(12) United States Patent
Chaki et al.

(10) Patent No.: US 7,772,285 B2
(45) Date of Patent: Aug. 10, 2010

(54) BENZOPHENONE DERIVATIVES OR SALTS THEREOF

(75) Inventors: Hisaaki Chaki, Ohyama-machi (JP); Hironori Kotsubo, Tateyama-machi (JP); Tadashi Tanaka, Toyama (JP); Yukihiko Aikawa, Toyama (JP); Shuichi Hirono, Tokyo (JP); Shunichi Shiozawa, Kobe (JP)

(73) Assignee: Toyama Chemical Co., Ltd., Tokyo (JP)

( * ) Notice: Subject to any disclaimer, the term of this patent is extended or adjusted under 35 U.S.C. 154(b) by 1387 days.

(21) Appl. No.: 10/493,223

(22) PCT Filed: Nov. 13, 2002

(86) PCT No.: PCT/JP02/11846

§ 371 (c)(1), (2), (4) Date: Dec. 15, 2004

(87) PCT Pub. No.: WO03/042150

PCT Pub. Date: May 22, 2003

(65) Prior Publication Data

US 2005/0113400 A1 May 26, 2005

(30) Foreign Application Priority Data

Nov. 16, 2001 (JP) ............................. 2001-351217
Jul. 18, 2002 (JP) ............................. 2002-209382

(51) Int. Cl.
*A61K 31/122* (2006.01)
*A61K 31/381* (2006.01)
*A61K 31/416* (2006.01)
*A61K 31/4245* (2006.01)
*A61K 31/428* (2006.01)
*A61K 31/433* (2006.01)
*A61K 31/44* (2006.01)
*A61K 31/517* (2006.01)
*A61K 31/5375* (2006.01)
*C07D 239/72* (2006.01)
*C07D 257/02* (2006.01)
*C07D 261/02* (2006.01)
*C07D 265/28* (2006.01)
*C07D 271/04* (2006.01)
*C07D 275/04* (2006.01)
*C07D 285/02* (2006.01)
*C07D 333/52* (2006.01)
*C07C 49/786* (2006.01)

(52) U.S. Cl. .................... 514/679; 568/308; 514/231.2; 514/258.1; 514/336; 514/362; 514/364; 514/372; 514/378; 514/379; 514/403; 514/443; 544/253; 546/268.1; 548/127; 548/131; 548/206; 548/207; 548/240; 548/241; 548/250; 549/49

(58) Field of Classification Search ................. 568/308; 514/679, 231.2, 258.1, 336, 362, 364, 372, 514/378, 379, 403, 443; 548/127, 131, 206, 548/207, 240, 241, 250, 356.1; 546/268.1; 544/253; 549/49
See application file for complete search history.

(56) References Cited

FOREIGN PATENT DOCUMENTS

| EP | 0 276 064 |    | 7/1988 |
|----|-----------|----|--------|
| EP | 0276064   | *  | 7/1988 |
| EP | 0 531 823 A1 |  | 3/1993 |
| JP | 2000-336063 |  | 12/2000 |
| JP | 2001-328958 |  | 11/2001 |
| WO | 00/27792  |    | 5/2000 |

* cited by examiner

*Primary Examiner*—Joseph McKane
*Assistant Examiner*—Janet L Coppins
(74) *Attorney, Agent, or Firm*—Oblon, Spivak, McClelland, Maier & Neustadt, L.L.P.

(57) ABSTRACT

A benzophenone derivative represented by the following formula:

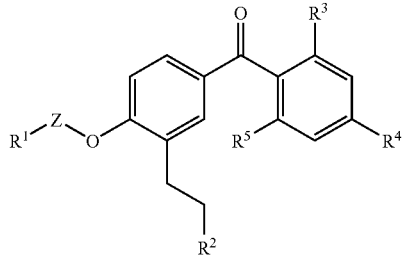

wherein
$R^1$ represents, for example, an optionally substituted heterocyclic group, or a substituted phenyl group; Z represents, for example, an alkylene group; $R^2$ represents, for example, a carboxyl group optionally protected with alkyl;
$R^3$ represents, for example, an optionally protected hydroxyl group; $R^4$ represents, for example, an optionally substituted cycloalkyloxy group; and $R^5$ represents, for example, a hydrogen atom,
or a salt thereof has anti-arthritic activity, inhibits bone destruction caused by arthritis, and provides high safety and excellent pharmacokinetics and thus is useful as therapeutic agent for arthritis. These compounds have inhibitory effect on AP-1 activity and are useful as preventive or therapeutic agent for diseases in which excessive expression of AP-1 is involved.

17 Claims, No Drawings

BENZOPHENONE DERIVATIVES OR SALTS THEREOF

TECHNICAL FIELD

The present invention relates to novel benzophenone derivatives or the salts thereof that have anti-arthritic activities and inhibitory effect on bone destruction caused by arthritis and provide preventive, therapeutic and improving effect against arthritic diseases. Further, the invention relates to preventive/therapeutic agent for diseases, in which excessive expression of AP-1 is involved, and inhibitors against AP-1 activity, which contain the above benzophenone derivatives or the salts thereof.

BACKGROUND ART

Arthritic disease such as connective tissue diseases, represented by rheumatoid arthritis, and osteoarthritis brings on joint dysfunction by the progression of cartilage/bone destruction and has a large effect on patients' daily life.

Up until now, for drug treatment for rheumatoid arthritis and other arthritis, have been used non-steroidal anti-inflammatory drugs (NSAIDs) such as aspirin and indomethacin, disease modifying antirheumatic drugs (DMARDs) such as gold preparation and D-penicillamine, immunosuppressive drugs such as methotrexate, and adrenocorticoids. However, therapies currently in use cannot completely inhibit the progress of bone destruction, which is the most important problem of concern with arthritis, and are difficult to apply to patients for a long period of time because of adverse effects occurring in association with the drugs used and thereby satisfactory treatment has not been given to patients to date.

To overcome the above problem, studies have been performed; for example, Japanese Patent Laid-Open No. 2000-336063 discloses benzophenone derivatives that are effective in the treatment for mouse collagen-induced arthritis. However, it is still expected that the benzophenone derivatives having anti-arthritic activities provide a further improvement in anti-arthritic activities and inhibitory effect on bone destruction caused by arthritis, safety, and pharmacokinetics.

Further, it has been hoped that preventive/therapeutic agent for diseases, in which excessive expression of AP-1 is involved, are developed which provide inhibitory effect on the activity of transcription factor AP-1, suppress excessive expression of a variety of genes based on their inhibitory effect on AP-1, and produce less adverse effects.

DISCLOSURE OF THE INVENTION

Under these conditions, the inventors of this invention directed tremendous research effort toward coming up to the above expectation and hope, and they have found that benzophenone derivatives represented by the following general formula:

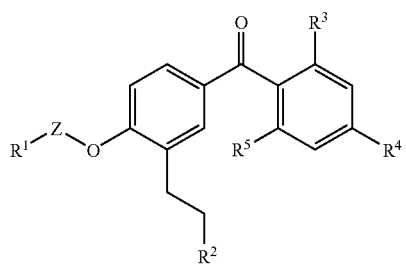

[1]

wherein
$R^1$ represents a substituted or unsubstituted heterocyclic group, a substituted phenyl group or a substituted or unsubstituted alkyl group;
Z represents a substituted or unsubstituted alkylene group;
$R^2$ represents a substituted or unsubstituted heterocyclic group, a substituted or unsubstituted heterocyclic carbonyl group or a protected or unprotected carboxyl group;
$R^3$ represents a hydrogen atom, a halogen atom, a cyano group, a nitro group, a protected or unprotected carboxyl group, a protected or unprotected hydroxyl group, a protected or unprotected amino group, a mercapto group, a carbamoyl group or a substituted or unsubstituted alkyl, alkenyl, cycloalkyl, aryl, aralkyl, alkoxy, aryloxy, acyl, alkoxycarbonyl, aryloxycarbonyl, alkylthio, alkylsulfinyl, alkylsulfonyl, alkylamino, acylamino, alkylsulfonylamino, arylsulfonylamino or heterocyclic group;
$R^4$ represents a substituted or unsubstituted alkoxy, cycloalkyloxy, cycloalkenyloxy, alkyl, cycloalkyl, heterocyclic-oxy or heterocyclic group;
$R^5$ represents a hydrogen atom, a halogen atom or a hydroxyl group;
provided that, when $R^1$ represents a substituted or unsubstituted alkyl group, $R^4$ represents a substituted or unsubstituted cycloalkyloxy group, an alkoxy group substituted with a substituted or unsubstituted phenyl or heterocyclic group, or a substituted or unsubstituted heterocyclic-oxy group,
or the salts thereof have excellent anti-arthritic action as well as inhibitory action against bone destruction caused by arthritis, and moreover, high safety and excellent pharmacokinetics. They also have found that the compounds of this invention provide AP-1 inhibitory action and are useful as preventive/therapeutic agent for diseases, in which excessive expression of AP-1 is involved. And they have finally accomplished this invention.

The compounds of this invention are expected to have AP-1 inhibitory action and be effective in the treatment and the prevention of diseases in which AP-1 related genes are involved.

In the following the compounds of this invention will be described in detail.

In this specification, unless otherwise specified, halogen atoms mean fluorine, chlorine, bromine and iodine atoms; alkyl groups mean straight- or branched-chain $C_{1-12}$ alkyl groups such as methyl, ethyl, n-propyl, isopropyl, n-butyl, sec-butyl, isobutyl, tert-butyl, pentyl, isopentyl, hexyl, heptyl and octyl groups; lower alkyl groups mean straight- or branched-chain $C_{1-6}$ alkyl groups such as methyl, ethyl, n-propyl, isopropyl, n-butyl, sec-butyl, isobutyl, tert-butyl, pentyl and isopentyl groups; halogeno lower alkyl groups mean straight- or branched-chain halogeno-$C_{1-6}$ alkyl groups such as fluoromethyl, chloromethyl, bromomethyl, dichloromethyl, trifluoromethyl, trichloromethyl, chloroethyl, dichloroethyl, trichloroethyl and chloropropyl groups; lower alkoxy lower alkyl groups mean straight- or branched-chain $C_{1-6}$ alkoxy-$C_{1-6}$ alkyl groups such as methoxymethyl, ethoxymethyl, n-propoxymethyl, methoxyethyl and ethoxyethyl groups; hydroxy lower alkyl groups mean straight- or branched-chain hydroxy-$C_{1-6}$ alkyl groups such as hydroxymethyl, hydroxyethyl and hydroxypropyl groups; amino lower alkyl groups mean amino-$C_{1-6}$ alkyl groups such as aminomethyl, aminoethyl and aminopropyl groups; alkenyl groups mean straight- or branched-chain $C_{2-12}$ alkenyl groups such as vinyl, allyl, propenyl, isopropenyl, butenyl, isobutenyl, pentenyl, hexenyl, heptenyl and octenyl groups; lower alkenyl groups mean straight- or branched-chain $C_{2-6}$ alkenyl groups such as vinyl, allyl, propenyl, isopropenyl, butenyl, isobutenyl and pentenyl groups; cycloalkyl groups mean $C_{3-7}$ cycloalkyl groups such as cyclopropyl, cyclobutyl, cyclopentyl, cyclohexyl or cycloheptyl group; cycloalkyloxy groups mean $C_{3-7}$ cycloalkyloxy groups such as cyclopropyloxy, cyclobutyloxy, cyclopentyloxy, cyclohexyloxy or cyclopentyloxy group; cycloalkenyloxy groups mean $C_{5-7}$ cycloalkenyloxy groups such as cyclopentenyloxy and cyclohexenyloxy groups; aryl groups mean, for example, phenyl, tolyl and naphthyl groups; aralkyl groups mean ar-$C_{1-12}$ alkyl groups such as benzyl, diphenylmethyl, trityl, phenethyl, 4-methylbenzyl and naphthylmethyl groups; ar-lower alkyl groups mean ar-$C_{1-6}$ alkyl groups such as benzyl, diphenylmethyl, trityl and phenethyl groups; aryloxy groups mean, for example, phenoxy and naphthoxy groups; aryloxycarbonyl groups mean, for example, phenoxycarbonyl and naphthoxycarbonyl groups; alkoxy groups mean straight- or branched-chain $C_{1-12}$ alkoxy groups such as methoxy, ethoxy, n-propoxy, isopropoxy, n-butoxy, isobutoxy, sec-butoxy, tert-butoxy, pentyloxy, isopentyloxy, hexyloxy, heptyloxy and octyloxy groups; lower alkoxy groups mean straight- or branched-chain $C_{1-6}$ alkoxy groups such as methoxy, ethoxy, n-propoxy, isopropoxy, n-butoxy, isobutoxy, sec-butoxy, tert-butoxy, pentyloxy and isopentyloxy groups; alkylene groups mean straight- or branched-chain $C_{1-12}$ alkylene groups such as methylene, ethylene and propylene groups; alkoxycarbonyl groups mean straight- or branched-chain $C_{1-12}$ alkoxycarbonyl groups such as methoxycarbonyl, ethoxycarbonyl, n-propoxycarbonyl, isopropoxycarbonyl, n-butoxycarbonyl, isobutoxycarbonyl, sec-butoxycarbonyl, tert-butoxycarbonyl and pentyloxycarbonyl groups; lower alkoxycarbonyl groups mean straight- or branched-chain $C_{1-6}$ alkyloxycarbonyl groups such as methoxycarbonyl, ethoxycarbonyl and propoxycarbonyl groups; lower alkoxycarbonyl lower alkyl groups mean straight- or branched-chain $C_{1-6}$ alkoxycarbonyl-$C_{1-6}$ alkyl groups such as methoxycarbonylmethyl, ethoxycarbonylmethyl, n-propoxycarbonylmethyl, methoxycarbonylethyl and ethoxycarbonylethyl groups; lower alkoxyimino groups mean straight- or branched-chain $C_{1-6}$ alkoxyimino groups such as methoxyimino and ethoxyimino groups; alkylamino groups mean straight- or branched-chain $C_{1-12}$ alkylamino groups such as methylamino, ethylamino, propylamino, butylamino, pentylamino, hexylamino, heptylamino and octylamino groups; lower alkylamino groups mean straight- or branched-chain mono- or di-$C_{1-6}$ alkylamino groups such as methylamino, ethylamino, propylamino, dimethylamino, diethylamino and methylethylamino groups; lower alkylamino lower alkyl groups mean mono- or di-$C_{1-6}$ alkylamino $C_{1-6}$ alkyl groups such as methylaminomethyl, methylaminoethyl, ethylaminomethyl, methylaminopropyl, propylaminoethyl, dimethylaminomethyl, diethylaminomethyl, diethylaminoethyl and dimethylaminopropyl groups; lower alkylidene groups mean $C_{1-6}$ alkylidene groups such as methylene, ethylidene, propylidene and isopropylidene groups; nitrogen-containing heterocyclic groups mean 5- or 6-membered-ring, condensed-ring or bridged-ring heterocyclic groups each of which contains one or more nitrogen atoms as hetero atoms forming the ring and optionally one or more oxygen atoms or sulfur atoms, such as pyrrolyl, pyrrolidinyl, piperidyl, piperazinyl, imidazolyl, pyrazolyl, pyridyl, tetrahydropyridyl, pyrimidinyl, morpholinyl, thiomorpholinyl, quinolyl, quinolizinyl, tetrahydroquinolinyl, tetrahydroisoquinolinyl, quinuclidinyl, quinazolyl, thiazolyl, tetrazolyl, thiadiazolyl, pyrrolinyl, imidazolinyl, imidazolidinyl, pyrazolinyl, pyrazolidinyl, purinyl and indazolyl groups; heterocyclic rings mean the above described nitrogen-containing heterocyclic groups and 5- or 6-membered-ring, condensed-ring or bridged-ring heterocyclic groups each of which contains at least one or more heteroatoms selected from the group consisting of nitrogen, oxygen and sulfur atoms and optionally one or more oxygen and sulfur atoms as heteroatoms forming the ring, such as furyl, thienyl, 4-methyl-2-oxo-1,3-dioxol, benzothienyl, pyranyl, isobenzofuranyl, oxazolyl, benzofuranyl, indolyl, benzimidazolyl, benzoxazolyl, benzisoxazolyl, benzothiazolyl, quinoxalyl, dihydroquinoxalinyl, 2,3-dihydrobenzothienyl, 2,3-dihydrobenzopyrrolyl, 2,3-dihydro-4H-1-thianaphthyl, 2,3-dihydrobenzofuranyl, benzo[b]dioxanyl, imidazo[2,3-a]pyridyl, benzo[b]piperazinyl, chromenyl, isothiazolyl, isoxazolyl, thiadiazolyl, oxadiazolyl, pyridazinyl, isoindolyl and isoquinolyl groups; heterocyclic carbonyl groups mean heterocyclic —CO— groups such as 4-hydroxy-2-(5H)-furanocarbonyl, morpholinocarbonyl, piperazinocarbonyl or pyrrolidinocarbonyl group; acyl groups mean, for example, formyl group, straight- or branched-chain $C_{2-12}$ alkanoyl groups such as acetyl, isovaleryl, propionyl and pivaloyl, aralkylcarbonyl groups such as benzylcarbonyl group, aroyl groups such as benzoyl and naphthoyl groups, and heterocyclic carbonyl groups such as nicotinoyl, thenoyl, pyrrolidinocarbonyl and furoyl groups; acylamino groups mean $C_{1-6}$ acylamino groups such as formylamino, acetylamino, propionylamino and butyrylamino groups; alkanoyloxy groups mean $C_{2-12}$ alkanoyloxy groups such as acetyloxy, propionyloxy and pivaloyloxy; cyclic amino groups mean both saturated and unsaturated cyclic amino groups, each of which optionally contains, in the ring, one or more heteroatoms such as nitrogen, oxygen and sulfur atoms and carbonyl-carbons and may be monocyclic or di- to tricyclic, in more particular, saturated or unsaturated 3- to 7-membered-ring monocyclic amino groups containing one nitrogen atom, such as aziridin-1-yl, azetizin-1-yl, pyrrolidin-1-yl, pyrrolin-1-yl, pyrrol-1-yl, dihydropyridin-1-yl, piperidin-1-yl, dihydroazepin-1-yl and perhydroazepin-1-yl groups, saturated or unsaturated 3- to 7-membered-ring monocyclic amino groups containing two nitrogen atoms, such as imidazol-1-yl, imidazolidin-1-yl, imidazolin-1-yl, pyrazolidin-1-yl, piperazin-1-yl, 1,4-dihydropyrazin-1-yl, 1,2-dihydropyrimidin-1-yl, perhydropyrazin-1-yl and homopiperazin-1-yl groups, saturated or unsaturated 3- to 7-membered-ring monocyclic amino groups containing 3 or more nitrogen atoms, such as 1,2,4-triazol-1-yl, 1,2,3-triazol-1-yl, 1,2-dihydro-1,2,4-triazin-1-yl and perhydro-S-triazin-1-yl, saturated or unsaturated 3- to 7-membered-ring monocyclic amino groups containing 1 to 4 heteroatoms selected from the group consisting of oxygen and sulfur atoms, besides nitrogen atoms, such as oxazolidin-3-yl, isoxazolidin-2-yl, morpholin-4-yl, thiazolidin-3-yl, isothiazolidin-2-yl, thiomorpholin-4-yl, homothiomorpholin-4-yl and 1,2,4-thiaziazolin-2-yl groups, saturated or unsaturated di- to tricyclic amino groups such as isoindolin-2-yl, indolin-1-yl, 1H-indazol-1-yl, purin-7-yl and tetrahydroquinolin-1-yl groups, and spiro or bridged saturated or unsaturated 5- to 12-membered cyclic amino groups such as 5-azaspiro[2.4]heptan-5-yl, 2,8-diazabicyclo[4.3.0]nonan-8-yl, 3-azabicyclo[3.1.0]hexan-3-yl, 2-oxa-5,8-diazabicyclo[4.3.0]nonan-8-yl, 2,8-diazaspiro[4.4]nonan-2-yl and 7-azabicyclo[2.2.1]heptan-7-yl groups; alkylthio groups mean straight- or branched-chain $C_{1-12}$ alkylthio groups such as methylthio, ethylthio, n-propylthio, isopropylthio, n-butylthio, isobutylthio, sec-butylthio, tert-butylthio, pentylthio, isopentylthio, hexylthio, heptylthio and octylthio groups; lower alkylthio groups mean straight- or branched-chain $C_{1-6}$ alkylthio groups such as methylthio, ethylthio, n-propylthio, isopropylthio, n-butylthio, isobutylthio, sec-butylthio, tert-butylthio, pentylthio and isopentylthio groups; alkylsulfinyl groups mean straight- or branched-chain $C_{1-12}$ alkylsulfinyl groups such as methylsulfinyl, ethylsulfinyl, n-propylsulfinyl, isopropylsulfinyl, n-butylsulfinyl, isobutylsulfinyl, sec-butylsulfinyl, tert-butylsulfinyl, pentylsulfinyl, isopentylsulfinyl, hexylsulfinyl, heptylsulfinyl and octylsulfinyl groups; alkylsulfonyl groups mean straight- or branched-chain $C_{1-12}$ alkylsulfonyl groups such as methylsulfonyl, ethylsulfonyl, n-propylsulfonyl, isopropylsulfonyl, n-butylsulfonyl, isobutylsulfonyl, sec-butylsulfonyl, tert-butylsulfonyl, pentylsulfonyl, isopentylsulfonyl, hexylsulfonyl, heptylsulfonyl and octylsulfonyl groups; alkylsulfonylamino groups mean straight- or branched-chain $C_{1-12}$ alkylsulfonylamino groups such as methylsulfonylamino, ethylsulfonylamino, n-propylsulfonylamino, isopropylsulfonylamino, n-butylsulfonylamino, isobutylsulfonylamino, sec-butylsulfonylamino, tert-butylsulfonylamino, pentylsulfonylamino, isopentylsulfonylamino, hexylsulfonylamino, heptylsulfonylamino and octylsulfonylamino groups; arylsulfonylamino groups mean aryl-$SO_2NH$-groups such as phenylsulfonylamino and naphthylsulfonylamino groups; lower alkylsulfinyl groups mean straight- or branched-chain $C_{1-6}$ alkylsulfinyl groups such as methylsulfinyl, ethylsulfinyl, n-propylsulfinyl, isopropylsulfinyl, n-butylsulfinyl, isobutylsulfinyl, sec-butylsulfinyl, tert-butylsulfinyl, pentylsulfinyl and hexylsulfinyl groups; lower alkylsulfonyl groups mean straight- or branched-chain $C_{1-6}$ alkylsulfonyl groups such as methylsulfonyl, ethylsulfonyl, n-propylsulfonyl, isopropylsulfonyl, n-butylsulfonyl, isobutylsulfonyl, sec-butylsulfonyl, tert-butylsulfonyl and pentylsulfonyl; lower alkylcarbamoyl groups mean mono- or di-$C_{1-6}$ alkylcarbamoyl groups such as methylcarbamoyl, ethylcarbamoyl, propylcarbamoyl, dimethylcarbamoyl, diethylcarbamoyl and methylethylcarbamoyl groups; lower alkylsulfonylamino groups mean straight- or branched-chain $C_{1-6}$ alkylsulfonylamino groups such as methylsulfonylamino, ethylsulfonylamino, n-propylsulfonylamino, isopropylsulfonylamino, n-butylsulfonylamino, isobutylsulfonylamino, sec-butylsulfonylamino, tert-butylsulfonylamino and pentylsulfonylamino groups; lower alkylsulfonylcarbamoyl groups mean straight- or branched-chain $C_{1-6}$ alkylsulfonylcarbamoyl groups such as methylsulfonylcarbamoyl, ethylsulfonylcarbamoyl, n-propylsulfonylcarbamoyl, isopropylsulfonylcarbamoyl, n-butylsulfonylcarbamoyl, isobutylsulfonylcarbamoyl, sec-butylsulfonylcarbamoyl, tert-butylsulfonylcarbamoyl and pentylsulfonylcarbamoyl groups; lower alkylaminosulfonyl groups mean mono- or di-$C_{1-6}$ alkylaminosulfonyl groups such as methylaminosulfonyl, ethylaminosulfonyl, propylaminosulfonyl, dimethylaminosulfonyl, diethylaminosulfonyl and methylethylaminosulfonyl groups; carboxyl-lower alkenyl groups mean, for example, straight- or branched-chain carboxyl-substituted $C_{2-6}$ alkenyl groups; hydroxyl-heterocyclic groups mean, for example, hydroxyl-substituted heterocyclyl groups; lower alkyl-heterocyclic groups mean, for example, heterocyclic groups each having been substituted with a straight- or branched-chain lower alkyl group; lower alkoxy-lower alkoxy groups mean straight- or branched-chain $C_{1-6}$ alkoxy groups each having been substituted with a lower alkoxy group; heterocyclic-lower alkyl groups mean heterocyclic —$CH_2$— groups such as pyrrolidinylmethyl, piperidylmethyl, piperazinylmethyl, pyrazolylmethyl, tetrahydropyridylmethyl, morpholinylmethyl, thiomorpholinylmethyl, tetrahydroquinolinylmethyl, tetrahydroisoquinolinylmethyl, quinuclidinylmethyl, tetrazolylmethyl, thiadiazolylmethyl, pyrazolidinylmethyl, purinylmethyl, indazolylmethyl, 2-thienylmethyl, furfuryl, 2-pyranylmethyl, 1-isobenzofurylmethyl, 2-pyrrolylmethyl, 1-imidazolylmethyl, 1-pyrazolylmethyl, 3-isothiazolylmethyl, 3-isoxazolylmethyl, 2-pyridylmethyl, 2-pyrazinylmethyl, 2-pyrimidinylmethyl, 2-pyridazinylmethyl, 1-isoindolylmethyl, 2-indolylmethyl, 1-isoquinolylmethyl, 2-quinolylmethyl, 1-phthalazinylmethyl, 2-naphthyridinylmethyl, 2-quinoxalinylmethyl, 2-quinazolinylmethyl, 3-cinnolinylmethyl, 2-oxazolylmethyl, 2-thiazolylmethyl, 2-benzo[b]furylmethyl, 2-benzo[b]thienylmethyl, 2-benz[d]imidazolylmethyl and 2-benz[d]oxazolylmethyl groups; leaving groups mean halogen atoms such as fluorine, chlorine, bromine and iodine atoms, alkoxysulfonyloxy groups such as methoxysulfonyloxy group, alkylsulfonyloxy groups such as methylsulfonyloxy group, and arylsulfonyloxy groups such as p-toluenesulfonyloxy and benzenesulfonyloxy groups; and heterocyclic oxy groups mean groups represented by heterocyclic-O— each of which binds via an oxygen atom, such as pyrrolidinyloxy, piperidinyloxy, tetrahydrofuranyloxy, tetrahydropyranyloxy and tetrahydrothiopyranyloxy groups.

Carboxyl-protecting groups include all the groups that can be used as ordinary carboxyl-protecting groups. Concrete examples are alkyl such as methyl, ethyl, n-propyl, isopropyl, 1,1-dimethylpropyl, n-butyl, and tert-butyl; aryl such as phenyl and naphthyl; aralkyl such as benzyl, diphenylmethyl, trityl, p-nitrobenzyl, p-methoxybenzyl, and bis(p-methoxyphenyl)methyl; acyl-alkyl such as acetylmethyl, benzoylmethyl, p-nitrobenzoylmethyl, p-bromobenzoylmethyl, and p-methanesulfonylbenzoylmethyl; oxygen-containing heterocyclyl such as 2-tetrahydropyranyl and 2-tetrahydrofuranyl; halogeno-alkyl such as 2,2,2-trichloroethyl; alkylsilylalkyl such as 2-(trimethylsilyl)ethyl; acyloxyalkyl such as acetoxymethyl, propionyloxymethyl, and pivaloyloxymethyl; nitrogen-containing heterocyclic alkyl such as phthalimidomethyl and succinimidomethyl; cycloalkyl such as cyclohexyl; alkoxyalkyl such as methoxymethyl, methoxyethoxymethyl, and 2-(trimethylsilyl)ethoxymethyl; ar-alkoxy-alkyl such as benzyloxymethyl; alkylthio-alkyl such as methylthiomethyl and 2-methylthioethyl; arylthioalkyl such as phenylthiomethyl; alkenyl such as 1,1-dimethyl-2-propenyl, 3-methyl-3-butenyl, and allyl; and substituted silyl such as trimethylsilyl, triethylsilyl, triisopropylsilyl, diethylisopropylsilyl, tert-butyldimethylsilyl, tert-butyldiphenylsilyl, diphenylmethylsilyl, and tert-butylmethoxyphenylsilyl. Of the above carboxyl-protecting groups, are preferred alkyl groups such as methyl, ethyl, isopropyl and isobutyl groups; aralkyl groups such as benzyl group; and substituted silyl groups such as trimethylsilyl group.

Amino-protecting groups include all the groups that can be used as ordinary amino-protecting groups. Concrete examples are acyl such as trichloroethoxycarbonyl, tribromoethoxycarbonyl, benzyloxycarbonyl, 2-ethylhexyloxycarbonyl, p-nitrobenzyloxycarbonyl, o-bromobenzyloxycarbonyl, (mono-, di-, tri-)chloroacetyl, trifluoroacetyl, phenylacetyl, formyl, acetyl, benzoyl, tert-pentyloxycarbonyl, tert-butoxycarbonyl, p-methoxybenzyloxycarbonyl, 3,4-dimethoxybenzyloxycarbonyl, 4-(phenylazo)benzyloxycarbonyl, 2-furfuryloxycarbonyl, diphenylmethoxycarbonyl, 1,1-dimethylpropoxycarbonyl, isopropoxycarbonyl, phthaloyl, succinyl, alanyl, leucyl, 1-adamantyloxycarbonyl, and 8-quinolyloxycarbonyl; aralkyl such as benzyl, diphenylmethyl, and trityl; alkoxy-alkyl such as methoxymethyl, benzyloxymethyl, 2-methoxyethoxymethyl, 2,2,2-trichloroethoxymethyl, 2-(trimethylsilyl)ethoxymethyl, and 1-ethoxyethyl; alkylthio-alkyl such as methylthiomethyl; arylthio such as 2-nitrophenylthio and 2,4-dinitrophenylthio; alkyl- or aryl-sulfonyl such as methanesulfonyl and p-toluenesulfonyl; dialkylamino-alkylidene such as N,N-dimethylaminomethylene; aralkylidene such as benzylidene, 2-hydroxybenzylidene, 2-hydroxy-5-chlorobenzylidene, and 2-hydroxy-1-naphthylmethylene; nitrogen-containing heterocyclic alkylidene such as 3-hydroxy-4-pyridylmethylene; cycloalkylidene such as cyclohexylidene, 2-ethoxycarbonylcyclohexylidene, 2-ethoxycarbonylcyclopentylidene, 2-acetylcyclohexylidene, and 3,3-dimethyl-5-oxycyclohexylidene; diaryl- or diaralkylphosphoryl such as diphenylphosphoryl and dibenzylphosphoryl; oxygen-containing heterocyclic alkyl such as 5-methyl-2-oxo-2H-1,3-dioxol-4-yl-methyl; substituted silyl such as trimethylsilyl; hydroxylamino; and nitroso and nitro. Of the above amino-protecting groups, are preferred acyl groups such as tert-butoxycarbonyl and 2-ethylhexyloxycarbonyl groups; aralkyl groups such as trityl group; alkoxyalkyl groups such as methoxymethyl group; alkyl- or aryl-sulfonyl groups such as methanesulfonyl and p-toluenesulfonyl groups; substituted silyl groups such as trimethylsilyl group; hydroxylamino group; nitroso group; and nitro group.

Hydroxyl-protecting groups include all the groups that can be used as ordinary hydroxyl-protecting groups. Concrete examples are acyl such as benzyloxycarbonyl, 4-nitrobenzyloxycarbonyl, 4-bromobenzyloxycarbonyl, 4-methoxybenzyloxycarbonyl, 3,4-dimethoxybenzyloxycarbonyl, methoxycarbonyl, ethoxycarbonyl, tert-butoxycarbonyl, 1,1-dimethylpropoxycarbonyl, isopropoxycarbonyl, isobutyloxycarbonyl, diphenylmethoxycarbonyl, 2,2,2-trichloroethoxycarbonyl, 2,2,2-tribromoethoxycarbonyl, 2-(trimethylsilyl)ethoxycarbonyl, 2-(phenylsulfonyl)ethoxycarbonyl, 2-(triphenylphosphonio)ethoxycarbonyl, 2-furfuryloxycarbonyl, 1-adamantyloxycarbonyl, vinyloxycarbonyl, allyloxycarbonyl, S-benzylthiocarbonyl, 4-ethoxy-1-naphthyloxycarbonyl, 8-quinolyloxycarbonyl, acetyl, formyl, chloroacetyl, dichloroacetyl, trichloroacetyl, trifluoroacetyl, methoxyacetyl, phenoxyacetyl, pivaloyl, and benzoyl; alkyl such as methyl, isopropyl, isobutyl, tert-butyl, 2,2,2-trichloroethyl, and 2-trimethylsilylethyl; alkenyl such as allyl; aralkyl such as benzyl, p-methoxybenzyl, 3,4-dimethoxybenzyl, diphenylmethyl, and trityl; oxygen-containing and sulfur-containing heterocyclyl such as tetrahydrofuryl, tetrahydropyranyl, and tetrahydrothiopyranyl; alkoxy-alkyl such as methoxymethyl, benzyloxymethyl, 2-methoxyethoxymethyl, 2,2,2-trichloroethoxymethyl, 2-(trimethylsilyl)ethoxymethyl, and 1-ethoxyethyl; alkylthio-alkyl such as methylthiomethyl; alkyl- and aryl-sulfonyl such as methanesulfonyl and p-toluenesulfonyl; and substituted silyl such as trimethylsilyl, triethylsilyl, triisopropylsilyl, diethylisopropylsilyl, tert-butyldimethylsilyl, tert-butyldiphenylsilyl, diphenylmethylsilyl, and tert-butylmethoxyphenylsilyl. Of the above hydroxyl-protecting groups, are preferred acyl groups such as acetyl group; alkyl groups such as methyl, isopropyl and isobutyl groups; aralkyl groups such as benzyl group; oxygen-containing heterocyclic groups such as tetrahydropyranyl group; alkoxyalkyl groups such as methoxymethyl group; and arylsulfonyl groups such as p-toluenesulfonyl group.

Phenolic hydroxyl-protecting groups include all the groups that can be used as ordinary phenol-protecting groups. Concrete examples are acyl such as benzyloxycarbonyl, 4-nitrobenzyloxycarbonyl, 4-bromobenzyloxycarbonyl, 4-methoxybenzyloxycarbonyl, 3,4-dimethoxybenzyloxycarbonyl, methoxycarbonyl, ethoxycarbonyl, tert-butoxycarbonyl, 1,1-dimethylpropoxycarbonyl, isopropoxycarbonyl, isobutyloxycarbonyl, diphenylmethoxycarbonyl, 2,2,2-trichloroethoxycarbonyl, 2,2,2-tribromoethoxycarbonyl, 2-(trimethylsilyl)ethoxycarbonyl, 2-(phenylsulfonyl)ethoxycarbonyl, 2-(triphenylphosphonio)ethoxycarbonyl, 2-furfuryloxycarbonyl, 1-adamantyloxycarbonyl, vinyloxycarbonyl, allyloxycarbonyl, S-benzylthiocarbonyl, 4-ethoxy-1-naphthyloxycarbonyl, 8-quinolyloxycarbonyl, acetyl, formyl, chloroacetyl, dichloroacetyl, trichloroacetyl, trifluoroacetyl, methoxyacetyl, phenoxyacetyl, pivaloyl, and benzoyl; alkyl such as methyl, isopropyl, isobutyl, tert-butyl, 2,2,2-trichloroethyl, and 2-trimethylsilylethyl; alkenyl such as allyl; aralkyl such as benzyl, p-methoxybenzyl, 3,4-dimethoxybenzyl, diphenylmethyl, and trityl; oxygen-containing and sulfur-containing heterocyclyl such as tetrahydrofuryl, tetrahydropyranyl, and tetrahydrothiopyranyl; alkoxy-alkyl such as methoxymethyl, benzyloxymethyl, 2-methoxyethoxymethyl, 2,2,2-trichloroethoxymethyl, 2-(trimethylsilyl)ethoxymethyl, and 1-ethoxyethyl; alkylthio-alkyl such as methylthiomethyl; alkyl-, and aryl-sulfonyl such as methanesulfonyl and p-toluenesulfonyl; and substituted silyl such as trimethylsilyl, triethylsilyl, triisopropylsilyl, diethylisopropylsilyl, tert-butyldimethylsilyl, tert-butyldiphenylsilyl, diphenylmethylsilyl, and tert-butylmethoxyphenylsilyl. Of the above phenolic hydroxyl-protecting groups, are preferred acyl groups such as acetyl group; alkyl groups such as methyl, isopropyl and isobutyl groups; aralkyl groups such as benzyl group; oxygen-containing heterocyclic groups such as tetrahydropyranyl group; alkoxyalkyl groups such as methoxymethyl group; and arylsulfonyl groups such as p-toluenesulfonyl group.

Phosphoryl-protecting groups include all the groups that can be used as ordinary phosphoryl-protecting groups. Concrete examples are alkyl such as methyl, ethyl, isopropyl, tert-butyl, 2-cyanoethyl, 2-(trimethylsilyl)ethyl, 2-(4-nitrophenyl)ethyl, 2-(benzylsulfonyl)ethyl, and 2,2,2-trichloroethyl; alkenyl such as allyl; aralkyl such as benzyl, 4-nitrobenzyl, and diphenylmethyl; aryl such as phenyl, 2-methylphenyl, 4-chlorophenyl, and 4-nitrophenyl; and amino such as anilino and isopropylamino.

Sulfo-protecting groups include all the groups that can be used as ordinary sulfonyloxy-protecting groups. Concrete examples are aryl groups such as phenyl and 2,4-dinitrophenyl groups; alkyl groups such as tert-butyl, neopentyl, isopropyl and isobutyl groups; and 1-adamantyl group.

In this invention, the improvement in pharmacokinetics means, for example, the reduction in enzyme inhibitory effect of cytochrome P450 and the improvement in metabolic stability, in more particular, the reduction in enzyme inhibitory effect of CYP2C9 etc. and the decrease of in vivo metabolite ratio.

Salts of the compounds represented by general formula [1] include, for example, commonly known salts produced in the compounds' basic groups such as amino group and produced in the compounds' acidic groups such as hydroxyl and carboxyl groups. Salts produced in the compounds' basic groups include, for example, salts produced with mineral acids such as hydrochloric acid, hydrobromic acid and sulfuric acid; salts produced with organic carboxylic acids such as tartaric acid, formic acid, citric acid, trichloroacetic acid and trifluoroacetic acid; and salts produced with sulfonic acids such as methanesulfonic acid, benzenesulfonic acid, p-toluenesulfonic acid, mesitylenesulfonic acid and naphthalenesulfonic acid. Salts produced in the compounds' acidic groups include, for example, salts produced with alkaline metals such as sodium and potassium; salts produced with alkaline earth metals such as calcium and magnesium; ammonium salts; and salts produced with nitrogen-containing organic bases such as trimethylamine, triethylamine, tributylamine, pyridine, N,N-dimethylaniline, N-methylpiperidine, N-methylmorpholine, diethylamine, dicyclohexylamine, procaine, dibenzylamine, N-benzyl-β-phenethylamine and N,N'-dibenzylethylenediamine. Of the above salts of the compounds represented by the general formula [1], preferable are pharmacologically acceptable salts.

Each substituent of the groups $R^1$, $R^2$, $R^3$ and $R^4$ is optionally substituted with one or more groups selected from the group consisting of cyano, nitro, halogen, carboxyl that may be protected, phosphoryl, hydroxyl, amino, carbamoyl, hydroxycarbamoyl, aminosulfonyl, sulfo, hydroxy lower alkyl, amino lower alkyl, cyclic amino, lower alkylamino and lower alkylamino lower alkyl, lower alkyl, lower alkenyl, lower alkoxy, lower alkoxycarbonyl, acyl, aryl, heterocyclyl, cycloalkyl, aralkyl, lower alkylidene, mercapto, lower alkylthio, lower alkylsulfinyl, lower alkylsulfonyl, lower alkylsulfonylcarbamoyl, lower alkylcarbamoyl, lower alkylsulfonylamino, lower alkylaminosulfonyl, carboxyl lower alkenyl, hydroxyheterocyclyl, lower alkyl heterocyclyl, lower alkoxy lower alkoxy, halogeno lower alkyl, lower alkoxy lower alkyl, lower alkoxycarbonyl lower alkyl, and lower alkoxyimino.

The alkylene group of Z is optionally substituted with one or more groups selected from the group consisting of cyano, nitro, halogen, carboxyl that may be protected, carbamoyl, hydroxycarbamoyl, hydroxy lower alkyl, amino lower alkyl and lower alkylamino lower alkyl, lower alkyl, lower alkoxycarbonyl, acyl, aryl, heterocyclyl, cycloalkyl, lower alkenyl, aralkyl, lower alkylsulfonylcarbamoyl, lower alkylcarbamoyl, halogeno lower alkyl, lower alkoxy lower alkyl, and lower alkoxycarbonyl lower alkyl.

The substituents of the above described substituents are further optionally substituted with the groups exemplified above as substituents.

The heterocyclic groups and cyclic amino groups of the substituents of the above described substituents are optionally substituted with keto groups.

Preferable substituents of the compounds of this invention are as follows.

In the compounds of this invention, $R^1$ is preferably an optionally substituted heterocyclyl group or a substituted phenyl group, more preferably an optionally substituted heterocyclyl group, much more preferably an optionally substituted benzisoxazolyl group, and most preferably hydroxyl-substituted benzisoxazolyl group.

In the compounds of this invention, $R^2$ is preferably a heterocyclic carbonyl group optionally substituted with a hydroxyl group or an alkyl group or a carboxyl group optionally protected with an alkyl group, more preferably a carboxyl group optionally protected with an alkyl group, much more preferably a carboxyl group optionally protected with an ethyl group, and most preferably a carboxyl group.

Further, in the compounds of this invention, $R^2$ is preferably a carboxyl group protected with a substituted alkyl group and more preferably a carboxyl group protected with an alkyl group that has been substituted with a 4-morpholinyl group.

In the compounds of this invention, $R^3$ is preferably a halogen atom, a lower alkyl group, or an optionally protected hydroxyl group, more preferably an optionally protected hydroxyl group, and much more preferably a hydroxyl group.

In the compounds of this invention, $R^4$ is preferably an optionally substituted cycloalkyloxy group, more preferably a cycloalkyloxy group optionally substituted with an alkyl, alkoxy or optionally protected hydroxyl group, and much more preferably a cycloalkyloxy group.

In the compounds of this invention, $R^5$ is preferably a hydrogen atom.

In the compounds of this invention, Z is preferably an alkylene group optionally substituted with a lower alkyl group, more preferably an alkylene group, and much more preferably a methylene group.

When the substituent of $R^2$ is a carboxyl group, any one of commonly used carboxyl-protecting groups can be used as a carboxyl-protecting group. Examples of such carboxyl-protecting groups are the above described carboxyl-protecting groups.

Specifically, the carboxyl-protecting groups include, for example, alkyl groups such as methyl, ethyl, n-propyl, isopropyl, n-butyl and tert-butyl groups; alkoxycarbonyloxyalkyl groups such as 1-[(methoxycarbonyl)oxy]ethyl, 1-[(ethoxycarbonyl)oxy]ethyl and 1-[(isopropoxycarbonyl)oxy]ethyl groups; cycloalkyloxycarbonyloxyalkyl groups such as 1-{[(cyclopentyloxy)carbonyl]oxy}ethyl and 1-{[(cyclohexyloxy)carbonyl]oxy}ethyl groups; heterocyclic-alkyl groups such as 2-(4-morpholinyl)ethyl, (5-methyl-2-oxo-1,3-dioxol-4-yl)methyl and (5-phenyl-2-oxo-1,3-dioxol-4-yl)methyl groups; and acyloxyalkyl groups such as acetoxymethyl, propionyloxymethyl and pivaloyloxymethyl groups. Of the above carboxyl-protecting groups, are preferably used alkyl groups such as methyl and ethyl groups; alkoxycarbonyloxyalkyl groups such as 1-[(ethoxycarbonyl)oxy]ethyl group; cycloalkyloxycarbonyloxyalkyl groups such as 1-{[(cyclohexyloxy)carbonyl]oxy}ethyl group; heterocyclic-alkyl groups such as 2-(4-morpholinyl)ethyl and (5-methyl-2-oxo-1,3-dioxol-4-yl)methyl groups; and acyloxyalkyl groups such as pivaloyloxymethyl group, and 2-(4-morpholinyl)ethyl group is more preferably used.

In the compounds of this invention, a preferable combination of substituents is such that $R^1$ is an optionally substituted heterocyclyl group, $R^2$ is a carboxyl group optionally protected with an optionally substituted alkyl group, $R^3$ is an optionally protected hydroxyl group, $R^4$ is a cycloalkyloxy group optionally substituted with an alkyl, alkoxy or optionally protected hydroxyl group, $R^5$ is a hydrogen atom, and Z is an alkylene group.

A more preferable combination of substituents is such that $R^1$ is an optionally substituted benzisoxazolyl group, $R^2$ is a carboxyl group protected with an optionally substituted alkyl group, $R^3$ is a hydroxyl group, $R^4$ is a cycloalkyloxy group, $R^5$ is a hydrogen atom, and Z is an alkylene group.

Another more preferable combination of substituents is such that $R^1$ is an optionally substituted benzisoxazolyl group, $R^2$ is a carboxyl group, $R^3$ is a hydroxyl group, $R^4$ is a cycloalkyloxy group, $R^5$ is a hydrogen atom, and Z is an alkylene group.

Diseases in which AP-1-related genes are involved include, for example, autoimmune diseases such as rheumatoid arthritis, systemic lupus erythematosus, scleroderma, Behcet's disease, rheumatic fever, polymyositis, periarteritis nodosa, Sjögren's syndrome, active chronic hepatitis and glomerulonephritis; a variety of intractable diseases based on inflammation such as osteoarthritis, gout, atherosclerosis, psoriasis, atopic dermatitis and encephalitis; pulmonary diseases accompanied by granuloma such as interstitial pneumonia; endotoxin shock; sepsis; inflammatory colitis; diabetes mellitus; acute myeloblast leukemia; meningitis; hepatitis; hepatic disorder; jaundice; liver cirrhosis; liver failure; atrialmyxoma; Castleman's syndrome; multiple myeloma; cancer; metastasis of cancer; AIDS; epilepsy; ischemic heart disease; endothelial proliferative disease (arteriosclerosis); Alzheimer's disease and ischemic neuronal death; allograft rejection in transplantation. The compounds of this invention are particularly suitably used for autoimmune diseases such as rheumatoid arthritis, systemic lupus erythematosus, scleroderma, Behcet's disease, rheumatic fever, polymyositis, periarteritis nodosa, Sjögren's syndrome, active chronic hepatitis and glomerulonephritis and more suitably used for rheumatoid arthritis.

Representative compounds of this invention include, for example, compounds shown in Table 1 to Table 11 below. In the tables abbreviations represent the following meanings.

BTP: benzothiophene, TZ: tetrazole, ODN: oxadiazolone, TDN: thiadiazolone, BOZ: benzisoxazole, BTZ: benzisothiazole, QN: quinazolidione, IOZ: isoxazolole, ITZ: isothiazolole, PZ: pyrazolole, c-Pent: cyclopentyl, Ms: methanesulfonyl, Ts: toluenesulfonyl, Ac: acetyl, Py: pyridyl, Me: methyl, Et: ethyl, Pr: propyl, Bu: butyl, Ph: phenyl, Bn: benzyl, Moe: 2-(4-morpholinyl)ethyl, Eoe: 1-[(ethoxycarbonyl)oxy]ethyl, Hoe: 1-{[(cyclohexyloxy)carbonyl]oxy}ethyl, Pvm: (pivaloyloxy)methyl, Dom: (5-methyl-2-oxo-1,3-dioxol-4-yl)methyl, i: iso

TABLE 1

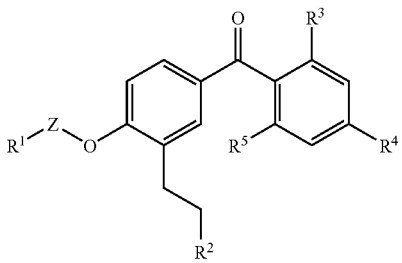

| $R^1$ | Z | $R^2$ | $R^3$ | $R^4$ | $R^5$ |
|---|---|---|---|---|---|
| 1-BTP-7-COOH-3-yl | $CH_2$ | COOH | OH | O-c-Pent | H |
| 1-BTP-7-COOH-3-yl | $(CH_2)_2$ | COOH | OH | O-c-Pent | H |
| 1-BTP-7-COOH-3-yl | $(CH_2)_3$ | COOH | OH | O-c-Pent | H |
| 1-BTP-7-COOEt-3-yl | $CH_2$ | COOH | OH | O-c-Pent | H |
| 1-BTP-6-COOH-3-yl | $CH_2$ | COOH | OH | O-c-Pent | H |
| 2-thiophenecarboxylic acid-4-yl | $CH_2$ | COOH | OH | O-c-Pent | H |
| 2-thiophenecarboxylic acid-5-yl | $CH_2$ | COOH | OH | O-c-Pent | H |
| 1-BTP-5-COOH-2-yl | $CH_2$ | COOH | OH | O-c-Pent | H |
| 1-BTP-6-COOH-2-yl | $CH_2$ | COOH | OH | O-c-Pent | H |
| 1-BTP-7-COOH-3-yl | CHMe | COOH | OH | O-c-Pent | H |
| 1-BTP-7-COOH-3-yl | $CH_2$ | 1,2,3,4-TZ-5-yl | OH | O-c-Pent | H |
| 1-BTP-7-COOH-3-yl | $CH_2$ | 1,2,4-ODN-03-yl | OH | O-c-Pent | H |
| 1-BTP-7-COOH-3-yl | $CH_2$ | tetronic acid-3-yl-CO | OH | O-c-Pent | H |
| 1-BTP-7-COOH-3-yl | $CH_2$ | 1,2,4-TDN-3-yl | OH | O-c-Pent | H |
| 1-BTP-7-COOH-3-yl | $CH_2$ | COOH | OH | $CH_2$-c-Pent | H |
| 1-BTP-7-COOH-3-yl | $CH_2$ | COOH | OH | O-i-Bu | H |
| 1-BTP-5-COOH-2-yl | $CH_2$ | 1,2,3,4-TZ-5-yl | OH | O-c-Pent | H |
| 1-BTP-5-COOH-2-yl | $CH_2$ | 1,2,4-ODN-3-yl | OH | O-c-Pent | H |
| 1-BTP-5-COOH-2-yl | $CH_2$ | 1,2,4-TDN-3-yl | OH | O-c-Pent | H |
| 1-BTP-7-COOH-3-yl | $CH_2$ | COOH | F | O-c-Pent | H |

TABLE 2

| $R^1$ | Z | $R^2$ | $R^3$ | $R^4$ | $R^5$ |
|---|---|---|---|---|---|
| 1-BTP-7-COOH-3-yl | $CH_2$ | COOH | CN | O-c-Pent | H |
| 1-BTP-7-COOH-3-yl | $CH_2$ | COOH | $NO_2$ | O-c-Pent | H |
| 1-BTP-7-COOH-3-yl | $CH_2$ | COOH | COOH | O-c-Pent | H |
| 1-BTP-7-COOH-3-yl | $CH_2$ | COOH | $NH_2$ | O-c-Pent | H |
| 1-BTP-7-COOH-3-yl | $CH_2$ | COOH | SH | O-c-Pent | H |
| 1-BTP-7-COOH-3-yl | $CH_2$ | COOH | $CONH_2$ | O-c-Pent | H |
| 1-BTP-7-COOH-3-yl | $CH_2$ | COOH | Me | O-c-Pent | H |
| 1-BTP-7-COOH-3-yl | $CH_2$ | COOH | $CH=CH_2$ | O-c-Pent | H |
| 1-BTP-7-COOH-3-yl | $CH_2$ | COOH | c-Pent | O-c-Pent | H |
| 1-BTP-7-COOH-3-yl | $CH_2$ | COOH | Ph | O-c-Pent | H |
| 1-BTP-7-COOH-3-yl | $CH_2$ | COOH | Bn | O-c-Pent | H |
| 1-BTP-7-COOH-3-yl | $CH_2$ | COOH | OMe | O-c-Pent | H |
| 1-BTP-7-COOH-3-yl | $CH_2$ | COOH | OPh | O-c-Pent | H |
| 1-BTP-7-COOH-3-yl | $CH_2$ | COOH | Ac | O-c-Pent | H |
| 1-BTP-7-COOH-3-yl | $CH_2$ | COOH | COOMe | O-c-Pent | H |
| 1-BTP-7-COOH-3-yl | $CH_2$ | COOH | COOPh | O-c-Pent | H |
| 1-BTP-7-COOH-3-yl | $CH_2$ | COOH | SMe | O-c-Pent | H |
| 1-BTP-7-COOH-3-yl | $CH_2$ | COOH | S(O)Me | O-c-Pent | H |
| 1-BTP-7-COOH-3-yl | $CH_2$ | COOH | $S(O)_2Me$ | O-c-Pent | H |
| 1-BTP-7-COOH-3-yl | $CH_2$ | COOH | $NMe_2$ | O-c-Pent | H |
| 1-BTP-7-COOH-3-yl | $CH_2$ | COOH | NHAc | O-c-Pent | H |
| 1-BTP-7-COOH-3-yl | $CH_2$ | COOH | NHMs | O-c-Pent | H |
| 1-BTP-7-COOH-3-yl | $CH_2$ | COOH | NHTs | O-c-Pent | H |
| 1-BTP-7-COOH-3-yl | $CH_2$ | COOH | 2-thienyl | O-c-Pent | H |
| 1-BTP-7-COOH-3-yl | $CH_2$ | COOH | OH | c-Pent | H |

TABLE 3

| $R^1$ | Z | $R^2$ | $R^3$ | $R^4$ | $R^5$ |
|---|---|---|---|---|---|
| 1-BTP-7-COOH-3-yl | $CH_2$ | COOH | OH | 2-thienyl | H |
| 1-BTP-7-COOH-3-yl | $CH_2$ | COOH | OH | i-Bu | H |
| 1-BTP-7-COOH-3-yl | $CH_2$ | COOH | OH | O-c-Pent | F |
| 1-BTP-7-COOH-3-yl | $CH_2$ | COOH | OH | O-c-Pent | OH |
| 3-OH-1,2-BOZ-6-yl | $CH_2$ | COOH | OH | O-c-Pent | H |
| 3-OH-1,2-BOZ-6-yl | $(CH_2)_2$ | COOH | OH | O-c-Pent | H |
| 3-OH-1,2-BOZ-6-yl | $(CH_2)_3$ | COOH | OH | O-c-Pent | H |
| 3-OH-1,2-BOZ-5-yl | $CH_2$ | COOH | OH | O-c-Pent | H |
| 2,4(1H,3H)-QN-7-yl | $CH_2$ | COOH | OH | O-c-Pent | H |
| 2,4(1H,3H)-QN-6-yl | $CH_2$ | COOH | OH | O-c-Pent | H |
| 3-OH-1,2-BTZ-6-yl | $CH_2$ | COOH | OH | O-c-Pent | H |
| 3-OH-1,2-BTZ-5-yl | $CH_2$ | COOH | OH | O-c-Pent | H |
| 3-OH-indazol-6-yl | $CH_2$ | COOH | OH | O-c-Pent | H |
| 3-OH-indazol-5-yl | $CH_2$ | COOH | OH | O-c-Pent | H |
| 1-BTP-2-COOH-5-yl | $CH_2$ | COOH | OH | O-c-Pent | H |
| 1-BTP-2-COOH-6-yl | $CH_2$ | COOH | OH | O-c-Pent | H |
| i-Pr | $CH_2$ | COOH | OH | O-c-Pent | H |
| i-Pr | $CH_2$ | COOH | OH | $OCH_2$-3-Py | H |
| 3-OH-1,2-BOZ-6-yl | CHMe | COOH | OH | O-c-Pent | H |
| 3-OH-1,2-BOZ-6-yl | $CH_2$ | 1,2,3,4-TZ-5-yl | OH | O-c-Pent | H |
| 3-OH-1,2-BOZ-6-yl | $CH_2$ | 1,2,4-ODN-3-yl | OH | O-c-Pent | H |
| 3-OH-1,2-BOZ-6-yl | $CH_2$ | tetronic acid-3-yl-CO | OH | O-c-Pent | H |
| 3-OH-1,2-BOZ-6-yl | $CH_2$ | 1,2,4-TDN-3-yl | OH | O-c-Pent | H |
| 3-OH-1,2-BOZ-6-yl | $CH_2$ | COOH | OH | O-i-Bu | H |
| 3-OH-1,2-BOZ-6-yl | $CH_2$ | COOH | OH | $CH_2$-c-Pent | H |

TABLE 4

| $R^1$ | Z | $R^2$ | $R^3$ | $R^4$ | $R^5$ |
|---|---|---|---|---|---|
| 2,4(1H,3H)-QN-6-yl | $CH_2$ | 1,2,3,4-TZ-5-yl | OH | O-c-Pent | H |
| 2,4(1H,3H)-QN-6-yl | $CH_2$ | 1,2,4-ODN-3-yl | OH | O-c-Pent | H |
| 2,4(1H,3H)-QN-6-yl | $CH_2$ | 1,2,4-TDN-3-yl | OH | O-c-Pent | H |
| 3-OH-1,2-BTZ-6-yl | $CH_2$ | 1,2,3,4-TZ-5-yl | OH | O-c-Pent | H |

TABLE 4-continued

| R¹ | Z | R² | R³ | R⁴ | R⁵ |
|---|---|---|---|---|---|
| 3-OH-1,2-BTZ-6-yl | CH₂ | 1,2,4-ODN-3-yl | OH | O-c-Pent | H |
| 3-OH-1,2-BTZ-6-yl | CH₂ | 1,2,4-TDN-3-yl | OH | O-c-Pent | H |
| 3-OH-indazol-6-yl | CH₂ | 1,2,3,4-TZ-5-yl | OH | O-c-Pent | H |
| 3-OH-indazol-6-yl | CH₂ | 1,2,4-ODN-3-yl | OH | O-c-Pent | H |
| 3-OH-indazol-6-yl | CH₂ | 1,2,4-TDN-3-yl | OH | O-c-Pent | H |
| 1-BTP-2-COOH-5-yl | CH₂ | 1,2,3,4-TZ-5-yl | OH | O-c-Pent | H |
| 1-BTP-2-COOH-5-yl | CH₂ | 1,2,4-ODN-3-yl | OH | O-c-Pent | H |
| 1-BTP-2-COOH-5-yl | CH₂ | 1,2,4-TDN-3-yl | OH | O-c-Pent | H |
| 3-OH-1,2-BOZ-6-yl | CH₂ | COOH | F | O-c-Pent | H |
| 3-OH-1,2-BOZ-6-yl | CH₂ | COOH | CN | O-c-Pent | H |
| 3-OH-1,2-BOZ-6-yl | CH₂ | COOH | NO₂ | O-c-Pent | H |
| 3-OH-1,2-BOZ-6-yl | CH₂ | COOH | COOH | O-c-Pent | H |
| 3-OH-1,2-BOZ-6-yl | CH₂ | COOH | NH₂ | O-c-Pent | H |
| 3-OH-1,2-BOZ-6-yl | CH₂ | COOH | SH | O-c-Pent | H |
| 3-OH-1,2-BOZ-6-yl | CH₂ | COOH | CONH₂ | O-c-Pent | H |
| 3-OH-1,2-BOZ-6-yl | CH₂ | COOH | Me | O-c-Pent | H |
| 3-OH-1,2-BOZ-6-yl | CH₂ | COOH | CH=CH₂ | O-c-Pent | H |
| 3-OH-1,2-BOZ-6-yl | CH₂ | COOH | c-Pent | O-c-Pent | H |
| 3-OH-1,2-BOZ-6-yl | CH₂ | COOH | Ph | O-c-Pent | H |
| 3-OH-1,2-BOZ-6-yl | CH₂ | COOH | Bn | O-c-Pent | H |

TABLE 5

| R¹ | Z | R² | R³ | R⁴ | R⁵ |
|---|---|---|---|---|---|
| 3-OH-1,2-BOZ-6-yl | CH₂ | COOH | OMe | O-c-Pent | H |
| 3-OH-1,2-BOZ-6-yl | CH₂ | COOH | OPh | O-c-Pent | H |
| 3-OH-1,2-BOZ-6-yl | CH₂ | COOH | Ac | O-c-Pent | H |
| 3-OH-1,2-BOZ-6-yl | CH₂ | COOH | COOMe | O-c-Pent | H |
| 3-OH-1,2-BOZ-6-yl | CH₂ | COOH | COOPh | O-c-Pent | H |
| 3-OH-1,2-BOZ-6-yl | CH₂ | COOH | SMe | O-c-Pent | H |
| 3-OH-1,2-BOZ-6-yl | CH₂ | COOH | S(O)Me | O-c-Pent | H |
| 3-OH-1,2-BOZ-6-yl | CH₂ | COOH | S(O)₂Me | O-c-Pent | H |
| 3-OH-1,2-BOZ-6-yl | CH₂ | COOH | NMe₂ | O-c-Pent | H |
| 3-OH-1,2-BOZ-6-yl | CH₂ | COOH | NHAc | O-c-Pent | H |
| 3-OH-1,2-BOZ-6-yl | CH₂ | COOH | NHMs | O-c-Pent | H |
| 3-OH-1,2-BOZ-6-yl | CH₂ | COOH | NHTs | O-c-Pent | H |
| 3-OH-1,2-BOZ-6-yl | CH₂ | COOH | 2-thienyl | O-c-Pent | H |
| 3-OH-1,2-BOZ-6-yl | CH₂ | COOH | OH | c-Pent | H |
| 3-OH-1,2-BOZ-6-yl | CH₂ | COOH | OH | 2-thienyl | H |
| 3-OH-1,2-BOZ-6-yl | CH₂ | COOH | OH | i-Bu | H |
| 3-OH-1,2-BOZ-6-yl | CH₂ | COOH | OH | O-c-Pent | F |
| 3-OH-1,2-BOZ-6-yl | CH₂ | COOH | OH | O-c-Pent | OH |
| 4-(3-IOZ-5-yl)Ph | CH₂ | COOH | OH | O-c-Pent | H |
| 4-(3-IOZ-5-yl)Ph | (CH₂)₂ | COOH | OH | O-c-Pent | H |
| 4-(3-IOZ-5-yl)Ph | (CH₂)₃ | COOH | OH | O-c-Pent | H |
| 4-(3-IOZ-5-yl)Ph | CHMe | COOH | OH | O-c-Pent | H |
| 4-(3-ITZ-5-yl)Ph | CH₂ | COOH | OH | O-c-Pent | H |
| 4-(3-ITZ-4-yl)Ph | CH₂ | COOH | OH | O-c-Pent | H |
| 4-(3-PZ-5-yl)Ph | CH₂ | COOH | OH | O-c-Pent | H |

TABLE 6

| R¹ | Z | R² | R³ | R⁴ | R⁵ |
|---|---|---|---|---|---|
| 4-(3-PZ-4-yl)Ph | CH₂ | COOH | OH | O-c-Pent | H |
| 4-(3-IOZ-4-yl)Ph | CH₂ | COOH | OH | O-c-Pent | H |
| 4-(1,2,4-ODN-3-yl)Ph | CH₂ | COOH | OH | O-c-Pent | H |
| 4-(1,2,3,4-TZ-5-yl)Ph | CH₂ | COOH | OH | O-c-Pent | H |
| 4-(3-IOZ-5-yl)Ph | CH₂ | 1,2,3,4-TZ-5-yl | OH | O-c-Pent | H |
| 4-(3-IOZ-5-yl)Ph | CH₂ | 1,2,4-ODN-3-yl | OH | O-c-Pent | H |
| 4-(3-IOZ-5-yl)Ph | CH₂ | tetronic acid-3-yl-CO | OH | O-c-Pent | H |

TABLE 6-continued

| R¹ | Z | R² | R³ | R⁴ | R⁵ |
|---|---|---|---|---|---|
| 4-(3-IOZ-5-yl)Ph | CH₂ | 1,2,4-TDN-3-yl | OH | O-c-Pent | H |
| 4-(3-IOZ-5-yl)Ph | CH₂ | COOH | OH | CH₂-c-Pent | H |
| 4-(3-IOZ-5-yl)Ph | CH₂ | COOH | OH | O-i-Bu | H |
| 4-(3-ITZ-5-yl)Ph | CH₂ | 1,2,3,4-TZ-5-yl | OH | O-c-Pent | H |
| 4-(3-ITZ-5-yl)Ph | CH₂ | 1,2,4-ODN-3-yl | OH | O-c-Pent | H |
| 4-(3-ITZ-5-yl)Ph | CH₂ | 1,2,4-TDN-3-yl | OH | O-c-Pent | H |
| 4-(3-PZ-5-yl)Ph | CH₂ | 1,2,3,4-TZ-5-yl | H | O-c-Pent | H |
| 4-(3-PZ-5-yl)Ph | CH₂ | 1,2,4-ODN-3-yl | OH | O-c-Pent | H |
| 4-(3-PZ-5-yl)Ph | CH₂ | 1,2,4-TDN-3-yl | OH | O-c-Pent | H |
| 4-(3-IOZ-5-yl)Ph | CH₂ | COOH | F | O-c-Pent | H |
| 4-(3-IOZ-5-yl)Ph | CH₂ | COOH | CN | O-c-Pent | H |
| 4-(3-IOZ-5-yl)Ph | CH₂ | COOH | NO₂ | O-c-Pent | H |
| 4-(3-IOZ-5-yl)Ph | CH₂ | COOH | COOH | O-c-Pent | H |
| 4-(3-IOZ-5-yl)Ph | CH₂ | COOH | NH₂ | O-c-Pent | H |
| 4-(3-IOZ-5-yl)Ph | CH₂ | COOH | SH | O-c-Pent | H |
| 4-(3-IOZ-5-yl)Ph | CH₂ | COOH | CONH₂ | O-c-Pent | H |
| 4-(3-IOZ-5-yl)Ph | CH₂ | COOH | Me | O-c-Pent | H |
| 4-(3-IOZ-5-yl)Ph | CH₂ | COOH | CH=CH₂ | O-c-Pent | H |

TABLE 7

| R¹ | Z | R² | R³ | R⁴ | R⁵ |
|---|---|---|---|---|---|
| 4-(3-IOZ-5-yl)Ph | CH₂ | COOH | c-Pent | O-c-Pent | H |
| 4-(3-IOZ-5-yl)Ph | CH₂ | COOH | Ph | O-c-Pent | H |
| 4-(3-IOZ-5-yl)Ph | CH₂ | COOH | Bn | O-c-Pent | H |
| 4-(3-IOZ-5-yl)Ph | CH₂ | COOH | OMe | O-c-Pent | H |
| 4-(3-IOZ-5-yl)Ph | CH₂ | COOH | OPh | O-c-Pent | H |
| 4-(3-IOZ-5-yl)Ph | CH₂ | COOH | Ac | O-c-Pent | H |
| 4-(3-IOZ-5-yl)Ph | CH₂ | COOH | COOMe | O-c-Pent | H |
| 4-(3-IOZ-5-yl)Ph | CH₂ | COOH | COOPh | O-c-Pent | H |
| 4-(3-IOZ-5-yl)Ph | CH₂ | COOH | SMe | O-c-Pent | H |
| 4-(3-IOZ-5-yl)Ph | CH₂ | COOH | S(O)Me | O-c-Pent | H |
| 4-(3-IOZ-5-yl)Ph | CH₂ | COOH | S(O)₂Me | O-c-Pent | H |
| 4-(3-IOZ-5-yl)Ph | CH₂ | COOH | NMe₂ | O-c-Pent | H |
| 4-(3-IOZ-5-yl)Ph | CH₂ | COOH | NHAc | O-c-Pent | H |
| 4-(3-IOZ-5-yl)Ph | CH₂ | COOH | NHMs | O-c-Pent | H |
| 4-(3-IOZ-5-yl)Ph | CH₂ | COOH | NHTs | O-c-Pent | H |
| 4-(3-IOZ-5-yl)Ph | CH₂ | COOH | 2-thienyl | O-c-Pent | H |
| 4-(3-IOZ-5-yl)Ph | CH₂ | COOH | OH | c-Pent | H |
| 4-(3-IOZ-5-yl)Ph | CH₂ | COOH | OH | 2-thienyl | H |
| 4-(3-IOZ-5-yl)Ph | CH₂ | COOH | OH | i-Bu | H |
| 4-(3-IOZ-5-yl)Ph | CH₂ | COOH | OH | O-c-Pent | F |
| 4-(3-IOZ-5-yl)Ph | CH₂ | COOH | OH | O-c-Pent | OH |
| Ph(4-COOH) | CH₂ | COOH | OH | O-c-Pent | H |
| Ph(4-COOH) | (CH₂)₂ | COOH | OH | O-c-Pent | H |
| Ph(4-COOH) | (CH₂)₃ | COOH | OH | O-c-Pent | H |
| Ph(4-COOEt) | CH₂ | COOH | OH | O-c-Pent | H |

TABLE 8

| R¹ | Z | R² | R³ | R⁴ | R⁵ |
|---|---|---|---|---|---|
| Ph(4-CH=CHCOOH) | CH₂ | COOH | OH | O-c-Pent | H |
| Ph(4-CH=CHCOOEt) | CH₂ | COOH | OH | O-c-Pent | H |
| Ph(4-(CH₂)₂COOH) | CH₂ | COOH | OH | O-c-Pent | H |
| Ph(4-(CH₂)₃COOH) | CH₂ | COOH | OH | O-c-Pent | H |
| Ph(3-OMe)(4-COOH) | CH₂ | COOH | OH | O-c-Pent | H |
| Ph(3-Me)(4-COOH) | CH₂ | COOH | OH | O-c-Pent | H |
| Ph(2-Me)(4-COOH) | CH₂ | COOH | OH | O-c-Pent | H |
| Ph(4-COOH) | CHMe | COOH | OH | O-c-Pent | H |
| Ph(4-COOH) | CH₂ | 1,2,3,4-TZ-5-yl | OH | O-c-Pent | H |
| Ph(4-COOH) | CH₂ | 1,2,4-ODN-3-yl | OH | O-c-Pent | H |
| Ph(4-COOH) | CH₂ | tetronic acid-3-yl-CO | OH | O-c-Pent | H |

TABLE 8-continued

| R¹ | Z | R² | R³ | R⁴ | R⁵ |
|---|---|---|---|---|---|
| Ph(4-COOH) | CH₂ | 1,2,4-TDN-3-yl | OH | O-c-Pent | H |
| Ph(3-OMe)(4-COOH) | CH₂ | 1,2,3,4-TZ-5-yl | OH | O-c-Pent | H |
| Ph(3-OMe)(4-COOH) | CH₂ | 1,2,4-ODN-3-yl | OH | O-c-Pent | H |
| Ph(3-OMe)(4-COOH) | CH₂ | tetronic acid-3-yl-CO | OH | O-c-Pent | H |
| Ph(3-OMe)(4-COOH) | CH₂ | 1,2,4-TDN-3-yl | OH | O-c-Pent | H |
| Ph(3-OMe)(4-COOH) | CH₂ | COOH | OH | O-i-Bu | H |
| Ph(3-OMe)(4-COOH) | CH₂ | COOH | OH | CH₂-c-Pent | H |
| Ph(4-COOH) | CH₂ | COOH | OH | O-i-Bu | H |
| Ph(4-COOH) | CH₂ | COOH | OH | CH₂-c-Pent | H |
| Ph(3-OMe)(4-COOEt) | CH₂ | COOH | OH | O-c-Pent | H |
| Ph(3-Me)(4-COOEt) | CH₂ | COOH | OH | O-c-Pent | H |
| Ph(2-Me)(4-COOEt) | CH₂ | COOH | OH | O-c-Pent | H |
| Ph(2,3-Me₂)(4-COOEt) | CH₂ | COOH | OH | O-c-Pent | H |

TABLE 9

| R¹ | Z | R² | R³ | R⁴ | R⁵ |
|---|---|---|---|---|---|
| Ph(4-CH=CHCOOH) | CH₂ | 1,2,3,4-TZ-5-yl | OH | O-c-Pent | H |
| Ph(4-CH=CHCOOH) | CH₂ | 1,2,4-ODN-3-yl | OH | O-c-Pent | H |
| Ph(4-CH=CHCOOH) | CH₂ | tetronic acid-3-yl-CO | OH | O-c-Pent | H |
| Ph(4-CH=CHCOOH) | CH₂ | 1,2,4-TDN-3-yl | OH | O-c-Pent | H |
| Ph(4-(CH₂)₂COOH) | CH₂ | 1,2,3,4-TZ-5-yl | OH | O-c-Pent | H |
| Ph(4-(CH₂)₂COOH) | CH₂ | 1,2,4-ODN-3-yl | OH | O-c-Pent | H |
| Ph(4-(CH₂)₂COOH) | CH₂ | 1,2,4-TDN-3-yl | OH | O-c-Pent | H |
| Ph(4-COOH) | CH₂ | COOH | F | O-c-Pent | H |
| Ph(4-COOH) | CH₂ | COOH | CN | O-c-Pent | H |
| Ph(4-COOH) | CH₂ | COOH | NO₂ | O-c-Pent | H |
| Ph(4-COOH) | CH₂ | COOH | COOH | O-c-Pent | H |
| Ph(4-COOH) | CH₂ | COOH | NH₂ | O-c-Pent | H |
| Ph(4-COOH) | CH₂ | COOH | SH | O-c-Pent | H |
| Ph(4-COOH) | CH₂ | COOH | CONH₂ | O-c-Pent | H |
| Ph(4-COOH) | CH₂ | COOH | Me | O-c-Pent | H |
| Ph(4-COOH) | CH₂ | COOH | CH=CH₂ | O-c-Pent | H |
| Ph(4-COOH) | CH₂ | COOH | c-Pent | O-c-Pent | H |
| Ph(4-COOH) | CH₂ | COOH | Ph | O-c-Pent | H |
| Ph(4-COOH) | CH₂ | COOH | Bn | O-c-Pent | H |
| Ph(4-COOH) | CH₂ | COOH | OMe | O-c-Pent | H |
| Ph(4-COOH) | CH₂ | COOH | OPh | O-c-Pent | H |

TABLE 9-continued

| R¹ | Z | R² | R³ | R⁴ | R⁵ |
|---|---|---|---|---|---|
| Ph(4-COOH) | CH₂ | COOH | Ac | O-c-Pent | H |
| Ph(4-COOH) | CH₂ | COOH | COOMe | O-c-Pent | H |
| Ph(4-COOH) | CH₂ | COOH | COOPh | O-c-Pent | H |

TABLE 10

| R¹ | Z | R² | R³ | R⁴ | R⁵ |
|---|---|---|---|---|---|
| Ph(4-COOH) | CH₂ | COOH | SMe | O-c-Pent | H |
| Ph(4-COOH) | CH₂ | COOH | S(O)Me | O-c-Pent | H |
| Ph(4-COOH) | CH₂ | COOH | S(O)₂Me | O-c-Pent | H |
| Ph(4-COOH) | CH₂ | COOH | NMe₂ | O-c-Pent | H |
| Ph(4-COOH) | CH₂ | COOH | NHAc | O-c-Pent | H |
| Ph(4-COOH) | CH₂ | COOH | NHMs | O-c-Pent | H |
| Ph(4-COOH) | CH₂ | COOH | NHTs | O-c-Pent | H |
| Ph(4-COOH) | CH₂ | COOH | 2-thienyl | O-c-Pent | H |
| Ph(4-COOH) | CH₂ | COOH | OH | c-Pent | H |
| Ph(4-COOH) | CH₂ | COOH | OH | 2-thienyl | H |
| Ph(4-COOH) | CH₂ | COOH | OH | i-Bu | H |
| Ph(4-COOH) | CH₂ | COOH | OH | O-c-Pent | F |
| Ph(4-COOH) | CH₂ | COOH | OH | O-c-Pent | OH |

TABLE 11

| R¹ | Z | R² | R³ | R⁴ | R⁵ |
|---|---|---|---|---|---|
| 3-OH-1,2-BOZ-6-yl | CH₂ | COOMe | OH | O-c-Pent | H |
| 3-OH-1,2-BOZ-6-yl | CH₂ | COOEt | OH | O-c-Pent | H |
| 3-OH-1,2-BOZ-6-yl | CH₂ | COO-n-Pr | OH | O-c-Pent | H |
| 3-OH-1,2-BOZ-6-yl | CH₂ | COO-i-Pr | OH | O-c-Pent | H |
| 3-OH-1,2-BOZ-6-yl | CH₂ | COOMoe | OH | O-c-Pent | H |
| 3-OH-1,2-BOZ-6-yl | CH₂ | COOEoe | OH | O-c-Pent | H |
| 3-OH-1,2-BOZ-6-yl | CH₂ | COOHoe | OH | O-c-Pent | H |
| 3-OH-1,2-BOZ-6-yl | CH₂ | COOPvm | OH | O-c-Pent | H |
| 3-OH-1,2-BOZ-6-yl | CH₂ | COODom | OH | O-c-Pent | H |

When isomers (e.g. optical isomers, geometrical isomers and tautomers) are present in compounds represented by the general formula [1] or the salts thereof, this invention embraces the isomers. This invention also embraces the solvates, the hydrates and the crystals in various forms of the compound or the salt thereof.

Then the process of producing the compounds of this invention will be described.

The compounds of this invention are produced by combining known processes; for example, they can be synthesized in accordance with the production processes A to Q shown below.

[Production Process A]

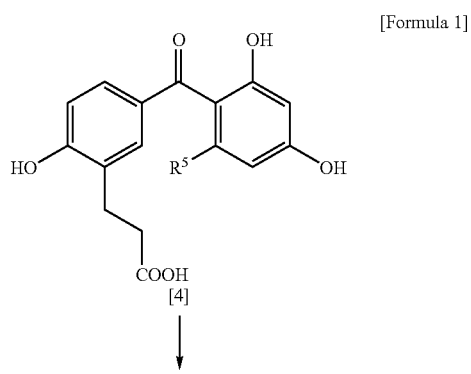

[Formula 1]

[4]

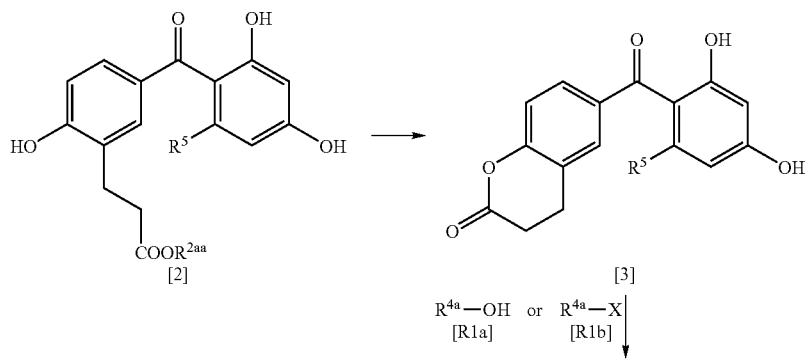
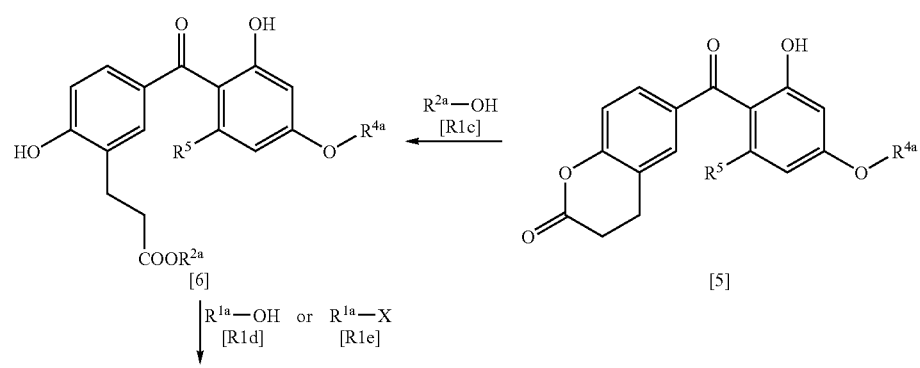
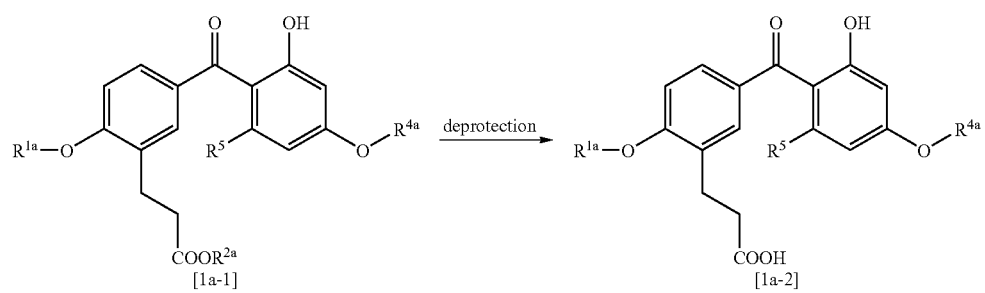
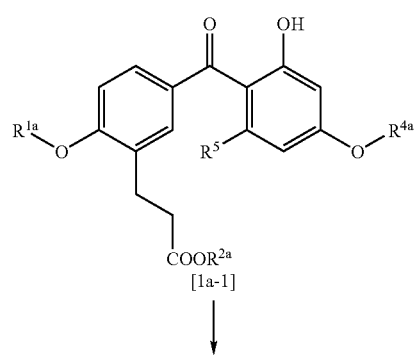

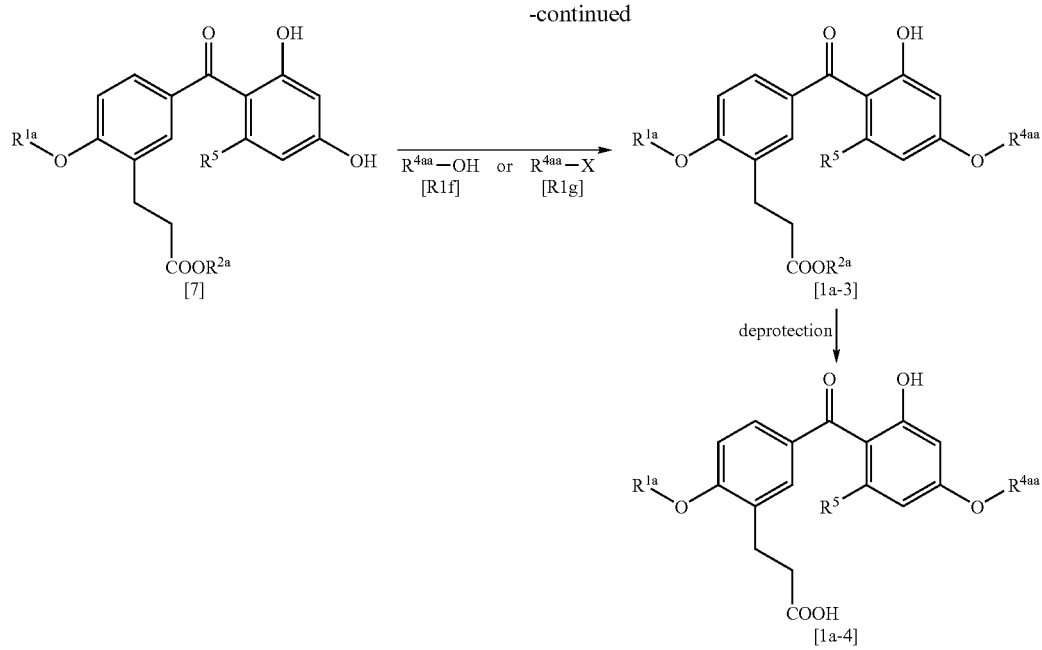

wherein $R^{2a}$ and $R^{2aa}$ each represent a carboxyl-protecting group; $R^{1a}$ represents a group represented by $R^1$—Z (wherein $R^1$ and Z represent the same meanings as above); $R^{4a}$ and $R^{4aa}$ each represent optionally substituted alkyl, cycloalkyl, heterocyclic, optionally substituted phenyl, or heterocyclyl-substituted alkyl; $R^5$ represents the same meaning as above; and X represents a leaving group.

A compound represented by the general formula [3] can be obtained by dehydrating a compound represented by the general formula [4]. This dehydration reaction is an ordinary dehydration reaction, and the reaction processes include, for example, processes in which dehydration is carried out in the presence or absence of acid or dehydrating agent, in which dehydration is carried out using base, condensing agent and additive, in which dehydration is carried out via acid chloride, and in which dehydration is carried out via acid anhydride.

Acids used in this reaction as the need arises include, for example, mineral acids such as hydrochloric acid, sulfuric acid, phosphoric acid and hydrobromic acid; organic acids such as p-toluenesulfonic acid and trifluoroacetic acid; and tin tetrachloride, aluminium chloride and boron trifluoride. The amount of acid used can be 0.01- to 100-fold of the mole of a compound represented by the general formula [4] and preferably 0.01- to 50-fold of the mole of the same. Dehydrating agents used in this reaction as the need arises include, for example, phosphorus pentoxide and polyphosphoric acid. The amount of dehydrating agent used can be 1- to 1000-fold of the mole of a compound represented by the general formula [4] and preferably 1- to 100-fold of the mole of the same.

When using base, condensing agent and additive in this reaction, bases used in the reaction include, for example, organic amines such as dimethylaminopyridine, triethylamine, pyridine and N-methylmorpholine; and alkaline metal carbonates such as potassium carbonate and sodium carbonate. The amount of base used can be 0.5- to 10-fold of the mole of a compound represented by the general formula [4] and preferably 1- to 3-fold of the mole of the same. Condensing agents used in the reaction include, for example, N,N'-dicyclohexylcarbodiimide, 1,1'-carbonyldiimidazole, 2-chloro-1-methylpyridinium iodide, 2,2'-dipyridyl disulfide and diphenylphosphoryl azide. The amount of condensing agent used can be 0.5- to 10-fold of the mole of a compound represented by the general formula [4] and preferably 1- to 3-fold of the mole of the same. Additives used in the reaction include, for example, 1-hydroxybenzotriazole, N-hydroxysuccinimide and triphenylphosphine. The amount of additive used can be 0.5- to 10-fold of the mole of a compound represented by the general formula [4] and preferably 1- to 3-fold of the mole of the same.

When using the processes via acid chloride or acid anhydride, the acid chloride or the acid anhydride of a compound represented by the general formula [4] can be obtained by reacting the compound represented by the general formula [4] with activating agent such as thionyl chloride, oxalyl chloride, phosphorus pentachloride, acetic anhydride or ethyl chloroformate. The amount of activating agent used can be 1- to 20-fold of the mole of a compound represented by the general formula [4] and preferably 1- to 5-fold of the mole of the same. In the reaction for obtaining the acid chloride of a compound represented by the general formula [4], N,N-dimethylformamide, as a catalyst, may be added in amounts of 0.001- to 10-fold of the mole of the compound represented by the general formula [4] and preferably 0.01- to 1-fold of the mole of the same.

Solvents used in this reaction are not limited to any specific ones as long as they do not adversely affect the reaction. They include, for example, aromatic hydrocarbons such as benzene and toluene; ethers such as 1,4-dioxane, tetrahydrofuran and diethyl ether; esters such as ethyl acetate and butyl acetate; nitrites such as acetonitrile; amides such as N,N-dimethylformamide and N,N'-dimethylacetamide; halogenated hydrocarbons such as chloroform and methylene chloride; sulfones such as sulfolane; and sulfoxides such as dimethyl sulfoxide. These solvents may be used independently or in the form of a mixture of two or more kinds.

Usually this reaction can be performed at −78° C. to the reflux temperature of the solvent used and preferably 0 to 150° C. for 30 minutes to 24 hours. The reaction can also be performed in an atmosphere of inert gas (e.g. argon, nitrogen).

The reaction for obtaining a compound represented by the general formula [3] from a compound represented by the general formula [2] can be carried out in the same manner as in the reaction for obtaining a compound represented by the general formula [3] from a compound represented by the general formula [4] in the production process A. Preferably the reaction is carried out in the presence or absence of acid.

A compound represented by the general formula [5] can be obtained by subjecting a compound represented by the general formula [3] and a compound represented by the general formula [R1a] to Mitsunobu reaction.

This reaction can be carried out using an azodicarbonyl compound such as diethyl azodicarboxylate, diisopropyl azodicarboxylate or azodicarbonyldipiperidine; and triarylphosphine such as triphenylphosphine or trialkylphosphine such as tri-n-butylphosphine. The amount of the compound represented by the general formula [R1a] used can be 1- to 5-fold of the mole of the compound represented by the general formula [3] and preferably 1- to 3-fold of the mole of the same.

Solvents used in this reaction are not limited to any specific ones as long as they do not adversely affect the reaction. They include, for example, aromatic hydrocarbons such as benzene, toluene and xylene; ethers such as 1,4-dioxane, tetrahydrofuran, anisole, diethylene glycol diethyl ether and dimethyl cellosolve; esters such as methyl acetate and ethyl acetate; nitrites such as acetonitrile; amides such as N,N-dimethylformamide and N,N'-dimethylacetamide; and halogenated hydrocarbons such as chloroform and methylene chloride. These solvents may be used independently or in the form of a mixture of two or more kinds.

Usually this reaction can be performed at −20 to 120° C. and preferably 0 to 50° C. for 30 minutes to 24 hours.

A compound represented by the general formula [5] can be obtained by reacting a compound represented by the general formula [3] and a compound represented by the general formula [R1b] in the presence of base.

The amount of the compound represented by the general formula [R1b] used can be 1- to 20-fold of the mole of the compound represented by the general formula [3] and preferably 1- to 5-fold of the mole of the same. Bases used in this reaction include, for example, organic amines such as dimethylaminopyridine, triethylamine and pyridine; alkaline metal hydrides such as sodium hydride; and alkaline metal carbonates such as potassium carbonate and sodium carbonate. The amount of base used can be 1- to 20-fold of the mole of the compound represented by the general formula [3] and preferably 1- to 5-fold of the mole of the same. Solvents used in this reaction are not limited to any specific ones as long as they do not adversely affect the reaction. They include, for example, aromatic hydrocarbons such as benzene, toluene and xylene; ethers such as 1,4-dioxane, tetrahydrofuran, anisole, diethylene glycol diethyl ether and dimethyl cellosolve; esters such as methyl acetate and ethyl acetate; nitrites such as acetonitrile; amides such as N,N-dimethylformamide; halogenated hydrocarbons such as chloroform and methylene chloride; and sulfoxides such as dimethyl sulfoxide. These solvents may be used independently or in the form of a mixture of two or more kinds.

Usually this reaction can be performed at 0 to 200° C. and preferably 25 to 150° C. for 10 minutes to 24 hours.

A compound represented by the general formula [6] can be obtained by reacting a compound represented by the general formula [R1c] and a compound represented by the general formula [5] in the presence of acid or base.

The compound represented by the general formula [R1c] used in this reaction can be used as a solvent in appropriate amount; however, when using some other solvent, the amount of the compound used can be 1- to 20-fold of the mole of the compound represented by the general formula [5] and preferably 1- to 5-fold of the mole of the same. Acids used in this reaction include, for example, hydrochloric acid, sulfuric acid, trimethylsilyl chloride and boron trifluoride. The amount of acid used can be 1- to 20-fold of the mole of the compound represented by the general formula [5] and preferably 1- to 5-fold of the mole of the same. Bases used in this reaction include, for example, alkaline metal alkoxides such as sodium methoxide, sodium ethoxide and potassium tert-butoxide; organic amines such as dimethylaminopyridine, triethylamine and pyridine; alkaline metal hydrides such as sodium hydride; and alkaline metal carbonates such as potassium carbonate and sodium carbonate. The amount of base used can be 1- to 20-fold of the mole of the compound represented by the general formula [5] and preferably 1- to 5-fold of the mole of the same. Solvents used in this reaction are not limited to any specific ones as long as they do not adversely affect the reaction. They include, for example, aromatic hydrocarbons such as benzene, toluene and xylene; ethers such as 1,4-dioxane, tetrahydrofuran, anisole, diethylene glycol diethyl ether and dimethyl cellosolve; nitrites such as acetonitrile; amides such as N,N-dimethylformamide; halogenated hydrocarbons such as chloroform and methylene chloride; and sulfoxides such as dimethyl sulfoxide. These solvents may be used independently or in the form of a mixture of two or more kinds.

Usually this reaction can be performed at −20 to 200° C. and preferably −10 to 150° C. for 10 minutes to 24 hours.

The reaction for obtaining a compound represented by the general formula [1a-1] from a compound represented by the general formula [6] can be carried out in the same manner as in the reaction for obtaining a compound represented by the general formula [5] from a compound represented by the general formula [3] in the production process A.

A compound represented by the general formula [1a-2] can be obtained by subjecting a compound represented by the general formula [1a-1] to deprotection reaction such as hydrolysis reaction in the presence of acid or base, dealkylation reaction using salt, or reductive dealkylation reaction including metal catalyst hydrogen addition reaction. Acids used in this reaction include, for example, formic acid, hydrochloric acid, sulfuric acid, hydrobromic acid, trifluoroacetic acid, aluminium chloride and trimethylsilyl iodide. The amount of acid used can be 1- to 1000-fold of the mole of the compound represented by the general formula [1a-1] and preferably 1- to 100-fold of the mole of the same. Bases used in this reaction include, for example, alkali hydroxides such as sodium hydroxide, potassium hydroxide and lithium hydroxide; alkaline metal alkoxides such as sodium methoxide, sodium ethoxide and potassium tert-butoxide; alkaline metal carbonates such as potassium carbonate and sodium carbonate; and tetrabutylammonium fluoride. The amount of base used can be 1- to 1000-fold of the mole of the compound represented by the general formula [1a-1] and preferably 1- to 50-fold of the mole of the same. Salts used in this reaction include, for example, lithium iodide and sodium chloride. The amount of salt used can be 1- to 100-fold of the mole of the compound represented by the general formula [1a-1] and preferably 1- to 10-fold of the mole of the same. Catalysts used in the reductive dealkylation reaction include, for example, palladium-carbon, palladium-black and palladium hydroxide. The amount of catalyst used can be 0.1- to 100% (w/w) the weight of the compound represented by the general formula [1a-1] and preferably 1- to 50% (w/w) the weight of the same. Reducing agents used in this reaction include, for example, hydrogen, formic acid, cyclohexene and zinc. The amount of reducing agent used can be 1- to 100-fold of the mole of the compound represented by the general formula [1a-1] and preferably 1- to 10-fold of the mole of the same. Solvents used in this reaction are not limited to any specific ones as long as they do not adversely affect the reaction. They include, for example, alcohols such as methanol, ethanol and isopropyl alcohol; ethers such as tetrahydrofuran, diethyl ether, 1,4-dioxane and anisole; halogenated hydrocarbons such as methylene chloride, chloroform and carbon tetrachloride; nitrites such as acetonitrile; aliphatic hydrocarbons such as n-hexane and cyclohexane; esters such as ethyl acetate; aromatic hydrocarbons such as toluene, benzene and xylene; dimethyl sulfoxide, N,N-dimethylformamide, nitromethane, pyridine and water. These solvents may be used independently or in the form of a mixture of two or more kinds.

Usually this reaction can be performed at −78 to 100° C. and preferably 0 to 80° C. for 10 minutes to 24 hours.

When the substituent $R^{1a}$, $R^{4a}$ or $R^5$ has a protecting group, the reaction can be carried out while appropriately deprotecting the substituent by conventional procedure.

A compound represented by the general formula [7] can be obtained by subjecting a compound represented by the general formula [1a-1] to reaction in the presence of acid, base or salt.

Acids used in this reaction include, for example, mineral acids such as hydrochloric acid, sulfuric acid and hydrobromic acid; organic acids such as trifluoroacetic acid; trimethylsilyl iodide, aluminium chloride, boron tribromide; and zinc chloride. These may be used in combination with each other. Bases used in this reaction include, for example, ethylmercaptan-sodium salt and lithium diisopropylamide. Salts used in this reaction include, for example, sodium cyanide, lithium iodide and pyridine hydrochloride.

The amounts of acid, base and salt used each can be 1- to 100-fold of the mole of the compound represented by the general formula [1a-1] and preferably 2- to 50-fold of the mole of the same. Solvents used in this reaction are not limited to any specific ones as long as they do not adversely affect the reaction. They include, for example, aromatic hydrocarbons such as benzene, toluene and xylene; ethers such as 1,4-dioxane, tetrahydrofuran, anisole, diethylene glycol diethyl ether and dimethyl cellosolve; esters such as methyl acetate and ethyl acetate; nitrites such as acetonitrile; alcohols such as methanol, ethanol and isopropyl alcohol; amides such as N,N-dimethylformamide and N,N-dimethylacetamide; and halogenated hydrocarbons such as chloroform and methylene chloride; and sulfoxides such as dimethyl sulfoxide. When using a mineral acid, water may also be used. These solvents may be used independently or in the form of a mixture of two or more kinds.

Usually this reaction can be performed at −78° C. to 150° C. and preferably 20 to 110° C. for 1 to 48 hours.

The reaction for obtaining a compound represented by the general formula [1a-3] from a compound represented by the general formula [7] can be carried out in the same manner as in the reaction for obtaining a compound represented by the general formula [5] from a compound represented by the general formula [3] in the production process A.

The reaction for obtaining a compound represented by the general formula [1a-4] from a compound represented by the general formula [1a-3] can be carried out in the same manner as in the reaction for obtaining a compound represented by the general formula [1a-2] from a compound represented by the general formula [1a-1] in the production process A. When the substituent $R^5$, $R^{1a}$ or $R^{4aa}$ has a protecting group, the reaction can be carried out while appropriately deprotecting the substituent by conventional procedure.

[Production Process B]

[Formula 3]

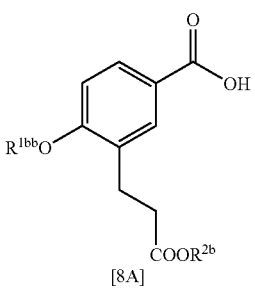

[8A]

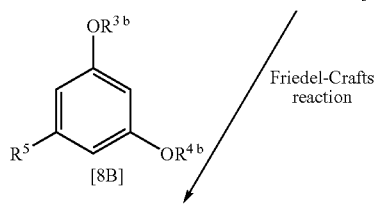

[8B]

Friedel-Crafts reaction

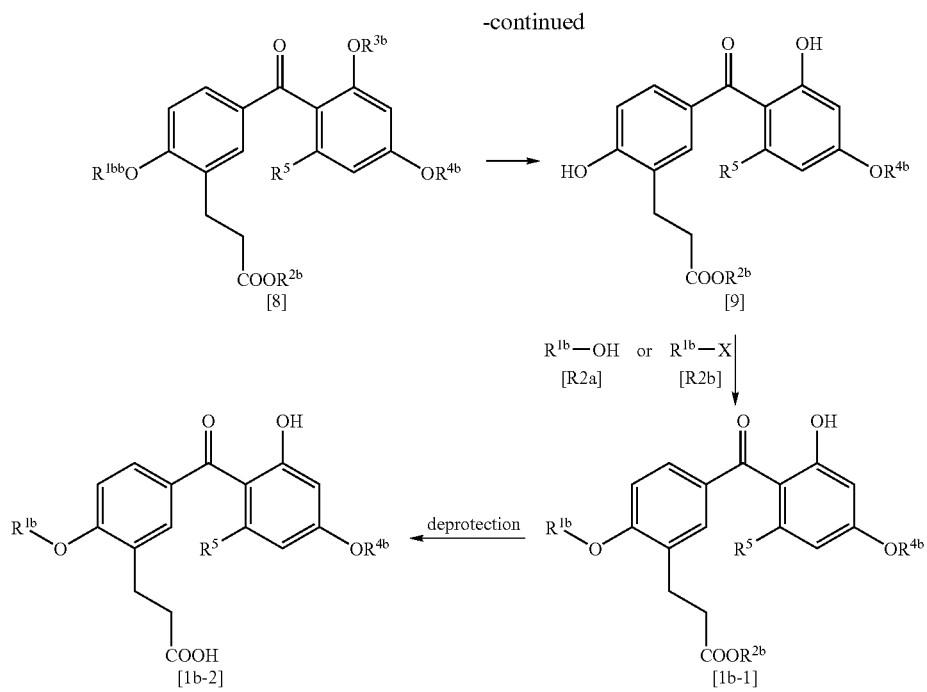

wherein $R^{2b}$ represents a carboxyl-protecting group; $R^{1b}$ represents the same meaning as $R^{1a}$; $R^{1bb}$, $R^{3b}$ and $R^{4b}$ each represent the same meaning as $R^{4a}$; and $R^5$ and X represent the same meaning as above.

A compound represented by the general formula [8] can be obtained by subjecting the acid chloride or acid anhydride of a compound represented by the general formula [8A] and a compound represented by the general formula [8B] to Friedel-Crafts reaction in the presence of acid.

The acid chloride or acid anhydride of a compound represented by the general formula [8A] used in the reaction can be obtained by allowing the compound represented by the general formula [8A] to react with activating agent such as thionyl chloride, oxalyl chloride, phosphorus pentachloride, acetic anhydride and ethyl chloroformate. The amount of activating agent used can be 1- to 10-fold of the mole of the compound represented by the general formula [8A] and preferably 1- to 3-fold of the mole of the same. In the reaction for obtaining the acid chloride of a compound represented by the general formula [8A], N,N-dimethylformamide as a catalyst may be added in amounts of 0.001- to 1-fold of the mole of the compound represented by the general formula [8A] and preferably 0.001- to 0.5-fold of the mole of the same. Acids used in this reaction include, for example, tin tetrachloride, aluminium chloride, boron trifluoride and zinc chloride. The amount of acid used can be 1- to 10-fold of the mole of a compound represented by the general formula [8A] and preferably 1- to 5-fold of the mole of the same. The amount of a compound represented by the general formula [8B] used can be 1 to 10-fold of the mole of a compound represented by the general formula [8A] and preferably 1- to 2-fold of the mole of the same. Solvents used in this reaction include, for example, halogenated hydrocarbons such as methylene chloride, chloroform, 1,2-dichloroethane and carbon tetrachloride; aliphatic hydrocarbons such as n-hexane and cyclohexane; nitromethane and nitrobenzene; and carbon disulfide. These solvents may be used independently or in the form of a mixture of two or more kinds.

Usually this reaction can be performed at −78° C. to 100° C. and preferably −50° C. to 30° C. for 10 minutes to 24 hours.

A compound represented by the general formula [9] can be obtained by subjecting a compound represented by the general formula [8] to reaction in the presence of acid, base or salt.

Acids used in this reaction include, for example, mineral acids such as hydrochloric acid, sulfuric acid and hydrobromic acid; organic acids such as trifluoroacetic acid; trimethylsilyl iodide, aluminium chloride, boron tribromide; and zinc chloride. These may be used in combination with each other. Bases used in this reaction include, for example, ethylmercaptan-sodium salt and lithium diisopropylamide. Salts used in this reaction include, for example, sodium cyanide, lithium iodide and pyridine hydrochloride. The amounts of acid, base and salt used each can be 2- to 100-fold of the mole of the compound represented by the general formula [8] and preferably 2- to 50-fold of the mole of the same. In this reaction, additives such as 2'-hydroxyacetophenone, anisole and ethyl acetate may be used. The amount of additive used can be 1- to 10-fold of the mole of the compound represented by the general formula [8] and preferably 1- to 5-fold of the mole of the same. Solvents used in this reaction are not limited to any specific ones as long as they do not adversely affect the reaction. They include, for example, aromatic hydrocarbons such as benzene, toluene and xylene; ethers such as 1,4-dioxane, tetrahydrofuran, anisole, diethylene glycol diethyl ether and dimethyl cellosolve; esters such as methyl acetate and ethyl acetate; nitriles such as acetonitrile; alcohols such as methanol, ethanol and isopropyl alcohol; amides such as N,N-dimethylformamide and N,N-dimethylacetamide; and halogenated hydrocarbons such as chloroform and methylene chloride; and sulfoxides such as dimethyl sulfoxide. When using a mineral acid, water may also be used. These solvents may be used independently or in the form of a mixture of two or more kinds.

Usually this reaction can be performed at −78° C. to 150° C. and preferably 20 to 110° C. for 1 to 48 hours.

A compound represented by the general formula [9] can also be obtained not by isolating a compound represented by the general formula [8] from a compound represented by the general formula [8A], but by carrying out the reactions continuously.

general formula [1a-2] from a compound represented by the general formula [1a-1] in the production process A. When the substituent $R^{1b}$ or $R^{4b}$ has a protecting group, the reaction can be carried out while appropriately deprotecting the substituent by conventional procedure.

[Production Process C]

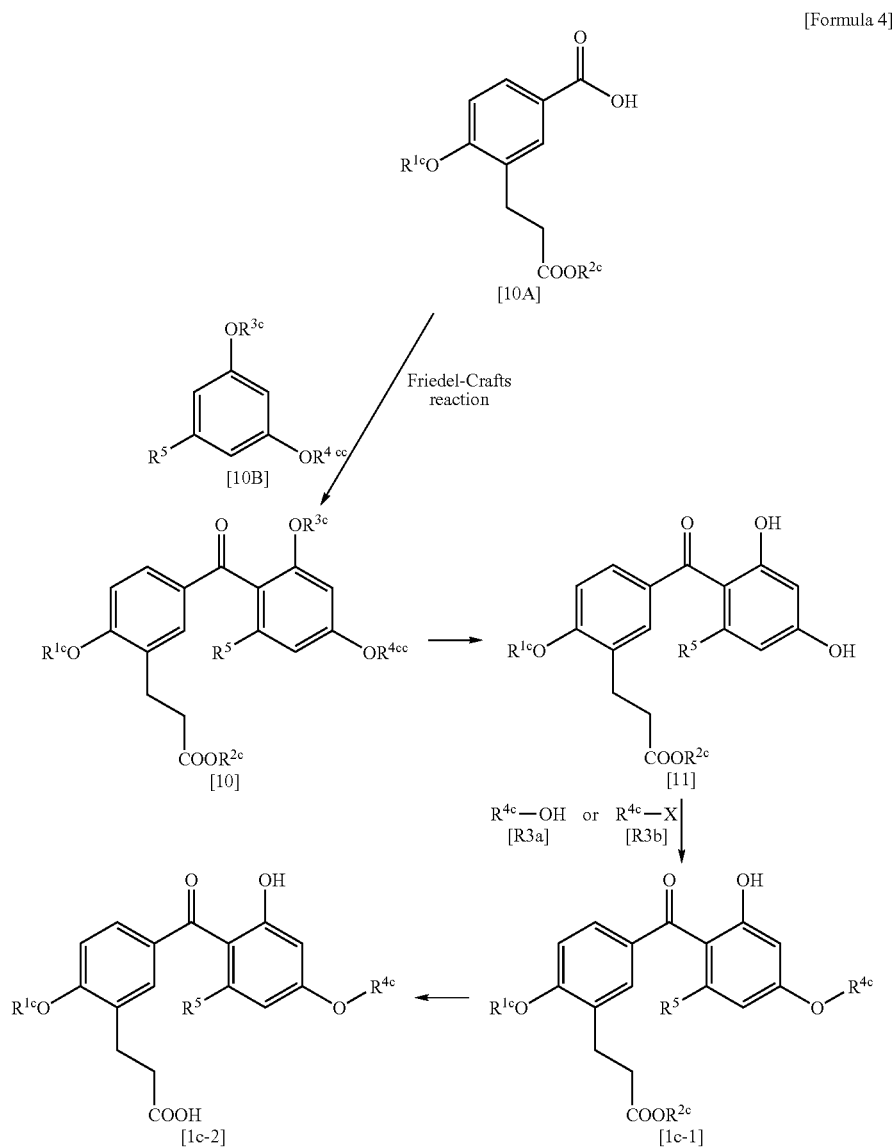

[Formula 4]

wherein $R^{2c}$ represents a carboxyl-protecting group; $R^{1c}$ represents the same meaning as $R^{1a}$; $R^{3c}$, $R^{4c}$ and $R^{4cc}$ each represent the same meaning as $R^{4a}$; and $R^5$ and X represent the same meaning as above.

The reaction for obtaining a compound represented by the general formula [1b-1] from a compound represented by the general formula [9] can be carried out in the same manner as in the reaction for obtaining a compound represented by the general formula [5] from a compound represented by the general formula [3] in the production process A.

The reaction for obtaining a compound represented by the general formula [1b-2] from a compound represented by the general formula [1b-1] can be carried out in the same manner as in the reaction for obtaining a compound represented by the The reaction for obtaining a compound represented by the general formula [10] from a compound represented by the general formula [10A] can be carried out in the same manner as in the reaction for obtaining a compound represented by the general formula [8] from a compound represented by the general formula [8A] in the production process B.

A compound represented by the general formula [11] can also be obtained not by isolating a compound represented by the general formula [10] from a compound represented by the general formula [10A], but by carrying out the reactions continuously.

The reaction for obtaining a compound represented by the general formula [11] from a compound represented by the general formula [10] can be carried out in the same manner as in the reaction for obtaining a compound represented by the general formula [9] from a compound represented by the general formula [8] in the production process B.

The reaction for obtaining a compound represented by the general formula [1c-1] from a compound represented by the general formula [11] can be carried out in the same manner as in the reaction for obtaining a compound represented by the general formula [5] from a compound represented by the general formula [3] in the production process A.

The reaction for obtaining a compound represented by the general formula [1c-2] from a compound represented by the general formula [1c-1] can be carried out in the same manner as in the reaction for obtaining a compound represented by the general formula [1a-2] from a compound represented by the general formula [1a-1] in the production process A.

When the substituent $R^{1c}$ or $R^{4c}$ has a protecting group, the reaction can be carried out while appropriately deprotecting the substituent by conventional procedure.

[Production Process D]

[Formula 5]

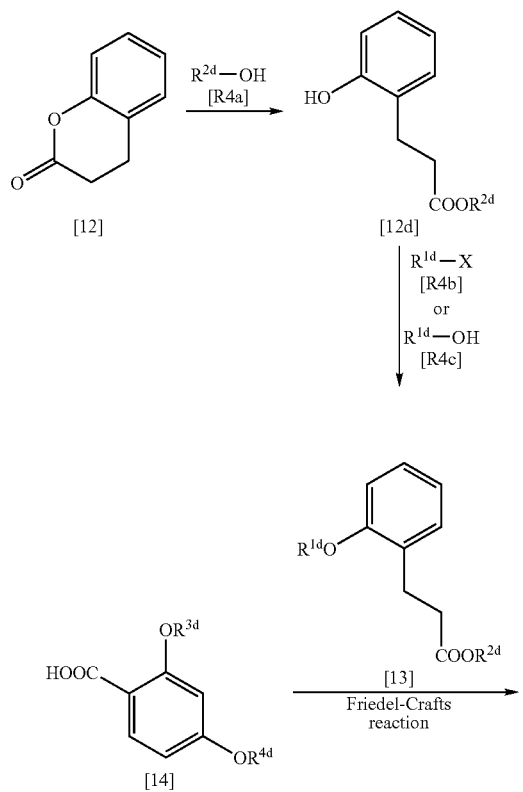

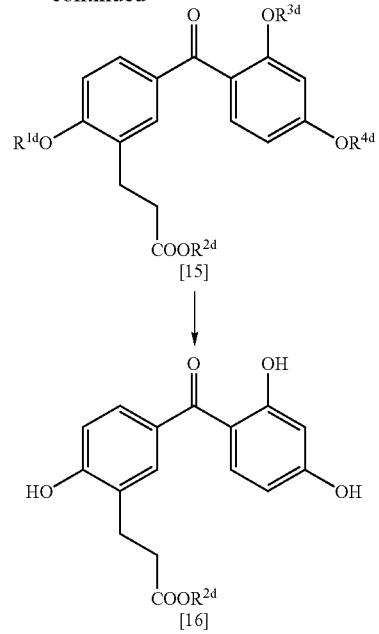

wherein $R^{2d}$ represents a carboxyl-protecting group; $R^{1d}$, $R^{3d}$ and $R^{4d}$ each represent the same meaning as $R^{4a}$; and X represents the same meaning as above.

The reaction for obtaining a compound represented by the general formula [12d] from a compound represented by the formula [12] can be carried out in the same manner as in the reaction for obtaining a compound represented by the general formula [6] from a compound represented by the general formula [5] in the production process A.

The reaction for obtaining a compound represented by the general formula [13] from a compound represented by the general formula [12d] can be carried out in the same manner as in the reaction for obtaining a compound represented by the general formula [5] from a compound represented by the general formula [3] in the production process A.

A compound represented by the general formula [13] can be obtained from a compound represented by the formula [12] via a compound represented by the general formula [12d] by carrying out the reactions continuously.

A compound represented by the general formula [15] can be obtained by subjecting the acid chloride or acid anhydride of a compound represented by the general formula [14] and a compound represented by the general formula [13] to Friedel-Crafts reaction in the presence of acid.

The acid chloride or the acid anhydride of a compound represented by the general formula [14] can be obtained by reacting the compound represented by the general formula [14] with activating agent such as thionyl chloride, oxalyl chloride, phosphorus pentachloride, acetic anhydride or ethyl chloroformate. The amount of activating agent used can be 1- to 10-fold of the mole of a compound represented by the general formula [14] and preferably 1- to 3-fold of the mole of the same. In the reaction for obtaining the acid chloride of a compound represented by the general formula [14], N,N-dimethylformamide, as a catalyst, may be added in amounts of 0.001- to 1-fold of the mole of the compound and preferably 0.001- to 0.5-fold of the mole of the same. Acids used in this reaction include, for example, tin tetrachloride, aluminium chloride, boron trifluoride and zinc chloride. The amount of acid used can be 1- to 10-fold of the mole of a compound represented by the general formula [14] and preferably 1- to 5-fold of the mole of the same. The amount of a compound represented by the general formula [13] used can be 1- to 10-fold of the mole of a compound represented by the general formula [14] and preferably 1- to 2-fold of the mole of the same. Solvents used in this reaction include, for example, halogenated hydrocarbons such as methylene chloride, chloroform 1,2-dichlorohexane and carbon tetrachloride; aliphatic hydrocarbons such as n-hexane and cyclohexane; nitromethane, nitrobenzene; and carbon disulfide. These solvents may be used independently or in the form of a mixture of two or more kinds.

Usually this reaction can be performed at −78° C. to 100° C. and preferably −50° C. to 30° C. for 10 minutes to 24 hours.

A compound represented by the general formula [16] can be obtained by subjecting a compound represented by the general formula [15] to reaction in the presence of acid, base or salt.

Acids used in this reaction include, for example, mineral acids such as hydrochloric acid, sulfuric acid and hydrobromic acid; organic acids such as trifluoroacetic acid and thiophenol; trimethylsilyl iodide, aluminium chloride, boron tribromide; and zinc chloride. Bases used in this reaction include, for example, ethylmercaptan-sodium salt and lithium diisopropylamide. Salts used in this reaction include, for example, sodium cyanide, lithium iodide and pyridine hydrochloride. The amounts of acid, base and salt used each can be 3- to 100-fold of the mole of the compound represented by the general formula [15] and preferably 3- to 50-fold of the mole of the same. In this reaction, additives such as 2'-hydroxyacetophenone, anisole and ethyl acetate may be used. The amount of additive used can be 1- to 10-fold of the mole of the compound represented by the general formula [14] and preferably 1- to 5-fold of the mole of the same. Solvents used in this reaction are not limited to any specific ones as long as they do not adversely affect the reaction. They include, for example, aromatic hydrocarbons such as benzene, toluene and xylene; ethers such as 1,4-dioxane, tetrahydrofuran, anisole, diethylene glycol diethyl ether and dimethyl cellosolve; esters such as methyl acetate and ethyl acetate; nitrites such as acetonitrile; alcohols such as methanol, ethanol and isopropyl alcohol; amides such as N,N-dimethylformamide and N,N-dimethylacetamide; and halogenated hydrocarbons such as chloroform and methylene chloride; and sulfoxides such as dimethyl sulfoxide. When using a mineral acid, water may also be used. These solvents may be used independently or in the form of a mixture of two or more kinds.

Usually this reaction can be performed at −78° C. to 150° C. and preferably 20 to 110° C. for 10 minutes to 48 hours.

A compound represented by the general formula [16] can also be obtained from a compound represented by the general formula [14] via a compound represented by the general formula [15] by carrying out the reactions continuously.

[Production Process E]

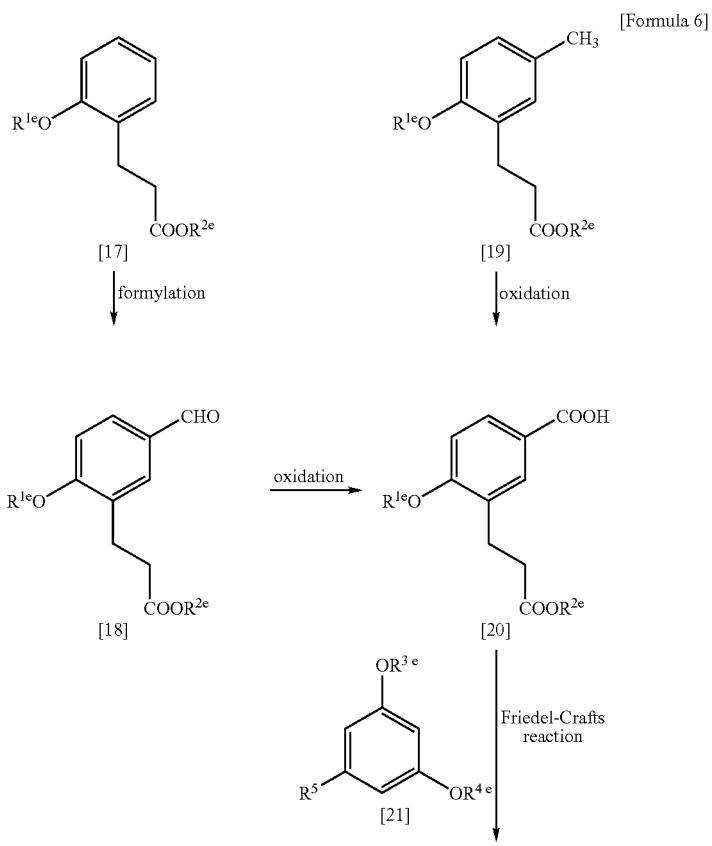

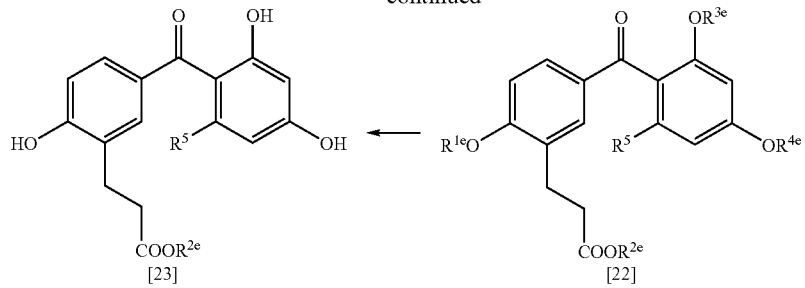

[23] [22]

wherein $R^{2e}$ represents a carboxyl-protecting group; $R^{1e}$, $R^{3e}$ and $R^{4e}$ each represent the same meaning as $R^{4a}$, and $R^5$ represents the same meaning as above.

A compound represented by the general formula [18] can be obtained by reacting a compound represented by the general formula [17] with a formylating agent in the presence of acid.

Acids used in this reaction include, for example, titanium tetrachloride, tin tetrachloride, aluminium chloride and phosphorus oxychloride. The amount of acid used can be 1- to 10-fold of the mole of the compound represented by the general formula [17] and preferably 1- to 3-fold of the mole of the same. Formylating agents used in this reaction include, for example, α,α-dichloromethyl methyl ether, N,N-dimethylformamide and ethyl orthoformate. The amount of formylating agent used can be 1- to 10-fold of the mole of the compound represented by the general formula [17] and preferably 1- to 5-fold of the mole of the same. Solvents used in this reaction include, for example, halogenated hydrocarbons such as methylene chloride, chloroform and carbon tetrachloride; and aliphatic hydrocarbons such as n-hexane and cyclohexane. These solvents may be used independently or in the form of a mixture of two or more kinds.

Usually this reaction can be performed at −78° C. to 150° C. and preferably −50° C. to 100° C. for 30 minutes to 24 hours.

A compound represented by the general formula [20] can be obtained by reacting a compound represented by the general formula [18] with an oxidizing agent in the presence or absence of acid or base.

Acids used in this reaction as the need arises include, for example, sodium dihydrogenphosphate, hydrochloric acid, sulfuric acid, acetic acid and sulfamic acid. The amount of acid used can be 1- to 1000-fold of the mole of a compound represented by the general formula [18] and preferably 1- to 100-fold of the mole of the same. Bases used in this reaction as the need arises include, for example, alkali hydroxides such as sodium hydroxide and potassium hydroxide; and pyridine. The amount of base used can be 1- to 1000-fold of the mole of a compound represented by the general formula [18] and preferably 1- to 100-fold of the mole of the same. Oxidizing agents used in this reaction include, for example, sodium chlorite, sodium hypochlorite, chromic acid, potassium permanganate, hydrogen peroxide, ruthenium oxide, nickel oxide, silver oxide and silver nitrate. The amount of oxidizing agent used can be 1- to 10-fold of the mole of a compound represented by the general formula [18] and preferably 1- to 5-fold of the mole of the same. Solvents used in this reaction are not limited to any specific ones as long as they do not adversely affect the reaction. They include, for example, ethers such as tetrahydrofuran, diethyl ether and 1,4-dioxane; halogenated hydrocarbons such as methylene chloride, chloroform and carbon tetrachloride; nitriles such as acetonitrile; aliphatic hydrocarbons such as n-hexane and cyclohexane; aromatic hydrocarbons such as toluene and benzene; dimethyl sulfoxide, pyridine; and water. These solvents may be used independently or in the form of a mixture of two or more kinds.

Usually this reaction can be performed at 0° C. to 100° C. and preferably 0° C. to 50° C. for 10 minutes to 24 hours.

A compound represented by the general formula [20] can also be obtained by reacting a compound represented by the general formula [19] with an oxidizing agent in the presence or absence of acid or base.

Acids used in this reaction as the need arises include, for example, sulfuric acid and acetic acid. The amount of acid used can be 1- to 1000-fold of the mole of a compound represented by the general formula [19] and preferably 1- to 100-fold of the mole of the same. Bases used in this reaction as the need arises include, for example, alkali hydroxides such as sodium hydroxide and potassium hydroxide; and pyridine. The amount of base used can be 1- to 1000-fold of the mole of a compound represented by the general formula [19] and preferably 1- to 100-fold of the mole of the same. Oxidizing agents used in this reaction include, for example, chromic acid and potassium permanganate. The amount of oxidizing agent used can be 1- to 50-fold of the mole of a compound represented by the general formula [19] and preferably 1- to 10-fold of the mole of the same. Solvents used in this reaction are not limited to any specific ones as long as they do not adversely affect the reaction. They include, for example, halogenated hydrocarbons such as methylene chloride, chloroform and carbon tetrachloride; aliphatic hydrocarbons such as n-hexane and cyclohexane; pyridine; and water. These solvents may be used independently or in the form of a mixture of two or more kinds.

Usually this reaction can be performed at 0° C. to 150° C. and preferably 20° C. to 100° C. for 30 minutes to 24 hours.

The reaction for obtaining a compound represented by the general formula [22] from a compound represented by the general formula [20] can be carried out in the same manner as in the reaction for obtaining a compound represented by the general formula [15] from a compound represented by the general formula [14] in the production process D.

The reaction for obtaining a compound represented by the general formula [23] from a compound represented by the general formula [22] can be carried out in the same manner as in the reaction for obtaining a compound represented by the general formula [16] from a compound represented by the general formula [15] in the production process D.

A compound represented by the general formula [23] can be obtained from a compound represented by the general formula [20] via a compound represented by the general formula [22] by carrying out the reactions continuously.

[Production Process F]
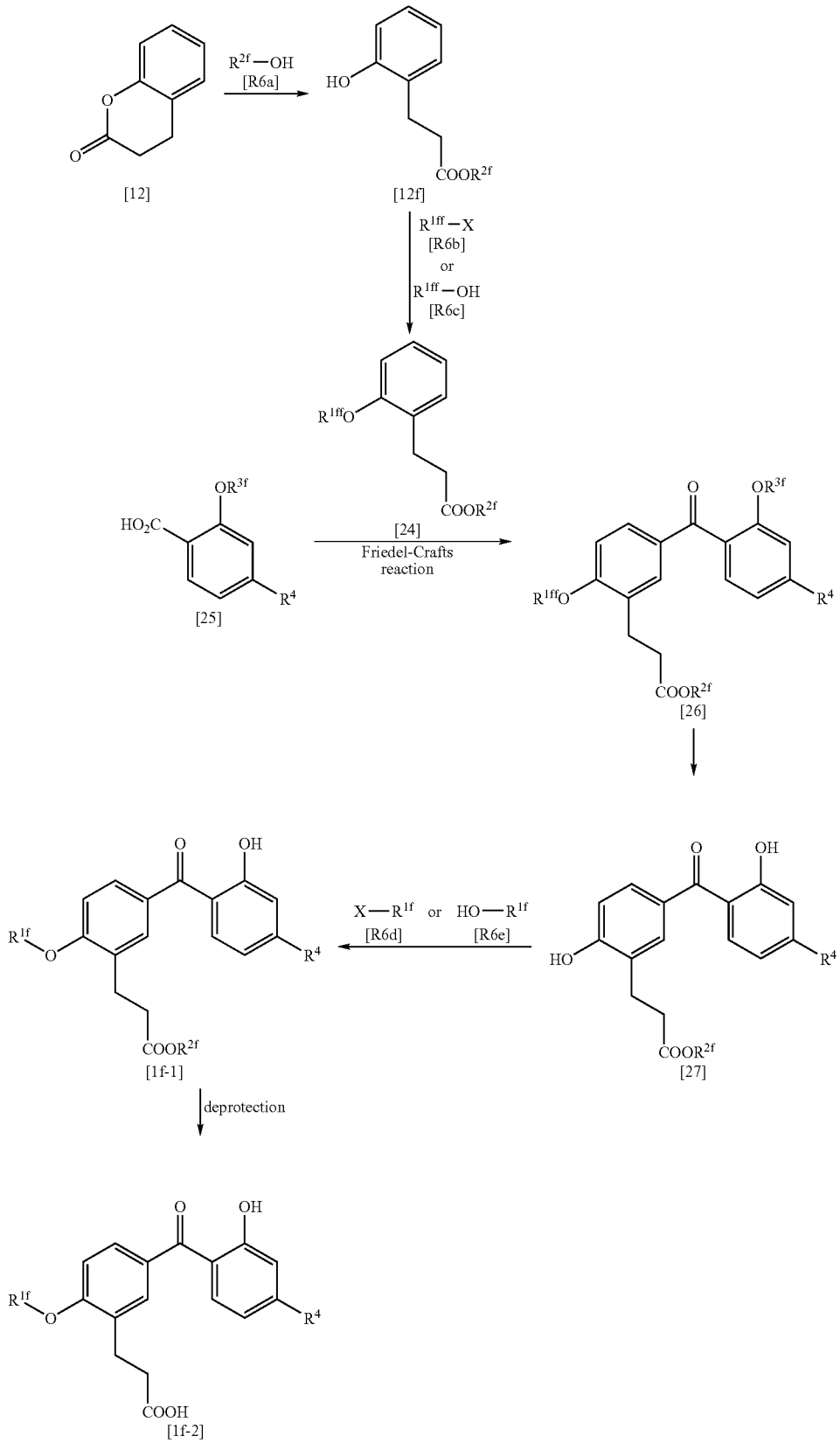

wherein $R^{2f}$ represents a carboxyl-protecting group; $R^{1f}$ represents the same meaning as $R^{1a}$; $R^{1ff}$ and $R^{3f}$ each represent the same meaning as $R^{4a}$; and $R^4$ and X represent the same meaning as above.

The reaction for obtaining a compound represented by the general formula [12f] from a compound represented by the formula [12] can be carried out in the same manner as in the reaction for obtaining a compound represented by the general formula [12d] from a compound represented by the formula [12] in the production process D.

The reaction for obtaining a compound represented by the general formula [24] from a compound represented by the general formula [12f] can be carried out in the same manner as in the reaction for obtaining a compound represented by the general formula [13] from a compound represented by the general formula [12d] in the production process D.

A compound represented by the general formula [24] can be obtained from a compound represented by the formula [12] via a compound represented by the general formula [12f] by carrying out the reaction for obtaining the compound represented by the general formula [12f] and the reaction of alkylating the same continuously.

The reaction for obtaining a compound represented by the general formula [26] from a compound represented by the general formula [25] can be carried out in the same manner as in the reaction for obtaining a compound represented by the general formula [15] from a compound represented by the general formula [14] in the production process D.

The reaction for obtaining a compound represented by the general formula [27] from a compound represented by the general formula [26] can be carried out in the same manner as in the reaction for obtaining a compound represented by the general formula [9] from a compound represented by the general formula [8] in the production process B.

A compound represented by the general formula [27] can also be obtained not by isolating a compound represented by the general formula [26] from a compound represented by the general formula [25], but by carrying out the reactions continuously.

The reaction for obtaining a compound represented by the general formula [1f-1] from a compound represented by the general formula [27] can be carried out in the same manner as in the reaction for obtaining a compound represented by the general formula [5] from a compound represented by the general formula [3] in the production process A.

The reaction for obtaining a compound represented by the general formula [1f-2] from a compound represented by the general formula [1f-1] can be carried out in the same manner as in the reaction for obtaining a compound represented by the general formula [1a-2] from a compound represented by the general formula [1a-1] in the production process A. When the substituent $R^{1f}$ or $R^4$ has a protecting group, the reaction can be carried out while appropriately deprotecting the substituent by conventional procedure.

[Production Process G]

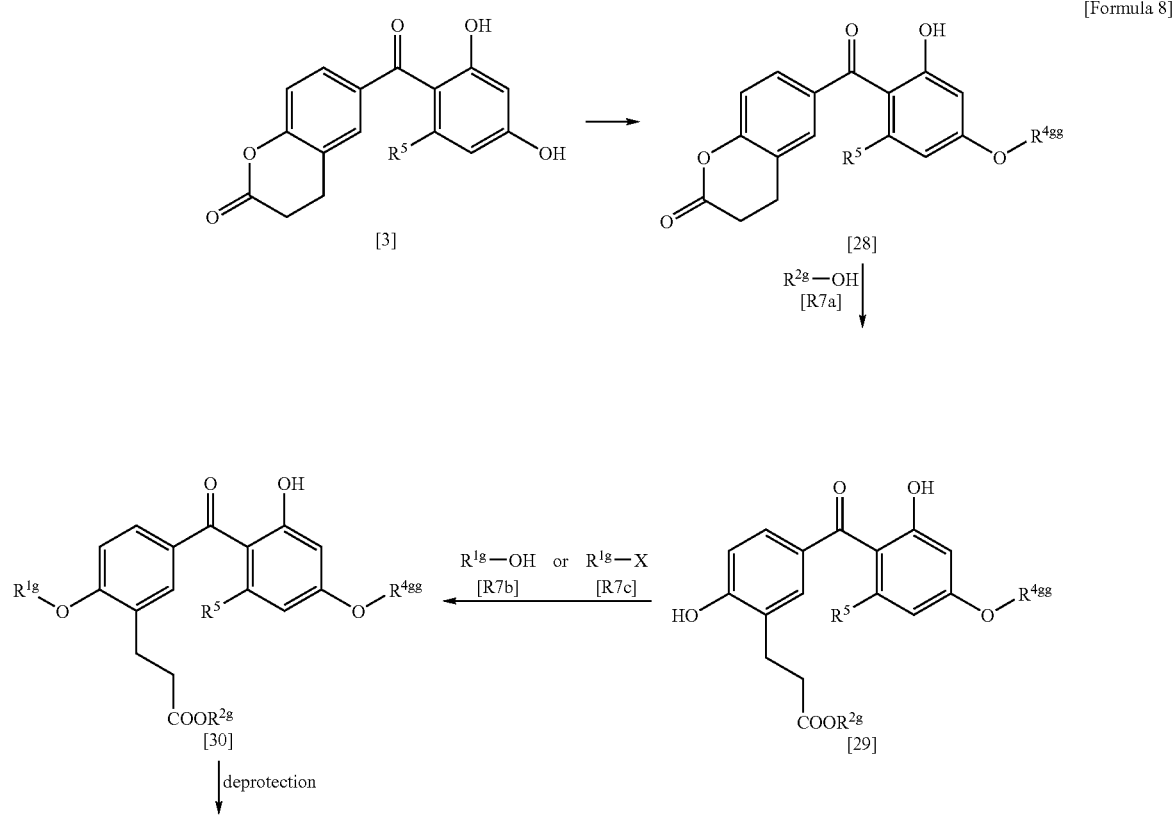

[Formula 8]

-continued

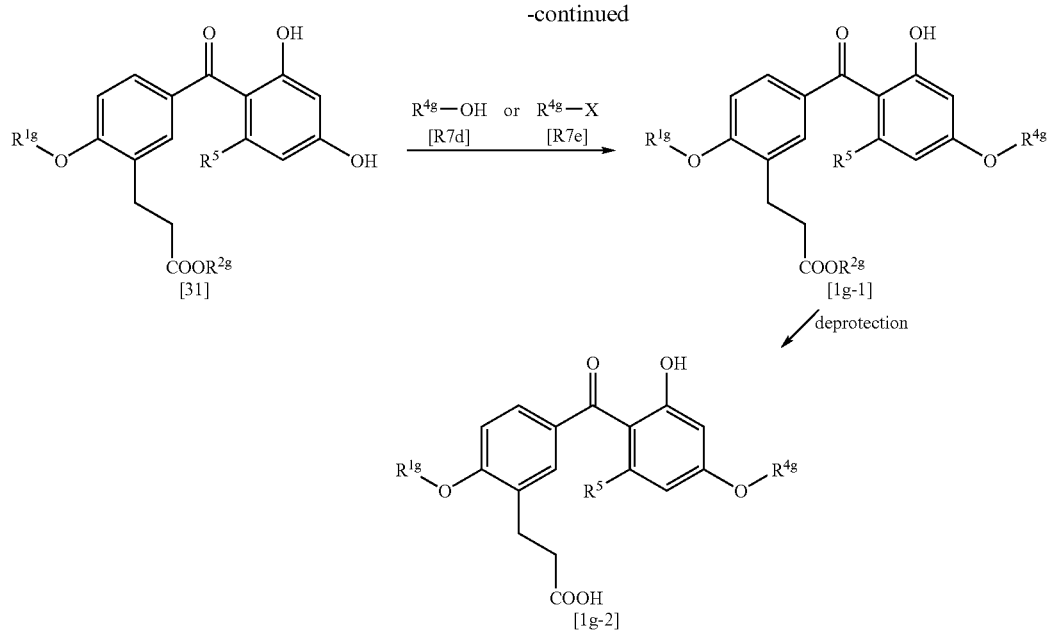

wherein $R^{2g}$ represents a carboxyl-protecting group; $R^{1g}$ represnts the same meaning as $R^{1a}$; $R^{4g}$ represents the same meaning as $R^{4a}$; $R^5$ and X represent the same meaning as above; and $R^{4gg}$ represents a phenol-protecting group.

A compound represented by the general formula [28] can be obtained by, for example, the process described in Greene et al., Protective Groups in Organic Synthesis, $3^{rd}$ edition, 1999, 249-280.

Specifically, when $R^{4gg}$ is a tetrahydropyranyl group, for example, a compound represented by the general formula [28] can be obtained by reacting a compound represented by the general formula [3] with 3,4-dihydro-2H-pyran in the presence of catalyst. The amount of 3,4-dihydro-2H-pyran used can be 1- to 20-fold of the mole of a compound represented by the general formula [3] and preferably 1- to 5-fold of the mole of the same. Catalysts used in this reaction include, for example, acids such as dry hydrogen chloride and p-toluenesulfonic acid; and salts such as pyridinium p-toluenesulfonate. The amount of catalyst used can be 0.01- to 10-fold of the mole of a compound represented by the general formula [3] and preferably 0.05- to 3-fold of the mole of the same. Solvents used in this reaction are not limited to any specific ones as long as they do not adversely affect the reaction. They include, for example, aromatic hydrocarbons such as benzene, toluene and xylene; ethers such as 1,4-dioxane, tetrahydrofuran, anisole, diethylene glycol diethyl ether and dimethyl cellosolve; esters such as methyl acetate and ethyl acetate; nitrites such as acetonitrile; amides such as N,N-dimethylformamide and N,N-dimethylacetamide; and halogenated hydrocarbons such as chloroform and methylene chloride. These solvents may be used independently or in the form of a mixture of two or more kinds.

Usually this reaction can be performed at 0° C. to 100° C. and preferably 0° C. to 50° C. for 10 minutes to 24 hours.

The reaction for obtaining a compound represented by the general formula [29] from a compound represented by the general formula [28] can be carried out in the same manner as in the reaction for obtaining a compound represented by the general formula [6] from a compound represented by the general formula [5] in the production process A.

The reaction for obtaining a compound represented by the general formula [30] from a compound represented by the general formula [29] can be carried out in the same manner as in the reaction for obtaining a compound represented by the general formula [1a-1] from a compound represented by the general formula [6] in the production process A.

A compound represented by the general formula [31] can be obtained from a compound represented by the general formula [30] by ordinary deprotection.

Specifically, when $R^{4gg}$ of a compound represented by the general formula [30] is tetrahydropyran, for example, a compound represented by the general formula [31] can be obtained by carrying out the reaction in the presence of acid. Acids used in this reaction include, for example, mineral acids such as hydrochloric acid; and organic acids such as p-toluenesulfonic acid and oxalic acid. The amount of acid used can be 0.01- to 100-fold of the mole of a compound represented by the general formula [30] and preferably 0.05- to 10-fold of the mole of the same. Solvents used in this reaction are not limited to any specific ones as long as they do not adversely affect the reaction. They include, for example, aromatic hydrocarbons such as benzene, toluene and xylene; ethers such as 1,4-dioxane, tetrahydrofuran, anisole, diethylene glycol diethyl ether and dimethyl cellosolve; alcohols such as methanol and ethanol; esters such as butyl acetate and ethyl acetate; nitrites such as acetonitrile; amides such as N,N-dimethylformamide and N,N-dimethylacetamide; halogenated hydrocarbons such as chloroform and methylene chloride; and water. These solvents may be used independently or in the form of a mixture of two or more kinds.

Usually this reaction can be performed at 0° C. to the reflux temperature of the solvent used and preferably 5 to 100° C. for 10 minutes to 24 hours.

The reaction for obtaining a compound represented by the general formula [1g-1] from a compound represented by the general formula [31] can be carried out in the same manner as in the reaction for obtaining a compound represented by the general formula [5] from a compound represented by the general formula [3] in the production process A.

The reaction for obtaining a compound represented by the general formula [1g-2] from a compound represented by the general formula [1g-1] can be carried out in the same manner as in the reaction for obtaining a compound represented by the general formula [1a-2] from a compound represented by the general formula [1a-1] in the production process A.

[Production Process H]

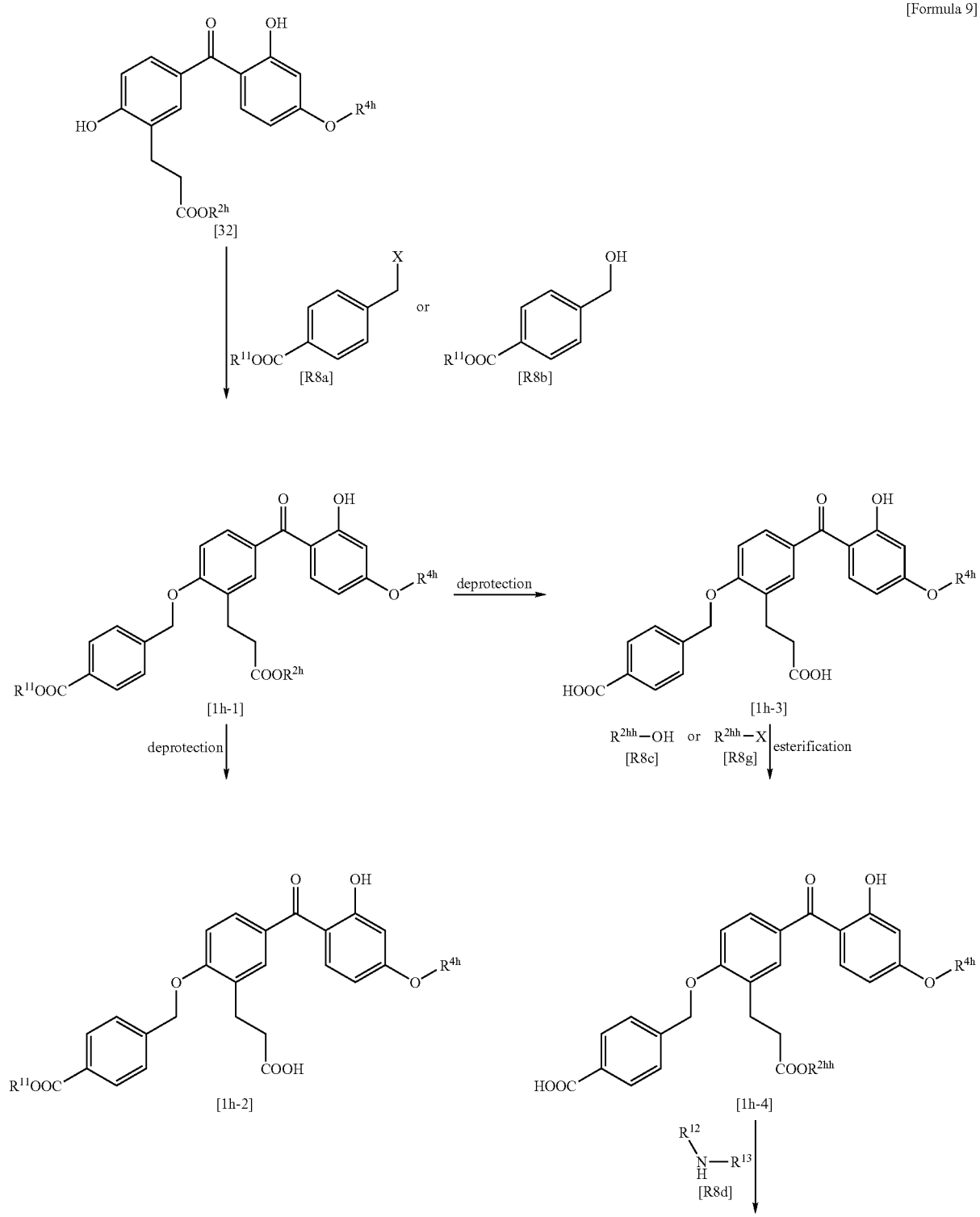

[Formula 9]

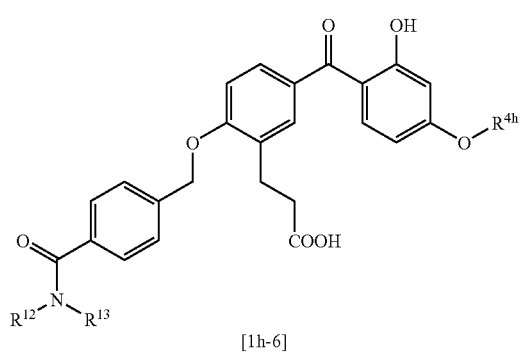

[1h-6]

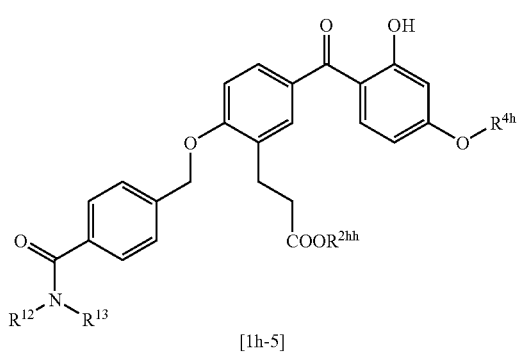

[1h-5]

[Formula 10]

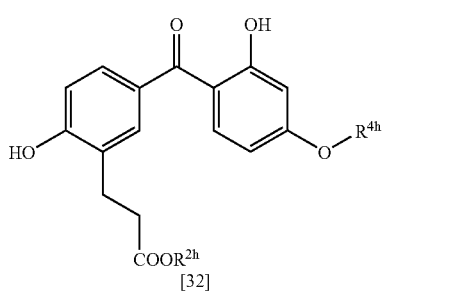

[32]

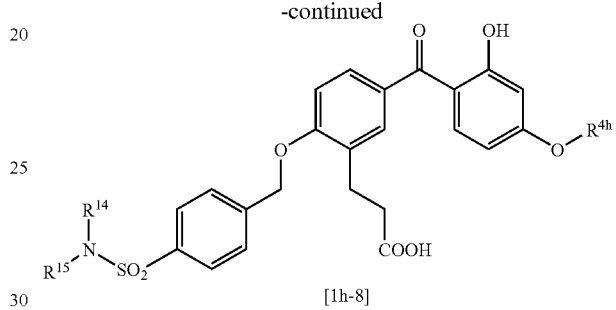

[1h-8]

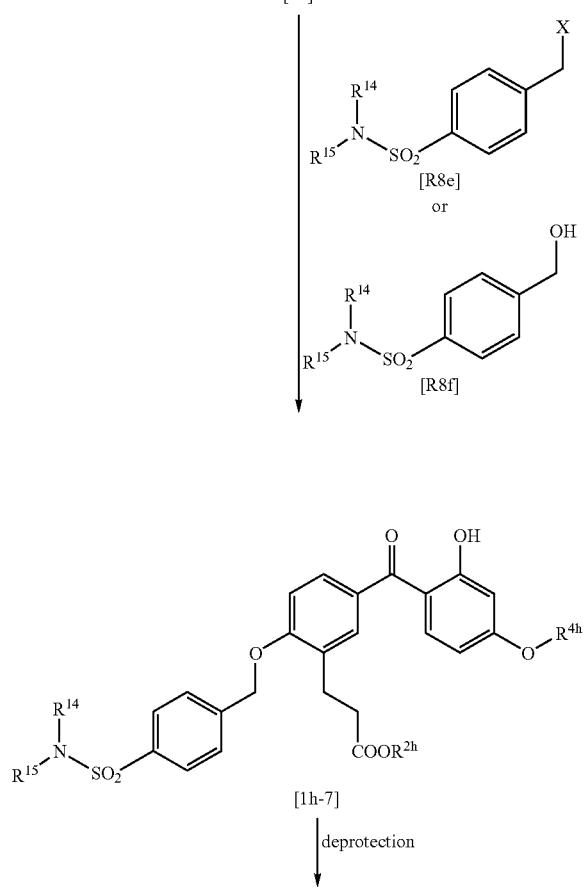

wherein $R^{4h}$ represents the same meaning as $R^{4a}$; $R^{2h}$, $R^{2hh}$ and $R^{11}$ each represent a carboxyl-protecting group; $R^{12}$, $R^{13}$, $R^{14}$ and $R^{15}$ each represent hydrogen, optionally substituted alkyl or an amino-protecting group; and X represent the same meaning as above.

The reaction for obtaining a compound represented by the general formula [1h-1] from a compound represented by the general formula [32] can be carried out in the same manner as in the reaction for obtaining a compound represented by the general formula [5] from a compound represented by the general formula [3] in the production process A.

The reaction for obtaining a compound represented by the general formula [1h-2] from a compound represented by the general formula [1h-1] can be carried out in the same manner as in the reaction for obtaining a compound represented by the general formula [1a-2] from a compound represented by the general formula [1a-1] in the production process A. When the substituent $R^{4h}$ or $R^{11}$ has a protecting group, the reaction can be carried out while appropriately deprotecting the substituent by conventional procedure.

The reaction for obtaining a compound represented by the general formula [1h-3] from a compound represented by the general formula [1h-1] can be carried out in the same manner as in the reaction for obtaining a compound represented by the general formula [1a-2] from a compound represented by the general formula [1a-1] in the production process A.

A compound represented by the general formula [1h-4] can be obtained by esterifying a compound represented by the general formula [1h-3].

In this reaction, common esterification methods can be used. Processes of esterification include: for example, processes in which an acid catalyst-additive combination is used, in which esterification is carried out via acid chloride, in which esterification is carried out via acid anhydride, in which a compound represented by the general formula [R8g]

is used with a base and in which a condensing agent-additive combination is used. For example, in the process in which an acid catalyst-additive combination is used, acid catalysts used include, for example, hydrochloric acid, sulfuric acid, hydrobromic acid, trimethylsilyl chloride, aluminium chloride, boron trifluoride and trifluoroacetic acid. The amount of catalyst used can be 0.01- to 100-fold of the mole of a compound represented by the general formula [1h-3] and preferably 0.5- to 50-fold of the mole of the same. Additives used include, for example, 2,2-dimethoxypropane and ethyl orthoformate. The amount of the additive used can be 0.1- to 100-fold of the mole of a compound represented by the general formula [1h-3] and preferably 1- to 50-fold of the mole of the same. A compound represented by the general formula [R8c] can be used as a solvent in an appropriate amount; however, when some other solvent is used, the amount of the compound used can be 1- to 100-fold of the mole of a compound represented by the general formula [1h-3] and preferably 1- to 50-fold of the mole of the same. Solvents used in this reaction are not limited to any specific ones as long as they do not adversely affect the reaction. They include, for example, aromatic hydrocarbons such as benzene, toluene and xylene; ethers such as 1,4-dioxane, tetrahydrofuran, anisole, diethylene glycol diethyl ether and dimethyl cellosolve; esters such as methyl acetate and ethyl acetate; nitrites such as acetonitrile; amides such as N,N-dimethylformamide; halogenated hydrocarbons such as chloroform and methylene chloride; and sulfoxides such as dimethyl sulfoxide. Usually this reaction can be performed at 0 to 200° C. and preferably 5 to 100° C. for 10 minutes to 24 hours.

In the process in which a base and a compound represented by the general formula [R8g] are used, bases used in this reaction include, for example, organic amines such as dimethylaminopyridine, triethylamine, pyridine and N-methylmorpholine; and alkaline metal carbonates such as potassium carbonate and sodium carbonate. The amount of base used can be 0.5- to 10-fold of the mole of a compound represented by the general formula [1h-3] and preferably 1- to 3-fold of the mole of the same. Compounds represented by the general formula [R8g] used in this reaction include, for example, methyl iodide, ethyl iodide and benzyl bromide. The amount of the compound used can be 0.5- to 10-fold of the mole of a compound represented by the general formula [1h-3] and preferably 1- to 3-fold of the mole of the same. Solvents used in this reaction are not limited to any specific ones as long as they do not adversely affect the reaction. They include, for example, aromatic hydrocarbons such as benzene, toluene and xylene; ethers such as 1,4-dioxane, tetrahydrofuran, anisole, diethylene glycol diethyl ether and dimethyl cellosolve; esters such as methyl acetate and ethyl acetate; nitrites such as acetonitrile; amides such as N,N-dimethylformamide; halogenated hydrocarbons such as chloroform and methylene chloride; and sulfoxides such as dimethyl sulfoxide. Usually this reaction can be performed at 0 to 200° C. and preferably 5 to 100° C. for 10 minutes to 24 hours.

In the process in which a condensing agent and an additive are used, a compound represented by the general formula [1h-4] can be obtained by subjecting a compound represented by the general formula [R8c] together with the condensing agent and the additive to condensation reaction. Condensing agents used in this reaction include, for example, 1,1'-carbonyldiimidazole, N,N'-dicyclohexylcarbodiimide, diisopropylcarbodiimide, N-ethyl-N'-3-dimethylaminopropylcarbodiimide and diphenylphosphoryl azide. Additives used in this reaction include, for example, 1-hydroxybenzotriazole and N-hydroxysuccinimide. The amounts of the alcohol, the condensing agent and the additive used in this reaction each can be 0.5- to 10-fold of the mole of a compound represented by the general formula [1h-3] and preferably 1- to 3-fold of the mole of the same. Solvents used in this reaction are not limited to any specific ones as long as they do not adversely affect the reaction. They include, for example, aromatic hydrocarbons such as benzene, toluene and xylene; ethers such as 1,4-dioxane, tetrahydrofuran, anisole, diethylene glycol diethyl ether and dimethyl cellosolve; esters such as methyl acetate and ethyl acetate; nitriles such as acetonitrile; amides such as N,N-dimethylformamide; halogenated hydrocarbons such as chloroform and methylene chloride; and sulfoxides such as dimethyl sulfoxide.

Usually this reaction can be performed at 0 to 200° C. and preferably 5 to 100° C. for 10 minutes to 24 hours.

A compound represented by the general formula [1h-5] can be obtained by subjecting a compound represented by the general formula [1h-4] together with a compound represented by the general formula [R8d] to amidation. This amidation is commonly used amidation. And processes of amidation include: for example, processes in which amidation is carried out via acid chloride, in which amidation is carried out via acid anhydride, and in which base, condensing agent and additive are used.

For example, in the process in which a base, a condensing agent and an additive are used, amines represented by the general formula [R8d] used in this reaction include, for example, ammonia and hydroxylamine; primary amines such as methyl amine, benzyl amine, aniline, phenethylamine, isopropylamine and aminothiazole; and secondary amines such as dimethyl amine, diethyl amine and di-n-propylamine and sulfonamides include, for example, methanesulfonamide. The amount of amine used can be 0.5- to 10-fold of the mole of a compound represented by the general formula [1h-4] and preferably 1- to 3-fold of the mole of the same. Bases used in this reaction include, for example, organic amines such as dimethylaminopyridine, triethylamine, pyridine, N-methylmorpholine and 1,8-diazabicyclo[5.4.0]undec-7-ene; and alkaline metal carbonates such as potassium carbonate and sodium carbonate. The amount of base used can be 0.5- to 10-fold of the mole of a compound represented by the general formula [1h-4] and preferably 1- to 5-fold of the mole of the same. Condensing agents used in this reaction include, for example, N,N'-dicyclohexylcarbodiimide, diisopropylcarbodiimide, N-ethyl-N'-3-dimethylaminopropylcarbodiimide and diphenylphosphoryl azide. The amount of the condensing agent used in this reaction can be 0.5- to 10-fold of the mole of a compound represented by the general formula [1h-4] and preferably 1- to 3-fold of the mole of the same. Additives used in this reaction include, for example, 1-hydroxybenzotriazole and N-hydroxysuccinimide. The amount of the additive used can be 0.5- to 10-fold of the mole of a compound represented by the general formula [1h-4] and preferably 1- to 3-fold of the mole of the same. Solvents used in this reaction are not limited to any specific ones as long as they do not adversely affect the reaction. They include, for example, aromatic hydrocarbons such as benzene, toluene and xylene; ethers such as 1,4-dioxane, tetrahydrofuran, anisole, diethylene glycol diethyl ether and dimethyl cellosolve; esters such as methyl acetate and ethyl acetate; nitrites such as acetonitrile; amides such as N,N-dimethylformamide; halogenated hydrocarbons such as chloroform and methylene chloride; and sulfoxides such as dimethyl sulfoxide.

Usually this reaction can be performed at −20 to 150° C. and preferably 0 to 120° C. for 10 minutes to 24 hours.

The reaction for obtaining a compound represented by the general formula [1h-6] from a compound represented by the general formula [1h-5] can be carried out in the same manner as in the reaction for obtaining a compound represented by the general formula [1a-2] from a compound represented by the general formula [1a-1] in the production process A. When the substituent $R^{12}$ or $R^{13}$ is an amino-protecting group or the substituent $R^{4h}$ has a protecting group, the reaction can be carried out while appropriately deprotecting the substituent by conventional procedure.

general formula [1a-2] from a compound represented by the general formula [1a-1] in the production process A. When the substituent $R^{14}$ or $R^{15}$ is an amino-protecting group or the substituent $R^{4h}$ has a protecting group, the reaction can be carried out while appropriately deprotecting the substituent by conventional procedure.

[Production Process I]

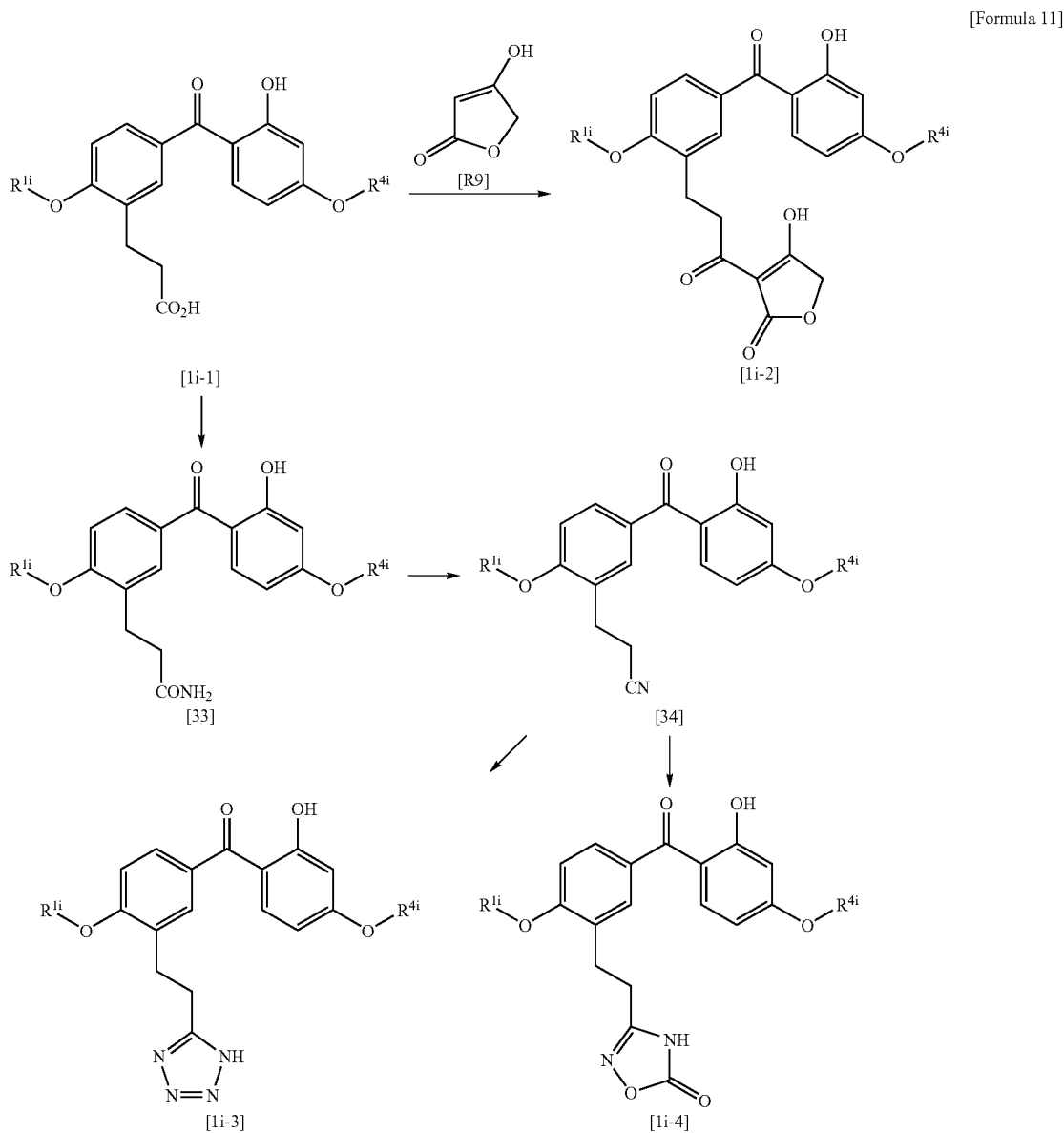

[Formula 11]

The reaction for obtaining a compound represented by the general formula [1h-7] from a compound represented by the general formula [32] can be carried out in the same manner as in the reaction for obtaining a compound represented by the general formula [5] from a compound represented by the general formula [3] in the production process A.

The reaction for obtaining a compound represented by the general formula [1h-8] from a compound represented by the general formula [1h-7] can be carried out in the same manner as in the reaction for obtaining a compound represented by the wherein $R^{1i}$ represents the same meaning as $R^{1a}$; and $R^{4i}$ represents the same meaning as $R^{4a}$.

A compound represented by the general formula [1i-2] can be obtained by reacting a compound represented by the general formula [1i-1] with a compound having the formula [R9] in accordance with the process described in Chemical and Pharmaceutical Bulletin, Vol. 34, 5188-5190, 1986. This reaction can be carried out, for example, by the process in which condensing agent and additive are used, in which the compound is obtained via acid chloride, or in which the compound is obtained via acid anhydride.

For example, in the process in which condensing agent and additive are used, condensing agents used in this reaction include, for example, N,N'-dicyclohexylcarbodiimide, diisopropylcarbodiimide, N-ethyl-N'-3-dimethylaminopropylcarbodiimide and diphenylphosphoryl azide. The amount of condensing agent used in this reaction can be 0.5- to 10-fold of the mole of a compound represented by the general formula [1i-1] and preferably 1- to 3-fold of the mole of the same. Additives used in this reaction include, for example, 1-hydroxybenzotriazole and N-hydroxysuccinimide. The amount of additive used can be 0.5- to 10-fold of the mole of a compound represented by the general formula [1i-1] and preferably 1- to 3-fold of the mole of the same. The amount of a compound represented by the formula [R9] used in this reaction can be 1- to 10-fold of the mole of a compound represented by the general formula [1i-1] and preferably 1- to 2-fold of the mole of the same. Solvents used in this reaction are not limited to any specific ones as long as they do not adversely affect the reaction. They include, for example, aromatic hydrocarbons such as benzene, toluene and xylene; ethers such as 1,4-dioxane, tetrahydrofuran, anisole, diethylene glycol diethyl ether and dimethyl cellosolve; esters such as methyl acetate and ethyl acetate; nitrites such as acetonitrile; amides such as N,N-dimethylformamide; halogenated hydrocarbons such as chloroform and methylene chloride; and sulfoxides such as dimethyl sulfoxide.

Usually this reaction can be performed at −20 to 150° C. and preferably 0 to 120° C. for 10 minutes to 24 hours.

In the process in which a compound represented by the general formula [1i-2] is obtained via acid chloride or via acid anhydride, the compound can be obtained by reacting the acid chloride or acid anhydride of a compound represented by the general formula [1i-1] with a compound represented by the formula [R9] in the presence of base. The acid chloride or acid anhydride of a compound represented by the general formula [1i-1] used in this reaction can be obtained by reacting the compound represented by the general formula [1i-1] with activating agent such as thionyl chloride, oxalyl chloride, phosphorus pentachloride, acetic anhydride or ethyl chloroformate. The amount of activating agent used can be 1- to 10-fold of the mole of a compound represented by the general formula [1i-1] and preferably 1- to 2-fold of the mole of the same. The amount of a compound represented by the formula [R9] used can be 1- to 20-fold of the mole of a compound represented by the general formula [1i-1] and preferably 1- to 5-fold of the mole of the same. Bases used in this reaction include, for example, organic amines such as dimethylaminopyridine, trimethylamine, pyridine and N-methylmorpholine; and alkaline metal carbonates such as potassium carbonate and sodium carbonate; organic lithiums such as n-butyllithium, methyllithium and lithium diisopropylamide; and organic magnesiums such as methylmagnesium bromide. The amount of base used can be 1- to 20-fold of the mole of a compound represented by the general formula [1i-1] and preferably 1- to 5-fold of the mole of the same. Solvents used in this reaction are not limited to any specific ones as long as they do not adversely affect the reaction. They include, for example, aromatic hydrocarbons such as benzene, toluene and xylene; halogenated hydrocarbons such as chloroform and methylene chloride; ethers such as 1,4-dioxane, tetrahydrofuran, anisole, diethylene glycol diethyl ether and dimethyl cellosolve; and aliphatic hydrocarbons such as hexane and cyclohexane. These solvents may be used independently or in the form of a mixture of two or more kinds.

Usually this reaction can be performed at −78 to 150° C. and preferably −78 to 120° C. for 10 minutes to 24 hours. When the substituent $R^{1i}$ or $R^{4i}$ has a protecting group, the reaction can be carried out while appropriately deprotecting the substituent by conventional procedure.

The reaction for obtaining a compound represented by the general formula [33] from a compound represented by the general formula [1i-1] can be carried out in the same manner as in the reaction for obtaining a compound represented by the general formula [1h-5] from a compound represented by the general formula [1h-4] in the production process H.

A compound represented by the general formula [34] can be obtained by dehydrating a compound represented by the general formula [33] in the presence or absence of dehydrating agent and bases.

Dehydrating agents used in this reaction as the need arises include, for example, phosphorus pentoxide, phosphorus pentachloride, phosphoryl chloride and thionyl chloride. The amount of dehydrating agent used can be 1- to 50-fold of the mole of a compound represented by the general formula [33] and preferably 1- to 10-fold of the mole of the same. Salts used in this reaction as the need arises include, for example, sodium chloride. The amount of salt used can be 1- to 50-fold of the mole of a compound represented by the general formula [33] and preferably 1- to 5-fold of the mole of the same. Solvents used in this reaction are not limited to any specific ones as long as they do not adversely affect the reaction. They include, for example, aromatic hydrocarbons such as benzene, toluene and xylene; ethers such as 1,4-dioxane, tetrahydrofuran, anisole, diethylene glycol diethyl ether and dimethyl cellosolve; aliphatic hydrocarbons such as hexane and cyclohexane; halogenated hydrocarbons such as chloroform and methylene chloride; esters such as methyl acetate and ethyl acetate; and amides such as N,N-dimethylformamide and N,N-dimethylacetamide. These solvents may be used independently or in the form of a mixture of two or more kinds.

Usually this reaction can be performed at −20 to 300° C. and preferably 0 to 220° C. for 30 minutes to 24 hours.

A compound represented by the general formula [1i-4] can be synthesized from a compound represented by the general formula [34] in accordance with the process described in Journal of Medicinal Chemistry, Vol. 39, 5228-5235, 1996.

Specifically, amidoxime can be obtained by reacting a compound represented by the general formula [34] with hydroxylamine in the presence of base. The amount of hydroxylamine used can be 1- to 20-fold of the mole of a compound represented by the general formula [34] and preferably 1- to 10-fold of the mole of the same. Bases used in this reaction include, for example, organic amines such as dimethylaminopyridine, triethylamine, pyridine and N-methylmorpholine; metal alkoxides such as sodium methoxide; and alkaline metal carbonates such as potassium carbonate and sodium carbonate. The amount of base used can be 1- to 10-fold of the mole of a compound represented by the general formula [34] and preferably 1- to 5-fold of the mole of the same. Solvents used in this reaction are not limited to any specific ones as long as they do not adversely affect the reaction. They include, for example, alcohols such as methanol and ethanol; aromatic hydrocarbons such as benzene, toluene and xylene; ethers such as 1,4-dioxane, tetrahydrofuran, anisole, diethylene glycol diethyl ether and dimethyl cellosolve; aliphatic hydrocarbons such as hexane and cyclohexane; halogenated hydrocarbons such as chloroform and methylene chloride; esters such as methyl acetate and ethyl acetate; sulfoxides such as dimethyl sulfoxide; and amides such as N,N-dimethylformamide and N,N-dimethylacetamide. These solvents may be used independently or in the form of a mixture of two or more kinds.

Usually this reaction can be performed at −20 to 200° C. and preferably 0 to 100° C. for 30 minutes to 24 hours.

The amidoxime compound obtained by the above method is then reacted with halogenated carbonate in the presence of base. Bases used in this reaction include, for example, organic amines such as dimethylaminopyridine, triethylamine, pyridine and N-methylmorpholine; alkaline metal carbonates such as potassium carbonate and sodium carbonate; and metal alkoxides such as potassium tert-butoxide. The amount of base used can be 1- to 10-fold of the mole of a compound represented by the general formula [34] and preferably 1- to 3-fold of the mole of the same. Halogenated carbonate used in this reaction include, for example, ethyl chloroformate, butyl chloroformate and 2-ethylhexyl chloroformate. The amount of halogenated carbonate used can be 1- to 10-fold of the mole of a compound represented by the general formula [34] and preferably 1- to 3-fold of the mole of the same. Solvents used in this reaction are not limited to any specific ones as long as they do not adversely affect the reaction. They include, for example, nitriles such as acetonitrile; aromatic hydrocarbons such as benzene, toluene and xylene; ethers such as 1,4-dioxane, tetrahydrofuran, anisole, diethylene glycol diethyl ether and dimethyl cellosolve; aliphatic hydrocarbons such as hexane and cyclohexane; halogenated hydrocarbons such as chloroform and methylene chloride; esters such as methyl acetate and ethyl acetate; amides such as N,N-dimethylformamide and N,N-dimethylacetamide; and sulfoxides such as dimethyl sulfoxide. These solvents may be used independently or in the form of a mixture of two or more kinds.

Usually this reaction can be performed at −20 to 200° C. and preferably 0 to 100° C. for 5 minutes to 24 hours.

Then the reaction product is heated in the presence or absence of solvent to give a compound represented by the general formula [1i-4]. Solvents used in this reaction are not limited to any specific ones as long as they do not adversely affect the reaction. They include, for example, nitriles such as acetonitrile; aromatic hydrocarbons such as benzene, toluene and xylene; ethers such as 1,4-dioxane, tetrahydrofuran, anisole, diethylene glycol diethyl ether and dimethyl cellosolve; aliphatic hydrocarbons such as hexane and cyclohexane; halogenated hydrocarbons such as chloroform and methylene chloride; esters such as methyl acetate and ethyl acetate; amides such as N,N-dimethylformamide and N,N-dimethylacetamide; and sulfoxides such as dimethyl sulfoxide. These solvents may be used independently or in the form of a mixture of two or more kinds.

Usually this reaction can be performed at 0° C. to the reflux temperature of the solvent used and preferably 0 to 150° C. for 30 minutes to 24 hours and preferably 30 minutes to 10 hours. When the substituent $R^{1i}$ or $R^{4i}$ has a protecting group, the reaction can be carried out while appropriately deprotecting the substituent by conventional procedure.

A compound represented by the general formula [1i-3] can be obtained by reacting a compound represented by the general formula [34] and an azide compound in the presence or absence of salts.

Azide compounds used in this reaction include, for example, sodium azide, trimethyltin azide and trimethylsilyl azide. The amount of azide compound used can be 1- to 30-fold of the mole of a compound represented by the general formula [34] and preferably 1- to 10-fold of the mole of the same. Salts used in this reaction as the need arises include, for example, triethylamine hydrochloride and ammonium chloride. The amount of salt used can be 1- to 30-fold of the mole of a compound represented by the general formula [34] and preferably 1- to 10-fold of the mole of the same. Solvents used in this reaction are not limited to any specific ones as long as they do not adversely affect the reaction. They include, for example, aromatic hydrocarbons such as benzene, toluene and xylene; ethers such as 1,4-dioxane, tetrahydrofuran, anisole, diethylene glycol diethyl ether and dimethyl cellosolve; aliphatic hydrocarbons such as hexane and cyclohexane; halogenated hydrocarbons such as chloroform and methylene chloride; esters such as butyl acetate and ethyl acetate; amides such as N,N-dimethylformamide and N,N-dimethylacetamide; and sulfoxides such as dimethyl sulfoxide. These solvents may be used independently or in the form of a mixture of two or more kinds.

Usually this reaction can be performed at −20 to 250° C. and preferably 0 to 150° C. for 30 minutes to 24 hours. When the substituent $R^{1i}$ or $R^{4i}$ has a protecting group, the reaction can be carried out while appropriately deprotecting the substituent by conventional procedure.

[Production Process J]

[Formula 12]

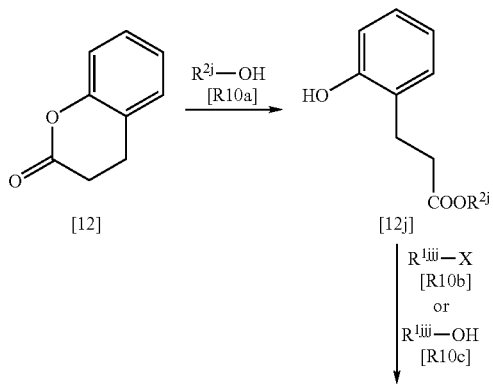

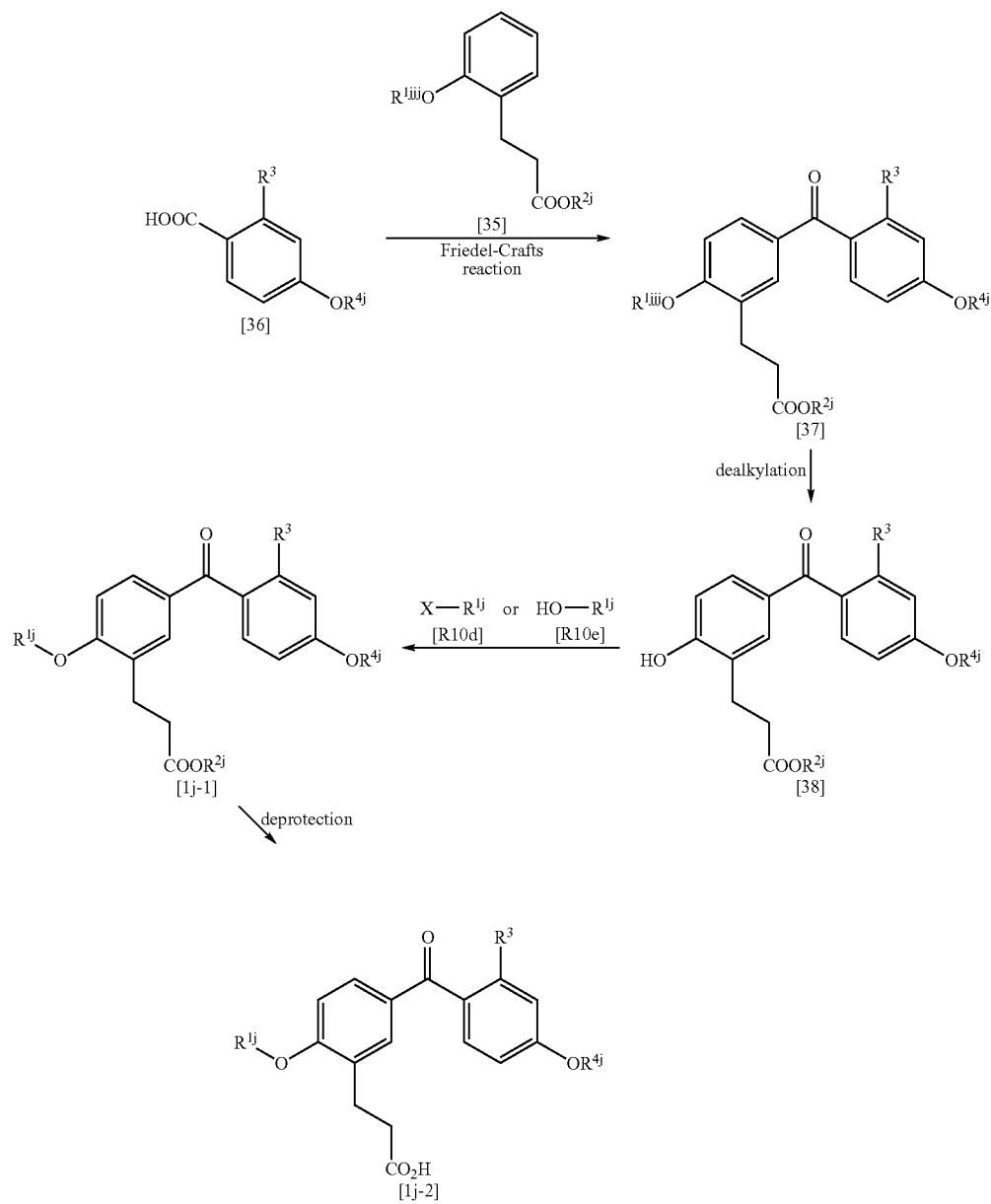
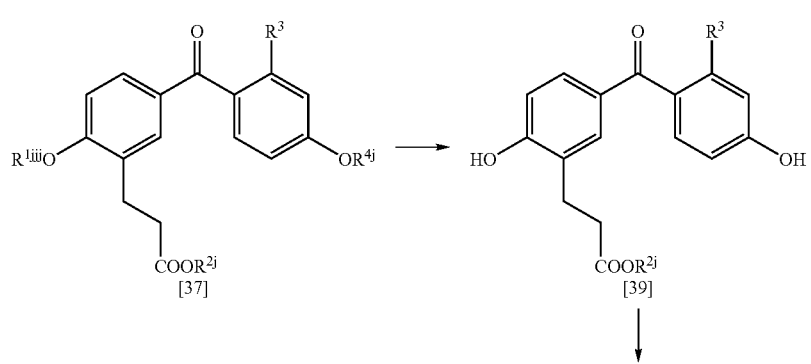
[Formula 13]

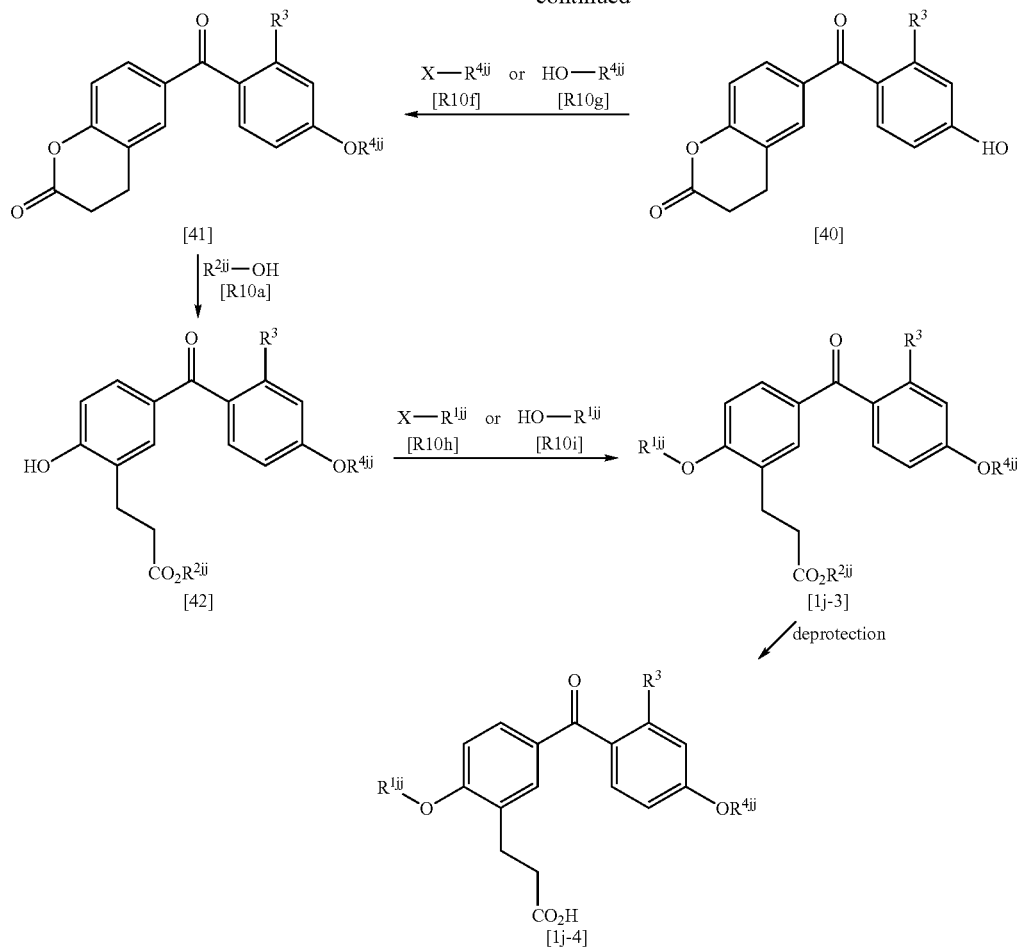

wherein $R^{2j}$ and $R^{2jj}$ each represent a carboxyl-protecting group; $R^{1j}$, $R^{1jj}$ and $R^{1jjj}$ each represent the same meaning as $R^{1a}$; $R^3$ and X represent the same meaning as above; $R^{4j}$ and $R^{4jj}$ each represent the same meaning as $R^{4a}$.

The reaction for obtaining a compound represented by the general formula [12j] from a compound represented by the formula [12] can be carried out in the same manner as in the reaction for obtaining a compound represented by the general formula [12d] from a compound represented by the formula [12] in the production process D.

The reaction for obtaining a compound represented by the general formula [35] from a compound represented by the general formula [12j] can be carried out in the same manner as in the reaction for obtaining a compound represented by the general formula [13] from a compound represented by the general formula [12d] in the production process D.

The reaction for obtaining a compound represented by the general formula [37] from a compound represented by the general formula [36] can be carried out in the same manner as in the reaction for obtaining a compound represented by the general formula [15] from a compound represented by the general formula [14] in the production process D.

The reaction for obtaining a compound represented by the general formula [38] from a compound represented by the general formula [37] can be carried out in the same manner as in the reaction for obtaining a compound represented by the general formula [7] from a compound represented by the general formula [1a-1] in the production process A.

A compound represented by the general formula [38] can also be obtained not by isolating a compound represented by the general formula [37] from a compound represented by the general formula [36], but by continuously carrying out Friedel-Crafts reaction and dealkylation.

The reaction for obtaining a compound represented by the general formula [1j-1] from a compound represented by the general formula [38] can be carried out in the same manner as in the reaction for obtaining a compound represented by the general formula [5] from a compound represented by the general formula [3] in the production process A.

The reaction for obtaining a compound represented by the general formula [1j-2] from a compound represented by the general formula [1j-1] can be carried out in the same manner as in the reaction for obtaining a compound represented by the general formula [1a-2] from a compound represented by the general formula [1a-1] in the production process A. When the substituent $R^{1j}$, $R^{4j}$ or $R^3$ has a protecting group, the reaction can be carried out while appropriately deprotecting the substituent by conventional procedure.

The reaction for obtaining a compound represented by the general formula [39] from a compound represented by the general formula [37] can be carried out in the same manner as in the reaction for obtaining a compound represented by the general formula [9] from a compound represented by the general formula [8] in the production process B.

The reaction for obtaining a compound represented by the general formula [40] from a compound represented by the general formula [39] can be carried out in the same manner as in the reaction for obtaining a compound represented by the general formula [3] from a compound represented by the general formula [2] in the production process A.

A compound represented by the general formula [40] can also be obtained from a compound represented by the general formula [36] by continuously carrying out Friedel-Crafts reaction, dealkylation and dehydration.

The reaction for obtaining a compound represented by the general formula [41] from a compound represented by the general formula [40] can be carried out in the same manner as in the reaction for obtaining a compound represented by the general formula [5] from a compound represented by the general formula [3] in the production process A.

The reaction for obtaining a compound represented by the general formula [42] from a compound represented by the general formula [41] can be carried out in the same manner as in the reaction for obtaining a compound represented by the general formula [6] from a compound represented by the general formula [5] in the production process A.

The reaction for obtaining a compound represented by the general formula [1j-3] from a compound represented by the general formula [42] can be carried out in the same manner as in the reaction for obtaining a compound represented by the general formula [5] from a compound represented by the general formula [3] in the production process A.

The reaction for obtaining a compound represented by the general formula [1j-4] from a compound represented by the general formula [1j-3] can be carried out in the same manner as in the reaction for obtaining a compound represented by the general formula [1a-2] from a compound represented by the general formula [1a-1] in the production process A. When the substituent $R^{1ij}$, $R^{4ij}$ or $R^3$ has a protecting group, the reaction can be carried out while appropriately deprotecting the substituent by conventional procedure.

[Production Process K]

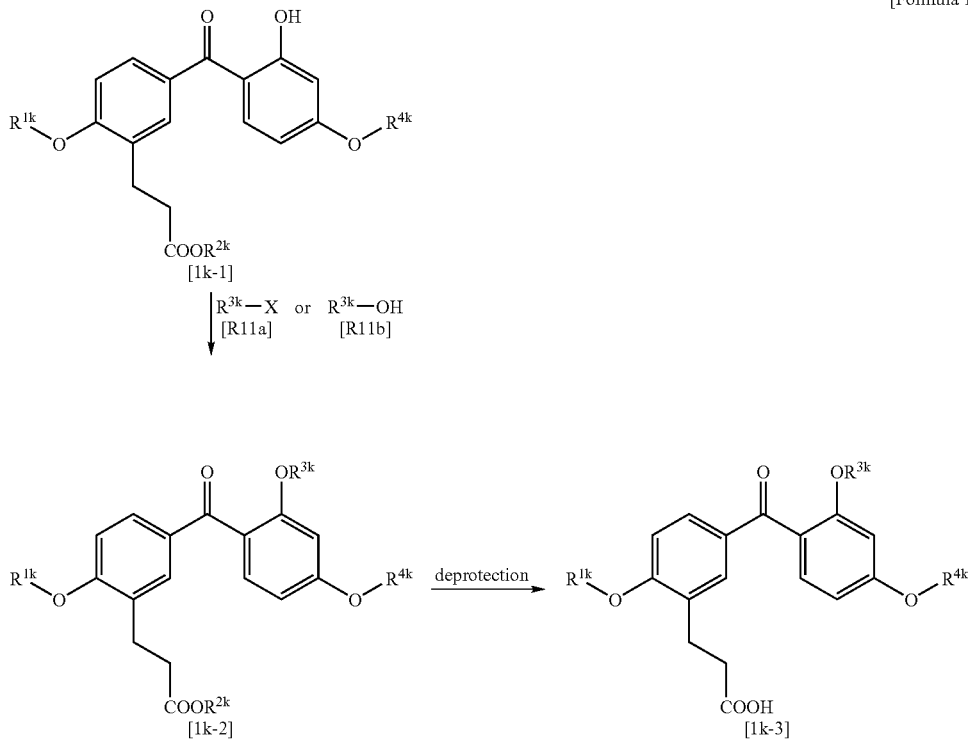

[Formula 14]

wherein $R^{2k}$ represents a carboxyl-protecting group; $R^{1k}$ represents the same meaning as $R^{1a}$; $R^{3k}$ represents optionally substituted alkyl; $R^{4k}$ represents the same meaning as $R^{4a}$; and X represents the same meaning as above.

The reaction for obtaining a compound represented by the general formula [1k-2] from a compound represented by the general formula [1k-1] can be carried out in the same manner as in the reaction for obtaining a compound represented by the general formula [5] from a compound represented by the general formula [3] in the production process A.

The reaction for obtaining a compound represented by the general formula [1k-3] from a compound represented by the general formula [1k-2] can be carried out in the same manner as in the reaction for obtaining a compound represented by the general formula [1a-2] from a compound represented by the general formula [1a-1] in the production process A. When the substituent $R^{1k}$, $R^{3k}$ or $R^{4k}$ has a protecting group, the reaction can be carried out while appropriately deprotecting the substituent by conventional procedure.

[Production Process L]

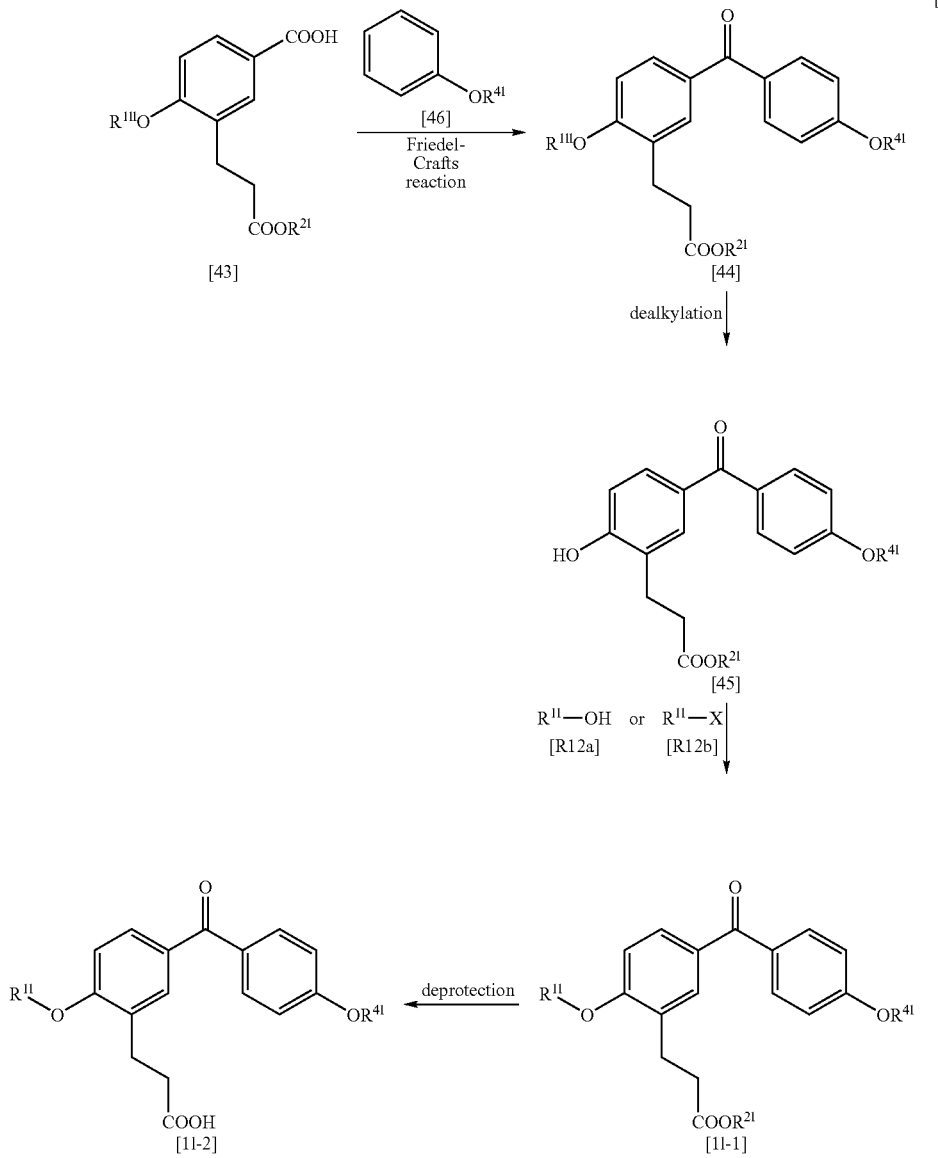

wherein $R^{2l}$ represents a carboxyl-protecting group; $R^{1l}$ and $R^{1ll}$ each represent the same meaning as $R^{1a}$; $R^{4l}$ represents the same meaning as $R^{4a}$; and X represents the same meaning as above.

The reaction for obtaining a compound represented by the general formula [44] from a compound represented by the general formula [43] can be carried out in the same manner as in the reaction for obtaining a compound represented by the general formula [15] from a compound represented by the general formula [14] in the production process D.

The reaction for obtaining a compound represented by the general formula [45] from a compound represented by the general formula [44] can be carried out in the same manner as in the reaction for obtaining a compound represented by the general formula [7] from a compound represented by the general formula [1a-1] in the production process A.

The reaction for obtaining a compound represented by the general formula [1l-1] from a compound represented by the general formula [45] can be carried out in the same manner as in the reaction for obtaining a compound represented by the general formula [5] from a compound represented by the general formula [3] in the production process A.

The reaction for obtaining a compound represented by the general formula [1l-2] from a compound represented by the general formula [1l-1] can be carried out in the same manner as in the reaction for obtaining a compound represented by the general formula [1a-2] from a compound represented by the general formula [1a-1] in the production process A. When the substituent $R^{1l}$ or $R^{4l}$ has a protecting group, the reaction can be carried out while appropriately deprotecting the substituent by conventional procedure.

[Production Process M]

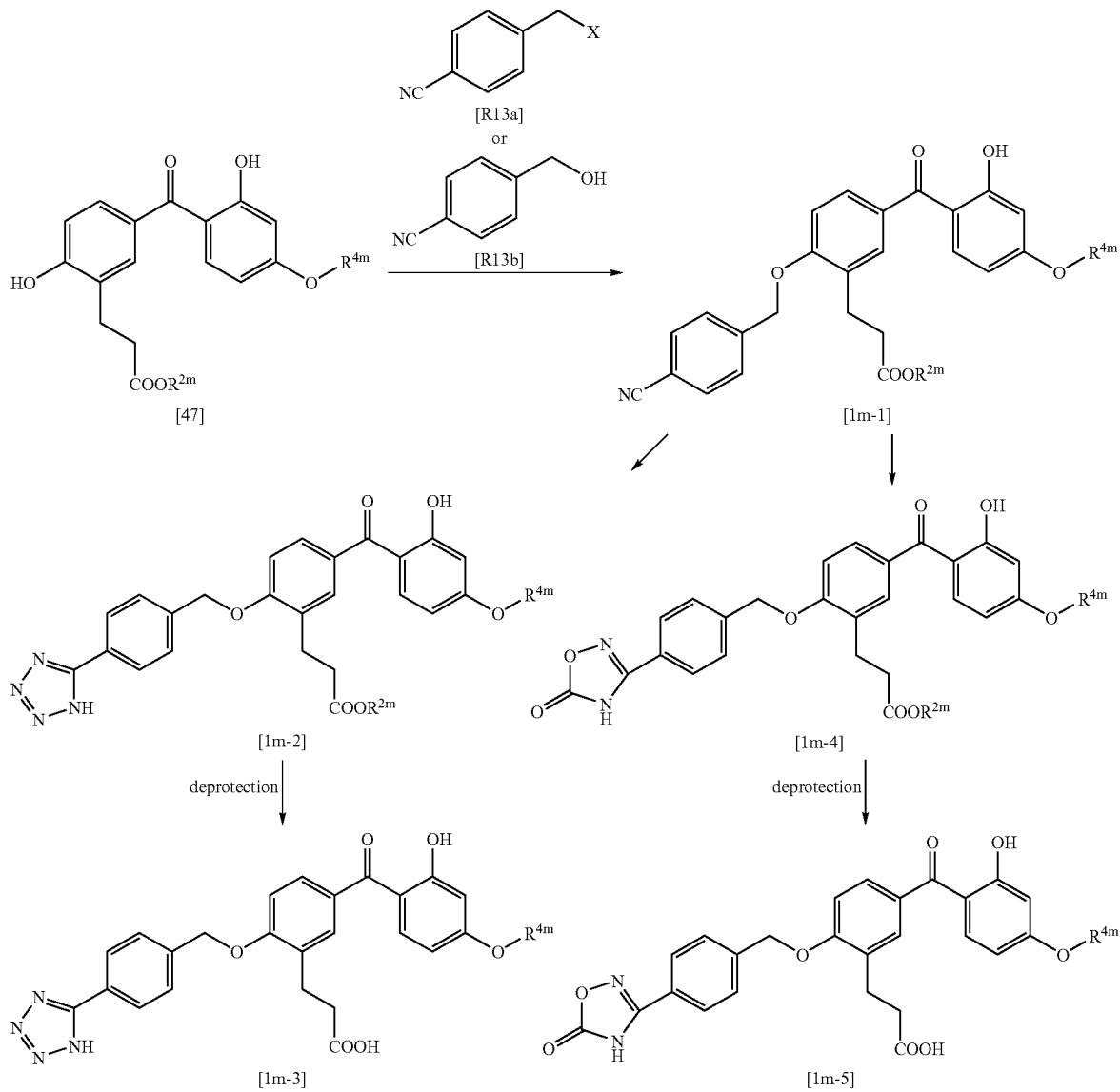

wherein $R^{2m}$ represents a carboxyl-protecting group; $R^{4m}$ represents the same meaning as $R^{4a}$; and X represents the same meaning as above.

The reaction for obtaining a compound represented by the general formula [1m-1] from a compound represented by the general formula [47] can be carried out in the same manner as in the reaction for obtaining a compound represented by the general formula [5] from a compound represented by the general formula [3] in the production process A.

The reaction for obtaining a compound represented by the general formula [1m-2] from a compound represented by the general formula [1m-1] can be carried out in the same manner as in the reaction for obtaining a compound represented by the general formula [1i-3] from a compound represented by the general formula [34] in the production process I.

The reaction for obtaining a compound represented by the general formula [1m-3] from a compound represented by the general formula [1m-2] can be carried out in the same manner as in the reaction for obtaining a compound represented by the general formula [1a-2] from a compound represented by the general formula [1a-1] in the production process A. When the substituent $R^{4m}$ has a protecting group, the reaction can be carried out while appropriately deprotecting the substituent by conventional procedure.

The reaction for obtaining a compound represented by the general formula [1m-4] from a compound represented by the general formula [1m-1] can be carried out in the same manner as in the reaction for obtaining a compound represented by the general formula [1i-4] from a compound represented by the general formula [34] in the production process I.

The reaction for obtaining a compound represented by the general formula [1m-5] from a compound represented by the general formula [1m-4] can be carried out in the same manner as in the reaction for obtaining a compound represented by the general formula [1a-2] from a compound represented by the general formula [1a-1] in the production process A. When the substituent $R^{4m}$ has a protecting group, the reaction can be carried out while appropriately deprotecting the substituent by conventional procedure.

[Production Process N]

general formula [5] from a compound represented by the general formula [3] in the production process A.

A compound represented by the general formula [1n-2] can be obtained by oxidizing a compound represented by the general formula [1n-1].

Oxidizing agents used in this reaction include, for example, organic peroxides such as peracetic acid, trifluoroperacetic acid, perbenzoic acid and m-chloroperbenzoic acid; hydrogen peroxide; chromic acid and potassium permanganate. The amount of oxidizing agent used can be 0.5- to 5-fold

[Formula 17]

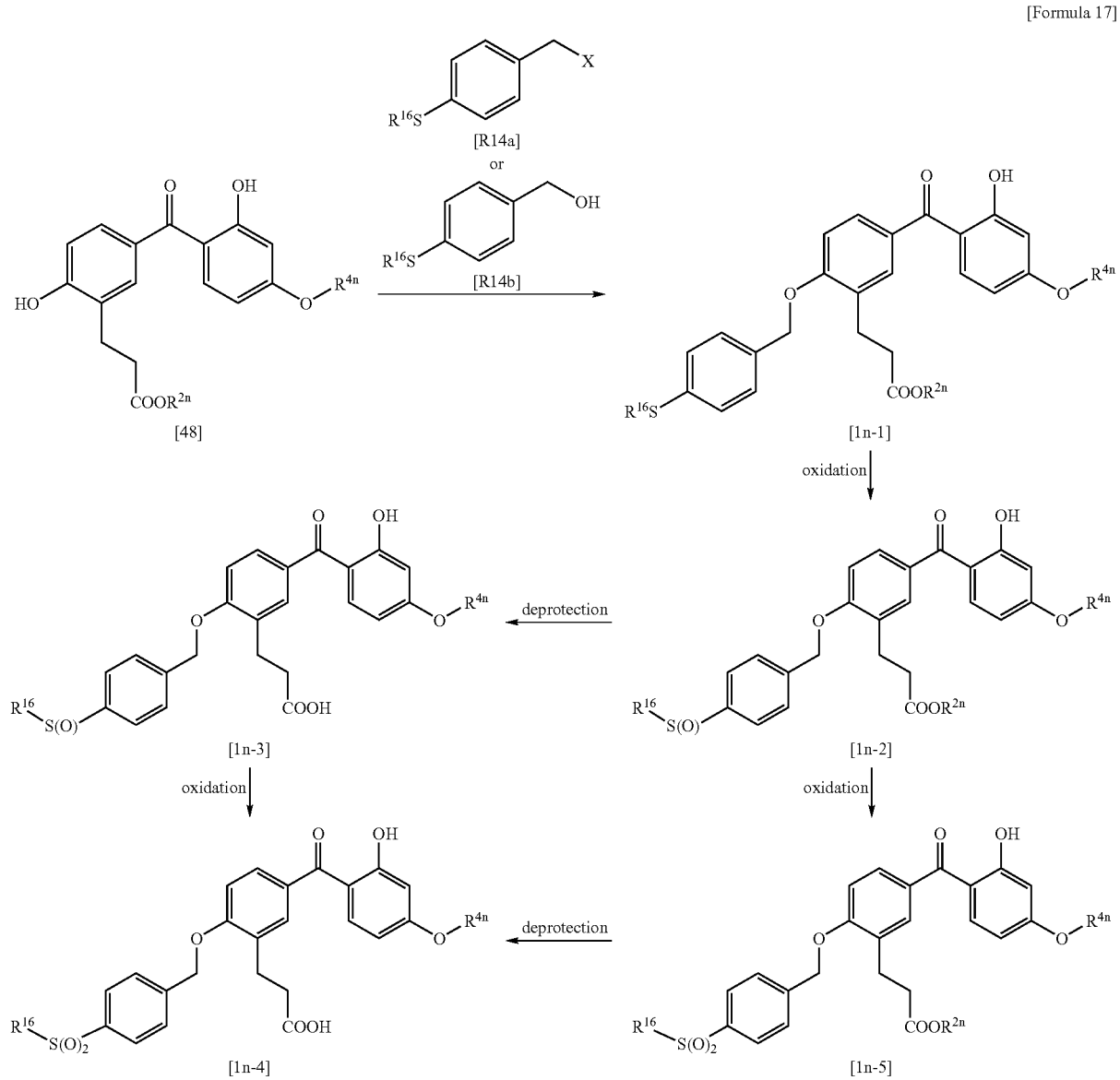

wherein $R^{2n}$ represents a carboxyl-protecting group; $R^{4n}$ represents the same meaning as $R^{4a}$; $R^{16}$ is optionally substituted alkyl or aryl; and X represents the same meaning as above.

The reaction for obtaining a compound represented by the general formula [1n-1] from a compound represented by the general formula [48] can be carried out in the same manner as in the reaction for obtaining a compound represented by the of the mole of a compound represented by the general formula [1n-1] and preferably 1- to 3-fold of the mole of the same. Solvents used in this reaction are not limited to any specific ones as long as they do not adversely affect the reaction. They include, for example, aromatic hydrocarbons such as benzene, toluene and xylene; ethers such as 1,4-dioxane, tetrahydrofuran, anisole, diethylene glycol diethyl ether and dimethyl cellosolve; alcohols such as methanol and ethanol; esters such as methyl acetate and ethyl acetate; nitriles such as acetonitrile; amides such as N,N-dimethylformamide and N,N-dimethylacetamide; halogenated hydrocarbons such as chloroform and methylene chloride; water; and sulfoxides such as dimethyl sulfoxide. These solvents may be used independently or in the form of a mixture of two or more kinds.

Usually this reaction can be performed at −78° C. to the reflux temperature of the solvent used and preferably −10 to 30° C. for 10 minutes to 24 hours.

The reaction for obtaining a compound represented by the general formula [1n-3] from a compound represented by the general formula [1n-2] can be carried out in the same manner as in the reaction for obtaining a compound represented by the general formula [1a-2] from a compound represented by the general formula [1a-1] in the production process A.

A compound represented by the general formula [1n-4] can be obtained by oxidizing a compound represented by the general formula [1n-3].

Oxidizing agents used in this reaction include, for example, organic peroxides such as peracetic acid, trifluoroperacetic acid, perbenzoic acid and m-chloroperbenzoic acid; hydrogen peroxide; chromic acid and potassium permanganate. The amount of oxidizing agent used can be 1- to 5-fold of the mole of a compound represented by the general formula [1n-3] and preferably 1- to 3-fold of the mole of the same. Solvents used in this reaction are not limited to any specific ones as long as they do not adversely affect the reaction. They include, for example, aromatic hydrocarbons such as benzene, toluene and xylene; ethers such as 1,4-dioxane, tetrahydrofuran, anisole, diethylene glycol diethyl ether and dimethyl cellosolve; alcohols such as methanol and ethanol; esters such as methyl acetate and ethyl acetate; nitriles such as acetonitrile; amides such as N,N-dimethylformamide and N,N-dimethylacetamide; halogenated hydrocarbons such as chloroform and methylene chloride; and water. These solvents may be used independently or in the form of a mixture of two or more kinds.

Usually this reaction can be performed at −78° C. to the reflux temperature of the solvent used and preferably −10 to 30° C. for 10 minutes to 24 hours.

The reaction for obtaining a compound represented by the general formula [1n-5] from a compound represented by the general formula [1n-2] can be carried out in the same manner as in the reaction for obtaining a compound represented by the general formula [1n-4] from a compound represented by the general formula [1n-3] in the production process N. When the substituent $R^{4n}$ or $R^{16}$ has a protecting group, the reaction can be carried out while appropriately deprotecting the substituent by conventional procedure.

A compound represented by the general formula [1n-5] can also be obtained by oxidizing a compound represented by the general formula [1n-1].

Oxidizing agents used in this reaction include, for example, organic peroxides such as peracetic acid, trifluoroperacetic acid, perbenzoic acid and m-chloroperbenzoic acid; hydrogen peroxide; chromic acid and potassium permanganate. The amount of oxidizing agent used can be 2- to 10-fold of the mole of a compound represented by the general formula [1n-1] and preferably 2- to 3-fold of the mole of the same. Solvents used in this reaction are not limited to any specific ones as long as they do not adversely affect the reaction. They include, for example, aromatic hydrocarbons such as benzene, toluene and xylene; ethers such as 1,4-dioxane, tetrahydrofuran, anisole, diethylene glycol diethyl ether and dimethyl cellosolve; alcohols such as methanol and ethanol; esters such as butyl acetate and ethyl acetate; nitriles such as acetonitrile; amides such as N,N-dimethylformamide and N,N-dimethylacetamide; halogenated hydrocarbons such as chloroform and methylene chloride; and water. These solvents may be used independently or in the form of a mixture of two or more kinds.

Usually this reaction can be performed at −78° C. to the reflux temperature of the solvent used and preferably −10 to 30° C. for 10 minutes to 24 hours.

The reaction for obtaining a compound represented by the general formula [1n-4] from a compound represented by the general formula [1n-5] can be carried out in the same manner as in the reaction for obtaining a compound represented by the general formula [1a-2] from a compound represented by the general formula [1a-1] in the production process A. When the substituent $R^{4n}$ or $R^{16}$ has a protecting group, the reaction can be carried out while appropriately deprotecting the substituent by conventional procedure.

[Production Process O]

[Formula 18]

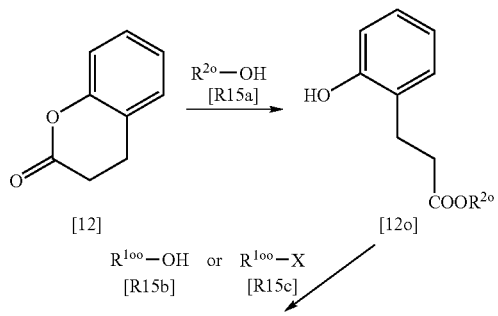

-continued
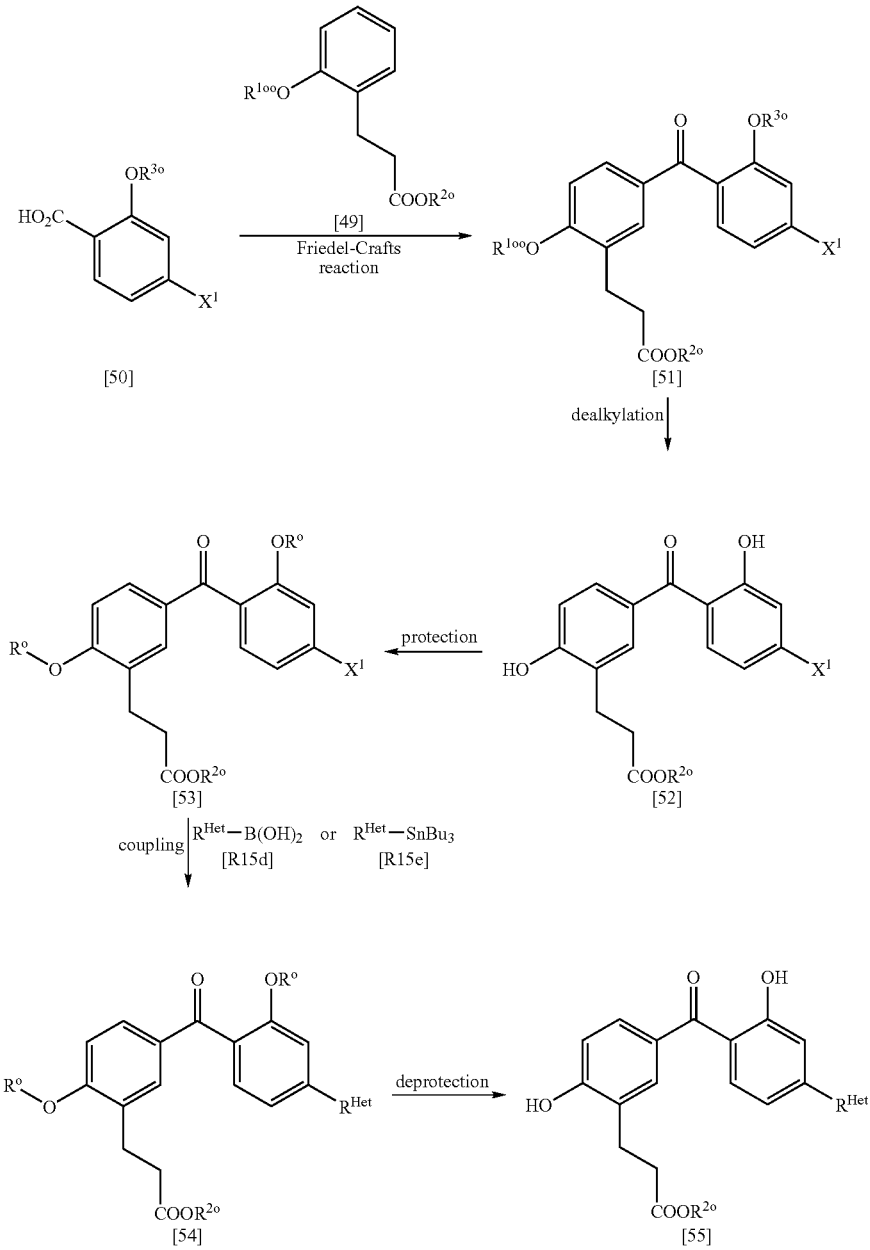
[Formula 19]
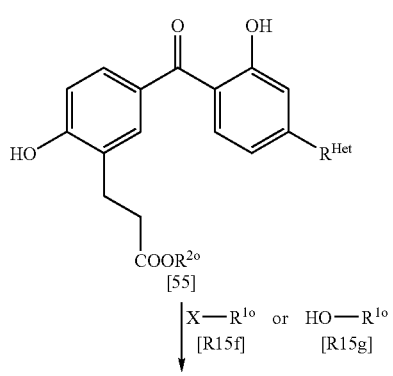

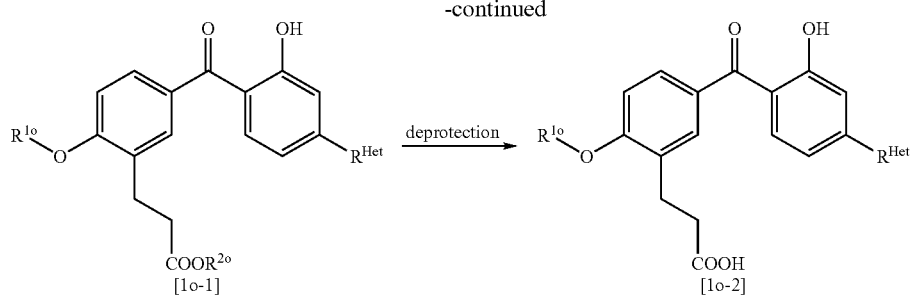

[1o-1] → deprotection → [1o-2]

wherein $R^{2o}$ represents a carboxyl-protecting group; $R^{1o}$ represents the same meaning as $R^{1a}$; $R^{1oo}$ and $R^{3o}$ are optionally substituted alkyl; $R^o$ is a phenol-protecting group; $R^{Het}$ is optionally substituted heterocyclyl; $X^1$ is a leaving group; and X represents the same meaning as above.

The reaction for obtaining a compound represented by the general formula [12o] from a compound represented by the formula [12] can be carried out in the same manner as in the reaction for obtaining a compound represented by the general formula [12d] from a compound represented by the formula [12] in the production process D.

The reaction for obtaining a compound represented by the general formula [49] from a compound represented by the general formula [12o] can be carried out in the same manner as in the reaction for obtaining a compound represented by the general formula [13] from a compound represented by the general formula [12d] in the production process D.

The reaction for obtaining a compound represented by the general formula [51] from a compound represented by the general formula [50] can be carried out in the same manner as in the reaction for obtaining a compound represented by the general formula [15] from a compound represented by the general formula [14] in the production process D.

The reaction for obtaining a compound represented by the general formula [52] from a compound represented by the general formula [51] can be carried out in the same manner as in the reaction for obtaining a compound represented by the general formula [9] from a compound represented by the general formula [8] in the production process B.

A compound represented by the general formula [52] can be obtained from a compound represented by the general formula [50] not by isolating a compound represented by the general formula [51], but by continuously carrying out Friedel-Crafts reaction and dealkylation reaction.

A compound represented by the general formula [53] can be obtained by the process disclosed in Greene et al., Protective Groups in Organic Synthesis, $3^{rd}$ edition, 1999, 249-280.

Specifically, when $R^o$ is an acetyl group, for example, a compound represented by the general formula [53] can be obtained by reacting a compound represented by the general formula [52] with acetic anhydride in the presence of base.

In this reaction, acetic anhydride can be used as a solvent; however, when some other solvent is used, the amount of acetic anhydride used can be 2- to 20-fold of the mole of a compound represented by the general formula [52] and preferably 2- to 3-fold of the mole of the same. Bases used in this reaction include, for example, organic amines such as dimethylaminopyridine, triethylamine, pyridine and N-methylmorpholine; and alkaline metal carbonates such as potassium carbonate and sodium carbonate. The amount of base used can be 2- to 10-fold of the mole of a compound represented by the general formula [52] and preferably 2- to 3-fold of the mole of the same. Solvents used in this reaction are not limited to any specific ones as long as they do not adversely affect the reaction. They include, for example, nitrites such as acetonitrile; aromatic hydrocarbons such as benzene, toluene and xylene; ethers such as 1,4-dioxane, tetrahydrofuran, anisole, diethylene glycol diethyl ether and dimethyl cellosolve; aliphatic hydrocarbons such as hexane and cyclohexane; halogenated hydrocarbons such as chloroform and methylene chloride; esters such as methyl acetate and ethyl acetate; amides such as N,N-dimethylformamide and N,N-dimethylacetamide; and sulfoxides such as dimethyl sulfoxide. These solvents may be used independently or in the form of a mixture of two or more kinds.

Usually this reaction can be performed at −20 to 200° C. and preferably 0 to 100° C. for 5 minutes to 24 hours.

When $R^o$ is a tetrahydropyranyl group, for example, a compound represented by the general formula [53] can be obtained by reacting a compound represented by the general formula [52] with 3,4-dihydro-2H-pyran in the presence of a catalyst.

The amount of the catalyst used in this reaction can be 2- to 20-fold of the mole of a compound represented by the general formula [52] and preferably 2- to 5-fold of the mole of the same. The catalysts used in this reaction include, for example, acids such as dry hydrogen chloride and p-toluenesulfonic acid; and salts such as pyridinium p-toluenesulfonate. The amount of catalyst used can be 0.01- to 10-fold of the mole of a compound represented by the general formula [52] and preferably 0.05- to 3-fold of the mole of the same. Solvents used in this reaction are not limited to any specific ones as long as they do not adversely affect the reaction. They include, for example, aromatic hydrocarbons such as benzene, toluene and xylene; ethers such as 1,4-dioxane, tetrahydrofuran, anisole, diethylene glycol diethyl ether and dimethyl cellosolve; esters such as methyl acetate and ethyl acetate; nitrites such as acetonitrile; amides such as N,N-dimethylformamide and N,N-dimethylacetamide; and halogenated hydrocarbons such as chloroform and methylene chloride. These solvents may be used independently or in the form of a mixture of two or more kinds.

Usually this reaction can be performed at 0° C. to 100° C. and preferably 0 to 50° C. for 10 minutes to 24 hours.

A compound represented by the general formula [54] can be obtained, for example, by the process described in Tetrahedron Letters, Vol. 28, 5093-5096, 1987.

Specifically, a compound represented by the general formula [54] can be obtained by reacting a compound represented by the general formula [53] and a compound represented by the general formula [R15d] in the presence of base and a palladium coordination compound as a catalyst.

Palladium coordination compounds used in this reaction include, for example, tetrakis(triphenylphosphine)palladium (0), bis(triphenylphosphine)palladium(II) chloride, benzyl (chloro)bis(triphenylphosphine)palladium(II) and palladium (II) acetate. The amount of catalyst used can be 0.001- to 1 mole per mole of a compound represented by the general formula [53] and preferably 0.01- to 0.1-fold of the mole of the same. Bases used in this reaction include, for example, alkali carbonates such as sodium hydrogencarbonate and sodium carbonate; alkali hydroxides such as sodium hydroxide and potassium hydroxide; alkaline metal alkoxides such as sodium methoxide and sodium tert-butoxide; and organic bases such as triethylamine and pyridine. The amount of base used can be 1- to 10-fold of the mole of a compound represented by the general formula [53] and preferably 2- to 4-fold of the mole of the same. Solvents used in this reaction are not limited to any specific ones as long as they do not adversely affect the reaction. They include, for example, aromatic hydrocarbons such as benzene, toluene and xylene; ethers such as 1,4-dioxane and tetrahydrofuran; halogenated hydrocarbons such as chloroform and methylene chloride; alcohols such as methanol and ethanol; esters such as ethyl acetate; amides such as N,N-dimethylformamide; sulfoxides such as dimethyl sulfoxide; and water. These solvents may be used independently or in the form of a mixture of two or more kinds.

Usually this reaction can be performed at 20° C. to the reflux temperature of the solvent used and preferably 30 to 120° C. for 30 minutes to 72 hours and preferably 30 minutes to 5 hours.

A compound represented by the general formula [54] can be obtained, for example, by the process described in Nippon Kagaku Kaishi, No. 3, 520-526, 1985.

Specifically, a compound represented by the general formula [54] can also be obtained by reacting a compound represented by the general formula [53] with a compound represented by the general formula [R15e] in the presence or absence of a palladium coordination compound as a catalyst.

Palladium coordination compounds used in this reaction include, for example, tetrakis(triphenylphosphine)palladium (0), bis(triphenylphosphine)palladium(II) chloride, benzyl (chloro)bis(triphenylphosphine)palladium(II) and palladium (II) acetate. The amount of catalyst used can be 0.001- to 1-fold of the mole of a compound represented by the general formula [53] and preferably 0.01- to 0.1-fold of the mole of the same. Solvents used in this reaction are not limited to any specific ones as long as they do not adversely affect the reaction. They include, for example, aromatic hydrocarbons such as benzene, toluene and xylene; ethers such as 1,4-dioxane and tetrahydrofuran; halogenated hydrocarbons such as chloroform and methylene chloride; alcohols such as methanol and ethanol; esters such as ethyl acetate; amides such as N,N-dimethylformamide; and sulfoxides such as dimethyl sulfoxide. These solvents may be used independently or in the form of a mixture of two or more kinds.

Usually this reaction can be performed at 20° C. to the reflux temperature of the solvent used and preferably 30 to 120° C. for 30 minutes to 72 hours and preferably 30 minutes to 5 hours.

A compound represented by the general formula [55] can be obtained from a compound represented by the general formula [54] by carrying out ordinary deprotection.

Specifically, when $R^o$ of a compound represented by the general formula [54] is acetyl, a compound represented by the general formula [55] can be obtained by deprotecting the substituents protected with $R^o$ in the presence of base.

Bases used in this reaction include, for example, alkaline metal carbonates such as potassium carbonate and sodium carbonate; and alkaline metal alkoxides such as potassium tert-butoxide and sodium methoxide. The amount of base used can be 2- to 10-fold of the mole of a compound represented by the general formula [54] and preferably 2- to 3-fold of the mole of the same. Solvents used in this reaction are not limited to any specific ones as long as they do not adversely affect the reaction. They include, for example, aromatic hydrocarbons such as benzene, toluene and xylene; ethers such as 1,4-dioxane and tetrahydrofuran; halogenated hydrocarbons such as chloroform and methylene chloride; alcohols such as methanol and ethanol; amides such as N,N-dimethylformamide; and sulfoxides such as dimethyl sulfoxide. These solvents may be used independently or in the form of a mixture of two or more kinds.

Usually this reaction can be performed at $-10°$ C. to $100°$ C. and preferably 0 to 30° C. for 5 minutes to 24 hours and preferably 10 minutes to 10 hours.

When $R^o$ of a compound represented by the general formula [54] is tetrahydropyran, for example, elimination thereof can be accomplished in the presence of acid. Acids used in this reaction include, for example, mineral acids such as hydrochloric acid; and organic acids such as p-toluenesulfonic acid and oxalic acid. The amount of acid used can be 0.01- to 100-fold of the mole of a compound represented by the general formula [54] and preferably 0.05- to 10-fold of the mole of the same. Solvents used in this reaction are not limited to any specific ones as long as they do not adversely affect the reaction. They include, for example, aromatic hydrocarbons such as benzene, toluene and xylene; ethers such as 1,4-dioxane, tetrahydrofuran, anisole, diethylene glycol diethyl ether and dimethyl cellosolve; alcohols such as methanol and ethanol; esters such as butyl acetate and ethyl acetate; nitrites such as acetonitrile; amides such as N,N-dimethylformamide and N,N-dimethylacetamide; halogenated hydrocarbons such as chloroform and methylene chloride; and water. These solvents may be used independently or in the form of a mixture of two or more kinds.

Usually this reaction can be performed at 0° C. to the reflux temperature of the solvent used and preferably 5 to 100° C. for 10 minutes to 24 hours.

The reaction for obtaining a compound represented by the general formula [1o-1] from a compound represented by the general formula [55] can be carried out in the same manner as in the reaction for obtaining a compound represented by the general formula [5] from a compound represented by the general formula [3] in the production process A.

The reaction for obtaining a compound represented by the general formula [1o-2] from a compound represented by the general formula [1o-1] can be carried out in the same manner as in the reaction for obtaining a compound represented by the general formula [1a-2] from a compound represented by the general formula [1a-1] in the production process A. When the substituent $R^{1o}$ or $R^{Het}$ has a protecting group, the reaction can be carried out while appropriately deprotecting the substituent by conventional procedure.

[Production Process P]
[Formula 20]
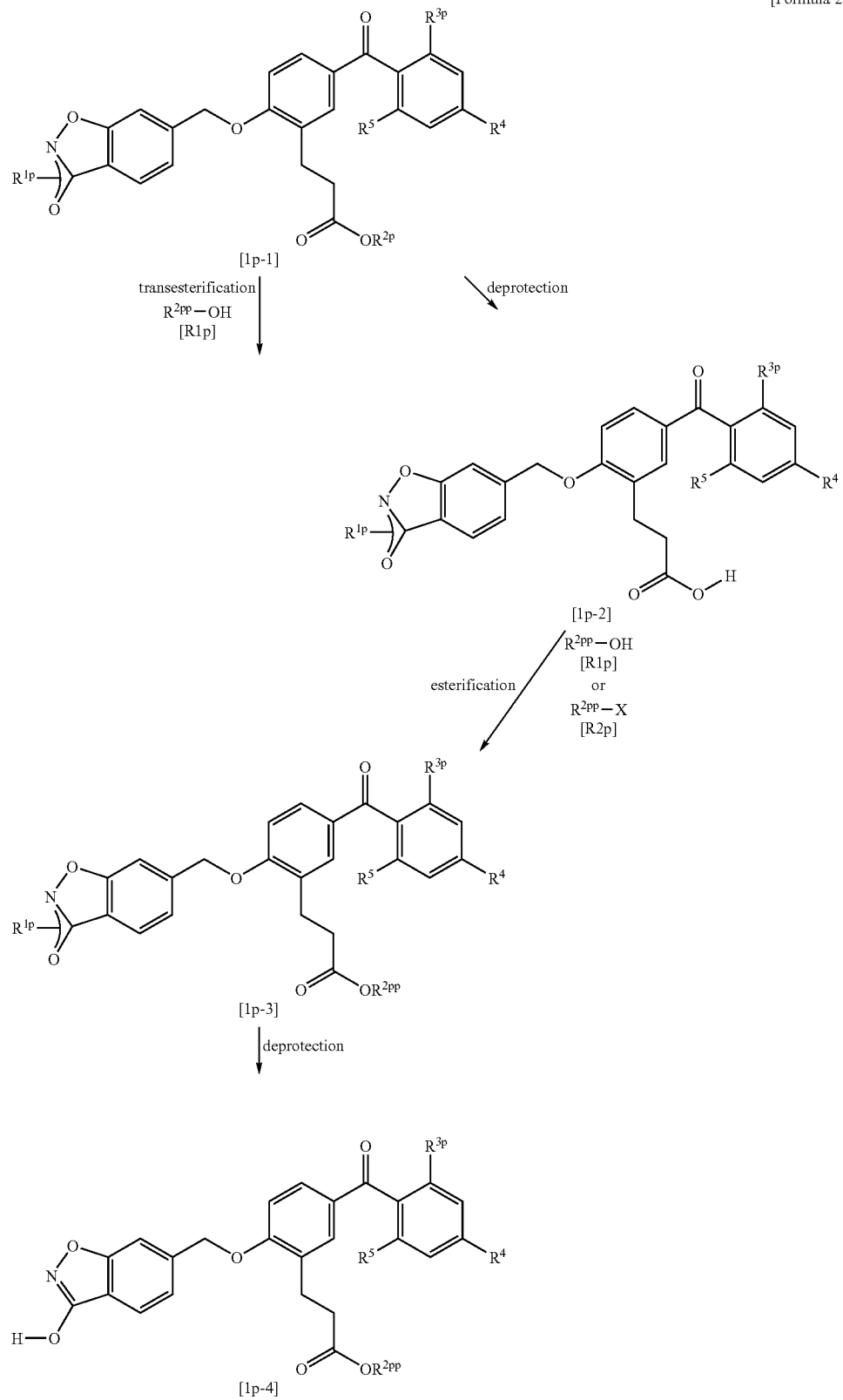

wherein $R^{1p}$ represents a hydroxyl- or amino-protecting group; $R^{2p}$ and $R^{2pp}$ each represent optionally substituted alkyl; $R^{3p}$ is hydrogen, halogen, cyano, nitro, optionally protected hydroxyl, optionally protected amino, mercapto, carbamoyl, or optionally substituted alkyl, alkenyl, cycloalkyl, aryl, aralkyl, alkoxy, aryloxy, acyl, alkylthio, alkylsulfinyl, alkylsulfonyl, alkylamino, acylamino, alkylsulfonylamino, arylsulfonylamino or heterocyclyl; $R^4$, $R^5$ and X represent the same meaning as above ($R^{1p}$ represents a group substituted for oxygen of a hydroxyl group as a substituent of benzisoxazole or nitrogen of benzisoxazole).

A compound represented by the general formula [1p-2] can be obtained by subjecting a compound represented by the general formula [1p-1] to deprotection reaction such as (1) hydrolysis with acid or base, (2) dealkylation with salt or (3) reductive dealkylation including hydrogen addition reaction with metal catalyst.

Acids used in the reaction (1) include, for example, mineral acids such as hydrochloric acid, sulfuric acid and hydrobromic acid; organic acids such as formic acid and trifluoroacetic acid; and Lewis acids such as aluminium chloride and trimethylsilyl iodide. The amount of acid used in the reaction can be 1- to 100-fold of the mole of a compound represented by the general formula [1p-1] and preferably 1- to 10-fold of the mole of the same.

Bases used in the reaction (1) include, for example, alkali hydroxides such as sodium hydroxide, potassium hydroxide and lithium hydroxide; alkaline metal alkoxides such as sodium methoxide, sodium ethoxide and potassium tert-butoxide; alkaline metal carbonates such as potassium carbonate and sodium carbonate; and tetrabutylammonium fluoride. The amount of base used can be 1- to 100-fold of the mole of a compound represented by the general formula [1p-1] and preferably 1- to 10-fold of the mole of the same.

Salts used in the reaction (2) include, for example, lithium iodide and sodium chloride. The amount of salt used can be 1- to 100-fold of the mole of a compound represented by the general formula [1p-1] and preferably 1- to 10-fold of the mole of the same.

Catalysts used in the reaction (3) include, for example, palladium carbon, palladium black and palladium hydroxide. The amount of catalyst used can be 0.1- to 100% (w/w) the weight of the compound represented by the general formula [1p-1] and preferably 1- to 50% (w/w) the weight of the same.

Reducing agents used in the reaction (3) include, for example, hydrogen, formic acid, cyclohexene and zinc. The amount of reducing agent used can be 1- to 100-fold of the mole of a compound represented by the general formula [1p-1] and preferably 1- to 10-fold of the mole of the same.

Solvents used in these reactions are not limited to any specific ones as long as they do not adversely affect the reaction. They include, for example, alcohols such as methanol, ethanol and isopropyl alcohol; ethers such as tetrahydrofuran, diethyl ether; 1,4-dioxane and anisole; halogenated hydrocarbons such as methylene chloride, chloroform and carbon tetrachloride; nitrites such as acetonitrile; aliphatic hydrocarbons such as n-hexane and cyclohexane; esters such as ethyl acetate; aromatic hydrocarbons such as toluene, benzene and xylene; dimethyl sulfoxide, N,N-dimethylformamide, nitromethane, pyridine and water. These solvents may be used independently or in the form of a mixture of two or more kinds.

Usually these reaction can be performed at −78 to 100° C. and preferably 0 to 80° C. for 10 minutes to 24 hours.

A compound represented by the general formula [1p-3] can be obtained by subjecting a compound represented by the general formula [1p-2] to esterification.

This can be carried out using ordinary esterification reaction, and the processes of esterification include, for example, processes (1) in which acid catalyst and additive are used, (2) in which esterification is carried out via acid chloride in the presence or absence of catalyst, (3) in which esterification is carried out via acid anhydride in the presence or absence of base, (4) in which base and a compound represented by the general formula [R2p] are used and (5) in which a compound represented by the general formula [R1p] together with condensing agent and additive is subjected to condensation reaction.

Acid catalysts used in the reaction (1) include, for example, hydrochloric acid, sulfuric acid, hydrobromic acid, trimethylsilyl chloride, aluminium chloride, boron trifluoride and trifluoroacetic acid. The amount of acid catalyst used in the reaction can be 0.01- to 100-fold of the mole of a compound represented by the general formula [1p-2] and preferably 0.5- to 50-fold of the mole of the same. Additives used in the reaction include, for example, 2,2-dimethoxypropane and ethyl orthoformate. The amount of additive used in the reaction can be 0.1- to 100-fold of the mole of a compound represented by the general formula [1p-2] and preferably 1- to 50-fold of the mole of the same.

Compounds represented by the general formula [R1p] include, for example, methanol, ethanol, benzyl alcohol, N-(2-hydroxyethyl)morpholine and 4-hydroxymethyl-5-methyl-1,3-dioxol-2-one. These compounds can be used as a solvent in appropriate amount; however, when some other solvent is used, the amount of such a compound used can be 1- to 100-fold of the mole of a compound represented by the general formula [1p-2] and preferably 1- to 50-fold of the mole of the same.

Solvents used in the reaction (1) are not limited to any specific ones as long as they do not adversely affect the reaction. They include, for example, aromatic hydrocarbons such as benzene, toluene and xylene; ethers such as 1,4-dioxane, tetrahydrofuran, anisole, diethylene glycol diethyl ether, and dimethyl cellosolve; esters such as methyl acetate and ethyl acetate; nitriles such as acetonitrile; amides such as N,N-dimethylformamide; halogenated hydrocarbons such as chloroform and methylene chloride; and sulfoxides such as dimethyl sulfoxide. Usually these reaction can be performed at 0 to 200° C. and preferably 5 to 100° C. for 10 minutes to 24 hours.

Carboxylic-activating agents used in the reaction (2) include, for example, oxalyl chloride and thionyl chloride. The amount of the agent used in the reaction can be 1- to 10-fold of the mole of a compound represented by the general formula [1p-2] and preferably 1- to 5-fold of the mole of the same.

Catalysts used in the reaction (2) as the need arises include, for example, N,N-dimethylformamide, and the amount of catalyst used in the reaction can be 0.001- to 1-fold of the mole of a compound represented by the general formula [1p-2] and preferably 0.01- to 0.5-fold of the mole of the same.

Solvents used in the reaction (2) are not limited to any specific ones as long as they do not adversely affect the reaction. They include, for example, aromatic hydrocarbons such as benzene, toluene and xylene; ethers such as 1,4-dioxane, tetrahydrofuran, anisole, diethylene glycol diethyl ether, and dimethyl cellosolve; esters such as methyl acetate and ethyl acetate; nitrites such as acetonitrile; amides such as N,N-dimethylformamide; and halogenated hydrocarbons such as chloroform and methylene chloride. Usually these reaction can be performed at 0 to 200° C. and preferably 5 to 100° C. for 10 minutes to 24 hours.

Activating agents used in the reaction (3) include, for example, acetic anhydride and ethyl chloroformate, and the amount of activating agent used in the reaction can be 1- to 10-fold of the mole of a compound represented by the general formula [1p-2] and preferably 1- to 5-fold of the mole of the same.

Bases used in the reaction (3) as the need arises include, for example, organic amines such as dimethylaminopyridine, triethylamine, pyridine, N-methylmorpholine and N-ethyldiisopropylamine; and alkaline metal carbonates such as potassium carbonate and sodium carbonate. The amount of base used can be 1- to 10-fold of the mole of a compound represented by the general formula [1p-2] and preferably 1- to 5-fold of the mole of the same. Solvents used in this reaction are not limited to any specific ones as long as they do not adversely affect the reaction. They include, for example, aromatic hydrocarbons such as benzene, toluene and xylene; ethers such as 1,4-dioxane, tetrahydrofuran, anisole, diethylene glycol diethyl ether and dimethyl cellosolve; esters such as methyl acetate and ethyl acetate; nitrites such as acetonitrile; amides such as N,N-dimethylformamide; and halogenated hydrocarbons such as chloroform and methylene chloride. Usually this reaction can be performed at 0 to 200° C. and preferably 5 to 100° C. for 10 minutes to 24 hours.

Bases used in the reaction (4) include, for example, organic amines such as dimethylaminopyridine, triethylamine, pyridine and N-methylmorpholine; and alkaline metal carbonates such as potassium carbonate and sodium carbonate. The amount of base used can be 0.5- to 10-fold of the mole of a compound represented by the general formula [1p-2] and preferably 1- to 5-fold of the mole of the same.

Compounds represented by the general formula [R2p] used in the reaction (4) include, for example, methyl iodide, ethyl iodide, benzyl bromide, ethyl carbonate 1-ethyl iodide, cyclohexyl carbonate 1-ethyl iodide, 4-bromomethyl-5-methyl-1,3-dioxol-2-one, N-(2-chloroethyl)morpholine and chloromethyl pivalate. The amount of such a compound used can be 0.5- to 10-fold of the mole of a compound represented by the general formula [1p-2] and preferably 1- to 3-fold of the mole of the same.

Solvents used in the reaction (4) are not limited to any specific ones as long as they do not adversely affect the reaction. They include, for example, aromatic hydrocarbons such as benzene, toluene and xylene; ethers such as 1,4-dioxane, tetrahydrofuran, anisole, diethylene glycol diethyl ether and dimethyl cellosolve; esters such as methyl acetate and ethyl acetate; nitrites such as acetonitrile; amides such as N,N-dimethylformamide; halogenated hydrocarbons such as chloroform and methylene chloride; and sulfoxides such as dimethyl sulfoxide. Usually this reaction can be performed at 0 to 200° C. and preferably 5 to 100° C. for 10 minutes to 24 hours.

Condensing agents used in the reaction (5) include, for example, 1,1'-carbonyldiimidazole, N,N'-dicyclohexylcarbodiimide, diisopropylcarbodiimide, N-ethyl-N'-3-dimethylaminopropylcarbodiimide, diisopropyl azodicarboxylate and diphenylphosphoryl azide.

Additives used in the reaction (5) include, for example, 1-hydroxybenzotriazole, triphenylphosphine and N-hydroxysuccinimide.

The amounts of a compound represented by the general formula [R1p], condensing agent and additive used in the reaction (5) each can be 0.01- to 10-fold of the mole of a compound represented by the general formula [1p-2] and preferably 0.1- to 3-fold of the mole of the same.

Solvents used in the reaction (5) are not limited to any specific ones as long as they do not adversely affect the reaction. They include, for example, aromatic hydrocarbons such as benzene, toluene and xylene; ethers such as 1,4-dioxane, tetrahydrofuran, anisole, diethylene glycol diethyl ether and dimethyl cellosolve; esters such as methyl acetate and ethyl acetate; nitrites such as acetonitrile; amides such as N,N-dimethylformamide; and halogenated hydrocarbons such as chloroform and methylene chloride. Usually this reaction can be performed at 0 to 200° C. and preferably 5 to 100° C. for 10 minutes to 24 hours.

A compound represented by the general formula [1p-3] can also be obtained from a compound represented by the general formula [1p-1] by continuously carrying out deprotection and esterification.

A compound represented by the general formula [1p-3] can also be obtained by reacting a compound represented by the general formula [1p-1] with a compound represented by the general formula [R1p] in the presence of acid or base.

Compounds represented by the general formula [R1p] used in this reaction include, for example, methanol, ethanol, benzyl alcohol, N-(2-hydroxyethyl)morpholine and 4-hydroxymethyl-5-methyl-1,3-dioxole-2-one. These compounds can be used as a solvent in appropriate amount; however, when some other solvent is used, the amount of such a compound used can be 1- to 100-fold of the mole of a compound represented by the general formula [1p-1] and preferably 1- to 10-fold of the mole of the same.

Acids used in this reaction include, for example, hydrochloric acid, sulfuric acid, p-toluenesulfonic acid, trimethylsilyl chloride and boron trifluoride. The amount of acid used in the reaction can be 0.01- to 100-fold of the mole of a compound represented by the general formula [1p-1] and preferably 0.1- to 10-fold of the mole of the same.

Bases used in this reaction include, for example, alkaline metal alkoxides such as sodium methoxide, sodium ethoxide and potassium tert-butoxide; organic amines such as dimethylaminopyridine, triethylamine and pyridine; alkaline metal hydrides such as sodium hydride; and alkaline metal carbonates such as potassium carbonate and sodium carbonate. The amount of base used can be 1- to 100-fold of the mole of a compound represented by the general formula [1p-1] and preferably 1- to 10-fold of the mole of the same.

Solvents used in this reaction are not limited to any specific ones as long as they do not adversely affect the reaction. They include, for example, aromatic hydrocarbons such as benzene, toluene and xylene; ethers such as 1,4-dioxane, tetrahydrofuran, anisole, diethylene glycol diethyl ether, and dimethyl cellosolve; nitrites such as acetonitrile; amides such as N,N-dimethylformamide; halogenated hydrocarbons such as chloroform and methylene chloride; and sulfoxides such as dimethyl sulfoxide. These solvents are used independently or in the form of a mixture of two or more kinds.

Usually this reaction can be performed at −50 to 200° C. and preferably −30 to 150° C. for 10 minutes to 24 hours.

A compound represented by the general formula [1p-4] can be obtained from a compound represented by the general formula [1p-3] by carrying out ordinary deprotection.

For example, when $R^{1p}$ of a compound represented by the general formula [1p-3] is tert-butoxycarbonyl, deprotection can be carried out in the presence of acid. Acids used in this reaction include, for example, mineral acids such as hydrochloric acid and sulfuric acid; and organic acids such as methanesulfonic acid, p-toluenesulfonic acid, acetic acid and trifluoroacetic acid. The amount of acid used in the reaction can be 0.01- to 100-fold of the mole of a compound represented by the general formula [1p-3] and preferably 1- to 10-fold of the mole of the same. Solvents used in this reaction are not limited to any specific ones as long as they do not adversely affect the reaction. They include, for example, aromatic hydrocarbons such as benzene, toluene and xylene; ethers such as 1,4-dioxane, tetrahydrofuran, anisole, diethylene glycol diethyl ether, and dimethyl cellosolve; alcohols such as methanol, ethanol and isopropyl alcohol; esters such as butyl acetate and ethyl acetate; nitrites such as acetonitrile; amides such as N,N-dimethylformamide and N,N-dimethylacetamide; halogenated hydrocarbons such as chloroform and methylene chloride; and water. These solvents are used independently or in the form of a mixture of two or more kinds. Usually this reaction can be performed at 0° C. to the reflux temperature of the solvent used and preferably 0 to 120° C. for 10 minutes to 24 hours.

For example, when $R^{1p}$ of a compound represented by the general formula [1p-3] is methoxymethyl or trityl, deprotection can be carried out in the presence of acid. Acids used in this reaction include, for example, mineral acids such as hydrochloric acid and sulfuric acid; and organic acids such as methanesulfonic acid, p-toluenesulfonic acid, acetic acid and trifluoroacetic acid. The amount of acid used in the reaction can be 0.01- to 100-fold of the mole of a compound represented by the general formula [1p-3] and preferably 1- to 10-fold of the mole of the same. Solvents used in this reaction are not limited to any specific ones as long as they do not adversely affect the reaction. They include, for example, aromatic hydrocarbons such as benzene, toluene and xylene; ethers such as 1,4-dioxane, tetrahydrofuran, anisole, diethylene glycol diethyl ether, and dimethyl cellosolve; alcohols such as methanol, ethanol and isopropyl alcohol; esters such as butyl acetate and ethyl acetate; nitrites such as acetonitrile; amides such as N,N-dimethylformamide and N,N-dimethylacetamide; halogenated hydrocarbons such as chloroform and methylene chloride; and water. These solvents are used independently or in the form of a mixture of two or more kinds. Usually this reaction can be performed at 0° C. to the reflux temperature of the solvent used and preferably 0 to 120° C. for 10 minutes to 24 hours.

A compound represented by the general formula [1p-4] can also be obtained from a compound represented by the general formula [1p-2] by continuously carrying out esterification and deprotection.

[Production Process Q]

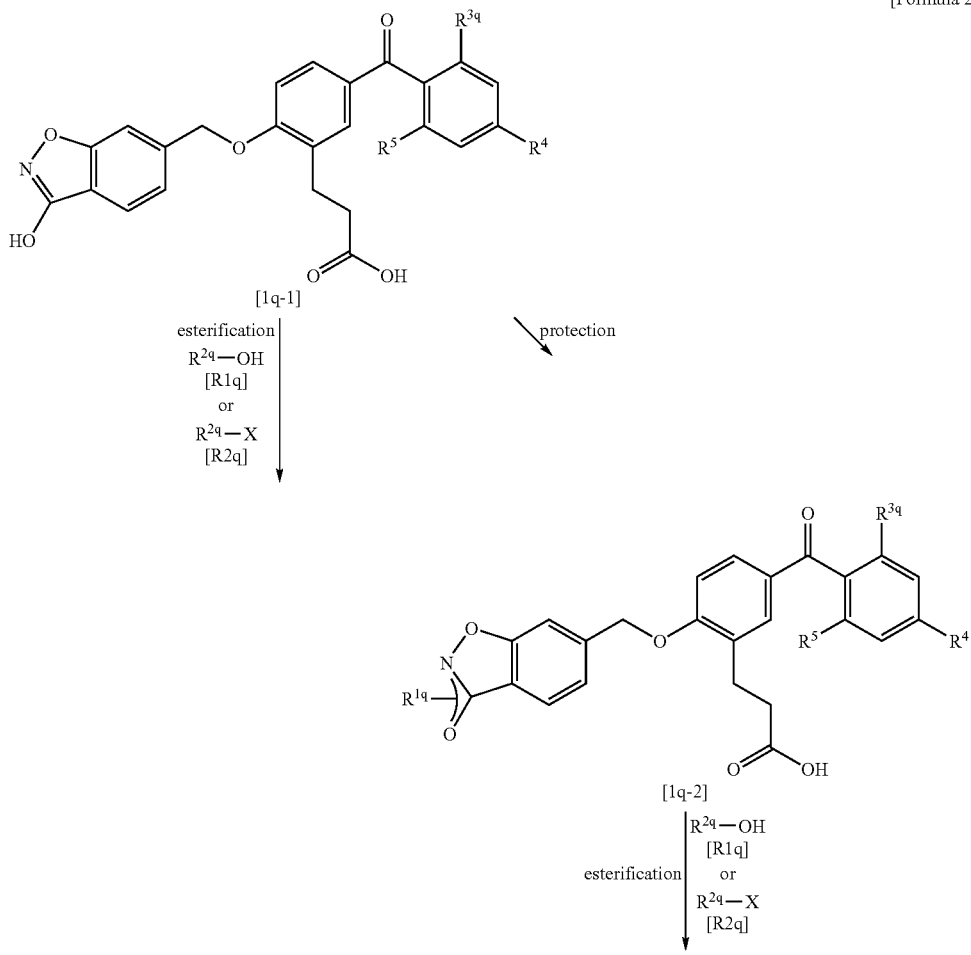

[Formula 21]

-continued

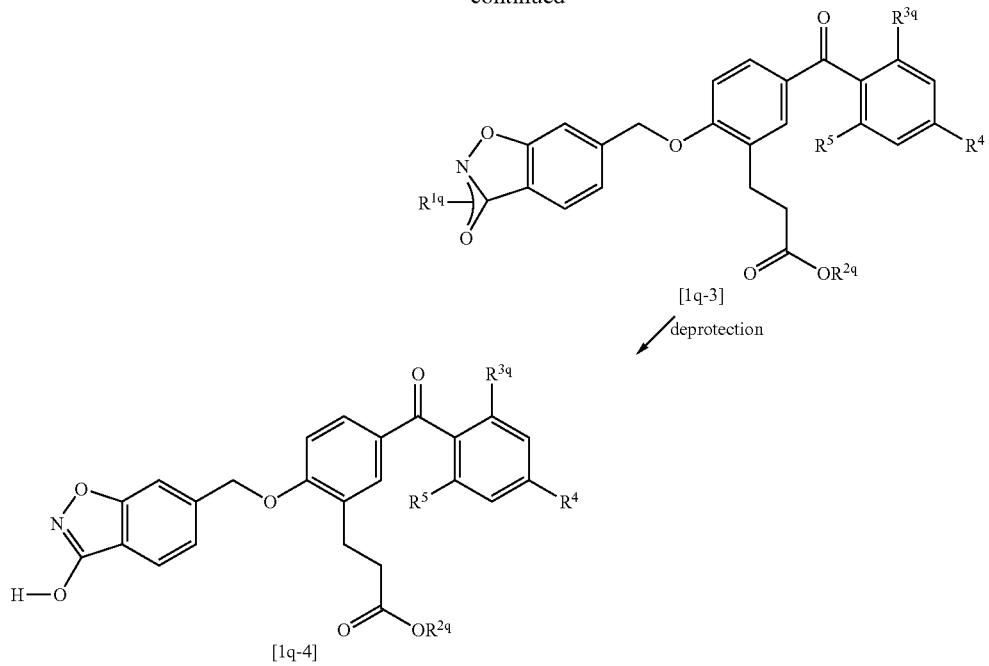

wherein $R^{1q}$ represents the same meaning as $R^{1p}$; $R^{2q}$ represents the same meaning as $R^{2p}$; $R^{3q}$ represents the same meaning as $R^{3p}$; and $R^4$, $R^5$ and X represent the same meaning as above ($R^{1q}$ represents a group substituted for oxygen of an oxo group as a substituent of benzisoxazole or nitrogen of benzisoxazole).

A compound represented by the general formula [1q-2] can be obtained, for example, by the process disclosed in Greene et al., Protective Groups in Organic Synthesis, 3$^{rd}$ edition, 1999, 17-292, 494-653.

Specifically, when $R^{1q}$ is a trityl group, for example, a compound represented by the general formula [1q-2] can be obtained by reacting a compound represented by the general formula [1q-1] with trityl chloride in the presence of base. The amount of trityl chloride used can be 1- to 10-fold of the mole of a compound represented by the general formula [1q-1] and preferably 1- to 3-fold of the mole of the same.

Bases used in this reaction include, for example, organic amines such as dimethylaminopyridine, triethylamine, pyridine and N-methylmorpholine; and alkaline metal carbonates such as potassium carbonate and sodium carbonate. The amount of base used can be 1- to 20-fold of the mole of a compound represented by the general formula [1q-1] and preferably 3- to 10-fold of the mole of the same.

Solvents used in this reaction are not limited to any specific ones as long as they do not adversely affect the reaction. They include, for example, nitrites such as acetonitrile; aromatic hydrocarbons such as benzene, toluene and xylene; ethers such as 1,4-dioxane, tetrahydrofuran, anisole, diethylene glycol diethyl ether and dimethyl cellosolve; aliphatic hydrocarbons such as hexane and cyclohexane; halogenated hydrocarbons such as chloroform and methylene chloride; esters such as methyl acetate and ethyl acetate; amides such as N,N-dimethylformamide and N,N-dimethylacetamide; and sulfoxides such as dimethyl sulfoxide. These solvents may be used independently or in the form of a mixture of two or more kinds.

Usually this reaction can be performed at −50 to 150° C. and preferably −30 to 100° C. for 5 minutes to 24 hours.

The reaction for obtaining a compound represented by the general formula [1q-3] from a compound represented by the general formula [1q-2] can be carried out in the same manner as in the reaction for obtaining a compound represented by the general formula [1p-3] from a compound represented by the general formula [1p-2] in the production process P.

The reaction for obtaining a compound represented by the general formula [1q-4] from a compound represented by the general formula [1q-1] can be carried out in the same manner as in the reaction for obtaining a compound represented by the general formula [1p-3] from a compound represented by the general formula [1p-2] in the production process P.

The reaction for obtaining a compound represented by the general formula [1q-4] from a compound represented by the general formula [1q-3] can be carried out in the same manner as in the reaction for obtaining a compound represented by the general formula [1p-4] from a compound represented by the general formula [1p-3] in the production process P.

In the compounds used in the above described production processes, those capable of taking the form of salts can be used as salts. Such salts include, for example, the same salts as described in the salts of compounds represented by the general formula [1].

When isomers (e.g. optical isomers, geometrical isomers and tautomers) are present in the compounds used in the above described production processes, the isomers can also be used. When solvates, hydrates and crystals in various forms are present in the compounds, the solvates, hydrates and crystals in various forms can also be used. In the compounds used in the above described production processes, for those having substituents that can be protected, such as amino, hydroxyl or carboxyl, the substituents can be protected with ordinary protecting groups in advance and deprotected by known processes after reaction.

Subjecting the compounds represented by the general formula [1] thus obtained to known reaction, such as oxidation, reduction, substitution, rearrangement, halogenation, dehydration or hydrolysis, or the combination thereof enables other compounds represented by the general formula [1] to be derived. Compounds represented by the general formula [1] or the salts thereof can be isolated and purified by conventional procedure such as extraction, crystallization and/or column chromatography.

When using the compounds of this invention as drugs, additives commonly used in preparation of drugs, such as excipient, carrier and diluent, can be appropriately mixed with the compounds. The resultant drugs can be administered orally or parenterally in a dosage form of tablet, capsule, powder, syrup, granule, pill, suspension, emulsion, solution, powder preparations, suppository, ointment or parenteral injection. The dosage, administration and dosing can be appropriately selected depending on the age, body weight and symptoms of patients. For adults, usually they can be administered orally or parenterally (e.g. injection, drip infusion, or administration into rectum) in a daily dose of 0.1 to 100 mg/kg in one to several divided portions.

Test Methods

Test Example 1 Effect on AP-1 Binding Activity to AP-1 Recognition Sequence (ELISA)

Jun peptide and Fos peptide with its N-terminal labeled with biotin via 4 glycine residues containing a DNA binding site [Nature, Vol. 373, 1995, 257-261] were synthesized. Each of the peptides was dissolved in Tris buffer [20 mM Tris-hydrochloric acid (pH 7.5), 50 mM potassium chloride, 1 mM ethylenediaminetetraacetic acid, 10 mM magnesium chloride, 1 mM dithiothreitol, 0.5 M guanidinohydrochloric acid, 30% glycerol], and equimolar amounts of the peptide solutions were mixed with each other to be used as an AP-1 complex (Fos/Jun peptide). The AP-1 complex was added onto a 96-well avidin-coated ELISA plate (10 pmol/well). The plate was washed, blocked by bovine serum albumin, and used for binding assay.

Digoxigenin-labeled double-stranded oligonucleotide (22mer) that contained AP-1 binding sequence (3'-TGAGTCA-5') synthesized by conventional procedure was reacted in binding reaction solution [25 mM tris-hydrochloric acid (pH 7.9), 0.5 mM ethylenediaminetetraacetic acid, 0.05% Nonidet P-40, 10% glycerol] for 30 minutes at room temperature in the presence or absence of samples. After the reaction, unbound labeled oligonucleotide was removed by washing with HEPES buffer containing 0.05% Tween-20. Then peroxidase-labeled anti-digoxigenin antibody was added to react with the labeled oligonucleotide bound to AP-1. After removing excess antibody by washing with HEPES buffer containing 0.05% Tween-20, incubation was conducted for a certain period with o-phenylene diamine as a substrate in 100 mM citric acid buffer (pH 5.0) containing hydrogen peroxide, sulfuric acid solution was added to each well, and the absorbance (492 nm) was measured. Inhibition rate of each sample was calculated from the absorbance obtained in the binding assay carried out in the presence of the sample, taking the absorbance obtained in the absence of the sample=100%.

The results are shown in Table 12.

TABLE 12

| Example no. | Concentration ($\mu$M) at 50% inhibition |
| --- | --- |
| 49(47) | 460 |
| 49(8) | 320 |
| 49(9) | 490 |
| 44 | 420 |
| 49(89) | 500 |
| 72(1) | 240 |
| 49(56) | 130 |
| 49(58) | 190 |
| 49(20) | 320 |
| 49(48) | 310 |
| 49(12) | 700 |
| 49(51) | 300 |
| 49(86) | 110 |
| 32(1) | 310 |
| 49(1) | 330 |
| 49(83) | 150 |
| 49(19) | 280 |
| 48 | 700 |
| 49(46) | 320 |
| 49(29) | 220 |
| 49(22) | 200 |
| 49(11) | 390 |
| 46 | 330 |
| 45 | 140 |
| 49(39) | 360 |
| 49(40) | 280 |
| 49(77) | 380 |
| 49(27) | 120 |
| 49(3) | 240 |
| 49(16) | 380 |
| 49(76) | 380 |
| 35 | 290 |
| 49(79) | 200 |
| 49(62) | 580 |
| 49(87) | 210 |
| 49(70) | 180 |
| 47 | 170 |
| 49(54) | 270 |
| 49(63) | 260 |

Test Example 2 Type II Collagen-Induced Arthritis in Mouse

Male DBA/1J mice aged 8 weeks (Charles River Japan) were used. To a solution of 2 mg/mL bovine type II collagen in 0.1 mol/L acetic acid (Koken), an equimolar amount of Freund's complete adjuvant (DIFCO) was added to prepare an emulsion, and 0.2 ml of the emulsion was subcutaneously injected in the tail root region of each mouse. The same treatment was given 21 days after the initial inoculation to induce arthritis in the mice. Test compounds were each suspended in 0.5% methylcellulose solution, and 10 mg/kg of each test compound was given orally to mice once a day from 21 to 35 days after the initial inoculation. To a control group (a negative control group), 0.5% methylcellulose solution was given in the same manner.

Taking the maximum score as 12, the arthritis score was calculated to evaluate the severity of arthritis that was evaluated in the following manner: score 0: no change; score 1: swelling on one or two toes, or slight swelling in the carpal and tarsal joints; score 2: swelling and rubor in more joints; score 3: extensive swelling over whole foreleg or hindleg; and total of the four legs was calculated.

X-ray photographs of four paws were taken 36 days after the initial inoculation, and the severity of bone destruction was evaluated as bone destruction score on a maximum scale, the sum of the points for extremities, of 105 points: 0 or 0.5 points in accordance with presence or absence of osteoporosis in the joints and their vicinity, and for bone erosion, no change at 0 point; "partial bone destruction" at 1 point and "complete bone destruction" at 2 points in the second to fifth interdigital joints, the first to fifth metacarpal and metatarsal joints, and carpal, tarsal and calcaneal regions. Inhibition rate was calculated using the following equation:

Inhibition rate(%)=100−(score of the group given the test compound/score of the control group)×100

Table 13 shows the arthritis inhibition rate and the bone destruction inhibition rate of each test compound on 36 days after initial inoculation.

TABLE 13

| Example no. | Arthritis inhibition rate | Bone destruction inhibition rate |
| --- | --- | --- |
| 35 | 76 | 92 |
| 45 | 55 | 81 |
| 48 | 57 | 64 |
| 49(12) | 50 | 76 |
| 54(2) | 65 | 78 |
| 76 | 90 | 99 |

BEST MODE FOR CARRYING OUT THE INVENTION

Compounds according to the present invention will now be described in the following Examples, however, the present invention is not intended to be limited to these examples. Abbreviations described in the Examples have meanings as follows, respectively.

Me: methyl, Et: ethyl, i-Pr: isopropyl, i-Bu: isobutyl, MOM: methoxymethyl, Bn: benzyl, Tr: trityl, Ph: phenyl, Boc: tert-butoxycarbonyl, $CDCl_3$: deuterated chloroform, DMSO-$d_6$: deuterated dimethylsulfoxide M represents a unit "mol/L".

Every mixing ratio of components used for the eluent is expressed by volume.

In addition, Silica gel BW-127ZH (produced by Fuji Silysia Chemical Ltd.) was used as a support for silica gel chromatography.

Example 1

Two grams of ethyl 3-[5-(2,4-diisopropoxybenzoyl)-2-isobutoxyphenyl] propanoate was dissolve in 20 mL of methylene chloride, and after the addition of 1.42 g of aluminum chloride at room temperature, the resultant mixture was stirred for 30 minutes at room temperature. This reaction mixture was added to ice water for the separation of an organic phase therefrom. After the resultant organic phase was washed with water and a saturated sodium chloride solution successively, the washed phase was dried over anhydrous magnesium sulfate and the solvent was distilled out thereof under reduced pressure. The resultant residue was purified by silica gel column chromatography [eluent; hexane:ethyl acetate=2:1] to yield 585 mg of ethyl 3-[5-(2-hydroxy-4-isopropoxybenzoyl)-2-isobutoxyphenyl] propanoate as light yellow oil.

NMR (90 MHz, $CDCl_3$) δ value: 1.07 (6H, d, J=6.8 Hz), 1.23 (3H, t, J=7.3 Hz), 1.38 (6H, d, J=6.1 Hz), 1.92-2.40 (1H, m), 2.61-2.72 (2H, m), 2.92-3.12 (2H, m), 3.82 (2H, d, J=6.1 Hz), 4.13 (2H, q, J=7.1 Hz), 4.50-4.77 (1H, m), 6.34-6.50 (2H, m), 6.88 (1H, d, J=9.3 Hz), 7.49-7.58 (3H, m), 12.70 (1H, s)

Example 2

545 mg of ethyl 3-[5-(2-hydroxy-4-isopropoxybenzoyl)-2-isobutoxyphenyl] propanoate was dissolve in 2.5 mL of ethanol, and after the addition of 1.5 mL of 5M sodium hydroxide thereto, the resultant mixture was stirred for 2.5 hours at room temperature. Following the addition of chloroform and water to the reaction mixture, which is then adjusted to pH 2 with 6M hydrochloric acid, and the organic phase was separate therefrom. After the resultant organic phase was washed with water and a saturated sodium chloride solution successively, the washed phase was dried over anhydrous magnesium sulfate and the solvent was distilled out thereof under reduced pressure. Consequently, 444 mg of 3-[5-(2-hydroxy-4-isopropoxybenzoyl)-2-isobutoxyphenyl] propanoic acid was obtained as light yellow solid.

NMR (90 MHz, $CDCl_3$) δ value: 1.07 (6H, d, J=6.6 Hz), 1.36 (6H, d, J=6.1 Hz), 1.95-2.31 (1H, m), 2.61-3.12 (4H, m), 3.82 (2H, d, J=6.1 Hz), 4.50-4.77 (1H, m), 6.32-6.49 (2H, m), 6.89 (1H, d, J=9.3 Hz), 7.48-7.62 (3H, m), 10.00 (1H, br), 12.68 (1H, s)

Example 3

Isopropyl 3-[5-(2-hydroxy-4-isopropoxybenzoyl)-2-isopropoxyphenyl] propanoate was obtained in a similar manner as in Example 1.

NMR (90 MHz, $CDCl_3$) δ value: 1.19 (6H, d, J=6.4 Hz), 1.38 (6H, d, J=6.1 Hz), 1.39 (6H, d, J=6.1 Hz), 2.56-2.66 (2H, m), 2.88-3.06 (2H, m), 4.42-5.13 (3H, m), 6.33-6.49 (2H, m), 6.89 (1H, d, J=9.3 Hz), 7.50-7.60 (3H, m), 12.70 (1H, s)

Example 4

3-[5-(2-hydroxy-4-isopropoxybenzoyl)-2-isopropoxyphenyl] propanoic acid was obtained in a similar manner as in Example 2.

NMR (90 MHz, $CDCl_3$) δ value: 1.36 (6H, d, J=6.1 Hz), 1.39 (6H, d, J=5.9 Hz), 2.61-3.08 (4H, m), 4.49-4.74 (2H, m), 6.33-6.49 (2H, m), 6.90 (1H, d, J=9.3 Hz), 7.50-7.60 (3H, m), 11.18 (1H, br), 12.69 (1H, s)

Example 5

5.0 g of methyl 3-[5-(2,4-dihydroxybenzoyl)-2-hydroxyphenyl] propanoate, 9.6 g of potassium carbonate, and 6.4 mL of isopropyl iodide were suspended in 50 mL of N,N-dimethylformamide, and stirred for 2 hours at temperatures of 50 to 60° C. This reaction mixture was added to a mixture of ethyl acetate and water, which is then adjusted to pH 2 with 6M hydrochloric acid, and the organic phase was separated therefrom. After the resultant organic phase was washed with water and a saturated sodium chloride solution successively, the washed phase was dried over anhydrous magnesium sulfate and the solvent was distilled out thereof under reduced pressure. The resultant residue was purified by silica gel column chromatography [eluent; hexane:ethyl acetate=5:1] to yield 4.7 g of methyl 3-[5-(2-hydroxy-4-isopropoxybenzoyl)-2-isopropoxyphenyl] propanoate as yellow oil.

NMR (90 MHz, $CDCl_3$) δ value: 1.36 (6H, d, J=6.1 Hz), 1.38 (6H, d, J=6.1 Hz), 2.52-3.06 (4H, m), 3.66 (3H, s), 4.49-4.80 (2H, m), 6.30-6.48 (2H, m), 6.88 (1H, d, J=9.3 Hz), 7.49-7.58 (3H, m), 12.69 (1H, s)

Example 6

6.5 g of methyl 3-[5-(2-hydroxy-4-isopropoxybenzoyl)-2-isopropoxyphenyl] propanoate was dissolved in 65 mL of methanol, and after the addition of 6.5 mL of 5M sodium hydroxide thereto, the resultant mixture was stirred for 4 hours at the temperature of 60° C. Ethyl acetate and water were added to the reaction mixture, which is then adjusted to pH 2 with 6M hydrochloric acid, and the organic phase was separated therefrom. After the resultant organic phase was washed with water and a saturated sodium chloride solution successively, the washed phase was dried over anhydrous magnesium sulfate and the solvent was distilled out thereof under reduced pressure, followed by purification with silica gel column chromatography to yield 4.3 g of 3-[5-(2-hydroxy-4-isopropoxybenzoyl)-2-isopropoxyphenyl] propanoic acid as light yellow solid.

NMR (90 MHz, CDCl$_3$) δ value: 1.36 (6H, d, J=6.1 Hz), 1.39 (6H, d, J=5.9 Hz), 2.61-3.08 (4H, m), 4.49-4.74 (2H, m), 6.33-6.49 (2H, m), 6.90 (1H, d, J=9.3 Hz), 7.50-7.60 (3H, m), 11.18 (1H, br), 12.69 (1H, s)

Example 7

5.12 g of 4-isobutoxy-3-(3-ethoxy-3-oxopropyl)benzoic acid was dissolved in 51 mL of methylene chloride, and after the consecutive addition thereto of 1.8 mL of oxalyl chloride and 20 µL of N,N-dimethylformamide at room temperature, the resultant mixture was stirred for one hour at room temperature. Then, 4.64 g of aluminum chloride and 3.30 g of 1,3-diisopropoxybenzene were successively added to the reaction mixture at temperatures of −30 to −20° C., followed by raising the temperature to 5° C., where the mixture was stirred for one hour. This reaction mixture was added to ice water for the separation of the organic phase therefrom. After the resultant organic phase was washed with water and a saturated sodium chloride solution successively, the washed phase was dried over anhydrous magnesium sulfate and the solvent was distilled out thereof under reduced pressure. The resultant residue was purified by silica gel column chromatography [eluent; hexane:ethyl acetate=5:1] to yield 5.05 g of ethyl 3-[5-(2,4-diisopropoxybenzoyl)-2-isobutoxyphenyl] propanoate as light yellow oil.

NMR (90 MHz, CDCl$_3$) δ value: 1.06 (6H, d, J=6.6 Hz), 1.10 (6H, d, J=6.1 Hz), 1.23 (3H, t, J=7.1 Hz), 1.38 (6H, d, J=6.1 Hz), 1.91-2.38 (1H, m), 2.47-2.69 (2H, m), 2.87-3.07 (2H, m), 3.80 (2H, d, J=6.4 Hz), 4.00-4.81 (4H, m), 6.46-6.58 (2H, m), 6.79 (1H, d, J=9.3 Hz), 7.33 (1H, d, J=8.6 Hz), 7.58-7.71 (2H, m)

Example 8

Isopropyl 3-[5-(2,4-diisopropoxybenzoyl)-2-isopropoxyphenyl] propanoate was obtained in a similar manner as in Example 7.

NMR (90 MHz, CDCl$_3$) δ value: 1.10 (6H, d, J=6.1 Hz), 1.20 (6H, d, J=6.4 Hz), 1.37 (12H, d, J=6.1 Hz), 2.43-2.62 (2H, m), 2.83-3.03 (2H, m), 4.02-5.20 (4H, m), 6.46-6.58 (2H, m), 6.80 (1H, d, J=9.3 Hz), 7.33 (1H, d, J=8.1 Hz), 7.55-7.67 (2H, m)

Example 9

15.0 g of 2,4-dimethoxybenzoic acid was dissolved in 150 mL of methylene chloride, and after the consecutive addition thereto of 8.6 mL of oxalyl chloride and 20 µL of N,N-dimethylformamide at room temperature, the resultant mixture was stirred for 4 hours at room temperature. After 32.9 g of aluminum chloride was added thereto at temperatures of −45 to −40° C., 19.2 g of methyl 3-(2-methoxyphenyl) propanoate was added dropwise at temperatures of −45 to −15° C., and then the temperature was raised to an ambient temperature over 3 hours. This reaction mixture was added to ice water for the separation of the organic phase therefrom. After the resultant organic phase was washed with water and a saturated sodium chloride solution successively, the washed phase was dried over anhydrous magnesium sulfate and the solvent was distilled out thereof under reduced pressure. The resultant residue was purified by silica gel column chromatography [eluent; hexane:ethyl acetate=1:2] to yield 15.1 g of methyl 3-[5-(2,4-dimethoxybenzoyl)-2-methoxyphenyl] propanoate as yellow oil.

NMR (90 MHz, CDCl$_3$) δ value: 2.48-2.68 (2H, m), 2.89-3.03 (2H, m), 3.66 (3H, s), 3.72 (3H, s), 3.86 (3H, s), 3.88 (3H, s), 6.47-6.57 (2H, m), 6.83 (1H, d, J=9.0 Hz), 7.32 (1H, d, J=9.0 Hz), 7.64-7.72 (2H, m)

Example 10

After 0.5 mL of 2'-hydroxyacetophenone and 1.86 g of aluminum chloride were added to a solution of 500 mg of methyl 3-[5-(2,4-dimethoxybenzoyl)-2-methoxyphenyl] propanoate in 5 mL of 1,2-dichloroethane, the resultant mixture was stirred for two hours at temperatures 35 to 55° C. The reaction mixture was added to ice water for the separation of the organic phase therefrom. After the resultant organic phase was washed with water and a saturated sodium chloride solution successively, the washed phase was dried over anhydrous magnesium sulfate and the solvent was distilled out thereof under reduced pressure. The resultant residue was purified by silica gel column chromatography [eluent; hexane:ethyl acetate=1:1] to yield 316 mg of methyl 3-[5-(2,4-dihydroxybenzoyl)-2-hydroxyphenyl] propanoate as light yellow solid.

Example 11

80.0 g of 2,4-dimethoxybenzoic acid was dissolved in 1040 mL of methylene chloride, and after the consecutive addition thereto of 0.7 mL of N,N-dimethylformamide and 46 mL of oxalyl chloride at room temperature, the resultant mixture was stirred for 2 hours at room temperature. After a solution of 102.3 g of methyl 3-(2-methoxyphenyl) propanoate in 80 mL of methylene chloride was added thereto, this solution was cooled to −30° C., followed by the addition of 146.4 g of aluminum chloride, and then stirred for one hour in an ice bath. Subsequently, 129 mL of ethyl acetate was added dropwise thereto, followed by the addition of 322.0 g of aluminum chloride in small portions at temperatures of 5 to 20° C., and then this solution was stirred for four hours while heating it under reflux. The reaction mixture was poured into a mixture of ice water, 6M hydrochloric acid, and methanol, then the organic phase was separated therefrom. After the resultant organic phase was washed with 6M hydrochloric acid, water was added thereto, and this phase was adjusted to pH 10 with a 10% aqueous solution of sodium hydroxide for separation of the aqueous phase. The aqueous phase was combined with ethyl acetate and then adjusted to pH 8 with 6M hydrochloric acid for the separation of the organic phase therefrom. After the resultant organic phase was washed with a saturated sodium chloride solution, the washed phase was dried over anhydrous magnesium sulfate and the solvent was distilled out thereof under reduced pressure. The resultant residue was purified by silica gel column chromatography [eluent; hexane:ethyl acetate=4:3] to yield 74.5 g of methyl 3-[5-(2,4-dihydroxybenzoyl)-2-hydroxyphenyl] propanoate as light yellow solid.

NMR (400 MHz, CDCl$_3$) δ value: 2.77 (2H, t, J=6.8 Hz), 2.96 (2H, t, J=6.8 Hz), 3.73 (3H, s), 5.78 (1H, s), 6.36 (1H, dd, J=8.8, 2.4 Hz), 6.46 (1H, d, J=2.4 Hz), 6.96 (1H, d, J=8.0 Hz), 7.45-7.49 (2H, m), 7.54 (1H, d, J=8.8 Hz), 7.90 (1H, s), 12.59 (1H, s)

Example 12

Compounds listed in Table 14 were obtained in a similar manner as in Example 11.

TABLE 14

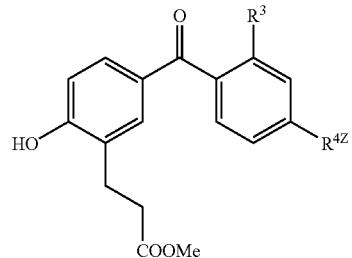

| Example Number | R³ | R⁴ᶻ |
|---|---|---|
| 12(1) | OH | issopropyl |
| 12(2) | OH | (1-methylcyclopentyl)methyl |
| 12(3) | OH | cyclopentyl |
| 12(4) | Me | OH |
| 12(5) | OH | cyclopenthylmethyl |
| 12(6) | OH | Br |

12(1)
NMR (400 MHz, CDCl₃) δ value: 1.27 (6H, d, J=6.8 Hz), 2.76-2.79 (2H, m), 2.89-2.98 (3H, m), 3.73 (3H, s), 6.75 (1H, dd, J=8.2, 2.0 Hz), 6.92 (1H, d, J=1.6 Hz), 6.97 (1H, d, J=9.2 Hz), 7.51-7.55 (3H, m), 7.92 (1H, s), 12.07 (1H, s)

12(2)
NMR (400 MHz, CDCl₃) δ value: 0.93 (3H, s), 1.31-1.38 (2H, m), 1.52-1.57 (2H, m), 1.66-1.70 (4H, m), 2.61 (2H, s), 2.77-2.80 (2H, m), 2.95-2.98 (2H, m), 3.73 (3H, s), 6.68 (1H, dd, J=8.0, 1.2 Hz), 6.86 (1H, d, J=1.2 Hz), 6.97 (1H, d, J=8.4 Hz), 7.50-7.53 (3H, m), 7.93 (1H, s), 12.07 (1H, s)

12(3)
NMR (400 MHz, CDCl₃) δ value: 1.57-1.75 (4H, m), 1.78-1.84 (2H, m), 2.07-2.11 (2H, m), 2.76-2.79 (2H, m), 2.95-3.03 (3H, m), 3.73 (3H, s), 6.76 (1H, dd, J=8.4, 1.6 Hz), 6.93-6.98 (2H, m), 7.50-7.54 (3H, m), 7.90 (1H, s), 12.06 (1H, s)

12(4)
NMR (400 MHz, DMSO-d₆) δ value: 2.16 (3H, s), 2.58 (2H, t, J=7.6 Hz), 2.81 (2H, t, J=7.6 Hz), 3.57 (3H, s), 6.65 (1H, dd, J=8.4, 2.4 Hz), 6.71 (1H, d, J=2.0 Hz), 6.88 (1H, d, J=8.4 Hz), 7.12 (1H, d, J=8.0 Hz), 7.42 (1H, dd, J=8.0, 2.4 Hz), 7.46 (1H, d, J=2.0 Hz), 9.87 (1H, brs), 10.44 (1H, brs)

12(5)
NMR (400 MHz, CDCl₃) δ value: 1.18-1.23 (2H, m), 1.52-1.75 (6H, m), 2.08-2.16 (1H, m), 2.62 (2H, d, J=7.6 Hz), 2.76-2.79 (2H, m), 2.95-2.98 (2H, m), 3.73 (3H, s), 6.69 (1H, dd, J=8.2, 1.6 Hz), 6.87 (1H, d, J=1.6 Hz), 6.97 (1H, d, J=8.8 Hz), 7.51-7.53 (3H, m), 7.91 (1H, s), 12.08 (1H, s)

12(6)
NMR (400 MHz, CDCl₃) δ value: 2.78 (2H, t, J=6.0 Hz), 2.96 (2H, t, J=6.0 Hz), 3.73 (3H, s), 6.98 (1H, d, J=8.4 Hz), 7.03 (1H, dd, J=8.4, 2.0 Hz), 7.47-7.52 (4H, m), 8.02 (1H, brs), 12.06 (1H, s)

Example 13

5.00 g of 2-fluoro-4-methoxybenzoic acid was dissolved in 50 mL of methylene chloride, and after the consecutive addition thereto of 20 μL of N,N-dimethylformamide and 3.9 mL of oxalyl chloride at room temperature, the resultant mixture was stirred for 2.5 hours at room temperature. After 8.23 g of aluminum chloride and 6.28 g of methyl 3-(2-methoxyphenyl) propanoate were successively added thereto in an ice bath, this solution was stirred for two hours in an ice bath. Further, 19.64 g of aluminum chloride was added thereto, and then this solution was stirred for two hours while heating it under reflux. After ethyl acetate was added to the reaction mixture, this mixture was poured into the icecooled 6M hydrochloric acid for the separation of the organic phase therefrom. After the resultant organic phase was washed with 6M hydrochloric acid, water, and a saturated sodium chloride solution successively, the washed phase was dried over anhydrous magnesium sulfate and the solvent was distilled out thereof under reduced pressure. The resultant residue was purified by silica gel column chromatography [eluent; hexane:ethyl acetate=1:2] to yield 2.52 g of 6-(2-fluoro-4-hydroxybenzoyl)-2-chromanone as yellow oil.

NMR (400 MHz, CDCl₃) δ value: 2.85 (2H, dd, J=8.2, 7.6 Hz), 3.08 (2H, t, J=7.6 Hz), 6.55 (1H, brs), 6.66 (1H, dd, J=11.4, 2.0 Hz), 6.75 (1H, dd, J=8.6, 2.4 Hz), 7.12 (1H, d, J=8.4 Hz), 7.52 (1H, t, J=8.4 Hz), 7.68-7.73 (2H, m)

Example 14

3.50 g of 4-isopropoxy-3-(3-isopropoxy-3-oxopropyl) benzoic acid was dissolved in 35 mL of methylene chloride, and after the consecutive addition thereto of 20 μL of N,N-dimethylformamide and 1.6 mL of oxalyl chloride at room temperature, the resultant mixture was stirred for 30 minutes at room temperature. The reaction mixture was cooled to −50° C., and 3.17 g of aluminum chloride and 2.91 g of 1,3-diisobutoxybenzene were successively added thereto, followed by raising its temperature to an ambient temperature over 30 minutes. Then this mixture was stirred for one hour while heating it under reflux. Further, 0.790 g of aluminum chloride was added thereto, and then this mixture was stirred for one hour while heating it under reflux. The reaction mixture was poured into a mixture of ice water and methanol for the separation of the organic phase therefrom. After the resultant organic phase was washed with 6M hydrochloric acid and a saturated sodium chloride solution successively, the washed phase was dried over anhydrous magnesium sulfate and the solvent was distilled out thereof under reduced pressure. The resultant residue was purified by silica gel column chromatography [eluent; hexane:ethyl acetate=3:1] to yield 4.01 g of isopropyl 3-[2-hydroxy-5-(2-hydroxy-4-isobutoxybenzoyl)phenyl] propanoate as yellow oil.

NMR (90 MHz, CDCl₃) δ value: 1.03 (6H, d, J=6.6 Hz), 1.23 (6H, d, J=6.1 Hz), 1.97-2.26 (1H, m), 2.71-2.92 (4H, m), 3.78 (2H, d, J=6.7 Hz), 4.91-5.18 (1H, m), 6.38-6.48 (2H, m), 6.95 (1H, d, J=9.0 Hz), 7.40-7.59 (3H, m), 8.18 (1H, brs), 12.65 (1H, s)

Example 15

The following compounds were obtained in a similar manner as in Example 14.
(1) isobutyl 3-[5-(2,4-dihydroxybenzoyl)-2-isobutoxyphenyl] propanoate
NMR (90 MHz, CDCl₃) δ value: 0.89 (6H, d, J=6.6 Hz), 1.07 (6H, d, J=6.8 Hz), 1.6-2.4 (2H, m), 2.6-3.2 (4H, m), 3.82

(2H, d, J=6.1 Hz), 3.87 (2H, d, J=6.6 Hz), 6.3-6.5 (2H, m), 6.88 (1H, d, J=9.3 Hz), 7.0-7.6 (4H, m), 12.63 (1H, s)

(2) isopropyl 3-[2-hydroxy-5-(4-isobutoxybenzoyl)phenyl]propanoate

NMR (90 MHz, CDCl$_3$) δ value: 1.05 (6H, d, J=6.6 Hz), 1.22 (6H, d, J=6.4 Hz), 1.90-2.35 (1H, m), 2.62-3.05 (4H, m), 3.80 (2H, d, J=6.4 Hz), 4.90-5.18 (1H, m), 6.89-7.00 (3H, m), 7.51-7.85 (4H, m), 8.34 (1H, brs)

Example 16

6.00 g of 4-isobutoxy-3-(3-methoxy-3-oxopropyl)benzoic acid was dissolved in 60 mL of methylene chloride, and after the consecutive addition thereto of 20 μL of N,N-dimethylformamide and 2.8 mL of oxalyl chloride at room temperature, the resultant mixture was stirred for 3 hours at room temperature. After the reaction mixture was cooled to −30° C., followed by the consecutive addition thereto of 5.17 g of aluminum chloride and 3.68 g of 1-fluoro-3,5-dimethoxybenzene, this mixture was stirred for 30 minutes in an ice bath. The reaction mixture was poured into an iced 6M hydrochloric acid for the separation of the organic phase therefrom. After the resultant organic phase was washed with 6M hydrochloric acid, water, and a saturated sodium chloride solution successively, the washed phase was dried over anhydrous magnesium sulfate and the solvent was distilled out thereof under reduced pressure. The resultant residue was purified by silica gel column chromatography [eluent; hexane:ethyl acetate=3:1] to yield 5.40 g of methyl 3-[5-(2-fluoro-4,6-dimethoxybenzoyl)-2-isobutoxyphenyl]propanoate as colorless oil.

NMR (400 MHz, CDCl$_3$) δ value: 1.05 (6H, d, J=6.8 Hz), 2.10-2.17 (1H, m), 2.61 (2H, t, J=7.8 Hz), 2.96 (2H, t, J=7.8 Hz), 3.66 (3H, s), 3.72 (3H, s), 3.80 (2H, d, J=6.4 Hz), 3.85 (3H, s), 6.28-6.32 (2H, m), 6.82 (1H, d, J=8.4 Hz), 7.69-7.73 (2H, m)

Example 17

5.00 g of methyl 3-[5-(2-fluoro-4,6-dimethoxybenzoyl)-2-isobutoxyphenyl] propanoate was dissolved in a mixed solvent of 50 mL of methylene chloride and 3.5 mL of ethyl acetate, and after the addition thereto of 12.7 g of aluminum chloride, the resultant mixture was stirred for 5 hours while heating it under reflux. The reaction mixture was poured into an iced 6M hydrochloric acid for the separation of the organic phase therefrom. After the resultant organic phase was washed with 6M hydrochloric acid, water, and a saturated sodium chloride solution successively, the washed phase was dried over anhydrous magnesium sulfate and the solvent was distilled out thereof under reduced pressure. The resultant residue was purified by silica gel column chromatography [eluent; hexane:ethyl acetate=2:1] to yield 2.82 g of methyl 3-[5-(2-fluoro-4,6-dihydroxybenzoyl)-2-hydroxyphenyl]propanoate as yellowish foam.

NMR (400 MHz, CDCl$_3$) δ value: 2.75 (2H, t, J=6.0 Hz), 2.95 (2H, t, J=6.8 Hz), 3.72 (3H, s), 6.13 (1H, dd, J=12.0, 2.4 Hz), 6.29-6.30 (1H, m), 6.89 (1H, d, J=8.4 Hz), 7.26 (1H, brs), 7.46-7.49 (2H, m), 7.95 (1H, brs), 11.82 (1H, s)

Example 18

74.2 g of methyl 3-[5-(2,4-dihydroxybenzoyl)-2-hydroxyphenyl] propanoate was suspended in 742 mL of toluene, and then 2.23 g of p-toluenesulfonic acid monohydrate was added thereto. This suspension was stirred for four hours while heating it under reflux. This reaction mixture was cooled to room temperature, followed by the consecutive addition thereto of ethyl acetate and a saturated aqueous solution of sodium hydrogen carbonate, and the organic phase was separated therefrom. After the resultant organic phase was washed with water and a saturated sodium chloride solution successively, the washed phase was dried over anhydrous magnesium sulfate and the solvent was distilled out thereof under reduced pressure. The resultant residue was solidified with diisopropyl ether and washed with ethanol to yield 56.3 g of 6-(2,4-dihydroxybenzoyl)-2-chromanone as light yellow solid.

NMR (400 MHz, DMSO-d$_6$) δ value: 2.85 (2H, t, J=6.8 Hz), 3.08 (2H, t, J=6.8 Hz), 6.37 (1H, d, J=2.2 Hz), 6.40 (1H, dd, J=8.6, 2.2 Hz), 7.20 (1H, d, J=8.3 Hz), 7.41 (1H, d, J=8.6 Hz), 7.56 (1H, dd, J=8.4, 2.2 Hz), 7.62 (1H, d, J=2.0 Hz), 10.70 (1H, s), 12.06 (1H, s)

Example 19

The following compounds were obtained in a similar manner as in Example 18.

(1) 6-(4-hydroxy-2-methylbenzoyl)-2-chromanone

NMR (400 MHz, CDCl$_3$) δ value: 2.36 (3H, s), 2.84 (2H, t, J=7.4 Hz), 3.07 (2H, t, J=7.4 Hz), 6.71 (1H, dd, J=8.4, 2.4 Hz), 6.78 (1H, d, J=2.4 Hz), 6.88 (1H, brs), 7.09 (1H, d, J=8.0 Hz), 7.25 (1H, d, J=8.4 Hz), 7.66 (1H, dd, J=8.0, 2.0 Hz), 7.67 (1H, s)

(2) 6-(2-fluoro-4,6-dihydroxybenzoyl)-2-chromanone

NMR (400 MHz, CDCl$_3$) δ value: 2.83-2.87 (2H, m), 3.08 (2H, t, J=8.0 Hz), 5.98 (1H, brs), 6.15 (1H, dd, J=12.2, 2.4 Hz), 6.30-6.31 (1H, m), 7.11 (1H, d, J=8.4 Hz), 7.54-7.57 (2H, m), 11.89 (1H, s)

Example 20

50.0 g of 6-(2,4-dihydroxybenzoyl)-2-chromanone, 17.6 mL of cyclopentanol, and 55.4 g of triphenylphosphine were dissolved in 500 mL of tetrahydrofuran, to which 41.6 mL of diisopropyl azodicarboxylate was added dropwise at temperatures of 15 to 32° C., and this solution was stirred for 30 minutes at room temperature. The reaction mixture was poured into a mixture of ethyl acetate and water for the separation of the organic phase therefrom. After the resultant organic phase was washed with water and a saturated sodium chloride solution successively, the washed phase was dried over anhydrous magnesium sulfate and the solvent was distilled out thereof under reduced pressure. The resultant residue was purified by silica gel column chromatography [eluent; hexane:ethyl acetate=3:1] to yield 54.7 g of 6-[4-(cyclopentyloxy)-2-hydroxybenzoyl]-2-chromanone as light yellow solid.

NMR (90 MHz, CDCl$_3$) δ value: 1.42-2.20 (8H, m), 2.74-3.10 (4H, m), 4.60-5.03 (1H, m), 6.31-6.48 (2H, m), 7.12 (1H, d, J=9.0 Hz), 7.30-7.58 (3H, m), 12.55 (1H, s)

Example 21

Compounds listed in Table 15 were obtained in a similar manner as in Example 20.

TABLE 15

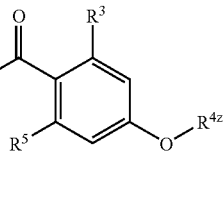

| Example Number | R4z | R3 | R5 |
|---|---|---|---|
| 21(1) | cyclopentyl | F | H |
| 21(2) | isopentyl | OH | H |
| 21(3) | neopentyl | OH | H |
| 21(4) | cyclohexyl | OH | H |
| 21(5) | cyclopentyl | OH | F |
| 21(6) | cyclopentyl | Me | H |
| 21(7) | CH(CH$_2$CH$_3$)$_2$ | OH | H |
| 21(8) | cyclohexylmeethyl | OH | H |
| 21(9) | cyclopropylmethyl | OH | H |
| 21(10) | cycloheptyl | OH | H |
| 21(11) | cyclopentylmethyl | OH | H |
| 21(12) | 3-pyridylmethyl | OH | H |
| 21(13) | cyclobutyl | OH | H |
| 21(14) | benzyl | OH | H |

21(1)

NMR (400 MHz, CDCl$_3$) δ value: 1.64-1.71 (2H, m), 1.78-1.99 (6H, m), 2.82-2.86 (2H, m), 3.06-3.09 (2H, m), 4.79-4.82 (1H, m), 6.62 (1H, dd, J=12.2, 2.0 Hz), 6.76 (1H, dd, J=8.6, 2.4 Hz), 7.11 (1H, d, J=8.4 Hz), 7.55 (1H, t, J=8.8 Hz), 7.68-7.72 (2H, m)

21(2)

NMR (400 MHz, CDCl$_3$) 5 value: 0.95 (6H, d, J=6.4 Hz), 1.68 (2H, q, J=6.8 Hz), 1.78-1.84 (1H, m), 2.82-2.85 (2H, m), 3.07 (2H, t, J=7.6 Hz), 4.04 (2H, t, J=6.8 Hz), 6.40 (1H, dd, J=9.2, 2.4 Hz), 6.49 (1H, d, J=2.0 Hz), 7.13 (1H, d, J=8.8 Hz), 7.45 (1H, d, J=8.8 Hz), 7.53-7.55 (2H, m), 12.53 (1H, s)

21(3)

NMR (400 MHz, CDCl$_3$) δ value: 1.05 (9H, s), 2.84-2.88 (2H, m), 3.08-3.11 (2H, m), 3.66 (2H, s), 6.44 (1H, dd, J=8.8, 3.6 Hz), 6.51 (1H, d, J=2.4 Hz), 7.16 (1H, d, J=8.8 Hz), 7.45-7.57 (3H, m), 12.54 (1H, s)

21(4)

NMR (90 MHz, CDCl$_3$) δ value: 1.1-2.2 (10H, m), 2.7-3.2 (4H, m), 4.1-4.5 (1H, m), 6.3-6.5 (2H, m), 7.14 (1H, d, J=8.8 Hz), 7.4-7.6 (3H, m), 12.54 (1H, s)

21(5)

NMR (400 MHz, CDCl$_3$) δ value: 1.59-1.71 (2H, m), 1.75-1.98 (6H, m), 2.82-2.86 (2H, m), 3.06-3.09 (2H, m), 4.79-4.81 (1H, m), 6.13 (1H, dd, J=13.2, 2.4 Hz), 6.32 (1H, t, J=1.2 Hz), 7.11 (1H, d, J=8.0 Hz), 7.53-7.57 (2H, m), 12.03 (1H, s)

21(6)

NMR (400 MHz, CDCl$_3$) δ value: 1.6-1.7 (2H, m), 1.7-2.0 (6H, m), 2.39 (3H, s), 2.83 (2H, t, J=7.4 Hz), 3.06 (2H, t, J=7.4 Hz), 4.80-4.85 (1H, m), 6.71 (1H, dd, J=8.8, 2.4 Hz), 6.79 (1H, d, J=2.4 Hz), 7.09 (1H, d, J=8.8 Hz), 7.29 (1H, d, J=8.4 Hz), 7.66 (1H, dd, J=8.4, 2.0 Hz), 7.70 (1H, d, J=2.0 Hz)

21(7)

NMR (90 MHz, CDCl$_3$) δ value: 0.96 (6H, t, J=7.2 Hz), 1.5-1.9 (4H, m), 2.7-3.2 (4H, m), 4.0-4.4 (1H, m), 6.4-6.5 (2H, m), 7.15 (1H, d, J=9.0 Hz), 7.4-7.6 (3H, m), 12.55 (1H, s)

21(8)

NMR (90 MHz, CDCl$_3$) δ value: 0.8-2.0 (11H, m), 2.7-3.2 (4H, m), 3.82 (2H, d, J=5.9 Hz), 6.3-6.5 (2H, m), 7.14 (1H, d, J=8.8 Hz), 7.4-7.6 (3H, m), 12.54 (1H, s)

21(9)

NMR (90 MHz, CDCl$_3$) δ value: 0.3-0.8 (4H, m), 1.1-1.4 (1H, m), 2.7-3.2 (4H, m), 3.87 (2H, d, J=6.8 Hz), 6.4-6.5 (2H, m), 7.13 (1H, d, J=9.0 Hz), 7.4-7.6 (3H, m), 12.53 (1H, s)

21(10)

NMR (90 MHz, CDCl$_3$) δ value: 1.2-2.2 (12H, m), 2.7-3.2 (4H, m), 4.4-4.7 (1H, m), 6.3-6.5 (2H, m), 7.14 (1H, d, J=9.0 Hz), 7.4-7.7 (3H, m), 12.55 (1H, s)

21(11)

NMR (400 MHz, CDCl$_3$) δ value: 1.33-1.41 (2H, m), 1.57-1.68 (4H, m), 1.81-1.89 (2H, m), 2.35-2.42 (1H, m), 2.84-2.87 (2H, m), 3.09 (2H, t, J=7.6 Hz), 3.90 (2H, d, J=6.8 Hz), 6.42 (1H, dd, J=9.2, 2.4 Hz), 6.51 (1H, d, J=2.4 Hz), 7.16 (1H, d, J=8.8 Hz), 7.47 (1H, d, J=9.2 Hz), 7.55-7.57 (2H, m), 12.55 (1H, s)

21(12)

NMR (90 MHz, CDCl$_3$) δ value: 2.70-3.20 (4H, m), 5.15 (2H, s), 6.40-6.60 (2H, m), 7.10-7.90 (6H, m), 8.60-8.70 (2H, m), 12.51 (1H, s)

21(13)

NMR (400 MHz, CDCl$_3$) δ value: 1.69-1.77 (1H, m), 1.87-1.94 (1H, m), 2.18-2.23 (2H, m), 2.48-2.51 (2H, m), 2.83-2.87 (2H, m), 3.09 (2H, t, J=6.8 Hz), 4.69-4.73 (1H, m), 6.36 (1H, dd, J=9.0, 2.4 Hz), 6.40 (1H, d, J=2.4 Hz), 7.15 (1H, d, J=8.5 Hz), 7.47 (1H, d, J=9.0 Hz), 7.54-7.57 (2H, m), 12.54 (1H, s)

21(14)

NMR (400 MHz, CDCl$_3$) δ value: 2.83-2.87 (2H, m), 3.10 (2H, t, J=8.0 Hz), 5.13 (2H, s), 6.51 (1H, dd, J=9.2, 2.4 Hz), 6.61 (1H, d, J=2.4 Hz), 7.16 (1H, d, J=8.4 Hz), 7.34-7.57 (8H, m), 12.53 (1H, s)

Example 22

54.7 g of 6-[4-(cyclopentyloxy)-2-hydroxybenzoyl]-2-chromanone was suspended in 274 mL of methanol, to which 71.9 g of a 28% solution of sodium methoxide in methanol was added dropwise at temperatures of 0 to 4° C., and this suspension was stirred for one hour at temperatures of 2 to 4° C. The reaction mixture was poured into a mixture of ethyl acetate and 6M hydrochloric acid, to which water was added, for the separation of the organic phase therefrom. After the resultant organic phase was washed with water and a saturated sodium chloride solution successively, the washed phase was dried over anhydrous magnesium sulfate and the solvent was distilled out thereof under reduced pressure. The resultant residue was solidified with a mixed solvent of diisopropylether and hexane (1:1) to yield 45.3 g of methyl 3-{5-(4-(cyclopentyloxy)-2-hydroxybenzoyl]-2-hydroxyphenyl} propanoate as white solid.

NMR (90 MHz, CDCl$_3$) δ value: 1.43-2.12 (8H, m), 2.73-2.96 (4H, m), 3.70 (3H, s), 4.68-4.92 (1H, m), 6.31-6.46 (2H, m), 6.89 (1H, d, J=8.1 Hz), 7.24-7.58 (3H, m), 9.90 (2H, brs)

Example 23

Compounds listed in Table 16 were obtained in a similar manner as in Example 22.

TABLE 16

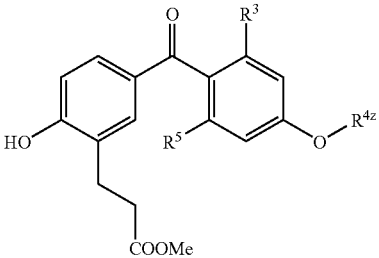

| 実施例番号 | R³ | R⁴ᶻ | R⁵ |
|---|---|---|---|
| 23(1) | F | cyclopentyl | H |
| 23(2) | OH | isopentyl | H |
| 23(3) | OH | neopentyl | H |
| 23(4) | OH | cyclohexyl | H |
| 23(5) | OH | cyclopentyl | F |
| 23(6) | Me | cyclopentyl | H |
| 23(7) | OH | CH(CH₂CH₃)₂ | H |
| 23(8) | OH | cyclohexylmethyl | H |
| 23(9) | OH | cyclopropylmethyl | H |
| 23(10) | OH | cycloheeptyl | H |
| 23(11) | OH | isobutyl | H |
| 23(12) | OH | cyclopenthylmethyl | H |
| 23(13) | OH | 3-pyridylmethyl | H |
| 23(14) | OH | cyclobutyl | H |
| 23(15) | OH | benzyl | H |

23(1)
NMR (400 MHz, CDCl₃) δ value: 1.63-1.69 (2H, m), 1.78-1.98 (6H, m), 2.74-2.77 (2H, m), 2.92-2.95 (2H, m), 3.72 (3H, s), 4.78-4.82 (1H, m), 6.61 (1H, dd, J=12.2, 2.4 Hz), 6.73 (1H, dd, J=8.8, 2.4 Hz), 6.91 (1H, d, J=8.4 Hz), 7.48 (1H, t, J=8.4 Hz), 7.58-7.61 (1H, m), 7.67 (1H, d, J=1.2 Hz), 7.98 (1H, s)

23(2)
NMR (400 MHz, CDCl₃) δ value: 0.95 (6H, d, J=6.6 Hz), 1.68 (2H, q, J=6.6 Hz), 1.76-1.86 (1H, m), 2.73-2.76 (2H, m), 2.92-2.95 (2H, m), 3.70 (3H, s), 4.03 (2H, t, J=6.6 Hz), 6.38 (1H, dd, J=6.3, 2.4 Hz), 6.47 (1H, d, J=1.7 Hz), 6.94 (1H, d, J=8.1 Hz), 7.32-7.52 (3H, m), 7.82 (1H, s), 12.64 (1H, s)

23(3)
NMR (400 MHz, CDCl₃) δ value: 1.04 (9H, s), 2.76-2.79 (2H, m), 2.90-2.97 (2H, m), 3.67 (2H, s), 3.70 (3H, s), 6.43 (1H, dd, J=9.0, 2.8 Hz), 6.50 (1H, d, J=2.4 Hz), 6.96 (1H, d, J=8.4 Hz), 7.46-7.49 (2H, m), 7.53 (1H, d, J=9.2 Hz), 7.87 (1H, s), 12.64 (1H, s)

23(4)
NMR (90 MHz, CDCl₃) δ value: 1.1-2.2 (10H, m), 2.6-3.1 (4H, m), 3.70 (3H, s), 4.1-4.5 (1H, m), 6.3-6.5 (2H, m), 6.90 (1H, d, J=8.5 Hz), 7.3-7.6 (3H, m), 8.12 (1H, s), 12.69 (1H, s)

23(5)
NMR (400 MHz, CDCl₃) δ value: 1.61-1.68 (2H, m), 1.78-1.95 (6H, m), 2.76 (2H, t, J=5.6 Hz), 2.93 (2H, t, J=6.4 Hz), 3.72 (3H, s), 4.77-4.80 (1H, m), 6.13 (1H, dd, J=13.2, 2.4 Hz), 6.31 (1H, t, J=1.2 Hz), 6.92 (1H, d, J=8.8 Hz), 7.48-7.52 (2H, m), 7.90 (1H, s), 11.90 (1H, s)

23(6)
NMR (400 MHz, CDCl₃) δ value: 1.6-2.0 (8H, m), 2.34 (3H, s), 2.73 (2H, t, J=6.4 Hz), 2.93 (2H, t, J=6.4 Hz), 3.68 (3H, s), 4.79-4.83 (1H, m), 6.70 (1H, dd, J=8.4, 2.4 Hz), 6.77 (1H, d, J=2.4 Hz), 6.89 (1H, d, J=8.8 Hz), 7.26 (1H, d, J=8.4 Hz), 7.53 (1H, dd, J=8.4, 2.0 Hz), 7.64 (1H, d, J=2.4 Hz), 8.13 (1H, s)

23(7)
NMR (90 MHz, CDCl₃) δ value: 0.96 (6H, t, J=7.2 Hz), 1.5-1.9 (4H, m), 2.7-3.1 (4H, m), 3.72 (3H, s), 4.1-4.4 (1H, m), 6.3-6.5 (2H, m), 6.95 (1H, d, J=9.0 Hz), 7.4-7.6 (3H, m), 7.86 (1H, s), 12.67 (1H, s)

23(8)
NMR (90 MHz, CDCl₃) δ value: 0.7-2.1 (11H, m), 2.6-3.1 (4H, m), 3.72 (3H, s), 3.82 (2H, d, J=5.9 Hz), 6.3-6.5 (2H, m), 6.93 (1H, d, J=9.0 Hz), 7.4-7.6 (3H, m), 7.96 (1H, brs), 12.67 (1H, s)

23(9)
NMR (90 MHz, CDCl₃) δ value: 0.2-1.6 (5H, m), 2.6-3.2 (4H, m), 3.71 (3H, s), 3.86 (2H, d, J=6.8 Hz), 6.3-6.5 (2H, m), 6.92 (1H, d, J=9.0 Hz), 7.2-7.7 (4H, m), 8.8-10.6 (1H, br)

23(10)
NMR (90 MHz, CDCl₃) δ value: 1.2-2.2 (12H, m), 2.6-3.1 (4H, m), 3.72 (3H, s), 4.3-4.7 (1H, m), 6.3-6.4 (2H, m), 6.94 (1H, d, J=9.0 Hz), 7.4-7.6 (3H, m), 7.89 (1H, s), 12.67 (1H, s)

23(11)
light yellow solid
NMR (90 MHz, CDCl₃) δ value: 1.03 (6H, d, J=6.6 Hz), 1.8-2.3 (1H, m), 2.6-3.7 (4H, m), 3.72 (3H, s), 3.78 (2H, d, J=6.6 Hz), 6.35-6.51 (2H, m), 6.92 (1H, d, J=9.0 Hz), 7.40-7.59 (3H, m), 7.8-8.2 (1H, br), 12.66 (1H, s)

23(12)
NMR (400 MHz, CDCl₃) δ value: 1.33-1.38 (2H, m), 1.57-1.68 (4H, m), 1.81-1.88 (2H, m), 2.34-2.41 (1H, m), 2.76-2.79 (2H, m), 2.95 (2H, t, J=6.6 Hz), 3.72 (3H, s), 3.89 (2H, d, J=6.9 Hz), 6.41 (1H, dd, J=8.8, 2.4 Hz), 6.49 (1H, d, J=2.4 Hz), 6.96 (1H, d, J=8.3 Hz), 7.45-7.54 (3H, m), 7.85 (1H, s), 12.64 (1H, s)

23(13)
NMR (90 MHz, CDCl₃) δ value: 2.60-3.10 (4H, m), 3.70 (3H, s), 5.15 (2H, s), 6.40-6.60 (2H, m), 6.93 (1H, d, J=8.3 Hz), 7.20-7.90 (6H, m), 8.60-8.70 (2H, m), 12.65 (1H, s)

23(14)
NMR (400 MHz, CDCl₃) δ value: 1.66-1.78 (1H, m), 1.86-1.94 (1H, m), 2.17-2.22 (2H, m), 2.45-2.52 (2H, m), 2.77 (2H, t, J=6.8 Hz), 2.96 (2H, t, J=6.8 Hz), 3.73 (3H, s), 4.68-4.72 (1H, m), 6.35 (1H, dd, J=8.8, 2.4 Hz), 6.38 (1H, d, J=2.4 Hz), 6.96 (1H, d, J=8.4 Hz), 7.45-7.48 (2H, m), 7.53 (1H, d, J=8.8 Hz), 7.85 (1H, s), 12.65 (1H, s)

23(15)
NMR (400 MHz, CDCl₃) δ value: 2.76-2.79 (2H, m), 2.96 (2H, t, J=6.4 Hz), 3.73 (3H, s), 5.12 (2H, s), 6.49 (1H, dd, J=9.0, 2.8 Hz), 6.59 (1H, d, J=2.8 Hz), 6.96 (1H, d, J=8.0 Hz), 7.33-7.49 (7H, m), 7.56 (1H, d, J=8.8 Hz), 7.86 (1H, s), 12.64 (1H, s)

Example 24

2.00 g of 6-(2,4-dihydroxybenzoyl)-2-chromanone was dissolved in 20 mL of tetrahydrofuran, to which 0.65 mL of 2-propanol and 2.21 g of triphenylphosphine were added and to which a solution of 1.7 mL of diisopropyl azodicarboxylate in 2 mL of tetrahydrofuran were added dropwise at 18-37° C., and the this mixture was stirred for one hour at room temperature. The reaction mixture was poured into a mixture of ethyl acetate and water, for the separation of the organic phase therefrom. After the resultant organic phase was washed with water and a saturated sodium chloride solution successively, the washed phase was dried over anhydrous magnesium sulfate and the solvent was distilled out thereof under reduced pressure. The resultant residue was dissolved in 20 mL of methanol, to which 3.39 g of a 28% solution of sodium methoxide in methanol was added dropwise in an ice bath, and then this mixture was stirred for one hour at temperatures of 5 to 10° C. The reaction mixture was poured into a mixture of chloroform and aqueous diluted hydrochloric acid. After the resultant organic phase was washed with water and a saturated sodium chloride solution successively, the washed phase was dried over anhydrous magnesium sulfate and the solvent was distilled out thereof under reduced pressure. The resultant residue was purified by silica gel column chromatography [eluent; toluene:ethyl acetate=4:1] and solidified with hexane to yield 2.36 g of methyl 3-[2-hydroxy-5-(2-hydroxy-4-isopropoxybenzoyl)phenyl] propanoate as light yellow solid.

NMR (400 MHz, DMSO-$d_6$) δ value: 1.36 (6H, d, J=6.0 Hz), 2.61 (2H, t, J=7.6 Hz), 2.84 (2H, t, J=7.6 Hz), 3.59 (3H, s), 4.70-4.76 (1H, m), 6.48 (1H, dd, J=8.8, 2.0 Hz), 6.52 (1H, d, J=2.4 Hz), 6.93 (1H, d, J=8.4 Hz), 7.43-7.48 (3H, m), 10.42 (1H, brs), 12.08 (1H, brs)

Example 25

10.0 g of 6-(2,4-dihydroxybenzoyl)-2-chromanone was suspended in 100 mL of methylene chloride, to which 3.53 mL of 3,4-dihydro-2H-pyran and 0.884 g of pyridinium p-toluenesulfonate were added, and this mixture was stirred for 18 hours at room temperature. The reaction mixture was poured into a saturated aqueous solution of sodium hydrogen carbonate, and the organic phase was separated therefrom. After the resultant organic phase was washed with water and a saturated sodium chloride solution successively, the washed phase was dried over anhydrous magnesium sulfate and the solvent was distilled out thereof under reduced pressure. The resultant residue was purified by silica gel column chromatography [eluent; hexane:ethyl acetate=3:1] to yield 6.99 g of 6-[2-hydroxy-4-(tetrahydro-2H-pyran-2-yloxy)benzoyl]-2-chromanon as light yellow solid.

NMR (400 MHz, CDCl$_3$) δ value: 1.5-2.1 (6H, m), 2.86 (2H, t, J=7.6 Hz), 3.10 (2H, t, J=7.6 Hz), 3.6-3.7 (1H, m), 3.8-3.9 (1H, m), 5.52 (1H, t, J=3.2 Hz), 6.55 (1H, dd, J=9.2, 2.4 Hz), 6.72 (1H, d, J=2.4 Hz), 7.14 (1H, d, J=8.4 Hz), 7.4-7.6 (3H, m), 12.39 (1H, s)

Example 26

3.20 g of 6-[2-hydroxy-4-(tetrahydro-2H-pyran-2-yloxy)benzoyl]-2-chromanone was suspended in 18.6 mL of methanol and was cooled to 0° C., to which 4.02 g of a 28% solution of sodium methoxide in methanol was added dropwise, and then this mixture was stirred for one hour at temperatures of −5 to 0° C. The reaction mixture was poured into a mixture of ethyl acetate and 6M hydrochloric acid, to which water was added, and the organic phase was separated therefrom. After the resultant organic phase was washed with water, a saturated aqueous solution of sodium hydrogen carbonate, and a saturated sodium chloride solution successively, the washed phase was dried over anhydrous magnesium sulfate and the solvent was distilled out thereof under reduced pressure. The resultant residue was purified by silica gel column chromatography [eluent; hexane:ethyl acetate=3:1] to yield 3.29 g of methyl 3-{2-hydroxy-5-[2-hydroxy-4-(tetrahydro-2H-pyran-2-yloxy)benzoyl]phenyl} propanoate as light yellow oil.

NMR (400 MHz, CDCl$_3$) δ value: 1.5-2.1 (6H, m), 2.77 (2H, t, J=6.0 Hz), 2.96 (2H, t, J=6.2 Hz), 3.6-3.7 (1H, m), 3.73 (3H, s), 3.8-3.9 (1H, m), 5.51 (1H, t, J=3.2 Hz), 6.54 (1H, dd, J=8.8, 2.4 Hz), 6.71 (1H, d, J=2.4 Hz), 6.96 (1H, d, J=8.8 Hz), 7.4-7.6 (3H, m), 7.87 (1H, s), 12.50 (1H, s)

Example 27

3.20 g of methyl 3-{2-hydroxy-5-[2-hydroxy-4-(tetrahydro-2H-pyran-2-yloxy)benzoyl]phenyl} propanoate, 1.83 g of methyl 4-(bromomethyl)benzoate, and 1.33 g of potassium carbonate were suspended in 32 mL of N,N-dimethylformamide, and this mixture was stirred for one hour at temperatures of 60 to 70° C. After the reaction mixture was cooled to room temperature, this mixture was added to a mixture of ethyl acetate and ice water, and then the organic phase was separated therefrom. After the resultant organic phase was washed with water and a saturated sodium chloride solution successively, the washed phase was dried over anhydrous magnesium sulfate and the solvent was distilled out thereof under reduced pressure. The resultant residue was purified by silica gel column chromatography [eluent; hexane:ethyl acetate=3:1] to yield 2.75 g of methyl 4-{[4-2-hydroxy-4-(tetrahydro-2H-pyran-2-yloxy)benzoyl]-2-(3-methoxy-3-oxopropyl)phenoxy]methyl} benzoate as light yellow solid.

NMR (400 MHz, CDCl$_3$) δ value: 1.5-2.1 (6H, m), 2.69 (2H, t, J=7.2 Hz), 3.08 (2H, t, J=7.2 Hz), 3.6-3.7 (1H, m), 3.67 (3H, s), 3.8-3.9 (1H, m), 3.93 (3H, s), 5.24 (2H, s), 5.4-5.6 (1H, m), 6.54 (1H, d, J=8.0 Hz), 6.71 (1H, s), 6.93 (1H, d, J=8.0 Hz), 7.4-7.6 (5H, m), 8.09 (2H, d, J=7.6 Hz), 12.51 (1H, s)

Example 28

2.70 g of methyl 4-{[4-[2-hydroxy-4-(tetrahydro-2H-pyran-2-yloxy)benzoyl]-2-(3-methoxy-3-oxopropyl)phenoxy]methyl} benzoate was suspended in 27 mL of tetrahydrofuran, to which 27 mL of 1M hydrochloric acid was added, and this suspension was stirred for 3 hours at room temperature and then for another one hour at temperatures of 30 to 40° C. After the reaction mixture was cooled to room temperature, this mixture was added to a mixture of ethyl acetate and water, and the organic phase was separated therefrom. After the resultant organic phase was washed with water and a saturated sodium chloride solution successively, the washed phase was dried over anhydrous magnesium sulfate and the solvent was distilled out thereof under reduced pressure. The resultant residue was solidified with diisopropyl ether, and the solid filtered out was washed with diisopropyl ether to yield 2.28 g of methyl 4-{[4-(2,4-dihydroxybenzoyl)-2-(3-methoxy-3-oxopropyl)phenoxy]methyl} benzoate as white solid.

NMR (400 MHz, CDCl$_3$) δ value: 2.70 (2H, t, J=7.6 Hz), 3.08 (2H, t, J=7.6 Hz), 3.67 (3H, s), 3.94 (3H, s), 5.24 (2H, s), 6.36 (1H, dd, J=8.8, 2.4 Hz), 6.45 (1H, d, J=2.4 Hz), 6.58 (1H, brs), 6.93 (1H, d, J=8.4 Hz), 7.49-7.55 (5H, m), 8.09 (2H, dd, J=6.8, 1.6 Hz), 12.60 (1H, s)

Example 29

32.0 g of methyl 3-{5-[4-(cyclopentyloxy)-2-hydroxybenzoyl]-2-hydroxyphenyl} propanoate and 23.0 g of potassium carbonate were suspended in 320 mL of N,N-dimethylformamide, and a temperature of this suspension was raised to 50° C. 28.5 g of 6-(bromomethyl)-3-(methoxymethoxy)-1,2-benzisoxazole was further added to this suspension, and which was stirred for one hour at 50° C. After the reaction mixture was cooled to room temperature, this mixture was added to a mixture of ethyl acetate and water, and was adjusted to pH 7 with 6M hydrochloric acid, then the organic phase was separated therefrom. After the resultant organic phase was washed with water and a saturated sodium chloride solution successively, the washed phase was dried over anhydrous magnesium sulfate and the solvent was distilled out thereof under reduced pressure. The resultant residue was purified by silica gel column chromatography [eluent; hexane:ethyl acetate=2:1] to yield 32.5 g of methyl 3-(5-[4-(cyclopentyloxy)-2-hydroxybenzoyl]-2-{[3-(methoxymethoxy)-1,2-benzisoxazol-6-yl]methoxy}phenyl) propanoate as yellow oil.

NMR (400 MHz, CDCl$_3$) δ value: 1.60-1.66 (2H, m), 1.74-1.99 (6H, m), 2.70 (2H, t, J=7.6 Hz), 3.09 (2H, t, J=7.6 Hz), 3.65 (3H, s), 3.68 (3H, s), 4.80-4.83 (1H, m), 5.33 (2H, s), 5.57 (2H, s), 6.37 (1H, dd, J=9.0, 2.8 Hz), 6.48 (1H, d, J=2.8 Hz), 6.95 (1H, d, J=8.4 Hz), 7.36 (1H, d, J=8.0 Hz), 7.45-7.57 (4H, m), 7.72 (1H, d, J=8.0 Hz), 12.69 (1H, s)

Example 30

32.0 g of methyl 3-(5-[4-(cyclopentyloxy)-2-hydroxybenzoyl]-2-{[3-(methoxymethoxy)-1,2-benzisoxazol-6-yl]methoxy}phenyl) propanoate was dissolved in a mixed solvent of 96 mL of methanol and 96 mL of 1,4-dioxane, to which 32 mL of 6M hydrochloric acid was added at room temperature, and then this mixture was stirred for 30 minutes at the same temperature. The resulting precipitate was filtered and solid was washed with water and diisopropyl ether successively to yield 26.3 g of methyl 3-{5-[4-(cyclopentyloxy)-2-hydroxybenzoyl]-2-[(3-hydroxy-1,2-benzisoxazol-6-yl)methoxy]phenyl}propanoate as light yellow solid.

NMR (400 MHz, DMSO-d$_6$) δ value: 1.60-1.74 (6H, m), 1.93-1.96 (2H, m), 2.67 (2H, t, J=7.6 Hz), 2.96 (2H, t, J=7.6 Hz), 3.58 (3H, s), 4.90-4.93 (1H, m), 5.42 (2H, s), 6.47-6.51 (2H, m), 7.20 (1H, d, J=8.4 Hz), 7.43-7.45 (2H, m), 7.55-7.57 (2H, m), 7.68 (1H, s), 7.79 (1H, d, J=8.4 Hz), 12.02 (1H, s), 12.41 (1H, brs)

Example 31

0.66 g of methyl 3-[5-[4-(cyclopentyloxy)-2-hydroxybenzoyl]-2-({4-[3-(methoxymethoxy)-5-isoxazolyl]benzyl}oxy)phenyl] propanoate was dissolved in a mixed solvent of 4 mL of methanol and 4 mL of 1,4-dioxane, to which 3 mL of 6M hydrochloric acid was added at room temperature, and then this mixture was stirred for 20 minutes at the same temperature and for another 20 minutes while heating it under reflux. Resultant precipitate was filtered out, and the resultant solid was washed with diisopropyl ether to yield 0.40 g of methyl 3-(5-[4-(cyclopentyloxy)-2-hydroxybenzoyl]-2-{[4-(3-hydroxy-5-isoxazolyl)benzyl]oxy}phenyl)propanoate as light yellow solid.

NMR (400 MHz, DMSO-d$_6$) δ value: 1.5-1.8 (6H, m), 1.9-2.0 (2H, m), 2.66 (2H, t, J=7.6 Hz), 2.95 (2H, t, J=7.6 Hz), 3.57 (3H, s), 4.92 (1H, m), 5.33 (2H, s), 6.48 (1H, dd, J=8.8, 2.4 Hz), 6.51 (1H, d, J=2.0 Hz), 6.58 (1H, s), 7.19 (1H, d, J=8.4 Hz), 7.44 (1H, d, J=8.8 Hz), 7.5-7.6 (2H, m), 7.62 (2H, d, J=8.0 Hz), 7.85 (2H, d, J=8.4 Hz), 11.41 (1H, br), 12.01 (1H, s)

Example 32

The following compounds were obtained in a similar manner as in Example 31.
(1) 4-({2-(2-carboxyethyl)-4-[4-(cyclopentyloxy)-2-hydroxybenzoyl]phenoxy}methyl)-3-hydroxybenzoic acid NMR (400 MHz, DMSO-d$_6$) δ value: 1.60-1.74 (6H, m), 1.90-2.00 (2H, m), 2.57 (2H, t, J=7.6 Hz), 2.89 (2H, t, J=7.6 Hz), 4.90-4.93 (1H, m), 5.23 (2H, s), 6.48-6.50 (2H, m), 7.17 (1H, d, J=8.4 Hz), 7.41-7.49 (4H, m), 7.54-7.57 (2H, m), 10.20 (1H, s), 12.05 (1H, s), 12.48 (2H, brs)
(2) methyl 3-{5-[4-(cyclopentyloxy)-2-hydroxybenzoyl]-2-[(3-hydroxy-1,2-benzisoxazol-5-yl)methoxy]phenyl}propanoate NMR (400 MHz, CDCl$_3$) δ value: 1.62-1.68 (2H, m), 1.78-1.98 (6H, m), 2.70 (2H, t, J=7.6 Hz), 2.75 (1H, brs), 3.08 (2H, t, J=7.6 Hz), 3.68 (3H, s), 4.81-4.84 (1H, m), 5.29 (2H, s), 6.37 (1H, dd, J=8.8, 2.4 Hz), 6.48 (1H, d, J=2.4 Hz), 6.99 (1H, d, J=8.8 Hz), 7.48 (1H, d, J=8.4 Hz), 7.51 (1H, d, J=8.8 Hz), 7.54-7.57 (2H, m), 7.68 (1H, dd, J=8.4, 2.0 Hz), 7.91 (1H, s), 12.69 (1H, s)

Example 33

3.00 g of methyl 3-{5-[4-(cyclopentyloxy)-2-hydroxybenzoyl]-2-hydroxyphenyl} propanoate and 2.16 g of potassium carbonate were suspended in 30 mL of N,N-dimethylformamide, and after this suspension was stirred for 30 minutes at room temperature, 2.55 g of 6-(bromomethyl)-2-(methoxymethyl)-1,2-benzisoxazol-3(2H)-one was added thereto at the same temperature and this mixture was stirred for 30 minutes at 50° C. The reaction mixture was cooled to room temperature, and was added to a mixture of ethyl acetate and water, which was adjusted to pH 5 with 6M hydrochloric acid, and then the organic phase was separated therefrom. After the resultant organic phase was washed with water and a saturated sodium chloride solution successively, the washed phase was dried over anhydrous magnesium sulfate and the solvent was distilled out thereof under reduced pressure. The resultant residue was purified by silica gel column chromatography [eluent; hexane:ethyl acetate=1:1] to yield 3.90 g of methyl 3-(5-[4-(cyclopentyloxy)-2-hydroxybenzoyl]-2-{[2-(methoxymethyl)-3-oxo-2,3-dihydro-1,2-benzisoxazol-6-yl]methoxy}phenyl)propanoate as yellow oil.

NMR (400 MHz, CDCl$_3$) δ value: 1.62-1.66 (2H, m), 1.78-1.96 (6H, m), 2.70 (2H, t, J=7.6 Hz), 3.10 (2H, t, J=7.6 Hz), 3.47 (3H, s), 3.68 (3H, s), 4.81-4.83 (1H, m), 5.31 (2H, s), 5.35 (2H, s), 6.37 (1H, dd, J=9.0, 2.4 Hz), 6.48 (1H, d, J=2.4 Hz), 6.93 (1H, d, J=8.4 Hz), 7.35 (1H, d, J=8.4 Hz), 7.39 (1H, s), 7.49-7.57 (3H, m), 7.90 (1H, d, J=8.4 Hz), 12.68 (1H, s)

Example 34

3.65 g of methyl 3-(5-[4-(cyclopentyloxy)-2-hydroxybenzoyl]-2-{[2-(methoxymethyl)-3-oxo-2,3-dihydro-1,2-benzisoxazol-6-yl]methoxy}phenyl) propanoate was dissolved in a mixed solvent of 40 mL of methanol and 40 mL of 1,4-dioxane, to which 30 mL of 6M hydrochloric acid was added at room temperature, and then this mixture was stirred for 4 hours while heating it under reflux. The reaction mixture was cooled to room temperature, to which chloroform and water were added, and then the organic phase was separated therefrom. After the resultant organic phase was washed with a saturated sodium chloride solution, the washed phase was dried over anhydrous magnesium sulfate and the solvent was distilled out thereof under reduced pressure. The resultant residue was purified by silica gel column chromatography [eluent; chloroform:ethanol=50:1] to yield 1.90 g of methyl 3-{5-[4-(cyclopentyloxy)-2-hydroxybenzoyl]-2-[(3-hydroxyl-1,2-benzisoxazol-6-yl)methoxy]phenyl}-propanoate as light yellow solid.

NMR (400 MHz, DMSO-$d_6$) δ value: 1.60-1.74 (6H, m), 1.93-1.96 (2H, m), 2.67 (2H, t, J=7.6 Hz), 2.96 (2H, t, J=7.6 Hz), 3.58 (3H, s), 4.90-4.93 (1H, m), 5.42 (2H, s), 6.47-6.51 (2H, m), 7.20 (1H, d, J=8.4 Hz), 7.43-7.45 (2H, m), 7.55-7.57 (2H, m), 7.68 (1H, s), 7.79 (1H, d, J=8.4 Hz), 12.02 (1H, s), 12.41 (1H, brs)

Example 35

26.0 g of methyl-3-{5-[4-(cyclopentyloxy)-2-hydroxybenzoyl]-2-[(3-hydroxy-1,2-benzisoxazol-6-yl)methoxy]phenyl} propanoate was suspended in 182 mL of methanol, to which a solution of 10.5 g of sodium hydroxide in 78 mL of water was added dropwise at room temperature, and then this mixture was stirred for 30 minutes at the same temperature. The reaction mixture was added to water, which was then adjusted to pH 1.5 with 6M hydrochloric acid, and resultant precipitate was filtered out. The resultant solid was dissolved in a mixed solvent of chloroform and methanol, and washed with water, and subsequently, a solvent in the separated organic phase was distilled out under reduced pressure. The resultant residue was washed with hexane to yield 22.5 g of 3-{5-[4-(cyclopentyloxy)-2-hydroxybenzoyl]-2-[(3-hydroxyl-1,2-benzisoxazol-6-yl)methoxy]phenyl}propanoic acid as light yellow solid.

NMR (400 MHz, DMSO-$d_6$) δ value: 1.60-1.74 (6H, m), 1.95-1.97 (2H, m), 2.59 (2H, t, J=7.2 Hz), 2.94 (2H, t, J=7.2 Hz), 4.88-4.95 (1H, m), 5.42 (2H, s), 6.48-6.51 (2H, m), 7.20 (1H, d, J=9.2 Hz), 7.43-7.47 (2H, m), 7.55-7.57 (2H, m), 7.69 (1H, s), 7.80 (1H, d, J=8.0 Hz), 12.06 (1H, s), 12.30 (2H, brs)

Example 36

40.0 g of methyl 3-{5-[4-(cyclopentyloxy)-2-hydroxybenzoyl]-2-hydroxyphenyl} propanoate, 23.8 g of methyl 4-(bromomethyl) benzoate, and 17.3 g of potassium carbonate were suspended in 400 mL of N,N-dimethylformamide, and this mixture was stirred for one hour at 60° C. The reaction mixture was cooled to room temperature, which was then added to a mixture of ethyl acetate and ice water, and the organic phase was separated therefrom. After the resultant organic phase was washed with water and a saturated sodium chloride solution successively, the washed phase was dried over anhydrous magnesium sulfate and the solvent was distilled out thereof under reduced pressure. The resultant residue was solidified with diisopropyl ether and filtered out. Crude crystals thus obtained were recrystallized from methanol to yield 40.1 g of methyl 4-{[4-[4-(cyclopentyloxy)-2-hydroxybenzoyl]-2-(3-methoxy-3-oxopropyl)phenoxy]methyl} benzoate as light yellow crystals.

NMR (90 MHz, CDCl$_3$) δ value: 1.50-2.04 (8H, m), 2.58-3.18 (4H, m), 3.67 (3H, s), 3.93 (3H, s), 4.71-4.93 (1H, m), 5.24 (2H, s), 6.30-6.49 (2H, m), 6.93 (1H, d, J=9.0 Hz), 7.47-7.56 (5H, m), 8.09 (2H, d, J=8.1 Hz), 12.68 (1H, s)

Example 37

1.00 g of methyl 3-{5-[4-(cyclopentyloxy)-2-hydroxybenzoyl]-2-hydroxyphenyl}propanoate, 0.809 g of methyl 4-(bromomethyl)-2-methoxy benzoate, and 0.539 g of potassium carbonate were suspended in 10 mL of N,N-dimethylformamide, and this suspension was stirred for 30 minutes at temperatures of 50 to 60° C. The reaction mixture was cooled to room temperature, which was then added to a mixture of ethyl acetate and water, and this mixture was adjusted to pH 2 with 6M hydrochloric acid for the separation of the organic phase therefrom. After the resultant organic phase was washed with water and a saturated sodium chloride solution successively, the washed phase was dried over anhydrous magnesium sulfate and the solvent was distilled out thereof under reduced pressure. The resultant residue was purified by silica gel column chromatography [eluent; hexane:ethyl acetate=2:1] to yield 1.08 g of methyl 4-{[4-[4-(cyclopentyloxy)-2-hydroxybenzoyl]-2-(3-methoxy-3-oxopropyl)phenoxy]methyl}-2-methoxybenzoate as yellow oil.

NMR (400 MHz, CDCl$_3$) δ value: 1.59-1.66 (2H, m), 1.76-1.98 (6H, m), 2.69 (2H, t, J=7.6 Hz), 3.08 (2H, t, J=7.6 Hz), 3.66 (3H, s), 3.90 (3H, s), 3.94 (3H, s), 4.80-4.83 (1H, m), 5.20 (2H, s), 6.37 (1H, dd, J=8.8, 2.4 Hz), 6.48 (1H, d, J=2.4 Hz), 6.93 (1H, d, J=8.4 Hz), 7.03 (1H, d, J=8.0 Hz), 7.09 (1H, s), 7.50 (1H, d, J=8.8 Hz), 7.52-7.55 (2H, m), 7.84 (1H, d, J=8.0 Hz), 12.68 (1H, s)

Example 38

1.36 g of methyl 3-{5-[4-(cyclopentyloxy)-2-hydroxybenzoyl]-2-hydroxyphenyl} propanoate, 1.43 g of 5-[4-(bromomethyl)phenyl]-3-isoxazolyl methoxymethyl ether, and 0.975 g of potassium carbonate were suspended in 12 mL of N,N-dimethylformamide, and this suspension was stirred for 30 minutes at 60° C. The reaction mixture was cooled to room temperature, which was then added to a mixture of ethyl acetate and water, and this mixture was adjusted to pH 2 with 6M hydrochloric acid for the separation of the organic phase therefrom. After the resultant organic phase was washed with water and a saturated sodium chloride solution successively, the washed phase was dried over anhydrous magnesium sulfate and the solvent was distilled out thereof under reduced pressure. The resultant residue was purified by silica gel column chromatography [eluent; ethyl acetate] to yield 0.76 g of methyl 3-[5-[4-(cyclopentyloxy)-2-hydroxybenzoyl]-2-({4-[3-(methoxymethoxy)-5-isoxazolyl]benzyl}oxy)phenyl] propanoate as yellow oil.

NMR (400 MHz, CDCl$_3$) δ value: 1.5-2.1 (8H, m), 2.69 (2H, t, J=7.6 Hz), 3.07 (2H, t, J=7.6 Hz), 3.59 (3H, s), 3.67 (3H, s), 4.7-4.9 (1H, m), 5.22 (2H, s), 5.38 (2H, s), 6.26 (1H, s), 6.37 (1H, dd, J=9.0, 2.4 Hz), 6.48 (1H, d, J=2.4 Hz), 6.95 (1H, d, J=8.4 Hz), 7.5-7.6 (5H, m), 7.78 (2H, d, J=8.4 Hz), 12.70 (1H, s)

Example 39

Compounds listed in Tables 17 to 21 were obtained in a similar manner as in Example 36.

Each of the compounds 39(47) and 39(61) to 39(64) in these tables was synthesized from a compound having a hydroxyl group as $R^4$, for the purpose of substitution of $R^4$.

TABLE 17

| Example Number | $R^{2z}$ | $R^3$ | $R^4$ | $R^5$ | $R^a$ | $R^b$ | $R^c$ | $R^d$ |
|---|---|---|---|---|---|---|---|---|
| 39(1) | Me | OH | 2-thienyl | H | H | H | COOMe | H |
| 39(2) | Me | F | O-cyclopentyl | H | H | H | COOMe | H |
| 39(3) | Me | OH | o-isoamyl | H | H | H | COOMe | H |
| 39(4) | Me | OH | O-neopentyl | H | H | H | COOMe | H |
| 39(5) | Me | OH | O-cyclohexyl | H | H | H | COOMe | H |
| 39(6) | Me | OH | O-cyclopentyl | H | OMOM | H | COOMe | H |
| 39(7) | Me | OH | cyclopentylmeethyl | H | H | H | COOMe | H |
| 39(8) | Me | OH | O-cyclopentyl | H | H | H | $SO_2N(Boc)_2$ | H |
| 39(9) | Me | OH | O-cyclopentyl | H | H | H | CN | H |
| 39(10) | Me | OH | O-isobutyl | H | H | H | CN | H |
| 39(11) | Me | OH | O-isobutyl | H | H | H | $NO_2$ | H |
| 39(12) | Me | OH | issopropyl | H | H | H | COOMe | H |
| 39(13) | Me | OH | (1-methylcyclopentyl)-methyl | H | H | H | COOMe | H |
| 39(14) | Me | OH | O-cyclopentyl | H | H | H | $SO_2NMe_2$ | H |
| 39(15) | Me | OH | O-cyclopentylmethyl | H | H | H | COOMe | H |
| 39(16) | Me | OH | O-(3-pyridyl)methyl | H | H | H | COOMe | H |
| 39(17) | Me | OH | O-cyclopentyl | H | H | MeO | COOMe | MeO |
| 39(18) | Me | OH | O-cyclopentyl | H | H | H | $CH_2COOEt$ | H |
| 39(19) | Me | OH | O-cyclobutyl | H | H | H | COOMe | H |
| 39(20) | Me | OH | O-benzyl | H | H | H | COOMe | H |
| 39(21) | Me | OH | O-cyclopentyl | H | H | H | $SO_2N(Boc)Me$ | H |
| 39(22) | Me | OH | O-cyclopentyl | H | H | H | $CONMe_2$ | H |
| 39(23) | Me | OH | O-cyclopentyl | H | H | H | $N(Boc)SO_2Me$ | H |
| 39(24) | Me | OH | O-cyclopentyl | H | H | H | $CON(Boc)Me$ | H |

TABLE 18

| Example Number | $R^{2z}$ | $R^3$ | $R^4$ | $R^5$ | $R^a$ | $R^b$ | $R^c$ | $R^d$ |
|---|---|---|---|---|---|---|---|---|
| 39(25) | Me | OH | cyclopentyl | H | H | H | COOMe | H |
| 39(28) | Me | OH | O-cyclopentyl | H | H | F | COOMe | H |
| 39(29) | Me | OH | O-cyclopentyl | H | H | COOMe | COOMe | H |
| 39(30) | i-Pr | H | O-isobutyl | H | H | H | COOMe | H |
| 39(31) | Me | OH | O-isobutyl | H | O-i-Pr | H | COO-i-Pr | H |
| 39(32) | Me | OH | O-cyclopentyl | H | H | O-i-Bu | COO-i-Bu | H |
| 39(33) | Me | OH | O-isobutyl | H | H | H | COOMe | H |
| 39(34) | i-Pr | OH | O-isobutyl | H | H | H | COOMe | H |
| 39(35) | i-Pr | OH | O-isobutyl | H | H | COOMe | H | H |
| 39(36) | i-Pr | OH | O-isobutyl | H | COOMe | H | H | H |
| 39(37) | Me | OH | O-cyclopentyl | H | F | H | COOMe | H |
| 39(38) | Me | OH | O-cyclopentyl | F | H | H | COOMe | H |
| 39(39) | Me | Me | O-cyclopentyl | H | H | H | COOMe | H |
| 39(40) | Me | OH | O-cyclopentyl | H | H | H | $SO_3Ph$ | H |
| 39(41) | Me | OH | O—$CH(CH_2CH_3)_2$ | H | H | H | COOMe | H |
| 39(42) | Me | OH | O-cyclohexylmethyl | H | H | H | COOMe | H |
| 39(43) | Me | OH | O-cyclopropylmethyl | H | H | H | COOMe | H |
| 39(44) | Me | OH | O-cycloheptyl | H | H | H | COOMe | H |
| 39(45) | Me | OH | O-cyclopentyl | H | H | H | $P(O)(OEt)_2$ | H |
| 39(46) | i-Pr | OH | O-isobutyl | H | H | H | CN | H |
| 39(47) | Me | OH | O-(2-pyradinyl)methyl | H | H | H | COOMe | H |

TABLE 19
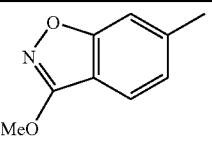
| Example Number | R¹ | R²ᶻ | R⁴ᶻ |
|---|---|---|---|
| 39(48) | 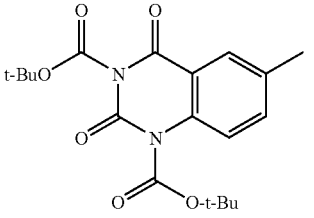 | methyl | cyclopentyl |
| 39(49) |  | methyl | cyclopentyl |
| 39(50) | 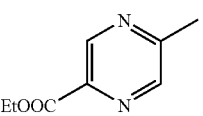 | methyl | cyclopentyl |
| 39(51) | 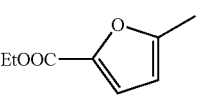 | methyl | cyclopentyl |
| 39(52) | 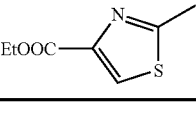 | methyl | cyclopentyl |
| 39(53) | 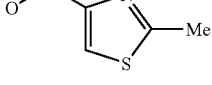 | methyl | cyclopentyl |
| 39(54) | 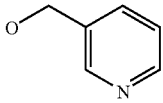 | methyl | cyclopentyl |
TABLE 20
| Example Number | R¹ | R²ᶻ | R⁴ᶻ |
|---|---|---|---|
| 39(55) | | methyl | cyclopentyl |
| 39(56) | | methyl | cyclopentyl |
| 39(57) | | isopropyl | isobutyl |
| 39(58) | | methyl | cyclopentyl |
| 39(59) | | methyl | cyclopentyl |
| 39(60) | | methyl | cyclopentyl |
TABLE 21
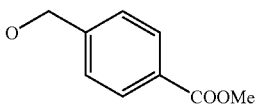
| Example Number | R⁴ᶻ |
|---|---|
| 39(61) | |
| 39(62) | |
| 39(63) | |

TABLE 21-continued

[Structure: a diaryl ketone with isobutoxy group, a propanoate chain (COO-i-Bu), a hydroxyl group, and R^4z substituent]

| Example Number | R^4z |
| --- | --- |
| 39(64) | -O-CH₂-(2-pyridyl) |

39(1)
NMR (400 MHz, CDCl₃) δ value: 2.70 (2H, t, J=7.6 Hz), 3.09 (2H, t, J=7.6 Hz), 3.68 (3H, s), 3.94 (3H, s), 5.26 (2H, s), 6.96 (1H, d, J=8.4 Hz), 7.1-7.2 (2H, m), 7.31 (1H, d, J=2.0 Hz), 7.40 (1H, dd, J=4.8, 0.8 Hz), 7.47 (1H, dd, J=3.6, 0.8 Hz), 7.52 (2H, d, J=8.0 Hz), 7.5-7.7 (3H, m), 8.10 (2H, d, J=8.4 Hz), 12.18 (1H, s)

39(2)
NMR (400 MHz, CDCl₃) δ value: 1.62-1.71 (2H, m), 1.77-1.98 (6H, m), 2.64-2.68 (2H, m), 3.03-3.07 (2H, m), 3.66 (3H, s), 3.93 (3H, s), 4.78-4.82 (1H, m), 5.23 (2H, s), 6.61 (1H, dd, J=12.4, 2.4 Hz), 6.73 (1H, dd, J=8.8, 2.4 Hz), 6.90 (1H, d, J=8.4 Hz), 7.47-7.51 (3H, m), 7.67-7.70 (2H, m), 8.06-8.09 (2H, m)

39(3)
NMR (400 MHz, CDCl₃) δ value: 0.97 (6H, d, J=6.8 Hz), 1.70 (2H, q, J=6.8 Hz), 1.79-1.87 (1H, m), 2.69 (2H, t, J=7.6 Hz), 3.07 (2H, t, J=8.0 Hz), 3.67 (3H, s), 3.94 (3H, s), 4.05 (2H, t, J=6.8 Hz), 5.24 (2H, s), 6.40 (1H, dd, J=8.8, 2.4 Hz), 6.50 (1H, d, J=2.4 Hz), 6.93 (1H, d, J=8.0 Hz), 7.51-7.55 (5H, m), 8.09 (2H, d, J=8.0 Hz), 12.67 (1H, s)

39(4)
NMR (400 MHz, CDCl₃) δ value: 1.04 (9H, s), 2.69 (2H, t, J=7.6 Hz), 3.07 (2H, t, J=7.6 Hz), 3.65 (2H, s), 3.67 (3H, s), 3.94 (3H, s), 5.25 (2H, s), 6.43 (1H, dd, J=9.0, 2.8 Hz), 6.50 (1H, d, J=2.8 Hz), 6.94 (1H, d, J=8.4 Hz), 7.51-7.56 (5H, m), 8.09 (2H, d, J=8.0 Hz), 12.65 (1H, s)

39(5)
NMR (90 MHz, CDCl₃) δ value: 1.1-2.2 (10H, m), 2.68 (2H, t, J=6.8 Hz), 3.08 (2H, t, J=6.6 Hz), 3.67 (3H, s), 3.93 (3H, s), 4.1-4.5 (1H, m), 5.24 (2H, s), 6.3-6.5 (2H, m), 6.93 (1H, d, J=9.0 Hz), 7.4-7.6 (5H, m), 8.09 (2H, d, J=8.3 Hz), 12.67 (1H, s)

39(6)
NMR (400 MHz, CDCl₃) δ value: 1.58-1.64 (2H, m), 1.76-1.98 (6H, m), 2.70 (2H, t, J=7.6 Hz), 3.08 (2H, t, J=7.6 Hz), 3.41 (3H, s), 3.52 (3H, s), 3.67 (3H, s), 3.93 (3H, s), 4.81-4.82 (1H, m), 5.27 (2H, s), 5.32 (2H, s), 6.37 (1H, dd, J=8.8, 2.0 Hz), 6.48 (1H, d, J=2.0 Hz), 6.99 (1H, d, J=8.4 Hz), 7.51-7.56 (4H, m), 7.75 (1H, d, J=8.0 Hz), 7.80 (1H, s), 12.70 (1H, s)

39(7)
NMR (400 MHz, CDCl₃) δ value: 1.17-1.26 (2H, m), 1.52-1.75 (6H, m), 2.04-2.16 (1H, m), 2.62 (2H, d, J=7.6 Hz), 2.69 (2H, t, J=7.3 Hz), 3.08 (2H, t, J=7.8 Hz), 3.67 (3H, s), 3.94 (3H, s), 5.25 (2H, s), 6.69 (1H, dd, J=8.2, 1.5 Hz), 6.87 (1H, d, J=1.5 Hz), 6.94 (1H, d, J=8.3 Hz), 7.49-7.52 (3H, m), 7.56-7.59 (2H, m), 8.09 (2H, d, J=8.3 Hz), 12.09 (1H, s)

39(8)
NMR (400 MHz, CDCl₃) δ value: 1.49 (18H, s), 1.63-1.68 (2H, m), 1.78-1.97 (6H, m), 2.69 (2H, t, J=7.6 Hz), 3.08 (2H, t, J=8.0 Hz), 3.67 (3H, s), 4.80-4.82 (1H, m), 5.28 (2H, s), 6.37 (1H, dd, J=8.8, 2.4 Hz), 6.48 (1H, d, J=2.0 Hz), 6.91 (1H, d, J=8.4 Hz), 7.49-7.56 (3H, m), 7.63 (2H, d, J=8.4 Hz), 8.14 (2H, d, J=8.8 Hz), 12.68 (1H, s)

39(9)
NMR (400 MHz, CDCl₃) δ value: 1.61-1.69 (2H, m), 1.76-1.98 (6H, m), 2.68 (2H, t, J=7.6 Hz), 3.08 (2H, t, J=7.6 Hz), 3.67 (3H, s), 4.80-4.84 (1H, m), 5.24 (2H, s), 6.37 (1H, dd, J=8.8, 2.4 Hz), 6.48 (1H, d, J=2.4 Hz), 6.91 (1H, d, J=8.4 Hz), 7.49 (1H, d, J=8.8 Hz), 7.53-7.58 (4H, m), 7.72 (2H, d, J=8.4 Hz), 12.69 (1H, s)

39(10)
NMR (90 MHz, CDCl₃) δ value: 1.03 (6H, d, J=6.6 Hz), 1.90-2.33 (1H, m), 2.60-2.75 (2H, m), 2.99-3.20 (2H, m), 3.67 (3H, s), 3.78 (2H, d, J=6.6 Hz), 5.24 (2H, s), 6.35-6.51 (2H, m), 6.92 (1H, d, J=9.3 Hz), 7.46-7.77 (7H, m), 12.64 (1H, s)

39(11)
NMR (90 MHz, CDCl₃) δ value: 1.03 (6H, d, J=6.6 Hz), 1.20 (6H, d, J=6.1 Hz), 1.8-2.4 (1H, m), 2.64 (2H, t, J=7.2 Hz), 3.09 (2H, t, J=7.2 Hz), 3.79 (2H, d, J=6.6 Hz), 4.8-5.2 (1H, m), 5.30 (2H, s), 6.3-6.6 (2H, m), 6.92 (1H, d, J=9.0 Hz), 7.4-7.8 (5H, m), 8.29 (2H, d, J=8.6 Hz), 12.64 (1H, s)

39(12)
NMR (400 MHz, CDCl₃) δ value: 1.27 (6H, d, J=6.8 Hz), 2.69 (2H, t, J=7.6 Hz), 2.88-2.95 (1H, m), 3.08 (2H, t, J=8.0 Hz), 3.67 (3H, s), 3.94 (3H, s), 5.25 (2H, s), 6.75 (1H, dd, J=8.2, 1.6 Hz), 6.92 (1H, d, J=2.0 Hz), 6.94 (1H, d, J=8.0 Hz), 7.51-7.59 (5H, m), 8.09 (2H, d, J=8.0 Hz), 12.09 (1H, s)

39(13)
NMR (400 MHz, CDCl₃) δ value: 0.93 (3H, s), 1.31-1.36 (2H, m), 1.50-1.55 (2H, m), 1.66-1.69 (4H, m), 2.61 (2H, s), 2.69 (2H, t, J=7.6 Hz), 3.08 (2H, t, J=7.6 Hz), 3.67 (3H, s), 3.94 (3H, s), 5.25 (2H, s), 6.67 (1H, dd, J=8.4, 1.6 Hz), 6.86 (1H, d, J=2.0 Hz), 6.94 (1H, d, J=8.4 Hz), 7.48-7.60 (5H, m), 8.09 (2H, d, J=8.0 Hz), 12.08 (1H, s)

39(14)
NMR (400 MHz, CDCl₃) δ value: 1.62-1.69 (2H, m), 1.78-1.98 (6H, m), 2.70 (2H, t, J=7.6 Hz), 2.75 (6H, s), 3.09 (2H, t, J=8.0 Hz), 3.68 (3H, s), 4.80-4.84 (1H, m), 5.26 (2H, s), 6.38 (1H, dd, J=9.0, 2.4 Hz), 6.48 (1H, d, J=2.4 Hz), 6.94 (1H, d, J=8.4 Hz), 7.50 (1H, d, J=8.8 Hz), 7.54-7.56 (2H, m), 7.62 (2H, d, J=8.4 Hz), 7.84 (2H, d, J=8.4 Hz), 12.68 (1H, s)

39(15)
NMR (400 MHz, CDCl₃) δ value: 1.33-1.38 (2H, m), 1.57-1.66 (4H, m), 1.82-1.87 (2H, m), 2.35-2.41 (1H, m), 2.69 (2H, t, J=7.6 Hz), 3.07 (2H, t, J=7.6 Hz), 3.67 (3H, s), 3.89 (2H, d, J=6.8 Hz), 3.94 (3H, s), 5.24 (2H, s), 6.41 (1H, dd, J=8.8, 2.4 Hz), 6.50 (1H, d, J=2.4 Hz), 6.93 (1H, d, J=8.4 Hz), 7.51-7.56 (5H, m), 8.09 (2H, d, J=8.4 Hz), 12.66 (1H, s)

39(16)
NMR (90 MHz, CDCl₃) δ value: 2.60-3.20 (4H, m), 3.67 (3H, s), 3.94 (3H, s), 5.14 (2H, s), 5.25 (2H, s), 6.40-6.70 (2H, m), 6.94 (1H, d, J=9.3 Hz), 7.30-7.90 (7H, m), 8.10 (2H, d, J=8.1 Hz), 8.60-8.80 (2H, m), 12.64 (1H, s)

39(17)

NMR (400 MHz, CDCl$_3$) δ value: 1.62-1.68 (2H, m), 1.76-1.98 (6H, m), 2.69 (2H, t, J=8.1 Hz), 3.07 (2H, t, J=8.1 Hz), 3.65 (3H, s), 3.84 (6H, s), 3.92 (3H, s), 4.80-4.83 (1H, m), 5.15 (2H, s), 6.38 (1H, dd, J=9.0, 2.4 Hz), 6.48 (1H, d, J=2.4 Hz), 6.65 (2H, s), 6.92 (1H, d, J=8.6 Hz), 7.50-7.55 (3H, m), 12.68 (1H, s)

39(18)

NMR (400 MHz, CDCl$_3$) δ value: 1.27 (3H, t, J=7.1 Hz), 1.56-1.64 (2H, m), 1.78-1.96 (6H, m), 2.68 (2H, t, J=7.6 Hz), 3.05 (2H, t, J=7.6 Hz), 3.64 (2H, s), 3.66 (3H, s), 4.17 (2H, q, J=7.1 Hz), 4.81-4.82 (1H, m), 5.16 (2H, s), 6.37 (1H, dd, J=8.8, 2.1 Hz), 6.47 (1H, d, J=2.0 Hz), 6.96 (1H, d, J=9.0 Hz), 7.33 (2H, d, J=7.8 Hz), 7.39 (2H, d, J=7.8 Hz), 7.50-7.54 (3H, m), 12.71 (1H, s)

39(19)

NMR (400 MHz, CDCl$_3$) δ value: 1.68-1.76 (1H, m), 1.86-1.92 (1H, m), 2.15-2.25 (2H, m), 2.45-2.53 (2H, m), 2.69 (2H, t, J=7.6 Hz), 3.07 (2H, t, J=7.6 Hz), 3.67 (3H, s), 3.94 (3H, s), 4.69-4.72 (1H, m), 5.24 (2H, s), 6.33-6.39 (2H, m), 6.93 (1H, d, J=8.4 Hz), 7.50-7.55 (5H, m), 8.09 (2H, d, J=8.4 Hz), 12.66 (1H, s)

39(20)

NMR (400 MHz, CDCl$_3$) δ value: 2.69 (2H, t, J=8.0 Hz), 3.07 (2H, t, J=8.0 Hz), 3.66 (3H, s), 3.94 (3H, s), 5.12 (2H, s), 5.24 (2H, s), 6.49 (1H, dd, J=8.8, 2.4 Hz), 6.60 (1H, d, J=2.4 Hz), 6.93 (1H, d, J=8.4 Hz), 7.35-7.44 (5H, m), 7.50-7.55 (5H, m), 8.09 (2H, d, J=8.0 Hz), 12.65 (1H, s)

39(21)

NMR (400 MHz, CDCl$_3$) δ value: 1.35 (9H, s), 1.62-1.66 (2H, m), 1.76-1.96 (6H, m), 2.68 (2H, t, J=7.6 Hz), 3.08 (2H, t, J=7.6 Hz), 3.36 (3H, s), 3.67 (3H, s), 4.80-4.83 (1H, m), 5.27 (2H, s), 6.37 (1H, dd, J=8.8, 2.4 Hz), 6.48 (1H, d, J=2.4 Hz), 6.91 (1H, d, J=8.4 Hz), 7.48-7.61 (5H, m), 7.95 (2H, d, J=8.4 Hz), 12.67 (1H, s)

39(22)

NMR (400 MHz, CDCl$_3$) δ value: 1.62-1.68 (2H, m), 1.77-1.98 (6H, m), 2.68 (2H, t, J=7.6 Hz), 3.01 (3H, brs), 3.06 (2H, t, J=7.6 Hz), 3.13 (3H, brs), 3.67 (3H, s), 4.80-4.83 (1H, m), 5.21 (2H, s), 6.37 (1H, dd, J=9.2, 2.4 Hz), 6.48 (1H, d, J=2.4 Hz), 6.94 (1H, d, J=8.4 Hz), 7.47-7.55 (7H, m), 12.69 (1H, s)

39(23)

NMR (400 MHz, CDCl$_3$) δ value: 1.48 (9H, s), 1.60-1.66 (2H, m), 1.81-1.96 (6H, m), 2.69 (2H, t, J=8.0 Hz), 3.07 (2H, t, J=8.0 Hz), 3.45 (3H, s), 3.66 (3H, s), 4.81-4.83 (1H, m), 5.21 (2H, s), 6.37 (1H, dd, J=8.8, 2.4 Hz), 6.48 (1H, d, J=2.4 Hz), 6.95 (1H, d, J=8.4 Hz), 7.29 (2H, d, J=8.4 Hz), 7.49-7.55 (5H, m), 12.69 (1H, s)

39(24)

NMR (400 MHz, CDCl$_3$) δ value: 1.17 (9H, s), 1.60-1.68 (2H, m), 1.77-1.98 (6H, m), 2.67 (2H, t, J=7.2 Hz), 3.05 (2H, t, J=7.6 Hz), 3.32 (3H, s), 3.66 (3H, s), 4.80-4.83 (1H, m), 5.22 (2H, s), 6.37 (1H, dd, J=8.8, 2.4 Hz), 6.48 (1H, d, J=2.4 Hz), 6.94 (1H, d, J=8.0 Hz), 7.46-7.57 (7H, m), 12.69 (1H, s)

39(25)

NMR (400 MHz, CDCl$_3$) δ value: 1.58-1.73 (4H, m); 1.79-1.84 (2H, m), 2.05-2.11 (2H, m), 2.69 (2H, t, J=7.6 Hz), 2.97-3.05 (1H, m), 3.08 (2H, t, J=8.0 Hz), 3.67 (3H, s), 3.94 (3H, s), 5.25 (2H, s), 6.76 (1H, dd, J=8.4, 1.6 Hz), 6.93-6.95 (2H, m), 7.51-7.59 (5H, m), 8.09 (2H, d, J=8.0 Hz), 12.09 (1H, s)

39(28)

NMR (400 MHz, CDCl$_3$) δ value: 1.62-1.66 (2H, m), 1.74-1.98 (6H, m), 2.69 (2H, t, J=7.6 Hz), 3.08 (2H, t, J=7.6 Hz), 3.68 (3H, s), 3.98 (3H, s), 4.80-4.83 (1H, m), 5.21 (2H, s), 6.37 (1H, dd, J=9.0, 2.2 Hz), 6.47 (1H, d, J=2.2 Hz), 6.90 (1H, d, J=8.3 Hz), 7.24-7.28 (2H, m), 7.49 (1H, d, J=9.0 Hz), 7.51-7.55 (2H, m), 7.99 (1H, t, J=7.8 Hz), 12.68 (1H, s)

39(29)

NMR (400 MHz, CDCl$_3$) δ value: 1.60-1.65 (2H, m), 1.80-1.95 (6H, m), 2.68 (2H, t, J=7.6 Hz), 3.07 (2H, t, J=7.6 Hz), 3.67 (3H, s), 3.93 (3H, s), 3.94 (3H, s), 4.78-4.83 (1H, m), 5.24 (2H, s), 6.37 (1H, dd, J=8.8, 2.4 Hz), 6.48 (1H, d, J=2.4 Hz), 6.91 (1H, d, J=8.4 Hz), 7.50 (1H, d, J=8.8 Hz), 7.51-7.56 (2H, m), 7.62-7.64 (1H, m), 7.79 (2H, d, J=8.0 Hz), 12.68 (1H, s)

39(30)

NMR (90 MHz, CDCl$_3$) δ value: 1.05 (6H, d, J=6.6 Hz), 1.19 (6H, d, J=6.3 Hz), 1.90-2.36 (1H, m), 2.52-2.77 (2H, m), 2.86-3.16 (2H, m), 3.80 (2H, d, J=6.6 Hz), 3.93 (3H, s), 4.86-5.14 (1H, m), 5.25 (2H, s), 6.86-7.02 (3H, m), 7.47-7.81 (6H, m), 8.09 (2H, d, J=8.3 Hz)

39(31)

NMR (90 MHz, CDCl$_3$) δ value: 1.03 (6H, d, J=6.6 Hz), 1.38 (6H, d, J=6.4 Hz), 1.40 (6H, d, J=6.1 Hz), 1.9-2.4 (1H, m), 2.6-2.8 (2H, m), 3.0-3.2 (2H, m), 3.68 (3H, s), 3.79 (2H, d, J=6.4 Hz), 4.5-5.0 (1H, m), 5.1-5.5 (1H, m), 5.25 (2H, s), 6.3-6.5 (2H, m), 6.97 (1H, d, J=9.3 Hz), 7.5-7.7 (6H, m), 12.68 (1H, s)

39(32)

NMR (400 MHz, CDCl$_3$) δ value: 1.01 (6H, d, J=6.6 Hz), 1.06 (6H, d, J=6.6 Hz), 1.64-1.73 (2H, m), 1.78-1.96 (6H, m), 2.08 (1H, sep, J=6.6 Hz), 2.15 (1H, sep, J=6.6 Hz), 2.69 (2H, t, J=7.6 Hz), 3.07 (2H, t, J=7.6 Hz), 3.66 (3H, s), 3.82 (2H, d, J=6.6 Hz), 4.10 (2H, d, J=6.6 Hz), 4.79-4.84 (1H, m), 5.18 (2H, s), 6.37 (1H, dd, J=8.8, 1.7 Hz), 6.48 (1H, d, J=1.7 Hz), 6.92 (1H, d, J=8.3 Hz), 7.00-7.03 (2H, m), 7.49-7.55 (3H, m), 7.82 (1H, d, J=7.8 Hz), 12.69 (1H, s)

39(33)

NMR (90 MHz, CDCl$_3$) δ value: 1.03 (6H, d, J=6.6 Hz), 1.95-2.23 (1H, m), 2.69 (2H, t, J=7.1 Hz), 3.09 (2H, t, J=7.1 Hz), 3.67 (3H, s), 3.79 (2H, d, J=6.1 Hz), 3.94 (3H, s), 5.25 (2H, s), 6.35-6.48 (2H, m), 6.93 (1H, d, J=8.5 Hz), 7.47-7.57 (5H, m), 8.09 (2H, d, J=7.8 Hz), 12.65 (1H, s)

39(34)

NMR (90 MHz, CDCl$_3$) δ value: 1.03 (6H, d, J=6.6 Hz), 1.19 (6H, d, J=6.1 Hz), 1.90-2.14 (1H, m), 2.52-2.72 (2H, m), 2.99-3.16 (2H, m), 3.78 (2H, d, J=6.6 Hz), 3.93 (3H, s), 4.87-5.16 (1H, m), 5.25 (2H, s), 6.35-6.51 (2H, m), 6.93 (1H, d, J=9.0 Hz), 7.47-7.57 (5H, m), 8.09 (2H, d, J=8.3 Hz), 12.65 (1H, s)

39(35)

NMR (90 MHz, CDCl$_3$) δ value: 1.03 (6H, d, J=6.6 Hz), 1.18 (6H, d, J=6.1 Hz), 1.86-2.33 (1H, m), 2.64 (2H, t, J=6.6 Hz), 3.07 (2H, t, J=6.6 Hz), 3.79 (2H, d, J=6.4 Hz), 3.94 (3H, s), 4.80-5.20 (1H, m), 5.23 (2H, s), 6.35-6.49 (2H, m), 6.95 (1H, d, J=9.0 Hz), 7.40-7.72 (5H, m), 7.99-8.11 (2H, m), 12.66 (1H, s)

39(36)

NMR (90 MHz, CDCl$_3$) δ value: 1.03 (6H, d, J=6.6 Hz), 1.20 (6H, d, J=6.1 Hz), 1.90-2.28 (1H, m), 2.58-2.74 (2H, m), 3.03-3.21 (2H, m), 3.79 (2H, d, J=6.4 Hz), 3.93 (3H, s), 4.88-5.17 (1H, m), 5.63 (2H, s), 6.35-6.51 (2H, m), 6.99 (1H, d, J=9.0 Hz), 7.26-7.83 (6H, m), 8.06 (1H, dd, J=7.3, 1.2 Hz), 12.68 (1H, s)

39(37)

NMR (400 MHz, CDCl$_3$) δ value: 1.62-1.67 (2H, m), 1.76-1.98 (6H, m), 2.68 (2H, t, J=7.6 Hz), 3.06 (2H, t, J=7.6 Hz), 3.67 (3H, s), 3.94 (3H, s), 4.80-4.83 (1H, m), 5.29 (2H, s), 6.37 (1H, dd, J=9.0, 2.4 Hz), 6.48 (1H, d, J=2.2 Hz), 6.98 (1H, d, J=9.3 Hz), 7.50 (1H, d, J=9.0 Hz), 7.53-7.56 (2H, m), 7.61 (1H, t, J=7.6 Hz), 7.78 (1H, dd, J=10.5, 1.2 Hz), 7.89 (1H, dd, J=8.0, 1.2 Hz), 12.68 (1H, s)

39(38)

NMR (400 MHz, CDCl$_3$) δ value: 1.60-1.67 (2H, m), 1.75-1.98 (6H, m), 2.67 (2H, t, J=7.6 Hz), 3.05 (2H, t, J=8.0 Hz), 3.66 (3H, s), 3.93 (3H, s), 4.78-4.80 (1H, m), 5.23 (2H, s), 6.12 (1H, dd, J=13.0, 2.4 Hz), 6.30 (1H, s), 6.90 (1H, d, J=8.4 Hz), 7.50-7.55 (4H, m), 8.08 (2H, d, J=8.4 Hz), 11.95 (1H, s)

39(39)

NMR (400 MHz, CDCl$_3$) δ value: 1.2-1.7 (2H, m), 1.7-2.0 (6H, m), 2.35 (3H, s), 2.65 (2H, t, J=8.0 Hz), 3.04 (2H, t, J=8.0 Hz), 3.66 (3H, s), 3.93 (3H, s), 4.79-4.83 (1H, m), 5.23 (2H, s), 6.69 (1H, dd, J=8.8, 2.4 Hz), 6.77 (1H, d, J=2.4 Hz), 6.87 (1H, d, J=8.8 Hz), 7.2-7.3 (1H, m), 7.50 (2H, d, J=8.4 Hz), 7.63 (1H, dd, J=8.4, 2.0 Hz), 7.67 (1H, d, J=2.4 Hz), 8.08 (2H, d, J=8.0 Hz)

39(40)

NMR (400 MHz, CDCl$_3$) δ value: 1.60-1.68 (2H, m), 1.77-1.97 (6H, m), 2.69 (2H, t, J=7.2 Hz), 3.08 (2H, t, J=8.0 Hz), 3.67 (3H, s), 4.80-4.82 (1H, m), 5.27 (2H, s), 6.37 (1H, dd, J=9.0, 2.4 Hz), 6.48 (1H, d, J=2.4 Hz), 6.91 (1H, d, J=8.3 Hz), 7.00-7.02 (2H, m), 7.27-7.32 (3H, m), 7.49 (1H, d, J=8.8 Hz), 7.54-7.62 (4H, m), 7.89 (2H, d, J=8.4 Hz), 12.66 (1H, s)

39(41)

NMR (90 MHz, CDCl$_3$) δ value: 0.96 (6H, t, J=7.2 Hz), 1.6-1.8 (4H, m), 2.68 (2H, t, J=6.8 Hz), 3.08 (2H, t, J=6.6 Hz), 3.67 (3H, s), 3.94 (3H, s), 4.1-4.3 (1H, m), 5.25 (2H, s), 6.3-6.5 (2H, m), 6.93 (1H, d, J=9.0 Hz), 7.4-7.6 (5H, m), 8.10 (2H, d, J=8.1 Hz), 12.67 (1H, s)

39(42)

NMR (90 MHz, CDCl$_3$) δ value: 0.7-2.0 (11H, m), 2.68 (2H, t, J=7.7 Hz), 3.08 (2H, t, J=8.1 Hz), 3.67 (3H, s), 3.81 (2H, d, J=5.9 Hz), 3.93 (3H, s), 5.24 (2H, 3), 6.3-6.5 (2H, m), 6.93 (1H, d, J=9.0 Hz), 7.4-7.6 (5H, m), 8.09 (2H, d, J=8.5 Hz), 12.67 (1H, s)

39(43)

NMR (90 MHz, CDCl$_3$) δ value: 0.3-0.8 (4H, m), 1.1-1.5 (1H, m), 2.6-2.8 (2H, m), 3.0-3.2 (2H, m), 3.67 (3H, s), 3.86 (2H, d, J=6.8 Hz), 3.94 (3H, s), 5.24 (2H, s), 6.3-6.5 (2H, m), 6.93 (1H, d, J=9.0 Hz), 7.4-7.6 (5H, m), 8.09 (2H, d, J=8.3 Hz), 12.67 (1H, s)

39(44)

NMR (90 MHz, CDCl$_3$) δ value: 1.3-2.0 (12H, m), 2.68 (2H, t, J=6.8 Hz), 3.08 (2H, t, J=6.8 Hz), 3.67 (3H, s), 3.93 (3H, s), 4.3-4.6 (1H, m), 5.24 (2H, s), 6.3-6.4 (2H, m), 6.93 (1H, d, J=9.3 Hz), 7.5-7.6 (5H, m), 8.09 (2H, d, J=8.3 Hz), 12.68 (1H, s)

39(45)

NMR (400 MHz, CDCl$_3$) δ value: 1.34 (6H, t, J=7.6 Hz), 1.60-1.98 (8H, m), 2.69 (2H, t, J=7.2 Hz), 3.08 (2H, t, J=8.0 Hz), 3.67 (3H, s), 4.10-4.19 (4H, m), 4.80-4.82 (1H, m), 5.23 (2H, s), 6.37 (1H, dd, J=8.8, 2.4 Hz), 6.48 (1H, d, J=2.4 Hz), 6.93 (1H, d, J=8.4 Hz), 7.50-7.56 (5H, m), 7.84-7.89 (2H, m), 12.69 (1H, s)

39(46)

NMR (90 MHz, CDCl$_3$) δ value: 1.03 (6H, d, J=6.6 Hz), 1.19 (6H, d, J=6.1 Hz), 1.96-2.20 (1H, m), 2.55-2.71 (2H, m), 2.99-3.17 (2H, m), 3.79 (2H, d, J=6.3 Hz), 4.86-5.14 (1H, m), 5.24 (2H, s), 6.37-6.48 (2H, m), 6.90 (1H, d, J=9.3 Hz), 7.46-7.77 (7H, m), 12.63 (1H, s)

39(47)

NMR (400 MHz, CDCl$_3$) δ value: 2.69 (2H, t, J=7.2 Hz), 3.08 (2H, t, J=7.6 Hz), 3.67 (3H, s), 3.94 (3H, s), 5.25 (2H, s), 5.30 (2H, s), 6.54 (1H, dd, J=8.8, 2.8 Hz), 6.62 (1H, d, J=2.4 Hz), 6.94 (1H, d, J=8.4 Hz), 7.51-7.60 (5H, m), 8.09 (2H, d, J=8.4 Hz), 8.58-8.60 (2H, m), 8.82 (1H, s), 12.62 (1H, s)

39(48)

NMR (400 MHz, CDCl$_3$) δ value: 1.61-1.68 (2H, m), 1.78-1.98 (6H, m), 2.67 (2H, t, J=7.6 Hz), 3.05 (2H, t, J=7.6 Hz), 3.65 (3H, s), 3.66 (3H, s), 4.81-4.84 (1H, m), 5.27 (2H, s), 5.57 (2H, s), 6.37 (1H, dd, J=8.8, 2.4 Hz), 6.48 (1H, d, J=2.4 Hz), 6.99 (1H, d, J=8.8 Hz), 7.50-7.57 (4H, m), 7.64 (1H, dd, J=8.8, 1.6 Hz), 7.75 (1H, s), 12.70 (1H, s)

39(49)

NMR (400 MHz, CDCl$_3$) δ value: 1.60-1.66 (2H, m), 1.67-1.98 (6H, m), 2.67 (3H, s), 2.70 (2H, t, J=7.6 Hz), 3.08 (2H, t, J=7.6 Hz), 3.67 (3H, s), 4.80-4.83 (1H, m), 5.25 (2H, s), 6.37 (1H, dd, J=8.8, 2.4 Hz), 6.48 (1H, d, J=2.4 Hz), 6.96 (1H, d, J=8.4 Hz), 7.48-7.57 (5H, m), 8.11 (2H, d, J=8.0 Hz), 12.70 (1H, s)

39(50)

NMR (400 MHz, CDCl$_3$) δ value: 1.63-1.67 (2H, m), 1.67 (9H, s), 1.78-1.96 (6H, m), 2.63 (2H, t, J=7.6 Hz), 3.00 (2H, t, J=7.6 Hz), 3.66 (3H, s), 4.81-4.83 (1H, m), 5.09 (2H, s), 6.38 (1H, dd, J=9.0, 2.4 Hz), 6.48 (1H, d, J=2.4 Hz), 6.97 (1H, d, J=8.6 Hz), 7.50 (1H, d, J=8.8 Hz), 7.53-7.57 (2H, m), 7.80 (1H, s), 8.18 (1H, s), 12.69 (1H, s)

39(51)

NMR (400 MHz, CDCl$_3$) δ value: 1.62-1.67 (2H, m), 1.76-1.98 (6H, m), 2.67 (2H, t, J=7.6 Hz), 3.04 (2H, t, J=7.6 Hz), 3.39 (6H, s), 3.66 (3H, s), 4.80-4.83 (1H, m), 5.20 (2H, s), 5.32 (2H, s), 5.34 (2H, s), 6.37 (1H, dd, J=9.2, 2.4 Hz), 6.48 (1H, d, J=2.4 Hz), 6.99 (1H, d, J=8.8 Hz), 7.18-7.32 (3H, m), 7.50-7.56 (3H, m), 12.70 (1H, s)

39(52)

NMR (400 MHz, CDCl$_3$) δ value: 1.63-1.68 (2H, m), 1.76-1.98 (6H, m), 2.70 (2H, t, J=7.6 Hz), 3.09 (2H, t, J=7.6 Hz), 3.36 (3H, s), 3.68 (3H, s), 4.80-4.84 (1H, m), 5.28 (2H, s), 6.37 (1H, dd, J=8.8, 2.4 Hz), 6.48 (1H, d, J=2.4 Hz), 6.95 (1H, d, J=8.0 Hz), 7.50 (1H, d, J=9.2 Hz), 7.54-7.56 (2H, m), 7.64-7.70 (4H, m), 12.68 (1H, s)

39(53)

NMR (400 MHz, CDCl$_3$) δ value: 1.60-1.68 (11H, m), 1.77-1.98 (6H, m), 2.69 (2H, t, J=7.2 Hz), 3.09 (2H, t, J=7.6 Hz), 3.68 (3H, s), 4.81-4.84 (1H, m), 5.33 (2H, s), 6.38 (1H, dd, J=8.8, 2.4 Hz), 6.48 (1H, d, J=2.4 Hz), 6.92 (1H, d, J=8.8 Hz), 7.48-7.57 (3H, m), 7.90 (1H, d, J=7.6 Hz), 8.00 (2H, d, J=8.0 Hz), 12.67 (1H, s)

39(54)

NMR (400 MHz, CDCl$_3$) δ value: 1.62-1.68 (2H, m), 1.76-1.98 (6H, m), 2.70 (2H, t, J=7.8 Hz), 3.09 (2H, t, J=7.6 Hz), 3.68 (3H, s), 3.69 (3H, s), 4.80-4.83 (1H, m), 5.30 (2H, s), 6.37 (1H, dd, J=9.0, 2.4 Hz), 6.48 (1H, d, J=2.4 Hz), 6.93 (1H, d, J=8.4 Hz), 7.31-7.35 (2H, m), 7.49-7.57 (3H, m), 7.87 (1H, d, J=7.6 Hz), 12.67 (1H, s)

39(55)

NMR (400 MHz, CDCl$_3$) δ value: 1.64-1.96 (8H, m), 2.70 (2H, t, J=7.6 Hz), 3.09 (2H, t, J=7.6 Hz), 3.68 (3H, s), 4.18 (3H, s), 4.80-4.83 (1H, m), 5.32 (2H, s), 6.37 (1H, dd, J=9.0, 2.8 Hz), 6.48 (1H, d, J=2.8 Hz), 6.95 (1H, d, J=8.4 Hz), 7.33 (1H, d, J=7.2 Hz), 7.49-7.56 (4H, m), 7.66 (1H, d, J=8.0 Hz), 12.69 (1H, s)

39(56)

NMR (400 MHz, CDCl$_3$) δ value: 1.66 (9H, s), 1.75 (9H, s), 1.77-1.98 (8H, m), 2.66 (2H, t, J=7.6 Hz), 3.04 (2H, t, J=8.0 Hz), 3.66 (3H, s), 4.80-4.83 (1H, m), 5.19 (2H, s), 6.37 (1H, dd, J=9.0, 2.4 Hz), 6.48 (1H, d, J=2.4 Hz), 6.95 (1H, d, J=9.2 Hz), 7.06 (1H, d, J=8.4 Hz), 7.51 (1H, d, J=9.2 Hz), 7.52-7.54 (2H, m), 7.66 (1H, dd, J=8.4, 2.0 Hz), 8.11 (1H, d, J=2.0 Hz), 12.69 (1H, s)

39(57)

NMR (90 MHz, CDCl$_3$) δ value: 1.04 (6H, d, J=6.6 Hz), 1.18 (6H, d, J=6.4 Hz), 1.86-2.34 (1H, m), 2.53-2.70 (2H, m), 2.97-3.14 (2H, m), 3.79 (2H, d, J=6.4 Hz), 4.80-5.30 (1H, m), 5.21 (2H, s), 6.38-6.49 (2H, m), 6.98 (1H, d, J=9.0 Hz), 7.28-7.58 (4H, m), 7.81 (1H, d, J=7.3 Hz), 8.63 (1H, d, J=4.6 Hz), 8.71 (1H, s), 12.66 (1H, s)

39(58)

NMR (400 MHz, CDCl$_3$) δ value: 1.48 (3H, t, J=7.3 Hz), 1.63-1.67 (2H, m), 1.76-1.98 (6H, m), 2.70 (2H, t, J=7.6 Hz), 3.10 (2H, t, J=7.6 Hz), 3.68 (3H, s), 4.53 (2H, q, J=7.2 Hz), 4.80-4.84 (1H, m), 5.43 (2H, s), 6.37 (1H, dd, J=8.8, 2.4 Hz), 6.48 (1H, d, J=2.4 Hz), 6.97 (1H, d, J=8.4 Hz), 7.49 (1H, d, J=8.8 Hz), 7.54-7.57 (2H, m), 8.98 (1H, s), 9.31 (1H, d, J=1.2 Hz), 12.66 (1H, s)

39(59)

NMR (90 MHz, CDCl$_3$) δ value: 1.39 (3H, t, J=7.1 Hz), 1.5-2.1 (8H, m), 2.6-2.7 (2H, m), 2.9-3.1 (2H, m), 3.66 (3H, s), 4.38 (2H, q, J=7.1 Hz), 4.7-4.9 (1H, m), 5.19 (2H, s), 6.3-6.6 (3H, m), 6.93 (1H, d, J=9.0 Hz), 7.17 (1H, d, J=3.4 Hz), 7.4-7.6 (3H, m), 12.67 (1H, s)

39(60)

NMR (90 MHz, CDCl$_3$) δ value: 1.2-2.1 (11H, m), 2.71 (2H, t, J=6.8 Hz), 3.11 (2H, t, J=8.0 Hz), 3.68 (3H, s), 4.46 (2H, q, J=7.1 Hz), 4.7-5.0 (1H, m), 5.52 (2H, s), 6.3-6.5 (2H, m), 6.98 (1H, d, J=9.0 Hz), 7.4-7.6 (3H, m), 8.24 (1H, s), 12.65 (1H, s)

39(61)

NMR (90 MHz, CDCl$_3$) δ value: 0.90 (6H, d, J=6.6 Hz), 1.08 (6H, d, J=6.6 Hz), 1.6-3.1 (6H, m), 2.74 (3H, s), 3.83 (2H, d, J=6.4 Hz), 3.86 (2H, d, J=6.6 Hz), 5.20 (2H, s), 6.4-6.7 (2H, m), 6.89 (1H, d, J=9.3 Hz), 7.18 (1H, s), 7.4-7.6 (3H, m), 12.67 (1H, s)

39(62)

NMR (90 MHz, CDCl$_3$) δ value: 0.90 (6H, d, J=6.6 Hz), 1.08 (6H, d, J=6.6 Hz), 1.63-2.40 (2H, m), 2.63-2.74 (2H, m), 2.94-3.12 (2H, m), 3.83 (2H, d, J=6.4 Hz), 3.86 (2H, d, J=6.6 Hz), 5.14 (2H, s), 6.46-6.61 (2H, m), 6.89 (1H, d, J=9.3 Hz), 7.33-7.82 (5H, m), 8.58-8.69 (2H, m), 12.67 (1H, s)

39(63)

NMR (90 MHz, CDCl$_3$) δ value: 0.90 (6H, d, J=6.6 Hz), 1.08 (6H, d, J=6.6 Hz), 1.68-2.32 (2H, m), 2.55-2.74 (2H, m), 2.94-3.13 (2H, m), 3.83 (2H, d, J=6.4 Hz), 3.86 (2H, d, J=6.6 Hz), 3.93 (3H, s), 5.18 (2H, s), 6.43-6.56 (2H, m), 6.89 (1H, d, J=9.0 Hz), 7.45-7.63 (5H, m), 8.08 (2H, d, J=8.3 Hz), 12.66 (1H, s)

39(64)

NMR (90 MHz, CDCl$_3$) δ value: 0.90 (6H, d, J=6.6 Hz), 1.08 (6H, d, J=6.6 Hz), 1.6-2.4 (2H, m), 2.5-2.8 (2H, m), 2.9-3.1 (2H, m), 3.83 (2H, d, J=6.1 Hz), 3.86 (2H, d, J=6.6 Hz), 5.27 (2H, s), 6.4-6.6 (2H, m), 6.89 (1H, d, J=9.0 Hz), 7.2-7.9 (6H, m), 8.61 (1H, d, J=4.6 Hz), 12.64 (1H, s)

Example 40

1.50 g of methyl 3-{5-[4-(cyclopentyloxy)-2-hydroxybenzoyl]-2-hydroxyphenyl} propanoate, 1.04 g of methyl 3-(hydroxymethyl)-1-benzothiophene-7-carboxylate, and 1.23 g of triphenylphosphine were dissolved in 15 mL of tetrahydrofuran, to which 0.92 mL of diisopropyl azodicarboxylate was added dropwise at temperatures of 19 to 32° C., and this mixture was stirred for one hour at room temperature. The reaction mixture was poured into a mixture of ethyl acetate and water, and the organic phase was separated therefrom. After the resultant organic phase was washed with water and a saturated sodium chloride solution successively, the washed phase was dried over anhydrous magnesium sulfate and the solvent was distilled out thereof under reduced pressure. The resultant residue was purified by silica gel column chromatography [eluent; hexane:ethyl acetate=3:1] to yield 1.70 g of methyl 3-{[4-[4-(cyclopentyloxy)-2-hydroxybenzoyl]-2-(3-methoxy-3-oxopropyl) phenoxy]methyl}-1-benzothiophene-7-carboxylate as light yellow solid.

NMR (400 MHz, CDCl$_3$) δ value: 1.61-1.68 (2H, m), 1.76-1.98 (6H, m), 2.61 (2H, t, J=7.6 Hz), 3.00 (2H, t, J=7.6 Hz), 3.62 (3H, s), 4.04 (3H, s), 4.80-4.84 (1H, m), 5.43 (2H, s), 6.38 (1H, dd, J=9.2, 2.4 Hz), 6.48 (1H, d, J=2.0 Hz), 7.10 (1H, d, J=8.4 Hz), 7.51-7.59 (4H, m), 7.67 (1H, s), 8.08 (1H, d, J=7.6 Hz), 8.18 (1H, d, J=7.6 Hz), 12.70 (1H, s)

Example 41

1.20 g of methyl 3-{5-[4-(cyclopentyloxy)-2-hydroxybenzoyl]-2-hydroxyphenyl} propanoate, 0.773 g of ethyl(E)-3-[4-(hydroxymethyl)phenyl]-2-propenoate, and 0.984 g of triphenylphosphine were dissolved in 12 mL of tetrahydrofuran, to which 0.74 mL of diisopropyl azodicarboxylate was added dropwise at temperatures of 20 to 31° C., and this mixture was stirred for 30 minutes at room temperature. The reaction mixture was poured into a mixture of ethyl acetate and water, and the organic phase was separated therefrom. After the resultant organic phase was washed with water and a saturated sodium chloride solution successively, the washed phase was dried over anhydrous magnesium sulfate and the solvent was distilled out thereof under reduced pressure. The resultant residue was purified by silica gel column chromatography [eluent; hexane:ethyl acetate=3:1] to yield 1.33 g of ethyl (E)-3-(4-{[4-[4-(cyclopentyloxy)-2-hydroxybenzoyl]-2-(3-methoxy-3-oxopropyl) phenoxy]methyl}phenyl)-2-propenoate as yellow oil.

NMR (400 MHz, CDCl$_3$) δ value: 1.35 (3H, t, J=7.1 Hz), 1.57-1.64 (2H, m), 1.76-1.98 (6H, m), 2.68 (2H, t, J=7.6 Hz), 3.06 (2H, t, J=7.6 Hz), 3.67 (3H, s), 4.28 (2H, q, J=7.1 Hz), 4.81-4.82 (1H, m), 5.20 (2H, s), 6.37 (1H, dd, J=8.8, 2.2 Hz), 6.46 (1H, d, J=15.6 Hz), 6.48 (1H, d, J=2.4 Hz), 6.94 (1H, d, J=8.0 Hz), 7.46 (2H, d, J=8.0 Hz), 7.50-7.55 (3H, m), 7.57 (2H, d, J=8.0 Hz), 7.70 (1H, d, J=16.0 Hz), 12.69 (1H, s)

Example 42

Compounds listed in Tables 22 to 25 and Table 25-2 were obtained in a similar manner to in Example 40.

Each of the compounds 42(6) and 42(22) to 42(25) in these Tables were synthesized from a compound having a hydrogen atom as $R^{4z}$, in order to replace the hydrogen by another $R^{4z}$ group.

TABLE 22

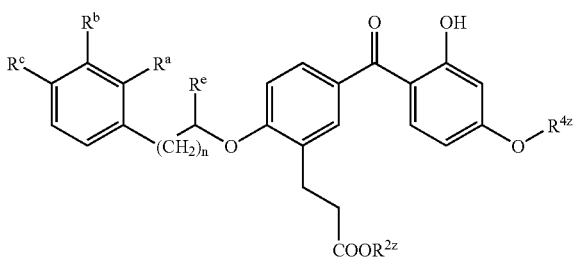

| Example Number | n | $R^{2z}$ | $R^{4z}$ | $R^a$ | $R^b$ | $R^c$ | $R^e$ |
|---|---|---|---|---|---|---|---|
| 42(1) | 0 | methyl | cyclopentyl | H | H | $CH_2CH_2COOEt$ | H |
| 42(2) | 0 | methyl | cyclopentyl | Me | H | COOMe | H |
| 42(3) | 0 | isopropyl | isobutyl | H | H | MeS | H |
| 42(4) | 0 | methyl | cyclopentyl | H | MeO | $CH_2CH_2COOEt$ | H |
| 42(5) | 0 | methyl | cyclopentyl | H | H | COOMe | Me |
| 42(6) | 0 | methyl | (methylcyclopentenyl) | H | H | COOMe | H |
| 42(7) | 1 | isopropyl | isobutyl | H | COOMe | H | H |
| 42(8) | 1 | issopropyl | isobutyl | H | H | COOMe | H |
| 42(9) | 0 | methyl | cyclopentyl | H | $CH_2CH_2COOMe$ | MeO | H |

TABLE 23

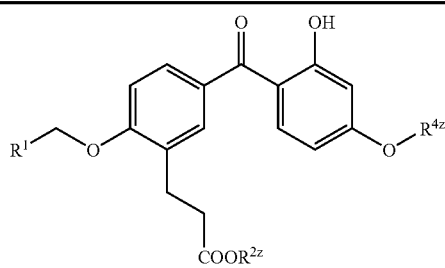

| Example Number | $R^1$ | $R^{2z}$ | $R^{4z}$ |
|---|---|---|---|
| 42(10) | mixture of (N-Tr benzimidazolyl) and (N-Tr benzimidazolyl) | Me | cyclopentyl |
| 42(11) | (N-Me dioxopiperazinyl-phenyl) | Me | cyclopentyl |

TABLE 23-continued

[Structure: benzophenone core with R¹-O-CH₂- on left ring, OH on right ring, O-R⁴ᶻ on right ring, and -CH₂CH₂-COOR²ᶻ substituent]

| Example Number | R¹ | R²ᶻ | R⁴ᶻ |
|---|---|---|---|
| 42(12) | 2-methyl-6-(MeOOC)-benzothiazol-yl | Me | cyclopentyl |
| 42(13) | 5-methyl-benzo[1,3]dioxol-yl | Me | cyclopentyl |
| 42(14) | 3-(4-methylphenyl)-oxazolidin-2-one-yl | Me | cyclopentyl |
| 42(15) | 3-methyl-5-(MeOOC)-benzothiophen-yl | Me | cyclopentyl |
| 42(16) | 2-methyl-5-(MeOOC)-benzothiophen-yl | i-Pr | isobutyl |

TABLE 24

| Example Number | R¹ | R²ᶻ | R⁴ᶻ |
|---|---|---|---|
| 42(17) | 2-methyl-5-(MeOOC)-benzothiophen-yl | Me | isopropyl |
| 42(18) | 2-methyl-5-(MeOOC)-benzothiophen-yl | Me | cyclopentyl |
| 42(19) | 5-methyl-2-(MeOOC)-thiophen-yl | Me | isobutyl |
| 42(20) | 5-methyl-2-(EtOOC)-pyridin-yl | Me | isobutyl |
| 42(21) | 5-methyl-2-(EtOOC)-benzothiophen-yl | Me | cyclopentyl |

TABLE 25

Structure: 2-hydroxy-4-(OR^4z)-phenyl ketone with 4-isobutoxy-3-(CH2CH2COO-i-Bu)-phenyl group

| Example Number | R^4z |
|---|---|
| 42(22) | 3-methyl-N-Boc-pyrrolidinyl |
| 42(23) | 4-nitrophenylpropyl |
| 42(24) | cyclopentylmethyl |
| 42(25) | (5-ethyl-2-COOEt-pyridinyl) |

TABLE 25-2

Structure: H3COOC-C6H4-(CH2)n-O- on one phenyl (with CH2CH2COOR^2z substituent) ketone-linked to 2-hydroxy-4-(OR^4z)-phenyl

| Example Number | n | R^2z | R^4z |
|---|---|---|---|
| 42(26) | 1 | methyl | O-furfuryl |
| 42(27) | 1 | methyl | O-2-thenyl |

42(1)

NMR (400 MHz, CDCl$_3$) δ value: 1.24 (3H, t, J=7.2 Hz), 1.62-1.66 (2H, m), 1.76-1.98 (6H, m), 2.64 (2H, t, J=7.6 Hz), 2.67 (2H, t, J=7.6 Hz), 2.98 (2H, t, J=7.6 Hz), 3.04 (2H, t, J=7.6 Hz), 3.66 (3H, s), 4.13 (2H, q, J=7.2 Hz), 4.80-4.83 (1H, m), 5.15 (2H, s), 6.37 (1H, dd, J=8.8, 2.4 Hz), 6.47 (1H, d, J=2.4 Hz), 6.96 (1H, d, J=9.0 Hz), 7.22 (2H, d, J=8.0 Hz), 7.36 (2H, d, J=8.0 Hz), 7.50-7.54 (3H, m), 12.70 (1H, s)

42(2)

NMR (400 MHz, CDCl$_3$) δ value: 1.5-2.0 (8H, m), 2.43 (3H, s), 2.66 (2H, t, J=7.6 Hz), 3.06 (2H, t, J=7.6 Hz), 3.66 (3H, s), 3.93 (3H, s), 4.8-4.9 (1H, m), 5.19 (2H, s), 6.37 (1H, dd, J=9.2, 2.4 Hz), 6.48 (1H, d, J=2.4 Hz), 6.97 (1H, d, J=9.2 Hz), 7.4-7.6 (4H, m), 7.91-7.92 (2H, m), 12.70 (1H, s)

42(3)

NMR (90 MHz, CDCl$_3$) δ value: 1.03 (6H, d, J=6.6 Hz), 1.19 (6H, d, J=6.4 Hz), 1.98-2.28 (1H, m), 2.50-2.70 (5H, m), 2.93-3.11 (2H, m), 3.78 (2H, d, J=6.6 Hz), 4.92-5.14 (3H, m), 6.35-6.50 (2H, m), 6.95 (1H, d, J=9.4 Hz), 7.32-7.57 (7H, m), 12.67 (1H, s)

42(4)

NMR (400 MHz, CDCl$_3$) δ value: 1.24 (3H, t, J=7.1 Hz), 1.60-1.67 (2H, m), 1.78-1.96 (6H, m), 2.61 (2H, t, J=7.8 Hz), 2.69 (2H, t, J=7.6 Hz), 2.95 (2H, t, J=7.8 Hz), 3.05 (2H, t, J=7.6 Hz), 3.65 (3H, s), 3.85 (3H, s), 4.13 (2H, q, J=7.1 Hz), 4.81-4.82 (1H, m), 5.14 (2H, s), 6.37 (1H, dd, J=8.8, 2.2 Hz), 6.47 (1H, d, J=2.0 Hz), 6.91-6.98 (3H, m), 7.17 (1H, d, J=7.3 Hz), 7.50-7.54 (3H, m), 12.70 (1H, s)

42(5)

NMR (400 MHz, CDCl$_3$) δ value: 1.57-1.63 (2H, m), 1.70 (3H, d, J=6.4 Hz), 1.75-1.95 (6H, m), 2.73 (2H, dt, J=7.6, 2.8 Hz), 3.10 (2H, dt, J=7.6, 2.8 Hz), 3.70 (3H, s), 3.91 (3H, s), 4.79-4.81 (1H, m), 5.45 (1H, q, J=6.4 Hz), 6.34 (1H, dd, J=8.8, 2.4 Hz), 6.45 (1H, d, J=2.4 Hz), 6.68 (1H, d, J=8.8 Hz), 7.37 (1H, dd, J=8.4, 2.0 Hz), 7.43-7.47 (3H, m), 7.51 (1H, d, J=1.6 Hz), 8.04 (2H, d, J=8.4 Hz), 12.72 (1H, s)

42(6)

NMR (400 MHz, CDCl$_3$) δ value: 2.59 (2H, d, J=17.6 Hz), 2.69 (2H, t, J=7.6 Hz), 2.85 (2H, dd, J=16.4, 6.4 Hz), 3.08 (2H, t, J=7.6 Hz), 3.67 (3H, s), 3.94 (3H, s), 5.0-5.1 (1H, m), 5.24 (2H, s), 5.77 (2H, s), 6.38 (1H, dd, J=9.0, 2.4 Hz), 6.48 (1H, d, J=2.4 Hz), 6.93 (1H, d, J=8.8 Hz), 7.5-7.6 (5H, m), 8.09 (2H, d, J=8.0 Hz), 12.70 (1H, s)

42(7)

NMR (90 MHz, CDCl$_3$) δ value: 1.03 (6H, d, J=6.6 Hz), 1.20 (6H, d, J=6.4 Hz), 1.97-2.25 (1H, m), 2.48-2.56 (2H, m), 2.85-3.28 (4H, m), 3.78 (2H, d, J=6.1 Hz), 3.92 (3H, s), 4.30 (2H, t, J=6.7 Hz), 4.88-5.15 (1H, m), 6.36-6.48 (2H, m), 6.82-6.95 (1H, m), 7.40-7.64 (5H, m), 7.90-8.00 (2H, m), 12.66 (1H, s)

42(8)

NMR (90 MHz, CDCl$_3$) δ value: 1.03 (6H, d, J=6.6 Hz), 1.22 (6H, d, J=6.4 Hz), 1.98-2.25 (1H, m), 2.40-2.56 (2H, m), 2.85-3.03 (2H, m), 3.15-3.28 (2H, m), 3.78 (2H, d, J=6.4 Hz), 3.91 (3H, s), 4.23-4.37 (2H, m), 4.94-5.08 (1H, m), 6.36-6.48 (2H, m), 6.88 (1H, d, J=9.1 Hz), 7.34-7.55 (5H, m), 8.01 (2H, d, J=8.1 Hz), 12.65 (1H, s)

42(9)

NMR (400 MHz, CDCl$_3$) δ value: 1.60-1.68 (2H, m), 1.78-1.96 (6H, m), 2.63 (2H, t, J=7.6 Hz), 2.66 (2H, t, J=7.6 Hz), 2.96 (2H, t, J=7.6 Hz), 3.02 (2H, t, J=7.6 Hz), 3.65 (3H, s), 3.66 (3H, s), 3.85 (3H, s), 4.79-4.84 (1H, m), 5.08 (2H, s), 6.37 (1H, d, J=9.3 Hz), 6.47 (1H, s), 6.87 (1H, d, J=8.3 Hz), 6.97 (1H, d, J=8.6 Hz), 7.22-7.28 (2H, m), 7.51-7.55 (3H, m), 12.71 (1H, s)

42(10)

R$^1$ is a 1-trityl-1H-benzimidazol-6-yl substituent.

NMR (400 MHz, CDCl$_3$) δ value: 1.62-1.66 (2H, m), 1.78-1.95 (6H, m), 2.66 (2H, t, J=7.6 Hz), 3.03 (2H, t, J=7.6 Hz), 3.63 (3H, s), 4.80-4.83 (1H, m), 5.21 (2H, s), 6.37 (1H, dd, J=9.0, 2.4 Hz), 6.47-6.53 (2H, m), 6.96-7.00 (1H, m), 7.14-7.35 (16H, m), 7.40 (1H, dd, J=8.4, 2.4 Hz), 7.47-7.53 (2H, m), 7.85 (1H, s), 7.92 (1H, s), 12.72 (1H, s)

R$^1$ is a 1-trityl-1H-benzimidazol-5-yl substituent.

NMR (400 MHz, CDCl$_3$) δ value: 1.62-1.66 (2H, m), 1.78-1.95 (6H, m), 2.44 (2H, t, J=7.6 Hz), 2.84 (2H, t, J=7.6 Hz), 3.66 (3H, s), 4.80-4.83 (1H, m), 5.00 (2H, s), 6.37 (1H, dd, J=9.0, 2.4 Hz), 6.47-6.49 (1H, m), 6.63 (1H, d, J=8.8 Hz), 6.96-7.00 (1H, m), 7.14-7.35 (16H, m), 7.47-7.53 (3H, m), 7.80 (1H, d, J=8.4 Hz), 7.89 (1H, s), 12.74 (1H, s)

42(11)

NMR (400 MHz, CDCl$_3$) δ value: 1.62-1.67 (2H, m), 1.76-1.98 (6H, m), 2.68 (2H, t, J=7.6 Hz), 3.05 (2H, t, J=7.6 Hz), 3.18 (3H, s), 3.67 (3H, s), 3.72 (2H, t, J=5.6 Hz), 4.01 (2H, t, J=5.6 Hz), 4.80-4.83 (1H, m), 5.18 (2H, s), 6.37 (1H, dd, J=9.0, 2.4 Hz), 6.48 (1H, d, J=2.4 Hz), 6.95 (1H, d, J=9.2 Hz), 7.40 (2H, d, J=8.4 Hz), 7.48-7.54 (5H, m), 12.69 (1H, s)

42(12)

NMR (400 MHz, CDCl$_3$) δ value: 1.62-1.67 (2H, m), 1.76-1.98 (6H, m), 2.76 (2H, t, J=7.6 Hz), 3.14 (2H, t, J=7.6 Hz), 3.70 (3H, s), 3.99 (3H, s), 4.79-4.83 (1H, m), 5.60 (2H, s), 6.37 (1H, dd, J=9.2, 2.4 Hz), 6.48 (1H, d, J=2.4 Hz), 7.03 (1H, d, J=8.8 Hz), 7.49 (1H, d, J=8.8 Hz), 7.52-7.59 (2H, m), 7.98 (1H, d, J=8.4 Hz), 8.11 (1H, dd, J=8.6, 2.4 Hz), 8.72 (1H, d, J=1.2 Hz), 12.66 (1H, s)

42(13)

NMR (400 MHz, CDCl$_3$) δ value: 1.60-1.68 (2H, m), 1.76-1.98 (6H, m), 2.66 (2H, t, J=7.8 Hz), 3.03 (2H, t, J=7.8 Hz), 3.66 (3H, s), 4.80-4.84 (1H, m), 5.07 (2H, s), 5.99 (2H, s), 6.37 (1H, dd, J=8.8, 2.4 Hz), 6.48 (1H, d, J=2.4 Hz), 6.83 (1H, d, J=8.0 Hz), 6.88-6.97 (3H, m), 7.50-7.55 (3H, m), 12.71 (1H, s)

42(14)

NMR (400 MHz, CDCl$_3$) δ value: 1.62-1.68 (2H, m), 1.76-1.98 (6H, m), 2.67 (2H, t, J=7.6 Hz), 3.04 (2H, t, J=7.6 Hz), 3.66 (3H, s), 4.09 (2H, t, J=8.0 Hz), 4.51 (2H, t, J=8.0 Hz), 4.80-4.83 (1H, m), 5.16 (2H, s), 6.37 (1H, dd, J=8.8, 2.4 Hz), 6.48 (1H, d, J=2.0 Hz), 6.96 (1H, d, J=8.8 Hz), 7.45 (2H, d, J=8.8 Hz), 7.50-7.56 (3H, m), 7.60 (2H, d, J=8.8 Hz), 12.70 (1H, s)

42(15)

NMR (400 MHz, CDCl$_3$) δ value: 1.62-1.68 (2H, m), 1.78-1.98 (6H, m), 2.64 (2H, t, J=7.6 Hz), 3.03 (2H, t, J=7.6 Hz), 3.61 (3H, s), 3.97 (3H, s), 4.80-4.84 (1H, m), 5.45 (2H, s), 6.38 (1H, dd, J=9.2, 2.4 Hz), 6.48 (1H, d, J=2.4 Hz), 7.09 (1H, d, J=8.4 Hz), 7.52-7.61 (4H, m), 7.95 (1H, d, J=8.4 Hz), 8.07 (1H, dd, J=8.6, 1.4 Hz), 8.56 (1H, s), 12.70 (1H, s)

42(16)

NMR (400 MHz, CDCl$_3$) δ value: 1.03 (6H, d, J=6.4 Hz), 1.18 (6H, d, J=6.4 Hz), 2.06-2.16 (1H, m), 2.66 (2H, t, J=7.6 Hz), 3.06 (2H, t, J=7.6 Hz), 3.78 (2H, d, J=6.8 Hz), 3.96 (3H, s), 4.95-5.04 (1H, m), 5.45 (2H, s), 6.42 (1H, dd, J=9.2, 2.4 Hz), 6.49 (1H, d, J=2.4 Hz), 7.02 (1H, d, J=8.8 Hz), 7.42 (1H, s), 7.51-7.57 (3H, m), 7.88 (1H, d, J=8.4 Hz), 8.01 (1H, dd, J=8.4, 1.6 Hz), 8.48 (1H, d, J=1.6 Hz), 12.66 (1H, s)

42(17)

NMR (400 MHz, CDCl$_3$) δ value: 1.38 (6H, d, J=6.0 Hz), 2.71 (2H, t, J=7.6 Hz), 3.06 (2H, t, J=7.6 Hz), 3.66 (3H, s), 3.97 (3H, s), 4.60-4.66 (1H, m), 5.45 (2H, s), 6.38 (1H, dd, J=8.8, 2.4 Hz), 6.48 (1H, d, J=2.4 Hz), 7.03 (1H, d, J=8.8 Hz), 7.43 (1H, s), 7.50-7.56 (3H, m), 7.88 (1H, d, J=8.4 Hz), 8.01 (1H, dd, J=8.4, 1.6 Hz), 8.48 (1H, d, J=1.6 Hz), 12.67 (1H, s)

42(18)

NMR (400 MHz, CDCl$_3$) δ value: 1.62-1.67 (2H, m), 1.76-1.98 (6H, m), 2.71 (2H, t, J=7.6 Hz), 3.06 (2H, t, J=7.6 Hz), 3.66 (3H, s), 3.96 (3H, s), 4.79-4.83 (1H, m), 5.45 (2H, s), 6.37 (1H, dd, J=9.2, 2.4 Hz), 6.48 (1H, d, J=2.4 Hz), 7.02 (1H, d, J=9.2 Hz), 7.42 (1H, s), 7.50 (1H, d, J=9.2 Hz), 7.54-7.56 (2H, m), 7.88 (1H, d, J=8.8 Hz), 8.01 (1H, dd, J=8.4, 1.6 Hz), 8.48 (1H, d, J=1.6 Hz), 12.68 (1H, s)

42(19)

NMR (90 MHz, CDCl$_3$) δ value: 1.03 (6H, d, J=6.6 Hz), 1.9-2.4 (1H, m), 2.6-3.2 (4H, m), 3.67 (3H, s), 3.78 (2H, d, J=6.6 Hz), 3.89 (3H, s), 5.34 (2H, s), 6.3-6.5 (2H, m), 6.97 (1H, d, J=9.0 Hz), 7.10 (1H, d, J=3.9 Hz), 7.4-7.6 (3H, m), 7.72 (1H, d, J=3.9 Hz), 12.68 (1H, s)

42(20)

NMR (90 MHz, CDCl$_3$) δ value: 1.03 (6H, d, J=6.7 Hz), 1.46 (3H, t, J=7.1 Hz), 1.98-2.15 (1H, m), 2.64-2.73 (2H, m), 2.97-3.06 (2H, m), 3.66 (3H, s), 3.79 (2H, d, J=6.6 Hz), 4.51 (2H, q, J=7.1 Hz), 5.28 (2H, s), 6.38-6.51 (2H, m), 6.96 (1H, d, J=9.3 Hz), 7.46-7.60 (3H, m), 7.9-8.0 (1H, m), 8.21 (1H, d, J=7.6 Hz), 8.85 (1H, d, J=1.5 Hz), 12.63 (1H, s)

42(21)

NMR (400 MHz, CDCl$_3$) δ value: 1.42 (3H, t, J=7.2 Hz), 1.62-1.66 (2H, m), 1.76-1.97 (6H, m), 2.69 (2H, t, J=7.6 Hz), 3.07 (2H, t, J=7.6 Hz), 3.66 (3H, s), 4.42 (2H, q, J=7.2 Hz), 4.80-4.83 (1H, m), 5.29 (2H, s), 6.37 (1H, dd, J=8.8, 2.0 Hz), 6.48 (1H, d, J=2.0 Hz), 6.99 (1H, d, J=8.4 Hz), 7.50-7.55 (4H, m), 7.90 (1H, d, J=8.4 Hz), 7.94 (1H, s), 8.07 (1H, s), 12.70 (1H, s)

42(22)

NMR (90 MHz, CDCl$_3$) δ value: 0.90 (6H, d, J=6.6 Hz), 1.08 (6H, d, J=6.8 Hz), 1.48 (9H, s), 1.7-2.4 (4H, m), 2.5-2.8 (2H, m), 2.9-3.2 (2H, m), 3.4-4.0 (4H, m), 3.83 (2H, d, J=6.4 Hz), 3.86 (2H, d, J=6.6 Hz), 4.9-5.1 (1H, m), 6.3-6.5 (2H, m), 6.89 (1H, d, J=9.3 Hz), 7.5-7.6 (3H, m), 12.67 (1H, brs)

42(23)

NMR (90 MHz, CDCl$_3$) δ value: 0.89 (6H, d, J=6.6 Hz), 1.08 (6H, d, J=6.6 Hz), 1.7-2.4 (2H, m), 2.5-2.8 (2H, m), 2.9-3.3 (4H, m), 3.83 (2H, d, J=6.4 Hz), 3.85 (2H, d, J=6.6 Hz), 4.29 (2H, t, J=6.4 Hz), 6.3-6.5 (2H, m), 6.88 (1H, d, J=9.3 Hz), 7.4-7.6 (5H, m), 8.19 (2H, d, J=8.8 Hz), 12.66 (1H, s)

42(24)

NMR (90 MHz, CDCl$_3$) δ value: 0.90 (6H, d, J=6.6 Hz), 1.08 (6H, d, J=6.6 Hz), 1.4-2.3 (10H, m), 2.5-2.8 (2H, m), 2.9-3.2 (2H, m), 3.83 (2H, d, J=6.4 Hz), 3.86 (2H, d, J=6.6 Hz), 4.7-4.9 (1H, m), 6.3-6.5 (2H, m), 6.88 (1H, d, J=9.3 Hz), 7.2-7.6 (3H, m), 12.71 (1H, s)

42(25)

NMR (90 MHz, CDCl$_3$) δ value: 0.7-1.2 (12H, m), 1.46 (3H, t, J=7.1 Hz), 1.7-2.5 (2H, m), 2.4-3.2 (4H, m), 3.7-4.0 (4H, m), 4.54 (2H, q, J=7.1 Hz), 5.22 (2H, s), 6.4-6.7 (2H, m), 6.8-7.0 (1H, m), 7.4-7.7 (3H, m), 7.8-8.0 (1H, m), 8.19 (1H, d, J=7.3 Hz), 8.82 (1H, d, J=1.5 Hz), 12.65 (1H, s)

42(26)

NMR (400 MHz, CDCl$_3$) δ value: 2.69 (2H, t, J=7.6 Hz), 3.08 (2H, t, J=8.0 Hz), 3.66 (3H, s), 3.94 (3H, s), 5.06 (2H, s), 5.25 (2H, s), 6.40-6.41 (1H, m), 6.47-6.50 (2H, m), 6.62 (1H, d, J=2.8 Hz), 6.93 (1H, d, J=8.4 Hz), 7.47-7.56 (6H, m), 8.09 (2H, d, J=8.0 Hz), 12.66 (1H, s)

42(27)

NMR (400 MHz, CDCl$_3$) δ value: 2.69 (2H, t, J=7.6 Hz), 3.08 (2H, t, J=7.6 Hz), 3.67 (3H, s), 3.94 (3H, s), 5.25 (2H, s), 5.28 (2H, s), 6.49 (1H, dd, J=8.8, 2.8 Hz), 6.61 (1H, d, J=2.4 Hz), 6.93 (1H, d, J=8.4 Hz), 7.02-7.04 (1H, m), 7.15 (1H, d, J=3.6 Hz), 7.36 (1H, dd, J=5.2, 1.2 Hz), 7.50-7.56 (5H, m), 8.09 (2H, d, J=8.4 Hz), 12.65 (1H, s)

Example 43

Isopropyl 3-(5-(2-hydroxy-4-isobutoxybenzoyl)-2-{[(2S)-5-oxopyrrolizinyl]methoxy}phenylpropanoate was obtained in a similar manner as in Example 40.

NMR (90 MHz, CDCl₃) δ value: 0.6-1.6 (12H, m), 1.6-3.3 (9H, m), 3.4-4.4 (5H, m), 4.7-5.3 (1H, m), 6.2-7.8 (6H, m), 12.30 (1H, s), 12.63 (1H, s)

Example 44

1.16 g of methyl 4-{[4-[4-(cyclopentyloxy)-2-hydroxybenzoyl]-2-(3-methoxy-3-oxopropyl)phenoxy]methyl} benzoate was dissolved in 10 mL of methanol, to which 2.6 mL of a 20% aqueous solution of sodium hydroxide was added at room temperature, and this mixture was stirred for 30 minutes at the same temperature. Water and chloroform were successively added to the reaction mixture which was adjusted to pH 2 with 6M hydrochloric acid, and then the organic phase was separated therefrom. After the resultant organic phase was washed with water and a saturated sodium chloride solution successively, the washed phase was dried over anhydrous magnesium sulfate and the solvent was distilled out thereof under reduced pressure. The resultant residue was washed with hexane to yield 0.64 g of 4-({2-(2-carboxyethyl)-4-[4-(cyclopentyloxy)-2-hydroxybenzoyl]phenoxy}methyl) benzoic acid as light yellow solid.

NMR (90 MHz, DMSO-d₆) δ value: 1.21-3.02 (12H, m), 4.77-5.03 (1H, m), 5.35 (2H, s), 6.44-6.52 (2H, m), 7.17 (1H, d, J=9.3 Hz), 7.41-7.89 (5H, m), 8.00 (2H, d, J=8.3 Hz), 12.09 (3H, br)

Example 45

1.15 g of methyl 3-{[4-[4-(cyclopentyloxy)-2-hydroxybenzoyl]-2-(3-methoxy-3-oxopropyl)phenoxy]methyl}-1-benzothiophene-7-carboxylate was dissolved in a mixed solvent of 10 mL of methanol and 10 mL of tetrahydrofuran, to which 2 mL of a 5M aqueous solution of sodium hydroxide was added at room temperature, and then this mixture was stirred for 30 minutes at the same temperature, followed by addition thereto of 2 mL of water, and this mixture was stirred for another 30 minutes at temperatures of 50 to 60° C. The reaction mixture was cooled to room temperature, to which water was added, and then adjusted to pH 2 with 6M hydrochloric acid. Chloroform was added to this reaction mixture, and then the organic phase was separated therefrom. After the resultant organic phase was washed with water, the organic phase was separated and the solvent was distilled out thereof under reduced pressure. The resultant residue was washed with hexane to yield 1.00 g of 3-({2-(2-carboxyethyl)-4-[4-(cyclopentyloxy)-2-hydroxybenzoyl]phenoxy}methyl)-1-benzothiophene-7-carboxilic acid as light yellow solid.

NMR (400 MHz, DMSO-d₆) δ value: 1.60-1.76 (6H, m), 1.91-1.96 (2H, m), 2.50 (2H, t, J=8.0 Hz), 2.84 (2H, t, J=7.6 Hz), 4.86-4.91 (1H, m), 5.56 (2H, s), 6.48-6.51 (2H, m), 7.38 (1H, d, J=8.8 Hz), 7.47 (1H, d, J=8.8 Hz), 7.54 (1H, d, J=1.6 Hz), 7.58-7.61 (2H, m), 8.02 (1H, s), 8.10 (1H, d, J=7.6 Hz), 8.22 (1H, d, J=7.6 Hz), 12.07 (1H, brs)

Example 46

1.20 g of ethyl (E)-3-(4-{[4-[4-(cyclopentyloxy)-2-hydroxybenzoyl]-2-(3-methoxy-3-oxopropyl)phenoxy]methyl}phenyl)-2-propenoate was dissolved in a mixed solvent of 12 mL of methanol and 12 mL of tetrahydrofuran, to which 2.4 mL of a 20% aqueous solution of sodium hydroxide was added at room temperature, and then this mixture was stirred for one hour at the same temperature. The reaction mixture was concentrated under reduced pressure, to which water was added, and then adjusted to pH 2 with 6M hydrochloric acid. The resultant precipitate was filtered out and washed with water to yield 0.841 g of (E)-3-(4-{[4-[4-(cyclopentyloxy)-2-hydroxybenzoyl]-2-(3-hydroxy-3-oxopropyl)phenoxy]methyl}phenyl)-2-propenoic acid as light yellow solid.

NMR (400 MHz, DMSO-d₆) δ value: 1.60-1.74 (6H, m), 1.93-1.96 (2H, m), 2.57 (2H, t, J=7.3 Hz), 2.91 (2H, t, J=7.3 Hz), 4.89-4.92 (1H, m), 5.29 (2H, s), 6.48-6.50 (2H, m), 6.56 (1H, d, J=16.1 Hz), 7.18 (1H, d, J=9.3 Hz), 7.46 (1H, d, J=8.6 Hz), 7.52-7.56 (4H, m), 7.60 (1H, d, J=15.9 Hz), 7.74 (2H, d, J=8.0 Hz), 12.07 (3H, brs)

Example 47

16.5 g of methyl 3-(5-[4-(cyclopentyloxy)-2-hydroxybenzoyl]-2-{[4-(3-hydroxy-5-isoxoazolyl)benzyl]oxy}phenyl) propanoate was dissolved in a mixed solvent of 160 mL of methanol and 160 mL of tetrahydrofuran, to which 20 mL of a 20% aqueous solution of sodium hydroxide was added at room temperature, and then this mixture was stirred for 2 hours at the same temperature. Water was added to the reaction mixture, and then adjusted to pH 1 with 6M hydrochloric acid. This mixture was concentrated under reduced pressure, then resultant precipitate was filtered out. The resultant precipitate was dissolved in a mixed solvent of chloroform and methanol, and washed with water. The solvent was distilled out under reduced pressure to yield 14.3 g of 3-(5-[4-(cyclopentyloxy)-2-hydroxybenzoyl]-2-{[4-(3-hydroxy-5-isoxazolyl)benzyl]oxy}phenyl) propanoic acid as light yellow solid.

NMR (400 MHz, DMSO-d₆) δ value: 1.5-1.8 (6H, m), 1.9-2.0 (2H, m), 2.58 (2H, t, J=7.6 Hz), 2.91 (2H, t, J=7.6 Hz), 4.8-5.0 (1H, m), 5.33 (2H, s), 6.49 (1H, dd, J=8.8, 2.4 Hz), 6.52 (1H, d, J=2.4 Hz), 6.59 (1H, s), 7.19 (1H, m), 7.44 (1H, d, J=8.4 Hz), 7.5-7.6 (2H, m), 7.62 (2H, d, J=8.4 Hz), 7.85 (2H, d, J=8.0 Hz), 11.45 (1H, brs), 11.97 (2H, brs)

Example 48

0.98 g of methyl 4-{[4-[4-(cyclopentyloxy)-2-hydroxybenzoyl]-2-(3-methoxy-3-oxopropyl)phenoxy]methyl}-2-methoxybenzoate was dissolved in a mixed solvent of 10 mL of methanol and 10 mL of tetrahydrofuran, to which 2 mL of a 20% aqueous solution of sodium hydroxide was added at room temperature, and then this mixture was stirred for one hour at the same temperature. The reaction mixture to which water was added was adjusted to pH 2 with 6M hydrochloric acid, followed by the addition of ethyl acetate thereto, and the organic phase was separated therefrom. After the resultant organic phase was washed with water and a saturated sodium chloride solution successively, this washed phase was dried over anhydrous magnesium sulfate and the solvent was distilled out under reduced pressure. The resultant residue was recrystallized from ethanol to yield 0.42 g of 4-({2-(2-carboxyethyl)-4-[4-(cyclopentyloxy)-2-hydroxybenzoyl]phenoxy}methyl)-2-methoxybenzoic acid as light yellow solid.

NMR (400 MHz, DMSO-d₆) δ value: 1.60-1.74 (6H, m), 1.93-1.96 (2H, m), 2.59 (2H, t, J=7.6 Hz), 2.93 (2H, t, J=7.6 Hz), 3.84 (3H, s), 4.90-4.93 (1H, m), 5.30 (2H, s), 6.48-6.50 (2H, m), 7.10 (1H, d, J=9.0 Hz), 7.18 (1H, d, J=9.2 Hz), 7.27 (1H, s), 7.46 (1H, d, J=8.4 Hz), 7.55-7.57 (2H, m), 7.68 (1H, d, J=8.0 Hz), 12.04 (1H, s), 12.39 (2H, brs)

Example 49

Compounds listed in Tables 26 to 32 were obtained in a similar manner as in Example 44.

TABLE 26

| Example Number | n | $R^3$ | $R^4$ | $R^5$ | $R^a$ | $R^b$ | $R^c$ | $R^d$ | $R^e$ |
|---|---|---|---|---|---|---|---|---|---|
| 49(1) | 0 | OH | O-cyclopentyl | H | H | H | $CH_2CH_2COOH$ | H | H |
| 49(2) | 0 | OH | O-cyclopentyl | H | H | Me | COOH | H | H |
| 49(3) | 0 | OH | O-cyclopentyl | H | Me | H | COOH | H | H |
| 49(4) | 0 | OH | O-isobutyl | H | H | H | MeS | H | H |
| 49(5) | 0 | OH | O-isobutyl | H | H | H | MeS(O) | H | H |
| 49(6) | 0 | OH | O-isobutyl | H | H | H | $MeS(O)_2$ | H | H |
| 49(7) | 0 | OH | O-isobutyl | H | H | H | $CONH_2$ | H | H |
| 49(8) | 0 | OH | O-isobutyl | H | H | H | $CONHSO_2Me$ | H | H |
| 49(9) | 0 | O-isobutyl | O-isobutyl | H | H | H | COOH | H | H |
| 49(10) | 0 | MeO | O-cyclopentyl | H | H | H | COOH | H | H |
| 49(11) | 0 | OH | O-cyclopentyl | H | H | MeO | $CH_2CH_2COOH$ | H | H |
| 49(12) | 0 | OH | O-cyclopentyl | H | H | H | COOH | H | Me |
| 49(13) | 0 | OH | O-(cyclopent-3-en-1-yl) | H | H | H | COOH | H | H |
| 49(14) | 1 | OH | O-isobutyl | H | H | COOH | H | H | H |
| 49(15) | 1 | OH | O-isobutyl | H | H | H | COOH | H | H |
| 49(16) | 0 | OH | 2-thienyl | H | H | H | COOH | H | H |
| 49(17) | 0 | F | O-cyclopentyl | H | H | H | COOH | H | H |
| 49(18) | 0 | OH | O-isoamyl | H | H | H | COOH | H | H |
| 49(19) | 0 | OH | O-neopentyl | H | H | H | COOH | H | H |
| 49(20) | 0 | OH | O-cyclohexyl | H | H | H | COOH | H | H |
| 49(21) | 0 | OH | O-cyclopentyl | H | OMOM | H | COOH | H | H |
| 49(22) | 0 | OH | cyclopenthylmethyl | H | H | H | COOH | H | H |
| 49(23) | 0 | OH | O-cyclopentyl | H | H | H | $SO_2NH_2$ | H | H |
| 49(24) | 0 | OH | O-isobutyl | H | H | H | CN | H | H |
| 49(25) | 0 | OH | O-isobutyl | H | H | H | $NO_2$ | H | H |
| 49(26) | 0 | OH | isopropyl | H | H | H | COOH | H | H |
| 49(27) | 0 | OH | (1-methylcyclopentyl)-methyl | H | H | H | COOH | H | H |
| 49(28) | 0 | OH | O-cyclopentyl | H | H | H | $SO_2NMe_2$ | H | H |
| 49(29) | 0 | OH | O-cyclopentylmethyl | H | H | H | COOH | H | H |
| 49(30) | 0 | OH | O-(3-pyridyl)methyl | H | H | H | COOH | H | H |
| 49(31) | 0 | OH | O-cyclopentyl | H | H | MeO | COOH | MeO | H |
| 49(32) | 0 | OH | O-cyclopentyl | H | H | H | $CH_2COOH$ | H | H |

TABLE 27

| Example Number | n | $R^3$ | $R^4$ | $R^5$ | $R^a$ | $R^b$ | $R^c$ | $R^d$ | $R^e$ |
|---|---|---|---|---|---|---|---|---|---|
| 49(33) | 0 | OH | O-cyclobutyl | H | H | H | COOH | H | H |
| 49(34) | 0 | OH | O-benzyl | H | H | H | COOH | H | H |
| 49(35) | 0 | OH | O-cyclopentyl | H | H | H | $SO_2NHMe$ | H | H |
| 49(36) | 0 | OH | O-cyclopentyl | H | H | H | $CONMe_2$ | H | H |
| 49(37) | 0 | OH | O-cyclopentyl | H | H | H | $NHSO_2Me$ | H | H |
| 49(38) | 0 | OH | O-cyclopentyl | H | H | H | CONHMe | H | H |
| 49(39) | 0 | OH | cyclopentyl | H | H | H | COOH | H | H |
| 49(40) | 0 | OH | O-furfuryl | H | H | H | COOH | H | H |
| 49(41) | 0 | OH | O-2-thenyl | H | H | H | COOH | H | H |
| 49(42) | 0 | OH | O-cyclopentyl | H | H | F | COOH | H | H |
| 49(43) | 0 | OH | O-cyclopentyl | H | H | COOH | COOH | H | H |
| 49(44) | 0 | H | O-isobutyl | H | H | H | COOH | H | H |
| 49(45) | 0 | OH | O-isobutyl | H | O-i-Pr | H | COOH | H | H |
| 49(46) | 0 | OH | O-cyclopentyl | H | H | O-i-Bu | COOH | H | H |
| 49(47) | 0 | OH | O-isobutyl | H | H | H | COOH | H | H |
| 49(48) | 0 | OH | O-isobutyl | H | H | H | CONHOH | H | H |

TABLE 27-continued

| Example Number | n | $R^3$ | $R^4$ | $R^5$ | $R^a$ | $R^b$ | $R^c$ | $R^d$ | $R^e$ |
|---|---|---|---|---|---|---|---|---|---|
| 49(49) | 0 | OH | O-isobutyl | H | H | COOH | H | H | H |
| 49(50) | 0 | OH | O-isobutyl | H | COOH | H | H | H | H |
| 49(51) | 0 | OH | O-cyclopentyl | H | F | H | COOH | H | H |
| 49(52) | 0 | OH | O-cyclopentyl | F | H | H | COOH | H | H |
| 49(53) | 0 | Me | O-cyclopentyl | H | H | H | COOH | H | H |
| 49(54) | 0 | OH | O-cyclopentyl | H | H | H | $SO_3H$ | H | H |
| 49(55) | 0 | OH | $O-CH(CH_2CH_3)_2$ | H | H | H | COOH | H | H |
| 49(56) | 0 | OH | O-cyclohexymethyl | H | H | H | COOH | H | H |
| 49(57) | 0 | OH | O-cyclopropylmethyl | H | H | H | COOH | H | H |
| 49(58) | 0 | OH | O-cycloheptyl | H | H | H | COOH | H | H |
| 49(59) | 0 | OH | O-cyclopentyl | H | H | H | $P(O)(OEt)_2$ | H | H |
| 49(60) | 0 | OH | O-(2-pyrazinyl)-methyl | H | H | H | COOH | H | H |
| 49(61) | 0 | OH | O-cyclopentyl | H | H | $CH_2CH_2COOH$ | MeO | H | H |
| 49(62) | 0 | OH | O-cyclopentyl | H | H | H | $CONHSO_2Me$ | H | H |

TABLE 28

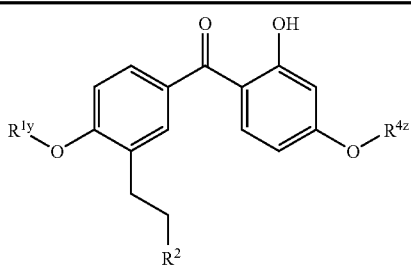

| Example Number | $R^{4z}$ | $R^{1y}$ | $R^2$ |
|---|---|---|---|
| 49(63) | cyclopentyl | 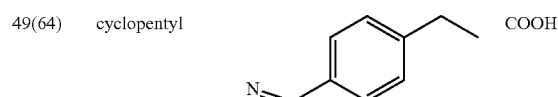 | COOH |
| 49(64) | cyclopentyl | 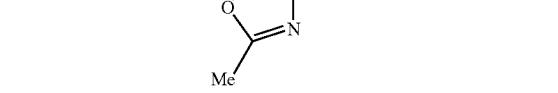 | COOH |
| 49(65) | cyclopentyl | | COOH |
| 49(66) | cyclopentyl | 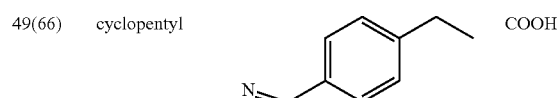 | COOH |

TABLE 28-continued

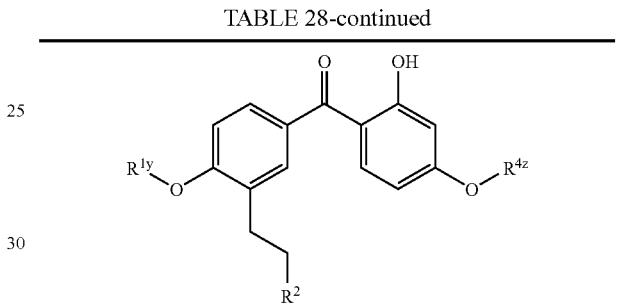

| Example Number | $R^{4z}$ | $R^{1y}$ | $R^2$ |
|---|---|---|---|
| 49(67) | cyclopentyl | 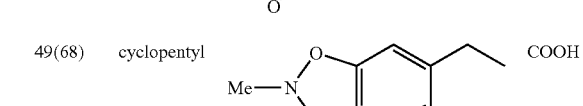 | COOH |
| 49(68) | cyclopentyl | 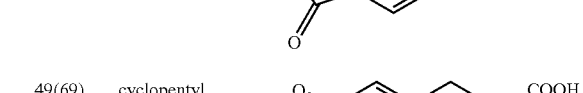 | COOH |
| 49(69) | cyclopentyl | | COOH |
| 49(70) | cyclopentyl | 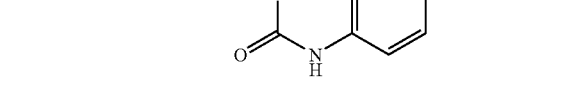 | COOH |
| 49(71) | isobutyl | 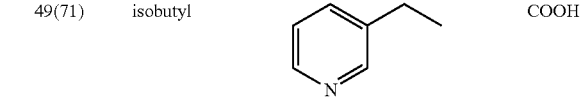 | COOH |

TABLE 29

| Example Number | $R^{4z}$ | $R^{1y}$ | $R^2$ |
|---|---|---|---|
| 49(72) | cyclopentyl | 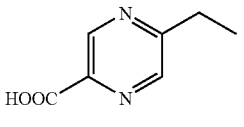 | COOH |
| 49(73) | cyclopentyl | 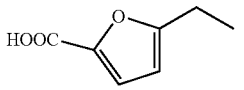 | COOH |
| 49(74) | cyclopentyl | 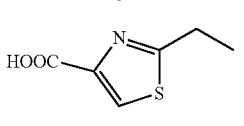 | COOH |
| 49(75) | cyclopentyl | 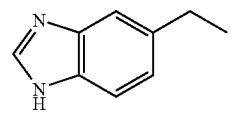 | COOH |
| 49(76) | cyclopentyl | 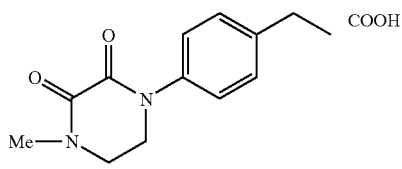 | COOH |
| 49(77) | cyclopentyl | 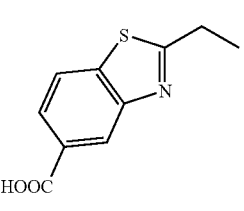 | COOH |
| 49(78) | cyclopentyl | 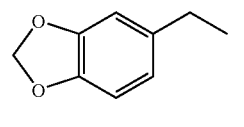 | COOH |
| 49(79) | cyclopentyl | 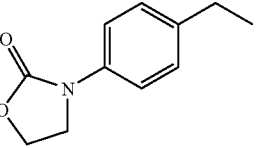 | COOH |
| 49(80) | cyclopentyl | 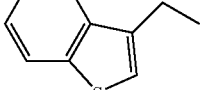 | COOH |

TABLE 30

| Example Number | $R^{4z}$ | $R^{1y}$ | $R^2$ |
|---|---|---|---|
| 49(81) | isobutyl | 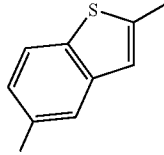 | COOH |
| 49(82) | isopropyl | 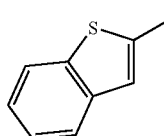 | COOH |
| 49(83) | cyclopentyl | 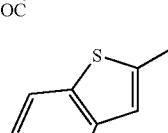 | COOH |
| 49(84) | isobutyl | 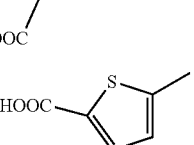 | COOH |
| 49(85) | isobutyl | 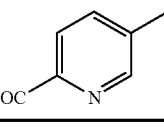 | COOH |

TABLE 31

| Example Number | $R^{4z}$ | $R^{1y}$ | $R^2$ |
|---|---|---|---|
| 49(86) | cyclopentyl | 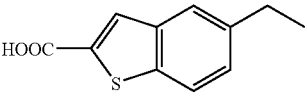 | COOH |
| 49(87) | cyclopentyl | 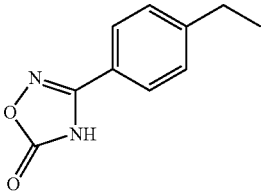 | COOH |

TABLE 31-continued

| Example Number | $R^{4z}$ | $R^{1y}$ | $R^2$ |
|---|---|---|---|
| 49(88) | isobutyl | (5-oxopyrrolidin-2-yl)ethyl | COOH |
| 49(89) | isobutyl | 4-ethylbenzoic acid | 5-methyl-1H-tetrazole |
| 49(90) | isobutyl | 4-(2H-tetrazol-5-yl)ethylphenyl | COOH |

TABLE 32

(Core structure: isobutoxy-benzoyl-hydroxyphenyl with propanoic acid and $OR^{4z}$ substituent)

| Example Number | $R^{4z}$ |
|---|---|
| 49(91) | 3-methylpyrrolidin-NH |
| 49(92) | 4-propylaniline |
| 49(93) | methylcyclopentyl |
| 49(94) | 5-ethylpyridine-2-carboxylic acid |
| 49(95) | 4-ethyl-2-methylthiazole |
| 49(96) | 3-ethylpyridine |

TABLE 32-continued

| Example Number | $R^{4z}$ |
|---|---|
| 49(97) | 4-ethylbenzoic acid |
| 49(98) | 2-ethylpyridine |

49(1)

NMR (400 MHz, DMSO-$d_6$) δ value: 1.60-1.74 (6H, m), 1.93-1.96 (2H, m), 2.55 (4H, t, J=7.6 Hz), 2.84 (2H, t, J=7.6 Hz), 2.88 (2H, t, J=7.6 Hz), 4.90-4.91 (1H, m), 5.21 (2H, s), 6.47-6.50 (2H, m), 7.19 (1H, d, J=8.4 Hz), 7.27 (2H, d, J=8.0 Hz), 7.40 (2H, d, J=8.0 Hz), 7.46 (1H, d, J=8.8 Hz), 7.53-7.55 (2H, m), 12.05 (1H, s), 12.13 (2H, brs)

49(2)

NMR (400 MHz, DMSO-$d_6$) δ value: 1.60-1.76 (6H, m), 1.94-1.96 (2H, m), 2.55 (3H, s), 2.58 (2H, t, J=7.2 Hz), 2.92 (2H, t, J=7.6 Hz), 4.89-4.91 (1H, m), 5.29 (2H, s), 6.48-6.50 (2H, m), 7.16-7.19 (1H, m), 7.39 (1H, d, J=8.0 Hz), 7.42 (1H, s), 7.46 (1H, d, J=8.4 Hz), 7.54-7.56 (2H, m), 7.87 (1H, d, J=8.0 Hz), 12.05 (1H, s), 12.47 (2H, brs)

49(3)

NMR (400 MHz, DMSO-$d_6$) δ value: 1.5-1.8 (6H, m), 1.8-2.0 (2H, m), 2.41 (3H, 3), 2.55 (2H, t, J=7.6 Hz), 2.90

(2H, t, J=7.6 Hz), 4.8-5.0 (1H, m), 5.30 (2H, s), 6.48-6.50 (2H, m), 7.25 (1H, d, J=8.4 Hz), 7.47 (1H, d, J=8.4 Hz), 7.5-7.6 (3H, m), 7.79 (1H, d, J=7.6 Hz), 7.82 (1H, s), 12.07 (3H, brs)

49(4)
NMR (90 MHz, CDCl$_3$) δ value: 1.01 (6H, d, J=6.6 Hz), 1.95-2.24 (1H, m), 2.49 (3H, s), 2.63-2.79 (2H, m), 2.95-3.10 (2H, m), 3.77 (2H, d, J=6.7 Hz), 5.12 (2H, s), 6.36-6.50 (2H, m), 6.95 (1H, d, J=9.1 Hz), 7.20-7.59 (7H, m), 12.66 (2H, brs)

49(5)
NMR (90 MHz, CDCl$_3$) δ value: 1.02 (6H, d, J=6.6 Hz), 1.95-2.30 (1H, m), 2.70-2.81 (5H, m), 3.00-3.20 (2H, m), 3.78 (2H, d, J=6.4 Hz), 5.24 (2H, s), 6.39-6.48 (2H, m), 6.95 (1H, d, J=9.3 Hz), 7.46-7.77 (7H, m), 12.63 (2H, brs)

49(6)
NMR (90 MHz, CDCl$_3$) δ value: 1.02 (6H, d, J=6.8 Hz), 1.95-2.30 (1H, m), 2.62-2.82 (2H, m), 2.96-3.16 (5H, m), 3.78 (2H, d, J=6.6 Hz), 5.27 (2H, s), 6.36-6.48 (2H, m), 6.93 (1H, d, J=9.3 Hz), 7.43-7.69 (5H, m), 8.00 (2H, d, J=8.4 Hz), 12.63 (2H, brs)

49(7)
NMR (400 MHz, DMSO-d$_6$) δ value: 0.98 (6H, d, J=6.8 Hz), 1.99-2.07 (1H, m), 2.57 (2H, t, J=7.6 Hz), 2.91 (2H, t, J=7.6 Hz), 3.83 (2H, d, J=6.6 Hz), 5.32 (2H, s), 6.52-6.55 (2H, m), 7.18 (1H, d, J=9.3 Hz), 7.38 (1H, brs), 7.47 (1H, d, J=9.5 Hz), 7.54-7.57 (4H, m), 7.91 (2H, d, J=8.3 Hz), 7.99 (1H, brs), 12.00 (1H, brs), 12.15 (1H, brs)

49(8)
NMR (90 MHz, DMSO-d$_6$) δ value: 0.99 (6H, d, J=6.6 Hz), 1.90-2.19 (1H, m), 2.50-2.64 (2H, m), 2.82-2.98 (2H, m), 3.32 (3H, s), 3.84 (2H, d, J=6.6 Hz), 5.36 (2H, s), 6.50-6.57 (2H, m), 7.13-7.68 (7H, m), 8.00 (2H, d, J=8.3 Hz), 11.99 (1H, s), 12.14 (1H, brs)

49(9)
NMR (90 MHz, DMSO-d$_6$) δ value: 0.67 (6H, d, J=6.8 Hz), 1.05 (6H, d, J=6.7 Hz), 1.60-1.88 (1H, m), 1.98-2.25 (1H, m), 2.67-2.75 (2H, m), 3.01-3.20 (2H, m), 3.61 (2H, d, J=6.3 Hz), 3.78 (2H, d, J=6.3 Hz), 5.22 (2H, s), 5.98 (2H, brs), 6.45-6.59 (2H, m), 6.87 (1H, d, J=9.3 Hz), 7.34-7.69 (5H, m), 8.12 (2H, d, J=8.1 Hz)

49(10)
NMR (400 MHz, DMSO-d$_6$) δ value: 1.5-1.8 (6H, m), 1.8-2.1 (2H, m), 2.53 (2H, t, J=7.6 Hz), 2.88 (2H, t, J=7.6 Hz), 3.65 (3H, s), 4.91-4.93 (1H, m), 5.33 (2H, s), 6.5-6.7 (2H, m), 7.11 (1H, d, J=8.8 Hz), 7.21 (1H, d, J=8.4 Hz), 7.51 (1H, dd, J=8.4, 2.4 Hz), 7.58-7.60 (3H, m), 7.89 (2H, d, J=8.4 Hz), 12.56 (2H, brs)

49(11)
NMR (400 MHz, DMSO-d$_6$) δ value: 1.60-1.74 (6H, m), 1.94-1.96 (2H, m), 2.48 (2H, t, J=7.3 Hz), 2.58 (2H, t, J=7.6 Hz), 2.78 (2H, t, J=7.6 Hz), 2.90 (2H, t, J=7.3 Hz), 3.82 (3H, s), 4.90-4.93 (1H, m), 5.21 (2H, s), 6.48-6.50 (2H, m), 6.98 (1H, d, J=7.3 Hz), 7.10 (1H, s), 7.16-7.21 (2H, m), 7.46 (1H, d, J=8.8 Hz), 7.54-7.57 (2H, m), 12.04 (1H, s), 12.13 (2H, brs)

49(12)
NMR (400 MHz, CDCl$_3$) δ value: 1.58-1.66 (2H, m), 1.71 (3H, d, J=6.4 Hz), 1.74-1.96 (6H, m), 2.84-2.88 (2H, m), 2.91-2.98 (1H, m), 3.33-3.41 (1H, m), 4.76-4.81 (1H, m), 5.51 (1H, q, J=6.4 Hz), 6.34 (1H, dd, J=8.8, 2.0 Hz), 6.44 (1H, d, J=2.4 Hz), 6.69 (1H, d, J=8.8 Hz), 7.37 (1H, dd, J=8.4, 1.2 Hz), 7.44 (1H, d, J=8.8 Hz), 7.51 (2H, d, J=8.4 Hz), 7.54 (1H, d, J=1.2 Hz), 8.12 (2H, d, J=8.0 Hz), 12.64 (1H, s)

49(13)
NMR (400 MHz, DMSO-d$_6$) δ value: 2.42 (2H, d, J=17.6 Hz), 2.57 (2H, t, J=7.6 Hz), 2.84 (2H, dd, J=16.8, 6.8 Hz), 2.92 (2H, t, J=7.6 Hz), 5.13-5.16 (1H, m), 5.35 (2H, s), 5.77 (2H, s), 6.48-6.52 (2H, m), 7.18 (1H, d, J=9.2 Hz), 7.46 (1H, d, J=8.4 Hz), 7.55-7.61 (4H, m), 7.98 (2H, d, J=8.0 Hz), 12.02 (3H, brs)

49(14)
NMR (90 MHz, DMSO-d$_6$) δ value: 0.98 (6H, d, J=6.6 Hz), 1.88-2.10 (1H, m), 2.38-2.52 (2H, m), 2.68-2.76 (2H, m), 3.09-3.23 (2H, m), 3.83 (2H, d, J=6.4 Hz), 4.26-4.33 (2H, m), 6.48-6.54 (2H, m), 7.12 (1H, d, J=9.5 Hz), 7.40-7.57 (5H, m), 7.77-7.94 (2H, m), 11.99 (1H, s), 12.46 (2H, brs)

49(15)
NMR (90 MHz, DMSO-d$_6$) δ value: 0.98 (6H, d, J=6.7 Hz), 1.90-2.18 (1H, m), 2.30-2.50 (2H, m), 2.67-2.86 (2H, m), 3.09-3.28 (2H, m), 3.83 (2H, d, J=6.4 Hz), 4.27-4.40 (2H, m), 6.50-6.54 (2H, m), 7.11 (1H, d, J=8.4 Hz), 7.40-7.58 (5H, m), 7.90 (2H, d, J=7.8 Hz), 11.99 (1H, s), 12.44 (2H, brs)

49(16)
NMR (400 MHz, DMSO-d$_6$) δ value: 2.90 (2H, t, J=7.6 Hz), 3.25 (2H, t, J=7.6 Hz), 5.69 (2H, s), 7.4-7.7 (4H, m), 7.75 (1H, d, J=8.4 Hz), 7.9-8.1 (6H, m), 8.31 (2H, d, J=8.0 Hz), 10.81 (1H, brs)

49(17)
NMR (400 MHz, DMSO-d$_6$) δ value: 1.61-1.76 (6H, m), 1.96-1.98 (2H, m), 2.55 (2H, t, J=7.2 Hz), 2.90 (2H, t, J=7.2 Hz), 4.93-4.94 (1H, m), 5.35 (2H, s), 6.85-6.91 (2H, m), 7.16 (1H, d, J=8.8 Hz), 7.45 (1H, t, J=8.8 Hz), 7.59-7.65 (4H, m), 7.98 (2H, d, J=8.0 Hz), 12.57 (2H, brs)

49(18)
NMR (400 MHz, DMSO-d$_6$) δ value: 0.94 (6H, d, J=6.8 Hz), 1.63 (2H, q, J=6.6 Hz), 1.74-1.79 (1H, m), 2.57 (2H, t, J=7.6 Hz), 2.92 (2H, t, J=7.6 Hz), 4.08 (2H, t, J=6.8 Hz), 5.35 (2H, s), 6.51-6.55 (2H, m), 7.18 (1H, d, J=9.3 Hz), 7.46 (1H, d, J=8.8 Hz), 7.54-7.56 (2H, m), 7.61 (2H, d, J=8.3 Hz), 7.99 (2H, d, J=8.3 Hz), 12.02 (3H, brs)

49(19)
NMR (400 MHz, DMSO-d$_6$) δ value: 1.00 (9H, s), 2.57 (2H, t, J=7.6 Hz), 2.92 (2H, t, J=7.6 Hz), 3.72 (2H, s), 5.35 (2H, s), 6.53-6.55 (2H, m), 7.18 (1H, d, J=9.2 Hz), 7.47 (1H, d, J=9.6 Hz), 7.54-7.56 (2H, m), 7.60 (2H, d, J=8.0 Hz), 7.98 (2H, d, J=8.0 Hz), 12.00 (3H, brs)

49(20)
NMR (90 MHz, DMSO-d$_6$) δ value: 1.0-2.2 (10H, m), 2.4-3.1 (4H, m), 4.3-4.7 (1H, m), 5.35 (2H, s), 6.4-6.6 (2H, m), 7.17 (1H, d, J-9.3 Hz), 7.4-7.7 (5H, m), 8.00 (2H, d, J=8.1 Hz), 11.6-12.9 (3H, br)

49(21)
NMR (400 MHz, DMSO-d$_6$) δ value: 1.60-1.74 (6H, m), 1.94-2.09 (2H, m), 2.56 (2H, t, J=7.6 Hz), 2.90 (2H, t, J=7.6 Hz), 3.43 (3H, s), 4.90-4.93 (1H, m), 5.30 (2H, s), 5.34 (2H, s), 6.48-6.50 (2H, m), 7.20 (1H, d, J=8.4 Hz), 7.47 (1H, d, J=8.4 Hz), 7.55-7.61 (3H, m), 7.64 (1H, dd, J=7.6, 1.2 Hz), 7.72 (1H, d, J=1.2 Hz), 12.05 (1H, s), 12.62 (2H, brs)

49(22)
NMR (400 MHz, DMSO-d$_6$) δ value: 1.16-1.21 (2H, m), 1.49-1.52 (2H, m), 1.60-1.68 (4H, m), 2.05-2.13 (1H, m), 2.54-2.59 (4H, m), 2.91 (2H, t, J=7.2 Hz), 5.35 (2H, s), 6.78 (1H, d, J=7.6 Hz), 6.81 (1H, s), 7.16 (1H, d, J=8.4 Hz), 7.32 (1H, d, J=8.0 Hz), 7.55 (1H, dd, J=8.4, 2.4 Hz), 7.59-7.62 (3H, m), 7.98 (2H, d, J=8.4 Hz), 10.81 (3H, brs)

49(23)

NMR (400 MHz, DMSO-d$_6$) δ value: 1.57-1.74 (6H, m), 1.80-1.98 (2H, m), 2.37 (2H, t, J=8.0 Hz), 2.85 (2H, t, J=7.6 Hz), 3.39 (2H, brs), 4.88-4.91 (1H, m), 5.33 (2H, s), 6.47-6.50 (2H, m), 7.14 (1H, d, J=8.4 Hz), 7.38 (2H, brs), 7.45 (1H, d, J=8.8 Hz), 7.51-7.54 (2H, m), 7.67 (2H, d, J=8.4 Hz), 7.86 (2H, d, J=8.4 Hz)

49(24)

NMR (90 MHz, CDCl$_3$) δ value: 1.02 (6H, d, J=6.6 Hz), 1.86-2.24 (1H, m), 2.64-3.18 (4H, m), 3.77 (2H, d, J=6.3 Hz), 5.23 (2H, s), 6.36-6.48 (2H, m), 6.92 (1H, d, J=9.0 Hz), 7.45-7.76 (7H, m), 8.74 (1H, brs), 12.62 (1H, s)

49(25)

NMR (90 MHz, CDCl$_3$) δ value: 1.02 (6H, d, J=6.6 Hz), 1.9-2.4 (1H, m), 2.75 (2H, t, J=6.8 Hz), 3.09 (2H, t, J=6.8 Hz), 3.77 (2H, d, J=6.3 Hz), 5.28 (2H, s), 6.3-6.6 (2H, m), 6.92 (1H, d, J=9.3 Hz), 7.4-7.8 (5H, m), 8.27 (2H, d, J=8.3 Hz), 12.61 (2H, brs)

49(26)

NMR (400 MHz, DMSO-d$_6$) δ value: 1.22 (6H, d, J=6.8 Hz), 2.56 (2H, t, J=7.6 Hz), 2.86-2.93 (3H, m), 5.35 (2H, s), 6.83-6.86 (2H, m), 7.16 (1H, d, J=8.8 Hz), 7.35 (1H, d, J=8.0 Hz), 7.56 (1H, dd, J=8.4, 2.4 Hz), 7.60-7.63 (3H, m), 7.98 (2H, d, J=8.4 Hz), 10.83 (3H, brs)

49(27)

NMR (400 MHz, DMSO-d$_6$) δ value: 0.90 (3H, s), 1.24-1.31 (2H, m), 1.48-1.55 (2H, m), 1.60-1.67 (4H, m), 2.54-2.58 (4H, m), 2.91 (2H, t, J=7.6 Hz), 5.34 (2H, s), 6.75 (1H, d, J=8.0 Hz), 6.79 (1H, s), 7.16 (1H, d, J=8.8 Hz), 7.31 (1H, d, J=8.0 Hz), 7.55 (1H, dd, J=8.4, 2.0 Hz), 7.60 (2H, d, J=8.4 Hz), 7.63 (1H, d, J=2.0 Hz), 7.98 (2H, d, J=8.4 Hz), 10.73 (3H, brs)

49(28)

NMR (400 MHz, DMSO-d$_6$) δ value: 1.57-1.78 (6H, m), 1.91-2.00 (2H, m), 2.58 (2H, t, J=7.6 Hz), 2.63 (6H, s), 2.94 (2H, t, J=7.2 Hz), 4.89-4.93 (1H, m), 5.40 (2H, s), 6.48-6.51 (2H, m), 7.19 (1H, d, J=9.6 Hz), 7.46 (1H, d, J=8.4 Hz), 7.56 (2H, s), 7.77 (2H, d, J=8.4 Hz), 7.81 (2H, d, J=8.4 Hz), 12.08 (2H, brs)

49(29)

NMR (400 MHz, DMSO-d$_6$) δ value: 1.30-1.35 (2H, m), 1.54-1.62 (4H, m), 1.74-1.80 (2H, m), 2.28-2.35 (1H, m), 2.57 (2H, t, J=7.6 Hz), 2.92 (2H, t, J=7.6 Hz), 3.93 (2H, d, J=7.2 Hz), 5.35 (2H, s), 6.51-6.54 (2H, m), 7.18 (1H, d, J=9.2 Hz), 7.46 (1H, d, J=9.2 Hz), 7.54-7.56 (2H, m), 7.61 (2H, d, J=8.4 Hz), 7.99 (2H, d, J=8.4 Hz), 12.00 (3H, brs)

49(30)

NMR (90 MHz, DMSO-d$_6$) δ value: 2.40-3.10 (4H, m), 5.25 (2H, s), 5.35 (2H, s), 6.40-6.70 (2H, m), 7.17 (1H, d, J=9.3 Hz), 7.4-7.7 (6H, m), 7.80-8.10 (3H, m), 8.50-8.80 (2H, m), 11.5-12.9 (3H, br)

49(31)

NMR (400 MHz, DMSO-d$_6$) δ value: 1.60-1.74 (6H, m), 1.94-1.99 (2H, m), 2.60 (2H, t, J=7.6 Hz), 2.93 (2H, t, J=7.6 Hz), 3.78 (6H, s), 4.90-4.91 (1H, m), 5.25 (2H, s), 6.49 (1H, dd, J=7.6, 2.2 Hz), 6.51 (1H, s), 6.84 (2H, s), 7.19 (1H, d, J=9.3 Hz), 7.46 (1H, d, J=9.3 Hz), 7.56-7.58 (2H, m), 12.02 (1H, s), 49(32)

NMR (400 MHz, DMSO-d$_6$) δ value: 1.60-1.74 (6H, m), 1.93-1.96 (2H, m), 2.56 (2H, t, J=7.3 Hz), 2.88 (2H, t, J=7.3 Hz), 3.59 (2H, s), 4.90-4.93 (1H, m), 5.23 (2H, s), 6.48-6.50 (2H, m), 7.19 (1H, d, J=8.3 Hz), 7.30 (2H, d, J=8.0 Hz), 7.43 (2H, d, J=8.0 Hz), 7.46 (1H, d, J=9.0 Hz), 7.54-7.56 (2H, m), 12.05 (1H, s), 12.25 (2H, brs)

49(33)

NMR (400 MHz, DMSO-d$_6$) δ value: 1.60-1.70 (1H, m), 1.77-1.83 (1H, m), 2.04-2.09 (2H, m), 2.42-2.50 (2H, m), 2.57 (2H, t, J=7.6 Hz), 2.91 (2H, t, J=7.6 Hz), 4.77-4.80 (1H, m), 5.35 (2H, s), 6.42 (1H, d, J=2.4 Hz), 6.45 (1H, dd, J=8.8, 2.4 Hz), 7.17 (1H, d, J=9.2 Hz), 7.45 (1H, d, J=8.8 Hz), 7.54-7.56 (2H, m), 7.60 (2H, d, J=8.4 Hz), 7.98 (2H, d, J=8.4 Hz), 11.92 (3H, brs)

49(34)

NMR (400 MHz, DMSO-d$_6$) δ value: 2.57 (2H, t, J=7.6 Hz), 2.92 (2H, t, J=7.6 Hz), 5.20 (2H, s), 5.35 (2H, s), 6.60-6.64 (2H, m), 7.18 (1H, d, J=9.2 Hz), 7.34-7.49 (6H, m), 7.55-7.62 (4H, m), 7.99 (2H, d, J=8.8 Hz), 11.93 (3H, brs)

49(35)

NMR (400 MHz, DMSO-d$_6$) δ value: 1.56-1.78 (6H, m), 1.90-1.99 (2H, m), 2.43 (3H, d, J=4.8 Hz), 2.58 (2H, t, J=7.2 Hz), 2.93 (2H, t, J=7.2 Hz), 4.90-4.93 (1H, m), 5.37 (2H, s), 6.48-6.50 (2H, m), 7.18 (1H, t, J=4.4 Hz), 7.45-7.50 (2H, m), 7.55-7.57 (2H, m), 7.72 (2H, d, J=8.4 Hz), 7.83 (2H, d, J=8.0 Hz), 12.05 (1H, s), 12.17 (1H, brs)

49(36)

NMR (400 MHz, DMSO-d$_6$) δ value: 1.57-1.75 (6H, m), 1.90-2.00 (2H, m), 2.58 (2H, t, J=7.6 Hz), 2.90-2.99 (8H, m), 4.89-4.93 (1H, m) 5.31 (2H, s), 6.48-6.50 (2H, m), 7.20 (1H, d, J=9.2 Hz), 7.44-7.47 (3H, m), 7.54-7.57 (4H, m), 12.06 (1H, s), 12.15 (1H, brs)

49(37)

NMR (400 MHz, DMSO-d$_6$) δ value: 1.60-1.70 (2H, m), 1.71-1.75 (4H, m), 1.93-1.99 (2H, m), 2.56 (2H, t, J=6.8 Hz), 2.88 (2H, t, J=6.8 Hz), 3.02 (3H, s), 4.91 (1H, m), 5.20 (2H, s), 6.48-6.50 (2H, m), 7.19 (1H, d, J=8.0 Hz), 7.25 (1H, d, J=8.0 Hz), 7.46 (2H, d, J=8.4 Hz), 7.47 (1H, s), 7.55 (2H, d, J=8.0 Hz), 9.85 (1H, brs), 12.07 (1H, s)

49(38)

NMR (400 MHz, CDCl$_3$) δ value: 1.59-1.66 (2H, m), 1.75-1.97 (6H, m), 2.73 (2H, t, J=7.6 Hz), 3.02 (3H, d, J=5.2 Hz), 3.06 (2H, t, J=7.6 Hz), 4.79-4.82 (1H, m), 5.22 (2H, s), 6.23 (1H, brs), 6.38 (1H, dd, J=9.2, 2.4 Hz), 6.47 (1H, d, J=2.4 Hz), 6.94 (1H, d, J=8.4 Hz), 7.49-7.56 (5H, m), 7.80 (2H, d, J=8.0 Hz), 12.68 (2H, brs)

49(39)

NMR (400 MHz, DMSO-d$_6$) δ value: 1.52-1.59 (2H, m), 1.64-1.70 (2H, m), 1.75-1.79 (2H, m), 1.99-2.03 (2H, m), 2.55 (2H, t, J=7.6 Hz), 2.90 (2H, t, J=7.6 Hz), 2.94-3.03 (1H, m), 3.34 (3H, brs), 5.32 (2H, s), 6.84 (1H, d, J=8.4 Hz), 6.87 (1H, s), 7.15 (1H, d, J=8.4 Hz), 7.34 (1H, d, J=8.0 Hz), 7.53-7.57 (3H, m), 7.62 (1H, d, J=2.4 Hz), 7.95 (2H, d, J=8.0 Hz)

49(40)

NMR (400 MHz, DMSO-d$_6$) δ value: 2.57 (2H, t, J=7.6 Hz), 2.91 (2H, t, J=6.8 Hz), 5.15 (2H, s), 5.33 (2H, s), 6.48-6.52 (1H, m), 6.60 (1H, d, J=8.4 Hz), 6.64 (1H, d, J=3.6 Hz), 6.68 (1H, d, J=2.4 Hz), 7.18 (1H, d, J=9.2 Hz), 7.47 (1H, d, J=8.8 Hz), 7.55-7.58 (7H, m), 7.72-7.73 (1H, m), 7.96 (2H, d, J=8.0 Hz)

49(41)

NMR (400 MHz, DMSO-d$_6$) δ value: 2.57 (2H, t, J=7.6 Hz), 2.92 (2H, t, J=7.6 Hz), 5.35 (2H, s), 5.39 (2H, s), 6.61 (1H, dd, J=9.2, 2.8 Hz), 6.67 (1H, d, J=2.0 Hz), 7.05-7.07

(1H, m), 7.18 (1H, d, J=9.6 Hz), 7.26 (1H, d, J=3.6 Hz), 7.47 (1H, d, J=8.8 Hz), 7.55-7.62 (5H, m), 7.99 (2H, d, J=8.0 Hz), 11.90 (3H, brs)

49(42)
NMR (400 MHz, DMSO-$d_6$) δ value: 1.60-1.74 (6H, m), 1.93-1.99 (2H, m), 2.58 (2H, t, J=7.6 Hz), 2.93 (2H, t, J=7.6 Hz), 4.90-4.93 (1H, m), 5.35 (2H, s), 6.48-6.50 (2H, m), 7.16 (1H, d, J=9.2 Hz), 7.40-7.47 (3H, m), 7.55-7.56 (2H, m), 7.91 (1H, t, J=8.0 Hz), 12.03 (1H, s)

49(43)
NMR (400 MHz, DMSO-$d_6$) δ value: 1.59-1.79 (6H, m), 1.83-2.00 (2H, m), 2.57 (2H, t, J=7.2 Hz), 2.91 (2H, t, J=7.2 Hz), 4.88-4.93 (1H, m), 5.36 (2H, s), 6.48-6.50 (2H, m), 7.16 (1H, d, J=9.2 Hz), 7.45 (1H, d, J=9.2 Hz), 7.55 (2H, s), 7.68-7.77 (3H, m), 12.06 (1H, s)

49(44)
NMR (90 MHz, CDCl$_3$) δ value: 1.05 (6H, d, J=6.6 Hz), 1.90-2.35 (1H, m), 2.56-3.14 (4H, m), 3.81 (2H, d, J=6.6 Hz), 5.26 (2H, s), 6.91-7.01 (4H, m), 7.41-7.80 (7H, m), 8.07 (2H, d, J=8.1 Hz)

49(45)
NMR (90 MHz, DMSO-$d_6$) δ value: 0.99 (6H, d, J=6.6 Hz), 1.33 (6H, d, J=6.1 Hz), 1.8-2.3 (1H, m), 2.5-3.0 (4H, m), 3.42 (2H, brs), 3.84 (2H, d, J=6.4 Hz), 4.6-4.9 (1H, m), 5.24 (2H, s), 6.4-6.6 (2H, m), 7.17 (1H, d, J=8.8 Hz), 7.4-7.6 (6H, m), 12.05 (1H, s)

49(46)
NMR (400 MHz, DMSO-$d_6$) δ value: 0.99 (6H, d, J=6.6 Hz), 1.60-1.74 (6H, m), 1.86-2.06 (3H, m), 2.58 (2H, t, J=7.6 Hz), 2.92 (2H, t, J=7.6 Hz), 3.83 (2H, d, J=6.4 Hz), 4.90-4.93 (1H, m), 5.29 (2H, s), 6.48-6.50 (2H, m), 7.08 (1H, d, J=8.0 Hz), 7.16 (1H, d, J=9.2 Hz), 7.23 (1H, s), 7.45 (1H, d, J=9.0 Hz), 7.54-7.56 (2H, m), 7.65 (1H, d, J=7.8 Hz), 12.04 (1H, s), 12.36 (2H, brs)

49(47)
NMR (90 MHz, DMSO-$d_6$) δ value: 0.99 (6H, d, J=6.6 Hz), 1.82-3.02 (5H, m), 3.83 (2H, d, J=6.3 Hz), 5.35 (2H, s), 6.47-6.55 (2H, m), 7.17 (1H, d, J=9.3 Hz), 7.42-7.66 (5H, m), 8.00 (2H, d, J=8.3 Hz), 12.03 (1H, s), 12.55 (2H, brs)

49(48)
NMR (90 MHz, DMSO-$d_6$) δ value: 0.99 (6H, d, J=6.7 Hz), 1.90-2.19 (1H, m), 2.48-2.64 (2H, m), 2.83-2.99 (2H, m), 3.84 (2H, d, J=6.7 Hz), 5.32 (2H, s), 6.47-6.57 (2H, m), 7.17 (1H, d, J=9.5 Hz), 7.42-7.70 (5H, m), 7.80 (2H, d, J=8.1 Hz), 9.02 (1H, brs), 11.20 (1H, brs), 11.96 (2H, brs)

49(49)
NMR (90 MHz, CDCl$_3$) δ value: 1.04 (6H, d, J=6.6 Hz), 1.90-2.35 (1H, m), 2.57-2.72 (2H, m), 2.98-3.13 (2H, m), 3.80 (2H, d, J=6.2 Hz), 5.25 (2H, s), 6.39-6.49 (2H, m), 7.00 (1H, d, J=9.2 Hz), 7.40-7.72 (6H, m), 7.98-8.12 (3H, m), 12.64 (1H, s)

49(50)
NMR (90 MHz, DMSO-$d_6$) δ value: 0.99 (6H, d, J=6.6 Hz), 1.90-2.95 (5H, m), 3.84 (2H, d, J=6.4 Hz), 5.59 (2H, s), 6.50-6.55 (2H, m), 7.10 (1H, d, J=8.6 Hz), 7.44-7.68 (6H, m), 7.98 (1H, d, J=7.1 Hz), 12.03 (1H, s), 12.62 (2H, brs)

49(51)
NMR (400 MHz, DMSO-$d_6$) δ value: 1.60-1.74 (6H, m), 1.93-1.96 (2H, m), 2.54 (2H, t, J=7.6 Hz), 2.88 (2H, t, J=7.6 Hz), 4.90-4.93 (1H, m), 5.38 (2H, s), 6.48-6.50 (2H, m), 7.25 (1H, d, J=8.8 Hz), 7.46 (1H, d, J=8.8 Hz), 7.55-7.58 (2H, m), 7.72-7.75 (2H, m), 7.83 (1H, dd, J=8.0, 1.2 Hz), 12.03 (1H, s), 12.55 (2H, brs)

49(52)
NMR (400 MHz, DMSO-$d_6$) δ value: 1.54-1.75 (6H, m), 1.88-1.96 (2H, m), 2.50 (2H, t, J=7.6 Hz), 2.89 (2H, t, J=7.6 Hz), 4.78-4.81 (1H, m), 5.33 (2H, s), 6.28 (1H, s), 6.33 (1H, dd, J=11.6, 2.0 Hz), 7.13 (1H, d, J=8.4 Hz), 7.54 (1H, dd, J=8.8, 2.0 Hz), 7.59 (2H, d, J=8.0 Hz), 7.68 (1H, d, J=2.0 Hz), 7.97 (2H, d, J=8.4 Hz), 10.23 (3H, brs)

49(53)
NMR (400 MHz, DMSO-$d_6$) δ value: 1.5-1.8 (6H, m), 1.9-2.0 (2H, m), 2.25 (3H, s), 2.55 (2H, t, J=7.4 Hz), 2.90 (2H, t, J=7.4 Hz), 4.8-5.0 (1H, m), 5.34 (2H, s), 6.80 (1H, dd, J=8.4, 2.4 Hz), 6.86 (1H, d, J=2.4 Hz), 7.15 (1H, d, J=8.4 Hz), 7.22 (1H, d, J=8.4 Hz), 7.52 (1H, dd, J=8.4, 2.4 Hz), 7.59-7.62 (3H, m), 7.98 (2H, d, J=8.4 Hz), 12.56 (2H, brs)

49(54)
NMR (400 MHz, DMSO-$d_6$) δ value: 1.55-1.75 (6H, m), 1.90-1.98 (2H, m), 2.56 (2H, t, J=7.6 Hz), 2.89 (2H, t, J=7.2 Hz), 4.31 (3H, brs), 4.89-4.92 (1H, m), 5.26 (2H, s), 6.48-6.50 (2H, m), 7.17 (1H, d, J=9.6 Hz), 7.43-7.47 (3H, m), 7.53-7.55 (2H, m), 7.63 (2H, d, J=8.0 Hz)

49(55)
NMR (90 MHz, DMSO-$d_6$) δ value: 0.91 (6H, t, J=7.1 Hz), 1.5-1.8 (4H, m), 2.5-3.0 (4H, m), 4.2-4.5 (1H, m), 5.36 (2H, s), 6.4-6.6 (2H, m), 7.17 (1H, d, J=9.0 Hz), 7.4-7.7 (5H, m), 8.00 (2H, d, J=8.0 Hz), 12.08 (1H, s), 12.55 (2H, brs)

49(56)
NMR (90 MHz, DMSO-$d_6$) δ value: 0.8-2.0 (11H, m), 2.4-3.1 (4H, m), 3.86 (2H, d, J=5.1 Hz), 5.35 (2H, s), 6.4-6.6 (2H, m), 7.1-7.7 (6H, m), 7.99 (2H, d, J=8.1 Hz), 11.4-12.9 (3H, br)

49(57)
NMR (90 MHz, DMSO-$d_6$) δ value: 0.3-0.7 (4H, m), 1.0-1.4 (1H, m), 2.5-3.0 (4H, m), 3.90 (2H, d, J=6.8 Hz), 5.35 (2H, s), 6.5-6.6 (2H, m), 7.17 (1H, d, J=9.0 Hz), 7.4-7.7 (5H, m), 7.99 (2H, d, J=7.8 Hz), 11.4-13.0 (3H, br)

49(58)
NMR (90 MHz, DMSO-$d_6$) δ value: 1.2-1.9 (12H, m), 2.5-3.0 (4H, m), 4.5-4.8 (1H, m), 5.35 (2H, s), 6.4-6.5 (2H, m), 7.1-7.7 (6H, m), 8.00 (2H, d, J=8.4 Hz), 11.4-13.0 (3H, br)

49(59)
NMR (400 MHz, CDCl$_3$) δ value: 1.34 (6H, t, J=7.2 Hz), 1.60-1.98 (8H, m) 2.74 (2H, t, J=7.6 Hz), 3.08 (2H, t, J=7.6 Hz), 4.10-4.18 (4H, m), 4.80-4.83 (1H, m), 5.23 (2H, s), 6.38 (1H, dd, J=8.8, 2.4 Hz), 6.48 (1H, d, J=2.4 Hz), 6.94 (1H, d, J=8.8 Hz), 7.49-7.57 (5H, m), 7.84-7.89 (2H, m), 12.68 (2H, brs)

49(60)
NMR (400 MHz, DMSO-$d_6$) δ value: 2.57 (2H, t, J=7.6 Hz), 2.91 (2H, t, J=7.6 Hz), 5.35 (4H, s), 6.66 (1H, dd, J=8.8, 2.8 Hz), 6.69 (1H, d, J=2.4 Hz), 7.18 (1H, d, J=8.4 Hz), 7.48 (1H, d, J=8.4 Hz), 7.55-7.61 (4H, m), 7.98 (2H, d, J=8.4 Hz), 8.66-8.70 (2H, m), 8.84 (1H, s), 11.82 (3H, brs)

49(61)
NMR (400 MHz, DMSO-$d_6$) δ value: 1.60-1.74 (6H, m), 1.93-1.96 (2H, m), 2.46-2.56 (4H, m), 2.80 (2H, t, J=7.6 Hz), 2.85 (2H, t, J=7.6 Hz), 3.81 (3H, s), 4.90-4.93 (1H, m), 5.13 (2H, s), 6.48-6.50 (2H, m), 6.99 (1H, d, J=8.6 Hz), 7.20 (1H, d, J=8.6 Hz), 7.28-7.33 (2H, m), 7.46 (1H, d, J=8.8 Hz), 7.52-7.56 (2H, m), 12.06 (1H, s), 12.10 (2H, brs)

49(62)
NMR (400 MHz, DMSO-$d_6$) δ value: 1.60-1.74 (6H, m), 1.95-1.96 (2H, m), 2.58 (2H, t, J=7.2 Hz), 2.92 (2H, t, J=7.2 Hz), 3.39 (3H, s), 4.87-4.95 (1H, m), 5.36 (2H, s), 6.48-6.50 (2H, m), 7.17 (1H, d, J=8.8 Hz), 7.46 (1H, d, J=8.8 Hz), 7.54-7.56 (2H, m), 7.63 (2H, d, J=8.0 Hz), 7.99 (2H, d, J=8.0 Hz), 12.05 (1H, s), 12.17 (2H, brs)

49(63)
NMR (400 MHz, DMSO-$d_6$) δ value: 1.60-1.74 (6H, m), 1.91-1.99 (2H, m), 2.56 (2H, t, J=7.6 Hz), 2.89 (2H, t, J=7.6 Hz), 3.42 (1H, brs), 4.90-4.93 (1H, m), 5.36 (2H, s), 6.48-6.50 (2H, m), 7.23 (1H, d, J=8.0 Hz), 7.46 (1H, d, J=8.4 Hz), 7.55-7.58 (2H, m), 7.62 (1H, d, J=8.4 Hz), 7.74 (1H, dd, J=8.8, 1.6 Hz), 7.88 (1H, s), 12.06 (1H, s), 12.30 (1H, brs)

49(64)
NMR (400 MHz, DMSO-$d_6$) δ value: 1.60-1.74 (6H, m), 1.93-1.99 (2H, m), 2.59 (2H, t, J=7.6 Hz), 2.68 (3H, s), 2.93 (2H, t, J=7.6 Hz), 4.90-4.91 (1H, m), 5.36 (2H, s), 6.48-6.50 (2H, m), 7.20 (1H, d, J=8.4 Hz), 7.46 (1H, d, J=8.4 Hz), 7.56-7.57 (2H, m), 7.67 (2H, d, J=8.4 Hz), 8.04 (2H, d, J=8.0 Hz), 12.07 (1H, s), 12.18 (1H, brs)

49(65)
NMR (400 MHz, CDCl$_3$) δ value: 1.63-1.95 (8H, m), 2.71 (2H, t, J=7.2 Hz), 3.07 (2H, t, J=7.2 Hz), 3.38 (3H, s), 3.39 (3H, s), 4.77-4.85 (1H, m), 5.21 (2H, s), 5.31 (2H, s), 5.35 (2H, s), 6.38 (1H, d, J=8.8 Hz), 6.47 (1H, d, J=2.0 Hz), 6.97 (1H, d, J=8.0 Hz), 7.17-7.19 (2H, m), 7.33 (1H, s), 7.49-7.55 (3H, m), 12.67 (2H, brs)

49(66)
NMR (400 MHz, DMSO-$d_6$) δ value: 1.58-1.74 (6H, m), 1.94-1.99 (2H, m), 2.59 (2H, t, J=7.6 Hz), 2.94 (2H, t, J=7.6 Hz), 3.24 (3H, s), 4.90-4.93 (1H, m), 5.39 (2H, s), 6.48-6.50 (2H, m), 7.20 (1H, d, J=9.2 Hz), 7.46 (1H, d, J=8.4 Hz), 7.56-7.58 (2H, m), 7.72 (2H, d, J=8.4 Hz), 7.80 (2H, d, 8.4), 12.06 (1H, s), 12.17 (1H, brs)

49(67)
NMR (400 MHz, DMSO-$d_6$) δ value: 1.59-1.78 (6H, m), 1.90-2.01 (2H, m) 2.58 (2H, t, J=7.6 Hz), 2.92 (2H, t, J=7.2 Hz), 4.90-4.93 (1H, m), 5.45 (2H, s), 6.48-6.50 (2H, m), 7.19 (1H, d, J=9.2 Hz), 7.45 (1H, d, J=−8.8 Hz), 7.56-7.57 (2H, m), 7.87-7.89 (1H, m), 7.92-7.95 (2H, m), 11.39 (1H, brs), 12.03 (1H, brs), 12.15 (1H, brs)

49(68)
NMR (400 MHz, DMSO-$d_6$) δ value: 1.60-1.74 (6H, m), 1.94-1.96 (2H, m), 2.58 (2H, t, J=7.4 Hz), 2.94 (2H, t, J=7.4 Hz), 3.59 (3H, s), 4.90-4.93 (1H, m), 5.42 (2H, s), 6.48-6.53 (2H, m), 7.10 (1H, d, J=8.4 Hz), 7.45 (2H, d, J=8.4 Hz), 7.55-7.61 (3H, m), 7.83 (1H, d, J=7.6 Hz), 12.04 (1H, s) 12.16 (1H, brs)

49(69)
NMR (400 MHz, DMSO-$d_6$) δ value: 1.60-1.74 (6H, m), 1.93-1.96 (2H, m), 2.58 (2H, t, J=7.2 Hz), 2.93 (2H, t, J=7.2 Hz), 4.12 (3H, s), 4.90-4.93 (1H, m), 5.43 (2H, s), 6.47-6.50 (2H, m), 7.13-7.27 (2H, m), 7.46 (1H, d, J=8.4 Hz), 7.48 (1H, d, J=8.8 Hz), 7.55-7.60 (2H, m), 7.75 (1H, s), 7.79 (1H, d, J=8.0 Hz), 12.05 (1H, brs)

49(70)
NMR (400 MHz, DMSO-$d_6$) δ value: 1.53-1.75 (6H, m), 1.90-1.98 (2H, m), 2.47 (2H, t, J=7.6 Hz), 2.84 (2H, t, J=7.6 Hz), 4.87-4.91 (1H, m), 5.26 (2H, s), 6.47-6.50 (2H, m), 7.17-7.23 (2H, m), 7.45 (1H, d, J=8.8 Hz), 7.53-7.55 (2H, m), 7.76 (1H, d, J=8.4 Hz), 8.00 (1H, s), 11.32 (4H, brs)

49(71)
NMR (90 MHz, CDCl$_3$) δ value: 1.04 (6H, d, J=6.6 Hz), 1.90-2.32 (1H, m), 2.54-2.70 (2H, m), 2.96-3.12 (2H, m), 3.80 (2H, d, J=6.6 Hz), 5.24 (2H, s), 6.41-6.49 (2H, m), 7.03 (1H, d, J=9.0 Hz), 7.36-7.88 (6H, m), 8.61 (1H, d, J=4.6 Hz), 8.72 (1H, s), 12.63 (1H, s)

49(72)
NMR (400 MHz, DMSO-$d_6$) δ value: 1.58-1.75 (6H, m), 1.92-1.98 (2H, m), 2.60 (2H, t, J=7.6 Hz), 2.93 (2H, t, J=7.6 Hz), 4.89-4.92 (1H, m), 5.44 (2H, s), 6.48-6.50 (2H, m), 7.22 (1H, d, J=8.0 Hz), 7.46 (1H, d, J=8.8 Hz), 7.54-7.56 (2H, m), 8.77 (1H, s), 9.06 (1H, s), 12.04 (3H, brs)

49(73)
NMR (90 MHz, DMSO-$d_6$) δ value: 1.4-2.1 (8H, m), 2.4-3.0 (4H, m), 4.8-5.0 (1H, m), 5.31 (2H, s), 6.4-6.6 (2H, m), 6.77 (1H, d, J=3.4 Hz), 7.20 (1H, d, J=3.4 Hz), 7.3-7.6 (4H, m), 12.06 (1H, brs), 12.2-13.0 (2H, br)

49(74)
NMR (90 MHz, DMSO-$d_6$) δ value: 1.5-2.2 (8H, m), 2.5-3.0 (4H, m), 4.8-5.0 (1H, m), 5.62 (2H, s), 6.4-6.6 (2H, m), 7.2-7.6 (4H, m), 8.54 (1H, s), 12.06 (1H, brs), 12.62 (2H, brs)

49(75)
NMR (400 MHz, DMSO-$d_6$) δ value: 1.59-1.74 (6H, m), 1.93-1.99 (2H, m), 2.57 (2H, t, J=7.6 Hz), 2.89 (2H, t, J=7.6 Hz), 3.53 (1H, brs), 4.89-4.92 (1H, m), 5.36 (2H, s), 6.47-6.51 (2H, m), 7.25 (1H, d, J=8.8 Hz), 7.35 (1H, dd, J=8.3, 1.5 Hz), 7.47 (1H, d, J=8.5 Hz), 7.52-7.57 (2H, m), 7.64 (1H, d, J=8.0 Hz), 7.74 (1H, s), 8.29 (1H, s), 12.08 (1H, s)

49(76)
NMR (400 MHz, DMSO-$d_6$) δ value: 1.60-1.74 (6H, m), 1.95-1.96 (2H, m), 2.57 (2H, t, J=7.8 Hz), 2.90 (2H, t, J=7.4 Hz), 3.00 (3H, s), 3.68 (2H, t, J=5.6 Hz), 3.97 (2H, t, J=5.6 Hz), 4.88-4.95 (1H, m), 5.26 (2H, s), 6.48-6.50 (2H, m), 7.20 (1H, d, J=8.4 Hz), 7.44-7.75 (7H, m), 12.06 (1H, s), 12.12 (1H, brs)

49(77)
NMR (400 MHz, DMSO-$d_6$) δ value: 1.60-1.76 (6H, m), 1.94-1.96 (2H, m), 2.66 (2H, t, J=7.6 Hz), 2.99 (2H, t, J=7.6 Hz), 4.90-4.92 (1H, m), 5.79 (2H, s), 6.49-6.51 (2H, m), 7.29 (1H, d, J=8.4 Hz), 7.46 (1H, d, J=8.4 Hz), 7.56-7.60 (2H, m), 8.02 (1H, dd, J=8.6, 1.6 Hz), 8.29 (1H, d, J=8.0 Hz), 8.53 (1H, d, J=1.6 Hz), 12.03 (3H, brs)

49(78)
NMR (400 MHz, CDCl$_3$) δ value: 1.59-1.67 (2H, m), 1.75-1.97 (6H, m), 2.72 (2H, t, J=7.6 Hz), 3.03 (2H, t, J=7.6 Hz), 4.78-4.83 (1H, m), 5.06 (2H, s), 5.98 (2H, s), 6.38 (1H, dd, J=9.0, 2.4 Hz), 6.47 (1H, d, J=2.4 Hz), 6.82 (1H, d, J=8.0 Hz), 6.87-6.90 (2H, m), 6.96 (1H, d, J=9.2 Hz), 7.50 (1H, d, J=9.2 Hz), 7.52-7.56 (2H, m), 12.69 (2H, brs)

49(79)
NMR (400 MHz, DMSO-$d_6$) δ value: 1.60-1.74 (6H, m), 1.93-1.98 (2H, m), 2.55 (2H, t, J=7.6 Hz), 2.87 (2H, t, J=7.2 Hz), 4.08 (2H, t, J=8.2 Hz), 4.45 (2H, t, J=8.0 Hz), 4.90-4.93 (1H, m), 5.23 (2H, s), 6.48-6.50 (2H, m), 7.20 (1H, d, J=8.4 Hz), 7.52 (1H, d, J=8.8 Hz), 7.54-7.56 (4H, m), 7.62 (2H, d, J=8.8 Hz), 12.05 (1H, s), 12.14 (1H, brs)

49(80)
NMR (400 MHz, DMSO-$d_6$) δ value: 1.60-1.77 (6H, m), 1.94-1.97 (2H, m), 2.51 (2H, t, J=7.6 Hz), 2.86 (2H, t, J=7.6 Hz), 4.90-4.92 (1H, m), 5.59 (2H, s), 6.49-6.51 (2H, m), 7.40

(1H, d, J=8.4 Hz), 7.49 (1H, d, J=8.4 Hz), 7.55 (1H, s), 7.60 (1H, dd, J=8.4, 1.6 Hz), 7.97 (1H, d, J=8.8 Hz), 8.02 (1H, s), 8.16 (1H, d, J=8.8 Hz), 8.56 (1H, s), 12.07 (1H, s), 12.54 (2H, brs)

49(81)

NMR (400 MHz, DMSO-$d_6$) δ value: 0.98 (6H, d, J=6.8 Hz), 1.98-2.09 (1H, m), 2.59 (2H, t, J=7.6 Hz), 2.90 (2H, t, J=7.6 Hz), 3.83 (2H, d, J=6.4 Hz), 5.62 (2H, s), 6.52-6.54 (2H, m), 7.29 (1H, d, J=8.8 Hz), 7.46 (1H, d, J=9.5 Hz), 7.50-7.60 (2H, m), 7.71 (1H, s), 7.90 (1H, dd, J=8.5, 1.7 Hz), 8.10 (1H, d, J=8.6 Hz), 8.47 (1H, s), 11.99 (1H, s), 12.58 (2H, brs)

49(82)

NMR (400 MHz, DMSO-$d_6$) δ value: 1.30 (6H, d, J=6.1 Hz), 2.59 (2H, t, J=7.5 Hz), 2.90 (2H, t, J=7.5 Hz), 4.69-4.76 (1H, m), 5.62 (2H, s), 6.48-6.52 (2H, m), 7.29 (1H, d, J=8.8 Hz), 7.45 (1H, d, J=8.8 Hz), 7.55-7.58 (2H, m), 7.71 (1H, s), 7.90 (1H, dd, J=8.4, 1.7 Hz), 8.09 (1H, d, J=8.5 Hz), 8.47 (1H, d, J=1.0 Hz), 12.02 (1H, s), 12.58 (2H, brs)

49(83)

NMR (400 MHz, DMSO-$d_6$) δ value: 1.60-1.74 (6H, m), 1.93-1.96 (2H, m), 2.59 (2H, t, J=7.6 Hz), 2.91 (2H, t, J=7.6 Hz), 4.88-4.94 (1H, m), 5.62 (2H, s), 6.47-6.50 (2H, m), 7.29 (1H, d, J=8.8 Hz), 7.46 (1H, d, J=8.8 Hz), 7.56-7.58 (2H, m), 7.72 (1H, s), 7.90 (1H, dd, J=8.8, 1.6 Hz), 8.10 (1H, d, J=8.4 Hz), 8.47 (1H, d, J=1.2 Hz), 12.04 (1H, s), 12.56 (2H, brs)

49(84)

NMR (90 MHz, DMSO-$d_6$) δ value: 0.99 (6H, d, J=6.6 Hz), 1.8-3.0 (5H, m), 3.84 (2H, d, J=6.6 Hz), 5.50 (2H, s), 6.4-6.5 (2H, m), 7.2-7.8 (6H, m), 12.00 (1H, s), 11.7-13.2 (2H, br)

49(85)

NMR (90 MHz, DMSO-$d_6$) δ value: 0.98 (6H, d, J=6.7 Hz), 1.90-2.18 (1H, m), 2.48-2.61 (2H, m), 2.83-2.90 (2H, m), 3.84 (2H, d, J=6.7 Hz), 5.41 (2H, s), 6.49-6.55 (2H, m), 7.16-7.54 (4H, m), 8.08 (1H, s), 8.83 (1H, s), 11.98 (3H, brs)

49(86)

NMR (400 MHz, DMSO-$d_6$) δ value: 1.59-1.74 (6H, m), 1.93-1.96 (2H, m), 2.58 (2H, t, J=7.4 Hz), 2.91 (2H, t, J=7.4 Hz), 4.89-4.91 (1H, m), 5.38 (2H, s), 6.47-6.50 (2H, m), 7.23 (1H, d, J=9.2 Hz), 7.46 (1H, d, J=8.8 Hz), 7.55-7.61 (3H, m), 8.07 (2H, d, J=8.8 Hz), 8.11 (1H, s), 12.05 (3H, brs)

49(87)

NMR (400 MHz, DMSO-$d_6$) δ value: 1.60-1.74 (6H, m), 1.94-1.99 (2H, m), 2.58 (2H, t, J=7.6 Hz), 2.93 (2H, t, J=7.6 Hz), 4.90-4.91 (1H, m), 5.36 (2H, s), 6.48-6.50 (2H, m), 7.18 (1H, d, J=9.2 Hz), 7.46 (1H, d, J=8.4 Hz), 7.55-7.56 (2H, m), 7.69 (2H, d, J=8.0 Hz), 7.87 (2H, d, J=8.4 Hz), 12.06 (1H, s), 12.17 (1H, brs), 12.99 (1H, brs)

49(88)

NMR (90 MHz, CDCl$_3$) δ value: 0.2-3.1 (15H, m), 3.1-4.5 (4H, m), 4.7-5.3 (1H, m), 6.0-8.0 (6H, m), 8.83 (1H, s), 12.2-12.4 (1H, br), 12.63 (1H, s)

49(89)

NMR (90 MHz, DMSO-$d_6$) δ value: 0.99 (6H, d, J=6.4 Hz), 1.90-2.19 (1H, m), 3.13-3.20 (4H, m), 3.84 (2H, d, J=6.4 Hz), 5.36 (2H, s), 6.47-6.55 (2H, m), 7.15-7.66 (6H, m), 8.00 (2H, d, J=7.9 Hz), 11.95 (3H, brs)

49(90)

NMR (90 MHz, DMSO-$d_6$) δ value: 0.99 (6H, d, J=6.8 Hz), 1.92-2.20 (1H, m), 2.50-2.66 (2H, m), 2.85-3.03 (2H, m), 3.84 (2H, d, J=6.8 Hz), 5.38 (2H, s), 6.50-6.57 (2H, m), 7.22 (1H, d, J=8.2 Hz), 7.42-7.77 (5H, m), 8.10 (2H, d, J=8.0 Hz), 12.01 (1H, s), 12.14 (2H, brs)

49(91)

NMR (90 MHz, DMSO-$d_6$) δ value: 1.02 (6H, d, J=6.6 Hz), 1.6-3.4 (11H, m), 3.85 (2H, d, J=5.6 Hz), 4.2-5.4 (4H, br), 6.4-6.5 (2H, m), 7.04 (1H, d, J=9.0 Hz), 7.4-7.5 (3H, m)

49(92)

NMR (90 MHz, CDCl$_3$) δ value: 1.06 (6H, d, J=6.8 Hz), 1.9-2.4 (1H, m), 2.6-3.1 (6H, m), 3.82 (2H, d, J=6.4 Hz), 4.15 (2H, t, J=7.0 Hz), 4.5-5.9 (4H, br), 6.3-6.5 (2H, m), 6.63 (2H, d, J=8.3 Hz), 6.88 (1H, d, J=9.3 Hz), 7.05 (2H, d, J=8.5 Hz), 7.4-7.6 (3H, m)

49(93)

NMR (90 MHz, CDCl$_3$) δ value: 1.07 (6H, d, J=6.6 Hz), 1.4-2.3 (9H, m), 2.6-3.1 (4H, m), 3.82 (2H, d, J=6.1 Hz), 4.7-4.9 (1H, m), 6.3-6.5 (2H, m), 6.89 (1H, d, J=9.3 Hz), 7.4-7.6 (3H, m), 8.3-9.6 (1H, br), 12.69 (1H, brs)

49(94)

NMR (90 MHz, DMSO-$d_6$) δ value: 1.03 (6H, d, J=6.6 Hz), 1.8-5.0 (10H, m), 5.30 (2H, s), 6.5-6.8 (2H, m), 6.9-7.3 (1H, m), 7.4-7.8 (3H, m), 8.01 (2H, s), 8.71 (1H, s)

49(95)

NMR (90 MHz, CDCl$_3$) δ value: 1.07 (6H, d, J=6.6 Hz), 1.9-3.1 (5H, m), 2.73 (3H, s), 3.82 (2H, d, J=6.1 Hz), 5.0-6.2 (1H, br), 5.20 (2H, s), 6.4-6.8 (2H, m), 6.89 (1H, d, J=9.3 Hz), 7.17 (1H, s), 7.5-7.7 (3H, m), 12.64 (1H, s)

49(96)

NMR (90 MHz, CDCl$_3$) δ value: 1.07 (6H, d, J=6.6 Hz), 1.90-2.43 (1H, m), 2.61-3.10 (4H, m), 3.82 (2H, d, J=6.4 Hz), 5.10 (2H, s), 6.43 (1H, dd, J=8.8, 2.4 Hz), 6.56 (1H, d, J=2.4 Hz), 6.89 (1H, d, J=9.0 Hz), 7.34-7.76 (5H, m), 8.57-8.68 (2H, m), 9.0-10.0 (1H, br), 12.32 (2H, brs)

49(97)

NMR (90 MHz, CDCl$_3$) δ value: 1.08 (6H, d, J=6.8 Hz), 2.03-2.32 (1H, m), 2.51-2.69 (2H, m), 2.91-3.06 (2H, m), 3.85 (2H, d, J=6.1 Hz), 5.22 (2H, s), 5.63 (2H, brs), 6.48-6.58 (2H, m), 6.93 (1H, d, J=9.0 Hz), 7.47-7.65 (5H, m), 8.07 (2H, d, J=8.1 Hz), 12.61 (1H, s)

49(98)

NMR (90 MHz, DMSO-$d_6$) δ value: 1.03 (6H, d, J=6.6 Hz), 1.9-3.0 (5H, m), 3.88 (2H, d, J=6.1 Hz), 5.27 (2H, s), 6.5-6.7 (2H, m), 7.07 (1H, d, J=9.3 Hz), 7.3-8.0 (6H, m), 8.60 (1H, d, J=4.9 Hz), 11.4-12.4 (2H, br)

Example 50

0.13 g of hydroxylamine hydrochloride was dissolved in 3 mL of methanol, to which 0.36 g of a 28% solution of sodium methoxide in methanol was added at room temperature, and then this mixture was stirred for 30 minutes. The mixture thus obtained was added to 0.31 g of methyl 3-{2-[(4-cyanobenzyl)oxy]-5-[4-(cyclopentyloxy)-2-hydroxybenzoyl]phenyl}propanoate which was dissolved in a mixed solution of 5 mL of methanol and 5 mL of tetrahydrofuran, and then stirred for 14 hours at room temperature and subsequently for another one hour at 50° C. The reaction mixture was cooled to room temperature, to which water and ethyl acetate were successively added, and the organic phase was separated therefrom. After the resultant organic phase was washed with water and a saturated sodium chloride solution successively, this washed phase was dried over anhydrous sodium sulfate and the solvent was distilled out under reduced pressure. 0.42 g of the resultant residue was dissolved in 2 mL of N,N- dimethylformamide, to which 55 mg of pyridine and 0.12 g of 2-ethylhexyl chloroformate were added at room temperature, then this mixture was stirred for 5 minutes at the same temperature. The reaction mixture was added to a mixed solution of water and ethyl acetate, and the organic phase was separated therefrom. After the resultant organic phase was washed with water and a saturated sodium chloride solution successively, this washed phase was dried over anhydrous sodium sulfate and the solvent was distilled out under reduced pressure. The resultant residue to which 4 mL of xylene was added was stirred for one hour while heating it under reflux. The reaction mixture was cooled to room temperature, and purified by silica gel column chromatography [eluent; hexane:ethyl acetate=1:1] to yield 0.19 g of methyl 3-(5-[4-(cyclopentyloxy)-2-hydroxybenzoyl]-2-{[4-(5-oxo-4,5-dihydro-1,2,4-oxadiazol-3-yl)benzyl]oxy}phenyl) propanoate as yellow solid.

NMR (400 MHz, CDCl$_3$) δ value: 1.61-1.98 (8H, m), 2.70 (2H, t, J=7.6 Hz), 3.09 (2H, t, J=7.6 Hz), 3.68 (3H, s), 4.81-4.84 (1H, m), 5.27 (2H, s), 6.37 (1H, dd, J=8.8, 2.4 Hz), 6.48 (1H, d, J=2.4 Hz), 6.94 (1H, d, J=8.0 Hz), 7.49-7.56 (3H, m), 7.62 (2H, d, J=8.8 Hz), 7.84 (2H, d, J=8.4 Hz), 11.01 (1H, brs), 12.68 (1H, s)

Example 51

1.85 g of 4-({2-(2-carboxyethyl)-4-[4-(cyclopentyloxy)-2-hydroxybenzoyl]phenoxy}methyl) benzoic acid was dissolved in a mixed solvent of 19 mL of methylene chloride and 0.1 mL of N,N-dimethylformamide, to which 1.6 mL of oxalyl chloride was added dropwise over 10 minutes at room temperature, and then this mixture was stirred for one hour at room temperature. After 19 mL of ethanol was added dropwise to the reaction mixture over 10 minutes and this mixture was stirred for one hour at room temperature and for another 30 minutes at 50° C., the reaction mixture was cooled to room temperature to which water was added, and then the organic phase was separated therefrom. After the resultant organic phase was washed with water and a saturated sodium chloride solution successively, this washed phase was dried over anhydrous magnesium sulfate and the solvent was distilled out under reduced pressure. The resultant residue was purified by silica gel column chromatography [eluent; hexane:ethyl acetate=4:1] to yield 2.00 g of ethyl 4-{[4-[4-(cyclopentyloxy)-2-hydroxybenzoyl]-2-(3-ethoxy-3-oxopropyl)phenoxy]methyl} benzoate as yellow oil.

NMR (400 MHz, CDCl$_3$) δ value: 1.22 (3H, t, J=7.2 Hz), 1.41 (3H, t, J=7.2 Hz), 1.62-1.67 (2H, m), 1.78-1.98 (6H, m), 2.67 (2H, t, J=7.6 Hz), 3.07 (2H, t, J=7.6 Hz), 4.12 (2H, q, J=7.2 Hz), 4.40 (2H, q, J=7.2 Hz), 4.80-4.83 (1H, m), 5.25 (2H, s), 6.37 (1H, dd, J=8.8, 2.4 Hz), 6.48 (1H, d, J=2.4 Hz), 6.93 (1H, d, J=8.4 Hz), 7.49-7.56 (5H, m), 8.09 (2H, d, J=8.0 Hz), 12.69 (1H, s)

Example 52

The following compounds were obtained in a similar manner as in Example 51.
(1) ethyl 4-{[2-(3-ethoxy-3-oxopropyl)-4-(2-hydroxy-4-isobutoxybenzoyl)phenoxy]methyl} benzoate NMR (90 MHz, CDCl$_3$) δ value: 1.03 (6H, d, J=6.6 Hz), 1.22 (3H, t, J=7.4 Hz), 1.40 (3H, t, J=7.4 Hz), 1.98-2.25 (1H, m), 2.58-2.74 (2H, m), 3.00-3.16 (1H, m), 3.78 (2H, d, J=6.7 Hz), 4.12 (2H, q, J=7.4 Hz), 4.39 (2H, q, J=7.4 Hz), 5.24 (2H, s), 6.34-6.48 (2H, m), 6.93 (1H, d, J=8.8 Hz), 7.47-7.57 (5H, m), 8.09 (2H, d, J=8.1 Hz), 12.65 (1H, s)

(2) ethyl 4-{[4-[4-(cyclopentyloxy)-2-hydroxybenzoyl]-2-(3-ethoxy-3-oxopropyl)phenoxy]methyl}-2-methoxybenzoate NMR (400 MHz, CDCl$_3$) δ value: 1.22 (3H, t, J=7.2 Hz), 1.39 (3H, t, J=7.2 Hz), 1.61-1.66 (2H, m), 1.78-1.96 (6H, m), 2.68 (2H, t, J=7.8 Hz), 3.08 (2H, t, J=7.8 Hz), 3.93 (3H, s), 4.11 (2H, q, J=7.2 Hz), 4.37 (2H, q, J=7.2 Hz), 4.80-4.82 (1H, m), 5.21 (2H, s), 6.37 (1H, dd, J=9.2, 2.4 Hz), 6.48 (1H, d, J=2.8 Hz), 6.92 (1H, d, J=8.4 Hz), 7.03 (1H, dd, J=8.0, 1.2 Hz), 7.09 (1H, s), 7.49-7.56 (3H, m), 7.83 (1H, d, J=7.6 Hz), 12.69 (1H, s)

Example 53

1.90 g of ethyl 4-{[4-[4-(cyclopentyloxy)-2-hydroxybenzoyl]-2-(3-ethoxy-3-oxopropyl)phenoxy]methyl} benzoate was dissolved in 25 mL of ethanol, to which 0.14 g of lithium hydroxide monohydrate dissolved in 5 mL of water was added dropwise over 5 minutes at room temperature, and then this mixture was stirred for 1.5 hour at the same temperature. Another 0.14 g of lithium hydroxide monohydrate dissolved in 5 mL of water was added dropwise over 5 minutes, then this mixture was stirred for 20 hours. The reaction mixture to which water and chloroform were successively added was adjusted to pH 2 with 6M hydrochloric acid, then the organic phase was separated therefrom. After the resultant organic phase was washed with water and a saturated sodium chloride solution successively, this washed phase was dried over anhydrous magnesium sulfate and the solvent was distilled out under reduced pressure. The resultant residue was purified by silica gel column chromatography [eluent; hexane:ethyl acetate=1:1] to yield 0.70 g of 3-(5-[4-(cyclopentyloxy)-2-hydroxybenzoyl]-2-{[4-(ethoxycarbonyl)benzyl]oxy}phenyl) propanoic acid as light yellow solid.

NMR (400 MHz, CDCl$_3$) δ value: 1.40 (3H, t, J=7.2 Hz), 1.55-1.66 (2H, m), 1.74-1.98 (6H, m), 2.75 (2H, t, J=7.6 Hz), 3.07 (2H, t, J=7.6 Hz), 4.39 (2H, q, J=7.2 Hz), 4.78-4.81 (1H, m), 5.23 (2H, s), 6.38 (1H, dd, J=9.0, 2.8 Hz), 6.47 (1H, d, J=2.8 Hz), 6.93 (1H, d, J=8.4 Hz), 7.48-7.57 (5H, m), 8.08 (2H, d, J=8.4 Hz), 12.68 (2H, brs)

Example 54

The following compounds were obtained in a similar manner as in Example 53.
(1) 3-(5-(2-hydroxy-4-isobutoxybenzoyl)-2-{[4-(methoxycarbonyl)benzyl]oxy}phenyl) propanoic acid NMR (90 MHz, CDCl$_3$) δ value: 1.02 (6H, d, J=6.7 Hz), 1.98-2.24 (1H, m), 2.72-2.83 (2H, m), 3.00-3.18 (2H, m), 3.77 (2H, d, J=6.3 Hz), 3.93 (3H, s), 5.24 (2H, s), 6.38-6.48 (2H, m), 6.93 (1H, d, J=9.3 Hz), 7.46-7.58 (5H, m), 8.09 (2H, d, J=8.3 Hz), 12.64 (2H, brs)

(2) 3-(5-[4-(cyclopentyloxy)-2-hydroxybenzoyl]-2-{[4-(ethoxycarbonyl)-3-methoxybenzyl]oxy}phenyl) propanoic acid NMR (400 MHz, CDCl$_3$) δ value: 1.38 (3H, t, J=6.8 Hz), 1.61-1.66 (2H, m), 1.77-1.95 (6H, m), 2.75 (2H, t, J=7.6 Hz), 3.08 (2H, t, J=7.6 Hz), 3.92 (3H, s), 4.36 (2H, q, J=6.8 Hz), 4.79-4.82 (1H, m), 5.20 (2H, s), 6.38 (1H, dd, J=8.8, 2.4 Hz), 6.47 (1H, d, J=2.4 Hz), 6.93 (1H, d, J=8.4 Hz), 7.02 (1H, d, J=8.0 Hz), 7.08 (1H, s), 7.48-7.57 (3H, m), 7.83 (1H, d, J=7.6 Hz), 12.67 (2H, brs)

(3) 3-[2-{[4-(ethoxycarbonyl)benzyl]oxy}-5-(2-hydroxy-4-isobutoxybenzoyl)phenyl] propanoic acid NMR (90 MHz, CDCl$_3$) δ value: 1.02 (6H, d, J=6.8 Hz), 1.40 (3H, t, J=7.1 Hz), 1.96-2.26 (1H, m), 2.71-2.82 (2H, m), 3.00-3.08 (2H, m), 3.77 (2H, d, J=6.4 Hz), 4.39 (2H, q, J=7.1

Hz), 5.24 (2H, s), 6.38-6.48 (2H, m), 6.93 (1H, d, J=9.3 Hz), 7.44-7.58 (5H, m), 8.09 (2H, d, J=8.4 Hz), 12.64 (2H, brs)

Example 55

1.00 g of methyl 3-{5-[4-(cyclopentyloxy)-2-hydroxybenzoyl]-2-hydroxyphenyl} propanoate, 0.56 g of methyl 4-(hydroxymethyl)-2-methylbenzoate, and 0.82 g of triphenylphosphine were dissolved in 10 mL of tetrahydrofuran, to which a solution of 0.6 mL of diisopropyl azodicarboxylate in 1 mL of tetrahydrofuran was added dropwise at room temperature, and then this mixture was stirred for one hour at the same temperature. The reaction mixture was added to a mixture of ethyl acetate and water, then the organic phase was separated therefrom. After the resultant organic phase was washed with water and a saturated sodium chloride solution successively, this washed phase was dried over anhydrous magnesium sulfate and the solvent was distilled out under reduced pressure. The resultant residue was purified by silica gel column chromatography [eluent; hexane:ethyl acetate=4:1] to yield 1.12 g of methyl 4-{[4-[4-(cyclopentyloxy)-2-hydroxybenzoyl]-2-(3-methoxy-3-oxopropyl)-phenoxy]methyl}-2-methylbenzoate as yellow oil.

NMR (400 MHz, CDCl$_3$) δ value: 1.61-1.67 (2H, m), 1.76-1.98 (6H, m), 2.64 (3H, s), 2.69 (2H, t, J=7.6 Hz), 3.07 (2H, t, J=7.6 Hz), 3.67 (3H, s), 3.91 (3H, s), 4.80-4.83 (1H, m), 5.19 (2H, s), 6.37 (1H, dd, J=9.2, 2.4 Hz), 6.48 (1H, d, J=2.4 Hz), 6.92 (1H, d, J=8.4 Hz), 7.30-7.32 (2H, m), 7.50-7.55 (3H, m), 7.96 (1H, d, J=8.8 Hz), 12.70 (1H, s)

Example 56

0.95 g of tert-butyl 4-{[4-[4-(cyclopentyloxy)-2-hydroxybenzoyl]-2-(3-methoxy-3-oxopropyl)phenoxy]methyl}-1H-pyrazole-1-carboxylate was dissolved in 4.8 mL of chloroform, to which 10 mL of 4M hydrogen chloride/ethanol was added dropwise at room temperature, and then this mixture was stirred for one hour at the same temperature. The reaction mixture was added to water, then the organic phase was separated therefrom. After the resultant organic phase was washed with water and a saturated sodium chloride solution successively, this washed phase was dried over anhydrous magnesium sulfate and the solvent was distilled out under reduced pressure. The resultant residue was purified by silica gel column chromatography [eluent; hexane:ethyl acetate=1:1] to yield 0.67 g of ethyl 3-[5-[4-(cyclopentyloxy)-2-hydroxybenzoyl]-2-(1H-pyrazol-4-ylmethoxy)phenyl] propanoate as light yellow oil.

NMR (400 MHz, CDCl$_3$) δ value: 1.22 (3H, t, J=7.2 Hz), 1.62-1.66 (2H, m), 1.78-1.96 (6H, m), 2.61 (2H, t, J=7.6 Hz), 2.99 (2H, t, J=7.6 Hz), 4.11 (2H, q, J=7.2 Hz), 4.81-4.83 (1H, m), 5.13 (2H, s), 6.37 (1H, dd, J=8.8, 2.4 Hz), 6.48 (1H, d, J=2.4 Hz), 7.00 (1H, d, J=8.3 Hz), 7.52-7.57 (3H, m), 7.71 (2H, s), 12.71 (2H, brs)

Example 57

The following compounds were obtained in a similar manner as in Example 56.
(1) methyl 3-{2-{[4-(aminosulfonyl)benzyl]oxy}-5-[4-(cyclopentyloxy)-2-hydroxybenzoyl]phenyl] propanoate NMR (400 MHz, CDCl$_3$) δ value: 1.62-1.68 (2H, m), 1.77-1.98 (6H, m), 2.68 (2H, t, J=7.2 Hz), 3.07 (2H, t, J=8.0 Hz), 3.68 (3H, s), 4.81 (3H, brs), 5.26 (2H, s), 6.37 (1H, dd, J=9.2, 2.4 Hz), 6.48 (1H, d, J=2.4 Hz), 6.92 (1H, d, J=8.4 Hz), 7.49-7.55 (3H, m), 7.61 (2H, d, J=8.4 Hz), 7.99 (2H, d, J=8.4 Hz), 12.67 (1H, s)

(2) methyl 3-[5-[4-(cyclopentyloxy)-2-hydroxybenzoyl]-2-({4-[(methylsulfonyl)amino]benzyl}oxy)phenyl] propanoate NMR (400 MHz, CDCl$_3$) δ value: 1.55-1.65 (2H, m), 1.78-2.05 (6H, m), 2.67 (2H, t, J=7.2 Hz), 3.05 (3H, s), 3.02 (2H, t, J=7.2 Hz), 3.67 (3H, s), 4.80-4.83 (1H, m), 5.30 (2H, s), 6.37 (1H, dd, J=9.2, 2.4 Hz), 6.48 (1H, d, J=2.4 Hz), 6.53 (1H, s), 6.96 (1H, d, J=9.2 Hz), 7.26 (2H, d, J=8.4 Hz), 7.43 (2H, d, J=8.4 Hz), 7.50-7.55 (3H, m), 12.69 (1H, s)

(3) ethyl 3-{2-(1H-benzimidazol-5-ylmethoxy)-5-[4-(cyclopentyloxy)-2-hydroxybenzoyl]phenyl} propanoate was obtained.

NMR (400 MHz, DMSO-d$_6$) δ value: 1.10 (3H, t, J=7.2 Hz), 1.60-1.71 (6H, m), 1.93-1.98 (2H, m), 2.63 (2H, t, J=7.6 Hz), 2.93 (2H, t, J=7.6 Hz), 4.01 (2H, q, J=7.2 Hz), 4.89-4.92 (1H, m), 5.45 (2H, s), 6.47 (1H, dd, J=8.8, 2.4 Hz), 6.51 (1H, d, J=2.4 Hz), 7.24 (1H, d, J=8.4 Hz), 7.43 (1H, d, J=8.8 Hz), 7.54-7.58 (2H, m), 7.69 (1H, d, J=7.6 Hz), 7.90 (1H, d, J=8.4 Hz), 7.96 (1H, s), 8.33 (1H, s), 9.49 (1H, s), 11.98 (1H, s)

(4) methyl 3-{5-[4-(cyclopentyloxy)-2-hydroxybenzoyl]-2-[(2,4-dioxo-1,2,3,4-tetrahydro-6-quinazolinyl)methoxy]phenyl} propanoate was obtained.

NMR (400 MHz, CDCl$_3$) δ value: 1.61-1.67 (2H, m), 1.77-1.98 (6H, m), 2.67 (2H, t, J=7.2 Hz), 3.05 (2H, t, J=7.6 Hz), 3.66 (3H, s), 4.80-4.83 (1H, m), 5.21 (2H, s), 6.37 (1H, dd, J=9.0, 2.4 Hz), 6.48 (1H, d, J=2.4 Hz), 6.96 (1H, d, J=9.2 Hz), 7.13 (1H, d, J=8.4 Hz), 7.50 (1H, d, J=9.2 Hz), 7.53-7.55 (2H, m), 7.76 (1H, d, J=6.4 Hz), 8.18 (1H, s), 8.27 (1H, brs), 8.52 (1H, brs), 12.69 (1H, s)

(5) methyl 3-[5-[4-(cyclopentyloxy)-2-hydroxybenzoyl]-2-({4-[(methylamino)sulfonyl]benzyl}oxy)phenyl} propanoate NMR (400 MHz, CDCl$_3$) δ value: 1.63-1.68 (2H, m), 1.76-1.98 (6H, m), 2.68-2.71 (5H, m), 2.88 (2H, brs), 3.08 (2H, t, J=7.6 Hz), 3.68 (3H, s), 4.80-4.84 (1H, m), 5.26 (2H, s), 6.38 (1H, dd, J=9.0, 2.4 Hz), 6.49 (1H, d, J=2.4 Hz), 6.93 (1H, d, J=8.4 Hz), 7.49-7.55 (3H, m), 7.61 (2H, d, J=8.4 Hz), 7.92 (2H, d, J=8.8 Hz)

(6) methyl 3-[5-[4-(cyclopentyloxy)-2-hydroxybenzoyl]-2-({4-[(methylamino)carbonyl]benzyl}oxy)phenyl] propanoate NMR (400 MHz, CDCl$_3$) δ value: 1.62-1.66 (2H, m), 1.78-1.96 (6H, m), 2.68 (2H, t, J=7.6 Hz), 3.05-3.08 (5H, m), 3.38 (1H, brs), 3.67 (3H, s), 4.80-4.84 (1H, m), 5.23 (2H, s), 6.33 (1H, brs), 6.37 (1H, dd, J=9.0, 2.4 Hz), 6.48 (1H, d, J=2.4 Hz), 6.93 (1H, d, J=8.4 Hz), 7.49-7.54 (5H, m), 7.79 (2H, d, J=8.0 Hz)

(7) methyl 3-{5-[4-(cyclopentyloxy)-2-hydroxybenzoyl]-2-[(1,3-dioxo-2,3-dihydro-1H-isoindol-5-yl)methoxy]phenyl} propanoate NMR (400 MHz, CDCl$_3$) δ value: 1.62-1.67 (2H, m), 1.77-2.00 (6H, m), 2.70 (2H, t, J=7.6 Hz), 3.09 (2H, t, J=7.6 Hz), 3.68 (3H, s), 4.81-4.84 (1H, m), 5.33 (2H, s), 6.38 (1H, dd, J=9.0, 2.4 Hz), 6.48 (1H, d, J=2.4 Hz), 6.93 (1H, d, J=8.4 Hz), 7.49-7.56 (3H, m), 7.72 (2H, brs), 7.86 (1H, d, J=7.6 Hz), 7.92-7.95 (2H, m)

Example 58

0.50 g of methyl 3-[5-[4-(cyclopentyloxy)-2-hydroxybenzoyl]-2-(1H-pyrazol-4-ylmethoxy)phenyl] propanoate was dissolved in 5 mL of 1,4-dioxane, to which 5 mL of 6M hydrochloric acid was added at room temperature, and then this mixture was stirred for 7 hours at the same temperature. The reaction mixture was added to a mixture of ethyl acetate and water, then the organic phase was separated therefrom. After the resultant organic phase was washed with water and a saturated sodium chloride solution successively, this washed phase was dried over anhydrous magnesium sulfate and the solvent was distilled out under reduced pressure. The resultant residue was purified by silica gel column chromatography [eluent; chloroform:ethanol=20:1] to yield 0.33 g of 3-[5-[4-(cyclopentyloxy)-2-hydroxybenzoyl]-2-(1H-pyrazol-4-ylmethoxy)phenyl] propanoic acid as yellow oil.

NMR (400 MHz, CDCl$_3$) δ value: 1.60-1.67 (2H, m), 1.76-1.98 (6H, m), 2.66 (2H, t, J=7.6 Hz), 3.02 (2H, t, J=7.6 Hz), 4.80-4.83 (1H, m), 5.11 (2H, s), 5.75 (2H, brs), 6.38 (1H, dd, J=8.8, 2.4 Hz), 6.48 (1H, d, J=2.4 Hz), 7.01 (1H, d, J=8.0 Hz), 7.52 (1H, d, J=8.8 Hz), 7.55-7.58 (2H, m), 7.71 (2H, s)

Example 59

1.00 g of 4-{[4-[4-(cyclopentyloxy)-2-hydroxybenzoyl]-2-(3-ethoxy-3-oxopropyl)phenoxy]methyl} benzoic acid was dissolved in 12 mL of tetrahydrofuran, to which 1.03 g of 1,1'-carbonyldiimidazole was added at room temperature, and then this mixture was stirred for one hour while heating it under reflux. After the reaction mixture was cooled to room temperature, 1.07 g of methanesulfonamide and 1.7 mL of 1,8-diazabicyclo[5.4.0]undec-7-ene were added to this mixture, which was stirred for 30 minutes at room temperature and for another 30 minutes at 50° C. The reaction mixture which was cooled to room temperature was added to a mixture of methylene chloride and water, and adjusted to pH 2 with 6M hydrochloric acid, and then the organic phase was separated therefrom. After the resultant organic phase was washed with water and a saturated sodium chloride solution successively, this washed phase was dried over anhydrous magnesium sulfate and the solvent was distilled out under reduced pressure. The resultant residue was purified by silica gel column chromatography [eluent; hexane:ethyl acetate=1:2] to yield 0.65 g of ethyl 3-{5-[4-(cyclopentyloxy)-2-hydroxybenzoyl]-2-[(4-{[(methylsulfonyl)amino]carbonyl}benzyl)oxy]phenyl}propanoate as light yellow solid.

NMR (400 MHz, CDCl$_3$) δ value: 1.23 (3H, t, J=7.2 Hz), 1.63-1.68 (2H, m), 1.76-1.96 (6H, m), 2.67 (2H, t, J=7.6 Hz), 3.07 (2H, t, J=7.6 Hz), 3.46 (3H, s), 4.13 (2H, q, J=7.2 Hz), 4.81-4.83 (1H, m), 5.26 (2H, s), 6.37 (1H, dd, J=9.2, 2.4 Hz), 6.48 (1H, d, J=2.4 Hz), 6.92 (1H, d, J=8.0 Hz), 7.48-7.61 (5H, m), 7.89 (2H, d, J=8.4 Hz), 8.57 (1H, brs), 12.67 (1H, s)

Example 60

The following compounds were obtained in a similar manner as in Example 59.
(1) methyl 3-{5-(2-hydroxy-4-isobutoxybenzoyl)-2-[(4-{[(methylsulfonyl)-amino]carbonyl}benzyl)oxy]phenyl} propanoate NMR (90 MHz, CDCl$_3$) δ value: 1.03 (6H, d, J=6.6 Hz), 1.96-2.26 (1H, m), 2.60-2.75 (2H, m), 2.98-3.15 (2H, m), 3.45 (3H, s), 3.67 (3H, s), 3.79 (2H, d, J=6.3 Hz), 5.25 (2H, s), 6.38-6.51 (2H, m), 6.92 (1H, d, J=9.4 Hz), 7.46-7.62 (5H, m), 7.92 (2H, d, J=8.6 Hz), 9.00 (1H, brs), 12.63 (1H, s)
(2) ethyl 3-[2-({4-[(hydroxyamino)-carbonyl]benzyl}oxy)-5-(2-hydroxy-4-isobutoxybenzoyl)phenyl]propanoate NMR (90 MHz, DMSO-d$_6$) δ value: 0.95-1.20 (9H, m), 1.92-2.16 (1H, m), 2.47-2.63 (2H, m), 2.82-2.94 (2H, m), 3.80-4.06 (4H, m), 5.32 (2H, s), 6.52-6.56 (2H, m), 7.23-7.85 (8H, m), 9.05 (1H, s), 11.24 (1H, s), 11.93 (1H, s)
(3) methyl 3-[2-{[4-(aminocarbonyl)benzyl]oxy}-5-(2-hydroxy-4-isobutoxybenzoyl)phenyl]propanoate NMR (90 MHz, DMSO-d$_6$) δ value: 0.99 (6H, d, J=6.6 Hz), 1.85-2.23 (1H, m), 2.46-2.95 (4H, m), 3.58 (3H, s), 3.83 (2H, d, J=6.4 Hz), 5.32 (2H, s), 6.53-6.56 (2H, m), 7.13-7.60 (8H, m), 7.92 (2H, d, J=7.8 Hz), 11.96 (1H, brs)

Example 61

1.85 g of methyl 3-[5-(4-bromo-2-hydroxybenzoyl)-2-hydroxyphenyl] propanoate was dissolved in 20 mL of methylene chloride, to which 1.5 mL of triethylamine and 1.0 mL of acetic anhydride were successively added at 5 to 10° C., and then this mixture was stirred for 2 hours at room temperature. Then, water and a saturated aqueous solution of sodium hydrogen carbonate were added to this mixture, and the organic phase was separated therefrom. After the resultant organic phase was washed with water and 1M hydrochloric acid successively, this washed phase was dried over anhydrous magnesium sulfate, and the solvent was distilled out under reduced pressure to yield 2.46 g of methyl 3-{2-(acetyloxy)-5-[2-(acetyloxy)-4-bromobenzoyl]phenyl} propanoate as brown oil.

NMR (400 MHz, CDCl$_3$) δ value: 1.96 (3H, s), 2.37 (3H, s), 2.59 (2H, t, J=7.8 Hz), 2.90 (2H, t, J=7.8 Hz), 3.67 (3H, s), 7.14 (1H, d, J=8.0 Hz), 7.39-7.51 (3H, m), 7.62-7.66 (2H, m)

Example 62

4-{[4-[2-(acetyloxy)-4-isobutoxybenzoyl]-2-(3-methoxy-3-oxopropyl)phenoxy]methyl} benzoic acid was obtained in a similar manner as in Example 61.

NMR (90 MHz, CDCl$_3$) δ value: 1.04 (6H, d, J=6.7 Hz), 1.86-2.25 (4H, m), 2.65-2.75 (2H, m), 2.99-3.14 (2H, m), 3.67 (3H, s), 3.78 (2H, d, J=6.4 Hz), 5.25 (2H, s), 6.67-6.94 (3H, m), 7.42-7.65 (5H, m), 8.15 (2H, d, J=7.8 Hz), 12.65 (1H, brs)

Example 63

1.20 g of methyl 3-{2-(acetyloxy)-5-[2-(acetyloxy)-4-bromobenzoyl]phenyl}propanoate was dissolved in 12 mL of toluene, to which 0.33 g of 2-thienylboronic acid, 0.69 g of potassium carbonate, and 0.10 g of bis(triphenylphosphine)palladium(II)dichloride were added at room temperature in a stream of nitrogen, and then this mixture was stirred for 3.5 hours while heating it under reflux. The reaction mixture was cooled to room temperature, followed by the addition thereto of ethyl acetate and water, and the organic phase was separated therefrom. After the resultant organic phase was washed with water and a saturated sodium chloride solution successively, this washed phase was dried over anhydrous magnesium sulfate, and the solvent was distilled out under reduced pressure. The resultant residue was purified by silica gel column chromatography [eluent; hexane:ethyl acetate=3:1] to yield 0.64 g of methyl 3-{2-(acetyloxy)-5-[2-(acetyloxy)-4-(2-thienyl)benzoyl]phenyl} propanoate as light yellow oil.

NMR (400 MHz, CDCl$_3$) δ value: 2.00 (3H, s), 2.37 (3H, s), 2.60 (2H, t, J=8.0 Hz), 2.91 (2H, t, J=8.0 Hz), 3.67 (3H, s), 7.1-7.2 (2H, m), 7.3-7.5 (3H, m), 7.57 (2H, s), 7.6-7.7 (2H, m)

Example 64

0.72 g of methyl 3-{2-(acetyloxy)-5-[2-(acetyloxy)-4-(2-thienyl)benzoyl]phenyl}propanoate was suspended in 8 mL of methanol, to which 0.66 g of a 28% solution of sodium methoxide in methanol was added dropwise at 5 to 7° C., and then this suspension was stirred for 30 minutes in an ice bath. The reaction mixture was added to a mixture of ethyl acetate and ice water, and adjusted to pH 3 with 1M hydrochloric acid, and the organic phase was separated therefrom. After the resultant organic phase was washed with water and a saturated sodium chloride solution successively, this washed phase was dried over anhydrous magnesium sulfate, and the solvent was distilled out under reduced pressure. The resultant solid was recrystallized from a mixed solvent of diisopropyl ether-hexane to yield 0.50 g of methyl 3-{2-hydroxy-5-[2-hydroxy-4-(2-thienyl)benzoyl]phenyl} propanoate as light yellow crystals.

NMR (400 MHz, CDCl$_3$) δ value: 2.79 (2H, t, J=6.2 Hz), 2.98 (2H, t, J=6.2 Hz), 3.74 (3H, s), 6.99 (1H, d, J=8.8 Hz), 7.1-7.2 (2H, m), 7.31 (1H, d, J=1.6 Hz), 7.39 (1H, dd, J=5.0, J=1.2 Hz), 7.46 (1H, dd, J=3.6, 1.2 Hz), 7.46-7.62 (2H, m), 7.63 (1H, d, J=8.4 Hz), 7.99 (1H, s), 12.16 (1H, s)

Example 65

1.00 g of methyl 4-{[4-[4-(cyclopentyloxy)-2-hydroxybenzoyl]-2-(3-methoxy-3-oxopropyl)phenoxy]methyl} benzoate was dissolved in 10 mL of N,N-dimethylformamide, to which 0.52 g of potassium carbonate and 0.23 mL of iodomethane were added at 5 to 10° C., and then this mixture was stirred for 4 hours at room temperature. The reaction mixture was added to a mixture of ethyl acetate and ice water, and the organic phase was separated therefrom. After the resultant organic phase was washed with water and a saturated sodium chloride solution successively, this washed phase was dried over anhydrous magnesium sulfate, and the solvent was distilled out under reduced pressure. The resultant solid was recrystallized from a mixed solvent of diisopropyl ether-hexane to yield 0.98 g of methyl 4-{[4-[4-(cyclopentyloxy)-2-methoxybenzoyl]-2-(3-methoxy-3-oxopropyl)phenoxy]methyl} benzoate as light yellow crystals.

NMR (400 MHz, CDCl$_3$) δ value: 1.6-1.7 (2H, m), 1.7-2.0 (6H, m), 2.64 (2H, t, J=7.8 Hz), 3.03 (2H, t, J=7.8 Hz), 3.65 (3H, s), 3.70 (3H, s), 3.93 (3H, s), 4.7-4.9 (1H, m), 5.22 (2H, s), 6.4-6.6 (2H, m), 6.86 (1H, d, J=8.4 Hz), 7.30 (1H, d, J=8.0 Hz), 7.50 (2H, d, J=8.4 Hz), 7.64-7.68 (2H, m), 8.07 (2H, d, J=8.0 Hz)

Example 66

1.00 g of isopropyl 3-(5-(2-hydroxy-4-isobutoxybenzoyl)-2-{[4-(methylsulfanyl)benzyl]oxy}phenyl) propanoate was dissolved in 10 mL of methylene chloride, to which 0.69 g of 70% m-chloroperbenzoic acid was added in small portions in an ice bath, and then this mixture was stirred for 1.5 hours at room temperature. A saturated aqueous solution of sodium hydrogen carbonate was added to the reaction mixture, and the organic phase was separated therefrom. After the resultant organic phase was washed with water and a saturated sodium chloride solution successively, this washed phase was dried over anhydrous magnesium sulfate, and the solvent was distilled out under reduced pressure. The resultant residue was purified by silica gel column chromatography [eluent; ethyl acetate] to yield 0.50 g of isopropyl 3-(5-(2-hydroxy-4-isobutoxybenzoyl)-2-{[4-(methylsulfonyl)benzyl]oxy}phenyl) propanoate as yellow oil and 0.54 g of isopropyl 3-(5-(2-hydroxy-4-isobutoxybenzoyl)-2-{[4-(methylsulfinyl)benzyl]oxy}phenyl) propanoate as yellow oil.

isopropyl 3-(5-(2-hydroxy-4-isobutoxybenzoyl)-2-{[4-(methylsulfinyl)benzyl]oxy}phenyl) propanoate NMR (90 MHz, CDCl$_3$) δ value: 1.03 (6H, d, J=6.6 Hz), 1.19 (6H, d, J=6.3 Hz), 1.98-2.30 (1H, m), 2.64-2.76 (5H, m), 2.99-3.17 (2H, m), 3.79 (2H, d, J=6.6 Hz), 4.80-5.15 (1H, m), 5.25 (2H, s), 6.38-6.51 (2H, m), 6.94 (1H, d, J=9.1 Hz), 7.48-7.77 (7H, m), 12.64 (1H, s)

isopropyl 3-(5-(2-hydroxy-4-isobutoxybenzoyl)-2-{[4-(methylsulfonyl)benzyl]oxy}phenyl) propanoate NMR (90 MHz, CDCl$_3$) δ value: 1.03 (6H, d, J=6.6 Hz), 1.20 (6H, d, J=6.4 Hz), 1.98-2.18 (1H, m), 2.56-2.72 (2H, m), 2.98-3.18 (5H, m), 3.79 (2H, d, J=6.4 Hz), 4.86-5.15 (1H, m), 5.28 (2H, s), 6.35-6.51 (2H, m), 6.92 (1H, d, J=9.3 Hz), 7.47-7.71 (5H, m), 8.01 (2H, d, J=8.6 Hz), 12.63 (1H, s)

Example 67

0.93 g of 3-(5-(2-hydroxy-4-isobutoxybenzoyl)-2-{[4-(methoxycarbonyl)benzyl]oxy}phenyl) propanoic acid was dissolved in 9.3 mL of tetrahydrofuran, to which 0.19 mL of oxalyl chloride and 20 μL of N,N-dimethylformamide were added at room temperature, and after this mixture was stirred for one hour, the reaction mixture was added dropwise to a 25% aqueous ammonia in an ice bath over 15 minutes. The reaction mixture was adjusted to pH 6 with 6M hydrochloric acid, to which ethyl acetate was added, and the organic phase was separated therefrom. After the resultant organic phase was washed with water and a saturated sodium chloride solution successively, this washed phase was dried over anhydrous magnesium sulfate, and the solvent was distilled out under reduced pressure. The resultant residue was dissolved in 18.6 mL of tetrahydrofuran, to which 0.27 mL of thionyl chloride was added, and this mixture was stirred for 6.5 hours while heating it under reflux. The reaction mixture was added to a mixture of ethyl acetate and ice water, followed by the separation of the organic phase therefrom. After the resultant organic phase was washed with water and a saturated sodium chloride solution successively, this washed phase was dried over anhydrous magnesium sulfate, and the solvent was distilled out under reduced pressure. The resultant residue was purified by silica gel column chromatography [eluent; ethyl acetate:hexane=2:1] to yield 0.36 g of methyl 4-{[2-(2-cyanoethyl)-4-(2-hydroxy-4-isobutoxybenzoyl)phenoxy]methyl} benzoate as light orange solid.

NMR (90 MHz, CDCl$_3$) δ value: 1.03 (6H, d, J=6.7 Hz), 1.98-2.26 (1H, m), 2.68-2.77 (2H, m), 3.00-3.08 (2H, m), 3.67-3.94 (5H, m), 5.25 (2H, s), 6.39-6.49 (2H, m), 6.99 (1H, d, J=9.0 Hz), 7.43-7.66 (5H, m), 8.11 (2H, d, J=8.1 Hz), 12.57 (1H, s)

Example 68

0.35 g of methyl 4-{[2-(2-cyanoethyl)-4-(2-hydroxy-4-isobutoxybenzoyl)phenoxy]methyl} benzoate, 0.42 g of sodium azide, and 0.89 g of triethylamine hydrochloride were suspended in 3.5 mL of xylene, and stirred for 7 hours at 110° C. The reaction mixture was cooled to room temperature, to which methylene chloride and water were added, and after this mixture was adjusted to pH 2 with 6M hydrochloric acid, the organic phase was separated therefrom. After the resultant organic phase was washed with water and a saturated sodium chloride solution successively, this washed phase was dried over anhydrous magnesium sulfate, and the solvent was distilled out under reduced pressure. The residue was purified by silica gel column chromatography [eluent; chloroform:ethanol=10:1] to yield 0.19 g of methyl 4-({4-(2-hydroxy-4-isobutoxybenzoyl)-2-[2-(1H-1,2,3,4-tetrazol-5-yl)ethyl]phenoxy}methyl) benzoate as light yellow solid.

NMR (90 MHz, CDCl$_3$) δ value: 1.02 (6H, d, J=6.5 Hz), 1.98-2.24 (1H, m), 3.23-3.34 (4H, m), 3.76 (2H, d, J=6.7 Hz), 3.91 (3H, s), 5.16 (2H, s), 6.38-6.46 (2H, m), 6.87 (1H, d, J=9.5 Hz), 7.29-7.50 (5H, m), 8.03 (2H, d, J=8.3 Hz), 12.49 (2H, brs)

Example 69 isopropyl 3-(5-(2-hydroxy-4-isobutoxybenzoyl)-2-{[4-(1H-1,2,3,4-tetrazol-5-yl)benzyl]oxy}phenyl) propanoate was obtained in a similar manner as in Example 68.

NMR (90 MHz, CDCl$_3$) δ value: 1.03 (6H, d, J=6.8 Hz), 1.20 (6H, d, J=6.4 Hz), 1.90-2.18 (1H, m), 2.62-2.98 (2H, m), 3.00-3.18 (2H, m), 3.78 (2H, d, J=6.4 Hz), 4.95-5.09 (2H, m), 5.21 (2H, s), 6.35-6.48 (2H, m), 6.91 (1H, d, J=7.4 Hz), 7.48-7.57 (5H, m), 8.10 (2H, d, J=8.3 Hz), 12.63 (1H, brs)

Example 70

0.580 g of isobutyl 3-(5-{2-hydroxy-4-[(4-nitrophenethyl)oxy]benzoyl}-2-isobutoxyphenyl) propanoate was dissolved in a mixed solvent of 3 mL of ethanol and 3 mL of tetrahydrofuran, to which 58 mg of 5% palladium-carbon was added, and this mixture was stirred for 3 hours at room temperature in a stream of hydrogen. After the reaction mixture was filtered through Celite, the solvent was distilled out under reduced pressure, and then the resultant residue was purified by silica gel column chromatography [eluent; hexane:ethyl acetate=2:1] to yield 0.515 g of isobutyl 3-(5-{4-[(4-aminophenethyl)oxy]-2-hydroxybenzoyl}-2-isobutoxyphenyl) propanoate as light yellow oil.

NMR (90 MHz, CDCl$_3$) δ value: 0.89 (6H, d, J=6.6 Hz), 1.07 (6H, d, J=6.6 Hz), 1.7-2.3 (2H, m), 2.5-2.8 (2H, m), 2.9-3.1 (4H, m), 3.60 (2H, brs), 3.82 (2H, d, J=6.3 Hz), 3.85 (2H, d, J=6.6 Hz), 4.17 (2H, t, J=7.1 Hz), 6.3-6.5 (2H, m), 6.65 (2H, d, J=8.5 Hz), 6.88 (1H, d, J=9.3 Hz), 7.07 (2H, d, J=8.3 Hz), 7.4-7.6 (3H, m), 12.66 (1H, s)

Example 71

3.32 g of 4-({2-(2-carboxyethyl)-4-[4-(cyclopentyloxy)-2-hydroxybenzoyl]phenoxy}-methyl)benzoic acid was suspended in 3.3 mL of methylene chloride, to which 3.3 mL of 4M hydrogen chloride-ethanol was added, and this mixture was stirred for 7 hours at room temperature. The reaction mixture was concentrated under reduced pressure, and then the resultant residue was purified by silica gel column chromatography [eluent; chloroform:ethanol=10:1] to yield 1.76 g of 4-{[4-[4-(cyclopentyloxy)-2-hydroxybenzoyl]-2-(3-ethoxy-3-oxopropyl)phenoxy]methyl} benzoic acid as white solid.

NMR (400 MHz, CDCl$_3$) δ value: 1.23 (3H, t, J=7.6 Hz), 1.62-1.66 (2H, m), 1.78-1.96 (6H, m), 2.69 (2H, t, J=7.6 Hz), 3.09 (2H, t, J=7.6 Hz), 4.13 (2H, q, J=7.2 Hz), 4.80-4.83 (1H, m), 5.27 (2H, s), 6.37 (1H, dd, J=8.8, 2.4 Hz), 6.48 (1H, d, J=2.4 Hz), 6.94 (1H, d, J=8.4 Hz), 7.50-7.57 (5H, m), 8.16 (2H, d, J=8.4 Hz), 12.69 (2H, brs)

Example 72

The following compounds were obtained in a similar manner as in Example 71.
(1) 4-{[2-(3-ethoxy-3-oxopropyl)-4-(2-hydroxy-4-isobutoxybenzoyl)phenoxy]methyl} benzoic acid NMR (90 MHz, CDCl$_3$) δ value: 1.03 (6H, d, J=6.8 Hz), 1.23 (3H, t, J=7.1 Hz), 1.98-2.27 (1H, m), 2.66-2.76 (2H, m), 3.00-3.09 (2H, m), 3.79 (2H, d, J=6.6 Hz), 4.13 (2H, q, J=7.1 Hz), 5.27 (2H, s), 6.35-6.51 (2H, m), 6.94 (1H, d, J=9.4 Hz), 7.48-7.61 (5H, m), 8.17 (2H, d, J=8.1 Hz), 12.65 (2H, brs)
(2) 4-{[4-(2-hydroxy-4-isobutoxybenzoyl)-2-(3-methoxy-3-oxopropyl)phenoxy]methyl} benzoic acid NMR (90 MHz, DMSO-d$_6$) δ value: 0.99 (6H, d, J=6.7 Hz), 1.92-2.19 (1H, m), 2.62-2.73 (2H, m), 2.86-3.14 (2H, m), 3.57 (3H, s), 3.84 (2H, d, J=5.9 Hz), 5.35 (2H, s), 6.48-6.55 (2H, m), 7.16-7.65 (6H, m), 8.00 (2H, d, J=7.8 Hz), 11.96 (1H, s), 12.80 (1H, brs)

Example 73

0.50 g of 4-{[2-(2-carboxyethyl)-4-(2-hydroxy-4-isobutoxybenzoyl)phenoxy]methyl} benzoic acid was dissolved in 15 mL of N,N-dimethylformamide, to which 1.54 g of potassium carbonate and 1.2 mL of isobutyl bromide were added at room temperature, and this mixture was stirred for one hour at 100° C. The reaction mixture was added to a mixture of chloroform and water, and adjusted to pH 3 with 6M hydrochloric acid, and then followed by separation of the organic phase therefrom. After the resultant organic phase was washed with water and a saturated sodium chloride solution successively, this washed phase was dried over anhydrous magnesium sulfate, and the solvent was distilled out under reduced pressure. The resultant residue was purified by silica gel column chromatography [eluent; chloroform:ethanol=10:1] to yield 0.64 g of isobutyl 4-{[4-(2,4-diisobutoxybenzoyl)-2-(3-isobutoxy-3-oxopropyl)phenoxy]methyl} benzoate as yellow oil.

NMR (90 MHz, CDCl$_3$) δ value: 0.68 (6H, d, J=6.8 Hz), 0.86-1.09 (18H, m), 1.75-2.25 (4H, m), 2.56-2.70 (2H, m), 2.93-3.12 (2H, m), 3.57-3.88 (6H, m), 4.12 (2H, d, J=6.4 Hz), 5.22 (2H, s), 6.46-6.55 (2H, m), 6.83 (1H, d, J=9.1 Hz), 7.32-7.66 (5H, m), 8.07 (2H, d, J=8.3 Hz)

Example 74

72.1 g of methyl 3-(5-[4-(cyclopentyloxy)-2-hydroxybenzoyl]-2-{[3-(methoxymethoxy)-1,2-benzisoxazol-6-yl]methoxy}phenyl) propanoate was dissolved in 220 mL of tetrahydrofuran and 140 mL of methanol, to which 125 g of a 20% aqueous solution of sodium hydroxide and 360 mL of water were added, and this mixture was stirred for 2 hours at room temperature. The reaction mixture to which water was added was adjusted to pH 2 with 6M hydrochloric acid, and then resultant precipitate was filtered out thereof. The precipitates thus obtained were washed with water and diisopropyl ether successively to yield 69.7 g of 3-(5-[4-(cyclopentyloxy)-2-hydroxybenzoyl]-2-{[3-(methoxymethoxy)-1,2-benzisoxazol-6-yl]methoxy}phenyl) propanoic acid as light yellow solid.

NMR (400 MHz, DMSO-d$_6$) δ value: 1.54-1.78 (6H, m), 1.89-2.02 (2H, m), 2.58 (2H, t, J=7.6 Hz), 2.93 (2H, t, J=7.6 Hz), 3.54 (3H, s), 4.87-4.94 (1H, m), 5.44 (2H, s), 5.55 (2H, s), 6.46-6.52 (2H, m), 7.20 (1H, d, J=9.2 Hz), 7.45 (1H, d, J=8.8 Hz), 7.51 (1H, d, J=8.0 Hz), 7.53-7.58 (2H, m), 7.78 (1H, s), 7.84 (1H, d, J=8.0 Hz), 11.93-12.34 (1H, br), 12.04 (1H, brs).

Example 75

69.7 g of 3-(5-[4-(cyclopentyloxy)-2-hydroxybenzoyl]-2-{[3-(methoxymethoxy)-1,2-benzisoxazol-6-yl]methoxy}phenyl) propanoic acid was dissolved in 700 mL of tetrahydrofuran, to which 16.5 mL of N-(2-hydroxyethyl)morpholine and 39.1 g of triphenylphosphine were added at room temperature followed by addition of diisopropyl azodicarboxylate, and this mixture was stirred for 20 minutes at the same temperature. The reaction mixture was added to a mixture of ethyl acetate and water, and then the organic phase was separated therefrom. After the resultant organic phase was washed with water and a saturated sodium chloride solution successively, this washed phase was dried over anhydrous magnesium sulfate, and the solvent was distilled out under reduced pressure. The resultant residue to which toluene was added was stirred in an ice bath, and resultant precipitate was filtered out thereof. The filtrate was concentrated under reduced pressure, and the resultant residue was purified by silica gel column chromatography [eluent; ethyl acetate] to yield 91.0 g of 2-(4-morpholinyl)ethyl 3-(5-[4-(cyclopentyloxy)-2-hydroxybenzoyl]-2-{[3-(methoxymethoxy)-1,2-benzisoxazol-6-yl]methoxy}phenyl) propanoate as yellow oil.

NMR (400 MHz, CDCl$_3$) δ value: 1.58-1.70 (2H, m), 1.74-2.01 (6H, m), 2.45 (4H, t, J=4.8 Hz), 2.58 (2H, t, J=6.4 Hz), 2.72 (2H, t, J=7.6 Hz), 3.09 (2H, t, J=7.6 Hz), 3.63-3.68 (4H, m), 3.65 (3H, s), 4.21 (2H, t, J=6.4 Hz), 4.77-4.85 (1H, m), 5.33 (2H, s), 5.57 (2H, s), 6.37 (1H, dd, J=9.3, 2.4 Hz), 6.48 (1H, d, J=2.4 Hz), 6.95 (1H, d, J=8.3 Hz), 7.36 (1H, d, J=7.6 Hz), 7.48-7.58 (4H, m), 7.72 (1H, d, J=8.3 Hz), 12.69 (1H, s).

Example 76

86.7 g of 2-(4-morpholinyl)ethyl 3-(5-[4-(cyclopentyloxy)-2-hydroxybenzoyl]-2-{[3-(methoxymethoxy)-1,2-benzisoxazol-6-yl]methoxy}phenyl) propanoate was dissolved in 200 mL of methylene chloride and 610 mL of isopropyl alcohol, to which 18.8 mL of methanesulfonic acid was added at room temperature, and this mixture was stirred for 30 minutes at the same temperature. The reaction mixture was added to a mixture of ice water and chloroform, followed by adjustment thereof to pH 6 with a saturated aqueous solution of sodium hydrogen carbonate, and the organic phase was separated therefrom. After the resultant organic phase was washed with a saturated sodium chloride solution, this washed phase was dried over anhydrous magnesium sulfate, and the solvent was distilled out under reduced pressure. The resultant residue was purified by silica gel column chromatography [eluent; chloroform:methanol=20:1] to yield 69.9 g of light yellow solid, which was recrystallized from acetone to yield 46.2 g of 2-(4-morpholinyl) ethyl 3-{5-[4-(cyclopentyloxy)-2-hydroxybenzoyl]-2-[(3-hydroxy-1,2-benzisoxazol-6-yl)methoxy]phenyl} propanoate as colorless crystals.

NMR (400 MHz, CDCl$_3$) δ value: 1.58-1.70 (2H, m), 1.74-2.01 (6H, m), 2.61 (2H, t, J=8.0 Hz), 2.68-2.78 (4H, m), 2.84 (2H, t, J=5.4 Hz), 3.00 (2H, t, J=8.0 Hz), 3.77 (4H, t, J=4.4 Hz), 4.32 (2H, t, J=5.4 Hz), 4.78-4.84 (1H, m), 5.23 (2H, s), 6.20-7.00 (1H, br), 6.36 (1H, dd, J=9.6, 2.4 Hz), 6.47 (1H, d, J=2.4 Hz), 6.90-6.93 (1H, m), 7.22 (1H, d, J=8.0 Hz), 7.40 (1H, s), 7.44-7.52 (3H, m), 7.74 (1H, d, J=8.4 Hz).

Example 77

5.80 g of 3-{5-[4-(cyclopentyloxy)-2-hydroxybenzoyl]-2-[(3-hydroxy-1,2-benzisoxazol-6-yl)methoxy]phenyl} propanoic acid was suspended in 58 mL of methylene chloride, to which 6.2 mL of triethylamine was added at room temperature followed by addition of 3.44 g of trityl chloride in an ice bath, and this mixture was stirred for 30 minutes at room temperature. The reaction mixture to which water was added was adjusted to pH 3 with 6M hydrochloric acid, and the organic phase was separated therefrom. After the resultant organic phase was washed with water, the solvent was distilled out under reduced pressure. The resultant residue was washed with hexane and then purified by silica gel column chromatography [eluent; chloroform:ethanol=50:1] to yield 6.83 g of 3-{5-[4-(cyclopentyloxy)-2-hydroxybenzoyl]-2-[(3-oxo-2-trityl-2,3-dihydro-1,2-benzisoxazol-6-yl)methoxy]phenyl} propanoic acid as yellow solid.

NMR (400 MHz, CDCl$_3$) δ value: 1.5-2.1 (8H, m), 2.72 (2H, t, J=7.4 Hz), 3.06 (2H, t, J=7.4 Hz), 4.75-4.85 (1H, m), 5.20 (2H, s), 6.37 (1H, dd, J=9.4, 2.6 Hz), 6.47 (1H, d, J=2.4 Hz), 6.87 (1H, d, J=8.0 Hz), 7.15-7.35 (11H, m), 7.45-7.60 (10H, m), 7.66 (1H, d, J=8.0 Hz), 12.67 (1H, s).

Example 78

50.0 g of 3-{5-[4-(cyclopentyloxy)-2-hydroxybenzoyl]-2-[(3-oxo-2-trityl-2,3-dihydro-1,2-benzisoxazol-6-yl)methoxy]phenyl} propanoic acid was dissolved in 500 mL of tetrahydrofuran, to which 8.8 mL of N-(2-hydroxyethyl)morpholine and 20.7 g of triphenylphosphine were added at room temperature followed by dropwise addition of 15.5 mL of diisopropyl azodicarboxylate, and this mixture was stirred for one hour at the same temperature. Then, water, ethyl acetate, and a saturated sodium chloride solution were added to the reaction mixture, and the organic phase was separated therefrom. After the resultant organic phase was washed with a saturated sodium chloride solution, this washed phase was dried over anhydrous sodium sulfate, and the solvent was distilled out under reduced pressure. The resultant residue was purified by silica gel column chromatography [eluent; ethyl acetate] to yield 59.0 g of 2-(4-morpholinyl)ethyl 3-{5-[4-(cyclopentyloxy)-2-hydroxybenzoyl]-2-[(3-oxo-2-trityl-2,3-dihydro-1,2-benzisoxazol-6-yl)methoxy]phenyl} propanoate as yellow oil.

NMR (400 MHz, CDCl$_3$) δ value: 1.5-2.1 (8H, m), 2.44 (4H, t, J=4.4 Hz), 2.55 (2H, t, J=6.0 Hz), 2.69 (2H, t, J=7.6 Hz), 3.06 (2H, t, J=7.6 Hz), 3.65 (4H, t, J=4.6 Hz), 4.17 (2H, t, J=5.8 Hz), 4.7-4.9 (1H, m), 5.22 (2H, s), 6.37 (1H, dd, J=8.8, 2.4 Hz), 6.48 (1H, d, J=2.4 Hz), 6.88 (1H, d, J=8.4 Hz), 7.16-7.34 (11H, m), 7.43-7.59 (9H, m), 7.67 (1H, d, J=8.4 Hz), 12.68 (1H, s).

Example 79

134 g of 2-(4-morpholinyl)ethyl 3-{5-[4-(cyclopentyloxy)-2-hydroxybenzoyl]-2-[(3-oxo-2-trityl-2,3-dihydro-1,2-benzisoxazol-6-yl)methoxy]phenyl} propanoate was dissolved in 1.3 L of 1,4-dioxane, to which 670 mL of 3M hydrochloric acid was added at room temperature, and this mixture was stirred for 1.5 hour at 40° C. The reaction mixture to which chloroform was added was adjusted to pH 5 with a saturated aqueous solution of sodium hydrogen carbonate, and the organic phase was separated therefrom. An aqueous phase was extracted with chloroform, and after the combined organic phases were washed with a saturated sodium chloride solution, the washed phases was dried over anhydrous magnesium sulfate, and the solvent was distilled out under reduced pressure. The resultant residue was purified by silica gel column chromatography [eluent; chloroform:methanol=40:1] to yield 38.6 g of 2-(4-morpholinyl) ethyl 3-{5-[4-(cyclopentyloxy)-2-hydroxybenzoyl]-2-[(3-hydroxy-1,2-benzisoxazol-6-yl)methoxy]phenyl} propanoate as colorless crystals.

NMR (400 MHz, CDCl$_3$) δ value: 1.58-2.00 (8H, m), 2.60 (2H, t, J=7.6 Hz), 2.71 (4H, brs), 2.82 (2H, t, J=5.6 Hz), 3.00 (2H, t, J=7.6 Hz), 3.77 (4H, t, J=4.6 Hz), 4.31 (2H, t, J=5.6 Hz), 4.78-4.84 (1H, m), 5.24 (2H, s), 5.7.-6.2 (1H, br), 6.36 (1H, dd, J=9.4, 2.6 Hz), 6.47 (1H, d, J=2.4 Hz), 6.92 (1H, d, J=8.8 Hz), 7.24 (1H, d, J=8.4 Hz), 7.40 (1H, s), 7.46-7.52 (3H, m), 7.74 (1H, d, J=8.0 Hz), 12.4-13.0 (1H, br)

Example 79 (2)

280 g of 2-(4-morpholinyl)ethyl 3-{5-[4-(cyclopentyloxy)-2-hydroxybenzoyl]-2-[(3-oxo-2-trityl-2,3-dihydro-1, 2-benzisoxazol-6-yl)methoxy]phenyl} propanoate was suspended in 560 mL of 1,4-dioxane, to which 92.5 g of methanesulfonic acid was added dropwise at 12 to 15° C., and this mixture was stirred for 15 minutes at 15° C. 20 mL of water was added to the reaction mixture, which was then stirred for one hour at 12 to 15° C., and the resultant precipitate was filtered out thereof. The filtrate was ice-cooled, to which methylene chloride and water were added, and was adjusted to pH 4.5 with a 20% aqueous solution of sodium hydroxide, and then the organic phase was separated therefrom. An aqueous phase was extracted with methylene chloride, and after the combined organic phases were washed with a saturated sodium chloride solution followed by filtration thereof through Celite, the organic phase was separated. The resultant organic phase was dried over anhydrous magnesium sulfate, and the solvent was distilled out under reduced pressure. The resultant residue, to which diisopropyl ether and ethyl acetate were added, was stirred for 30 minutes at room temperature, and then resultant precipitate was filtered out thereof to yield 180 g of light yellow solid.

Then, 170 g of the resultant solid was recrystallized from acetone to yield 142 g of 2-(4-morpholinyl)ethyl 3-{5-[4-(cyclopentyloxy)-2-hydroxybenzoyl]-2-[(3-hydroxy-1,2-benzisoxazol-6-yl)methoxy]phenyl} propanoate as light yellow needle crystals.

melting point: 131-132.5° C.

IR(KBr): 1742, 1625 cm$^{-1}$

NMR (400 MHz, CDCl$_3$) δ value: 1.6-2.0 (8H, m), 2.61 (2H, t, J=7.5 Hz), 2.74 (4H, brs), 2.85 (2H, t, J=5.6 Hz), 3.00 (2H, t, J=7.5 Hz), 3.78 (4H, t, J=4.6 Hz), 4.32 (2H, t, J=5.6 Hz), 4.78-4.84 (1H, m), 5.23 (2H, s), 6.36 (1H, dd, J=9.2, 2.4 Hz), 6.47 (1H, d, J=2.4 Hz), 6.91 (1H, d, J=9.2 Hz), 7.23 (1H, dd, J=8.0, 1.2 Hz), 7.40 (1H, s), 7.47-7.52 (3H, m), 7.74 (1H, d, J=8.0 Hz)

Example 80

(1) 3.00 g of 1-chloroethyl ethyl carbonate was dissolved in 90 mL of acetonitrile, to which 13.3 g of sodium iodide was added, and this mixture was stirred for 1.5 hours at 60° C. This mixture was cooled to room temperature, followed by concentration thereof under reduced pressure, and then insoluble substances were filtered out thereof by adding diethyl ether to the residue. The resultant filtrate was concentrated under reduced pressure to yield 4.60 g of ethyl 1-iodoethyl carbonate as orange oil.

(2) 1.50 g of 3-(5-[4-(cyclopentyloxy)-2-hydroxybenzoyl]-2-{[3-(methoxymethoxy)-1,2-benzisoxazol-6-yl]methoxy}phenyl) propanoic acid and 1.85 g of potassium carbonate were suspended in 15 mL of N,N-dimethylformamide, to which 2.00 g of 1-iodoethyl ethyl carbonate prepared in (1) was added, and this mixture was stirred for one hour at room temperature. The reaction mixture, to which water and ethyl acetate were added, was adjusted to pH 5 with 6M hydrochloric acid, and the organic phase was separated therefrom. After the resultant organic phases was washed with an aqueous solution of sodium thiosulfate and a saturated sodium chloride solution, the washed phase was dried over anhydrous sodium sulfate, and the solvent was distilled out under reduced pressure. The resultant residue was purified by silica gel column chromatography [eluent; hexane:ethyl acetate=4:1] to yield 1.42 g of 1-[(ethoxycarbonyl)oxy]ethyl 3-(5-[4-(cyclopentyloxy)-2-hydroxybenzoyl]-2-{[3-(methoxymethoxy)-1,2-benzisoxazol-6-yl]methoxy}phenyl) propanoate as yellow oil.

NMR (400 MHz, CDCl$_3$) δ value: 1.28 (3H, t, J=7.0 Hz), 1.49 (3H, d, J=5.6 Hz), 1.6-2.1 (8H, m), 2.70-2.76 (2H, m), 3.09 (2H, t, J=7.6 Hz), 3.65 (3H, s), 4.14-4.23 (2H, m), 4.79-4.86 (1H, m), 5.33 (2H, s), 5.57 (2H, s), 6.38 (1H, dd, J=8.8, 2.8 Hz), 6.48 (1H, d, J=2.4 Hz), 6.74-6.80 (1H, m), 6.94 (1H, d, J=8.4 Hz), 7.37 (1H, dd, J=8.2, 1.0 Hz), 7.48-7.59 (4H, m), 7.72 (1H, d, J=8.4 Hz), 12.68 (1H, s).

Example 81

1.40 g of 1-[(ethoxycarbonyl)oxy]ethyl 3-(5-[4-(cyclopentyloxy)-2-hydroxybenzoyl]-2-{[3-(methoxymethoxy)-1,2-benzisoxazol-6-yl]methoxy}phenyl) propanoate was dissolved in 28 mL of 1,4-dioxane, to which 6 mL of 3M hydrochloric acid was added, and this mixture was stirred for 3.5 hours at room temperature. Then, water and ethyl acetate were added to the reaction mixture, and the organic phase was separated therefrom. After the resultant organic phases was washed with water and a saturated sodium chloride solution, the washed phase was dried over anhydrous sodium sulfate, and the solvent was distilled out under reduced pressure. The resultant residue was purified by silica gel column chromatography [eluent; chloroform] to yield 1.12 g of 1-[(ethoxycarbonyl)oxy]ethyl 3-{5-[4-(cyclopentyloxy)-2-hydroxybenzoyl]-2-[(3-hydroxy-1,2-benzisoxazol-6-yl)methoxy]phenyl} propanoate as light yellow solid.

NMR (400 MHz, CDCl$_3$) δ value: 1.29 (3H, t, J=7.2 Hz), 1.49 (3H, d, J=5.4 Hz), 1.5-2.0 (8H, m), 2.70-2.80 (2H, m), 3.10 (2H, t, J=7.6 Hz), 4.1-4.3 (2H, m), 4.8-4.9 (1H, m), 5.33 (2H, s), 6.39 (1H, dd, J=9.2, 2.4 Hz), 6.47 (1H, d, J=2.2 Hz), 6.75-6.85 (1H, m), 6.95 (1H, d, J=8.4 Hz), 7.39 (1H, d, J=8.4 Hz), 7.47-7.62 (4H, m), 7.82 (1H, d, J=8.0 Hz), 9.5-10.0 (1H, br), 12.69 (1H, brs).

Example 82

(1) 9.15 g of cyclohexanol was dissolved in 150 mL of methylene chloride, to which 7.4 mL of pyridine was added followed by dropwise addition of 10 mL of 1-chloroethyl chloroformate in an ice bath, and this mixture was stirred for 2 hours at room temperature. Then, a sodium chloride solution was added to the reaction mixture and the organic phase was separated therefrom. After the resultant organic phase was dried over anhydrous magnesium sulfate, the solvent was distilled out under reduced pressure to yield 18.6 g of 1-chloroethyl cyclohexyl carbonate as colorless oil. 5.00 g of this 1-chloroethyl cyclohexyl carbonate was dissolved in 150 mL of acetonitrile, to which 16.3 g of sodium iodide was added, and this mixture was stirred for one hour at 60° C. The mixture was cooled to room temperature, followed by concentration thereof under reduced pressure, and then insoluble substances were filtered out therefrom by adding diethyl ether to the residue. The resultant filtrate was concentrated under reduced pressure to yield 5.90 g of cyclohexyl 1-iodoethyl carbonate as red oil.

(2) 1.50 g of 3-(5-[4-(cyclopentyloxy)-2-hydroxybenzoyl]-2-{[3-(methoxymethoxy)-1,2-benzisoxazol-6-yl]methoxy}phenyl) propanoic acid and 1.85 g of potassium carbonate were suspended in 15 mL of N,N-dimethylformamide, to which 4.00 g of 1-iodoethyl cyclohexyl carbonate prepared in (1) was added, and this mixture was stirred for one hour at room temperature. The reaction mixture, to which water and ethyl acetate were added, was adjusted to pH 5 with 6M hydrochloric acid, and the organic phase was separated therefrom. An aqueous phase was extracted with ethyl acetate, and then after the combined organic phases were washed with an aqueous solution of sodium thiosulfate and a saturated sodium chloride solution, the washed phase was dried over anhydrous sodium sulfate, and the solvent was distilled out under reduced pressure. The resultant residue was purified by silica gel column chromatography [eluent; hexane:ethyl acetate=5:1] to yield 1.47 g of 1-{[(cyclohexyloxy)carbonyl]oxy}ethyl 3-(5-[4-(cyclopentyloxy)-2-hydroxybenzoyl]-2-{[3-(methoxymethoxy)-1,2-benzisoxazol-6-yl]methoxy}phenyl) propanoate as red oil.

(3) 1.40 g of the resultant oil was dissolved in 42 mL of 1,4-dioxane, to which 9 mL of 3M hydrochloric acid was added, and this mixture was stirred for one hour at room temperature. Then, water and ethyl acetate were added to the reaction mixture and the organic phase was separated therefrom. After the resultant organic phase was washed with water and a saturated sodium chloride solution, the washed phase was dried over anhydrous sodium sulfate, the solvent was distilled out under reduced pressure. The resultant residue was purified by silica gel column chromatography [eluent; chloroform:ethyl acetate=1:1] to yield 1.04 g of 1-{[(cyclohexyloxy)carbonyl]oxy}ethyl 3-{5-[4-(cyclopentyloxy)-2-hydroxybenzoyl]-2-[(3-hydroxy-1,2-benzisoxazol-6-yl)methoxy]phenyl} propanoate as yellow solid.

NMR (400 MHz, CDCl$_3$) δ value: 1.1-2.0 (21H, m), 2.7-2.8 (2H, m), 3.10 (2H, t, J=7.4 Hz), 4.55-4.65 (1H, m), 4.78-4.86 (1H, m), 5.34 (2H, s), 6.39 (1H, dd, J=9.0, 2.6 Hz), 6.48 (1H, d, J=2.4 Hz), 6.74-6.82 (1H, m), 6.95 (1H, d, J=8.8 Hz), 7.40 (1H, d, J=8.0 Hz), 7.45-7.65 (4H, m), 7.83 (1H, d, J=8.0 Hz), 8.0-9.0 (1H, br), 12.68 (1H, brs).

Example 83

1.04 g of 3-(5-[4-(cyclopentyloxy)-2-hydroxybenzoyl]-2-{[3-(methoxymethoxy)-1,2-benzisoxazol-6-yl]methoxy}phenyl) propanoic acid and 512 mg of potassium carbonate were suspended in 10 mL of N,N-dimethylformamide, to which 0.29 mL of chloromethyl pivalate was added, and this mixture was stirred for 2 hours at 40° C. Then, water and ethyl acetate were added to the reaction mixture, and the organic phase was separated therefrom. The remaining aqueous phase was extracted with ethyl acetate, and organic phases were combined together. After the resultant organic phase was washed with a saturated sodium chloride solution, the washed phase was dried over anhydrous magnesium sulfate, and the solvent was distilled out under reduced pressure. The resultant residue was purified by silica gel column chromatography [eluent; hexane:ethyl acetate=3:1] to yield 1.02 g of {[3-(5-[4-(cyclopentyloxy)-2-hydroxybenzoyl]-2-{[3-(methoxymethoxy)-1,2-benzisoxazol-6-yl]methoxy}phenyl) propanoyl]oxy}methyl pivalate as light yellow oil.

NMR (400 MHz, CDCl$_3$) δ value: 1.16 (9H, s), 1.58-2.02 (8H, m), 2.75 (2H, t, J=7.6 Hz), 3.09 (2H, t, J=7.6 Hz), 3.65 (3H, s), 4.75-4.85 (1H, m), 5.32 (2H, s), 5.57 (2H, s), 5.75 (2H, s), 6.38 (1H, dd, J=9.2, 2.4 Hz), 6.48 (1H, d, J=2.8 Hz), 6.95 (1H, d, J=8.4 Hz), 7.36 (1H, d, J=8.0 Hz), 7.45-7.60 (4H, m), 7.72 (1H, d, J=8.4 Hz), 12.68 (1H, s).

Example 84

1.02 g of {[3-(5-[4-(cyclopentyloxy)-2-hydroxybenzoyl]-2-{[3-(methoxymethoxy)-1,2-benzisoxazol-6-yl]methoxy}phenyl) propanoyl]oxy}methyl pivalate was dissolved in 8 mL of 1,4-dioxane and 8 mL of methanol, to which 6 mL of 6M hydrochloric acid was added at room temperature, and this mixture was stirred for 50 minutes at the same temperature. The reaction mixture, to which water was added, was adjusted to pH 7 with an aqueous solution of sodium hydroxide, and then ethyl acetate was added to this mixture and the organic phase was separated therefrom. The remaining aqueous phase was extracted with ethyl acetate, and organic phases were combined together. After the resultant organic phase was washed with a saturated sodium chloride solution, the washed phase was dried over anhydrous magnesium sulfate, and the solvent was distilled out under reduced pressure. The resultant residue, to which a mixture of hexane and ethyl acetate [3:1] was added, was filtered out to yield 0.56 g of [(3-{5-[4-(cyclopentyloxy)-2-hydroxybenzoyl]-2-[(3-hydroxy-1,2-benzisoxazol-6-yl)methoxy]phenyl} propanoyl)oxy]methyl pivalate as white solid.

NMR (400 MHz, DMSO-d$_6$) δ value: 1.04 (9H, s), 1.53-1.80 (6H, m), 1.89-2.00 (2H, m), 2.74 (2H, t, J=7.2 Hz), 2.96 (2H, t, J=7.2 Hz), 3.1-3.7 (1H, br), 4.88-4.94 (1H, m), 5.38 (2H, s), 5.67 (2H, s), 6.4-6.6 (2H, m), 7.20 (1H, d, J=8.4 Hz), 7.35 (1H, d, J=8.0 Hz), 7.45 (1H, d, J=8.4 Hz), 7.50-7.35 (3H, m), 7.80 (1H, d, J=8.0 Hz), 12.10 (1H, brs).

Example 85

1.80 g of 3-(5-[4-(cyclopentyloxy)-2-hydroxybenzoyl]-2-{[3-(methoxymethoxy)-1,2-benzisoxazol-6-yl]methoxy}phenyl) propanoic acid was dissolved in 20 mL of N,N-dimethylformamide, to which 0.9 g of potassium carbonate and 0.3 mL of ethyl iodide were added at room temperature, and this mixture was stirred for one hour at 30 to 35° C. The reaction mixture was added to a mixture of ethyl acetate and ice water, and adjusted to pH 3 with 6M hydrochloric acid, and then the organic phase was separated therefrom. After the resultant organic phase was washed with water, a saturated aqueous solution of sodium hydrogen carbonate, and a saturated sodium chloride solution successively, the washed phase was dried over anhydrous magnesium sulfate, and the solvent was distilled out under reduced pressure. The resultant residue was purified by silica gel column chromatography [eluent; hexane:ethyl acetate=30:1] to yield 1.50 g of ethyl 3-(5-[4-(cyclopentyloxy)-2-hydroxybenzoyl]-2-{[3-(methoxymethoxy)-1,2-benzisoxazol-6-yl]methoxy}phenyl) propanoate as light yellow solid.

NMR (400 MHz, CDCl$_3$) δ value: 1.23 (3H, t, J=7.1 Hz), 1.58-1.72 (2H, m), 1.75-2.02 (6H, m), 2.69 (2H, t, J=7.7 Hz), 3.09 (2H, t, J=7.7 Hz), 3.65 (3H, s), 4.13 (2H, q, J=7.1 Hz), 4.78-4.86 (1H, m), 5.33 (2H, s), 5.57 (2H, s), 6.37 (1H, dd, J=9.2, 2.4 Hz), 6.48 (1H, d, J=2.8 Hz), 6.94 (1H, d, J=8.8 Hz), 7.36 (1H, d, J=8.4 Hz), 7.48-7.60 (4H, m), 7.71 (1H, d, J=8.4 Hz), 12.68 (1H, s).

Example 86

0.70 g of ethyl 3-(5-[4-(cyclopentyloxy)-2-hydroxybenzoyl]-2-{[3-(methoxymethoxy)-1,2-benzisoxazol-6-yl]methoxy}phenyl) propanoate was dissolved in 5 mL of 1,4-dioxane, to which 5 mL of 3M hydrochloric acid was added in an ice bath, and further, 7 mL of ethanol, 5 mL of 1,4-dioxane and 2 mL of 3M hydrochloric acid were added to the mixture, which was stirred for 2 hours at room temperature. The reaction mixture was added to a mixture of ice water and ethyl acetate, and the organic phase was separated therefrom. After the resultant organic phase was washed with a saturated sodium chloride solution, the washed phase was dried over anhydrous magnesium sulfate, and the solvent was distilled out under reduced pressure. The resultant residue, to which diisopropyl ether was added, was filtered out to yield 0.56 g of ethyl 3-{5-[4-(cyclopentyloxy)-2-hydroxybenzoyl]-2-[(3-hydroxy-1,2-benzisoxazol-6-yl)methoxy]phenyl} propanoate as white solid.

NMR (400 MHz, CDCl$_3$) δ value: 1.23 (3H, t, J=7.1 Hz), 1.58-1.72 (2H, m), 1.74-2.04 (6H, m), 2.70 (2H, t, J=7.9 Hz), 3.10 (2H, t, J=7.9 Hz), 4.14 (2H, q, J=7.1 Hz), 4.78-4.90 (1H, m), 5.34 (2H, s), 6.37 (1H, dd, J=8.8, 2.4 Hz), 6.48 (1H, d, J=2.4 Hz), 6.95 (1H, d, J=8.8 Hz), 7.39 (1H, d, J=8.0 Hz), 7.48-7.63 (4H, m), 7.83 (1H, d, J=7.6 Hz), 12.68 (2H, brs).

Example 87

5.50 g of methyl 3-(5-[4-(cyclopentyloxy)-2-hydroxybenzoyl]-2-{[3-(methoxymethoxy)-1,2-benzisoxazol-6-yl]methoxy}phenyl) propanoate was dissolved in 17 mL of 1,4-dioxane and 17 mL of methanol, to which 5.5 mL of 6M hydrochloric acid was added at room temperature, and this mixture was stirred for 20 minutes at the same temperature. Then, water was added to the reaction mixture, and resultant precipitate was filtered out therefrom. The precipitate thus obtained was washed with water to yield 4.99 g of methyl 3-{5-[4-(cyclopentyloxy)-2-hydroxybenzoyl]-2-[(3-hydroxy-1,2-benzisoxazol-6-yl)methoxy]phenyl} propanoate as white solid.

NMR (400 MHz, CDCl$_3$) δ value: 1.57-1.71 (2H, m), 1.74-2.01 (6H, m), 2.71 (2H, t, J=7.6 Hz), 3.11 (2H, t, J=7.6 Hz), 3.69 (3H, s), 4.77-4.85 (1H, m), 5.34 (2H, s), 6.37 (1H, dd, J=8.8, 2.4 Hz), 6.48 (1H, d, J=2.4 Hz), 6.95 (1H, d, J=8.8 Hz), 7.39 (1H, dd, J=8.0, 0.8 Hz), 7.48-7.58 (4H, m), 7.83 (1H, d, J=8.0 Hz), 12.68 (1H, s).

Example 88

(1) 2.08 g of 4,5-dimethyl-1,3-dioxol-2-one was dissolved in 24 mL of benzene, to which 3.25 g of N-bromosuccinimide and 86 mg of 2,2'-azobis(isobutyronitrile) were added at room temperature, and this mixture was stirred for 30 minutes while heating it under reflux. The reaction mixture was cooled to room temperature, and consequently, a solution of 4-bromomethyl-5-methyl-1,3-dioxol-2-one in benzene was obtained.

(2) 3.00 g of methyl 3-(5-[4-(cyclopentyloxy)-2-hydroxybenzoyl]-2-{[3-(methoxymethoxy)-1,2-benzisoxazol-6-yl]methoxy}phenyl) propanoate was dissolved in 15 mL of methanol and 15 mL of tetrahydrofuran, to which a solution of 1.08 g of potassium hydroxide in 4.5 mL of water was added, and this mixture was stirred for one hour at room temperature, and then the solvent was distilled out under reduced pressure. The resultant residue was dissolved in 40 mL of N,N-dimethylformamide, to which 3.60 g of potassium carbonate was added. Then, the benzene solution prepared in (1) was added thereto, and was stirred for one hour at room temperature. The reaction mixture was poured into a mixture of ethyl acetate and water, and adjusted to pH 7 with 6M hydrochloric acid, and then the organic phase was separated therefrom. After the resultant organic phase was washed with water and a saturated sodium chloride solution successively, the washed phase was dried over anhydrous sodium sulfate, and the solvent was distilled out under reduced pressure. The resultant residue was purified by silica gel column chromatography [eluent; toluene:ethyl acetate=5:1] to yield 1.58 g of (5-methyl-2-oxo-1,3-dioxol-4-yl)methyl 3-(5-[4-(cyclopentyloxy)-2-hydroxybenzoyl]-2-{[3-(methoxymethoxy)-1,2-benzisoxazol-6-yl]methoxy}phenyl) propanoate as yellow oil.

NMR (400 MHz, CDCl$_3$) δ value: 1.5-2.0 (8H, m), 2.16 (3H, s), 2.75 (2H, t, J=7.6 Hz), 3.10 (2H, t, J=7.6 Hz), 3.65 (3H, s), 4.5-5.0 (3H, m), 5.33 (2H, s), 5.57 (2H, s), 6.37 (1H, dd, J=8.8, 2.4 Hz), 6.47 (1H, d, J=2.4 Hz), 6.95 (1H, d, J=8.4 Hz), 7.35 (1H, dd, J=8.4, 1.2 Hz), 7.4-7.6 (4H, m), 7.72 (1H, d, J=8.0 Hz), 12.67 (1H, s).

Example 89

1.40 g of (5-methyl-2-oxo-1,3-dioxol-4-yl)methyl 3-(5-[4-(cyclopentyloxy)-2-hydroxybenzoyl]-2-{[3-(methoxymethoxy)-1,2-benzisoxazol-6-yl]methoxy}phenyl) propanoate was dissolved in 28 mL of 1,4-dioxane, to which 14 mL of 3M hydrochloric acid was added, and this mixture was stirred for 2 hours at room temperature. Then, water and chloroform were added to the reaction mixture, and the organic phase was separated therefrom. After the resultant organic phase was washed with a saturated sodium chloride solution, the washed phase was dried over anhydrous sodium sulfate, and the solvent was distilled out under reduced pressure. The resultant residue, to which 15 mL of methylene chloride and 45 mL of hexane were added, was stirred for 30 minutes at room temperature and then filtered out to yield 1.20 g of (5-methyl-2-oxo-1,3-dioxol-4-yl)methyl 3-{5-[4-(cyclopentyloxy)-2-hydroxybenzoyl]-2-[(3-hydroxy-1,2-benzisoxazol-6-yl)methoxy]phenyl} propanoate as light yellow solid.

NMR (400 MHz, CDCl$_3$) δ value: 1.5-2.1 (8H, m), 2.15 (3H, s), 2.76 (2H, t, J=7.6 Hz), 3.11 (2H, t, J=7.6 Hz), 4.7-5.0 (3H, m), 5.35 (2H, s), 6.37 (1H, dd, J=9.2, 2.4 Hz), 6.48 (1H, d, J=2.0 Hz), 6.96 (1H, d, J=8.4 Hz), 7.38 (1H, d, J=7.6 Hz), 7.4-7.7 (4H, m), 7.83 (1H, d, J=8.4 Hz), 12.66 (2H, brs)

Reference Example 1

5.0 g of 3-(2-hydroxyphenyl) propanoic acid, 12.5 g of potassium carbonate, and 7.5 mL of isopropyl iodide were suspended in 50 mL of N,N-dimethylformamide, and this suspension was stirred for 5 hours at 80 to 120° C. After the reaction mixture was filtered out, 10.4 g of potassium carbonate and 6 mL of isopropyl iodide were added to the filtrate, and this mixture was stirred for 3 hours at 80 to 120° C. The reaction mixture was added to a mixture of ethyl acetate and water, and adjusted to pH 2 with 6M hydrochloric acid, and then the organic phase was separated therefrom. After the resultant organic phase was washed with water and a saturated sodium chloride solution successively, the washed phase was dried over anhydrous magnesium sulfate, and the solvent was distilled out under reduced pressure. The resultant residue was purified by silica gel column chromatography [eluent; hexane:ethyl acetate=10:1] to yield 4.55 g of isopropyl 3-(2-isopropoxyphenyl) propanoate as colorless oil.

NMR (90 MHz, CDCl$_3$) δ value: 1.20 (6H, d, J=6.1 Hz), 1.34 (6H, d, J=6.1 Hz), 2.46-2.68 (2H, m), 2.84-3.01 (2H, m), 4.42-4.69 (1H, m), 4.85-5.14 (1H, m), 6.74-6.89 (2H, m), 7.10-7.25 (2H, m)

Reference Example 2

4.38 g of isopropyl 3-(2-isopropoxyphenyl) propanoate was dissolved in 44 mL of methylene chloride, followed by successive dropwise addition of 3.84 mL of titanium tetrachloride at −5° C. and 1.9 mL of (α,α-dichloromethyl methyl ether at 0 to 15° C., and this mixture was stirred for one hour at −5 to −3° C. The reaction mixture was added to a mixture of chloroform and water, then the organic phase was separated therefrom. After the resultant organic phase was washed with water and a saturated sodium chloride solution successively, the washed phase was dried over anhydrous magnesium sulfate, and the solvent was distilled out under reduced pressure. The resultant residue was dissolved in 20 mL of acetonitrile, to which 7.34 g of sodium dihydrogen phosphate dihydrate dissolved in 9 mL of water and 3.17 g of a 80% sodium chlorite dissolved in 5.6 mL of water and 2.9 mL of a 30% hydrogen peroxide solution were successively added at 5 to 10° C., and this mixture was stirred for one hour at room temperature. Then, ethyl acetate and water were added to the reaction mixture, and the organic phase was separated therefrom. After the resultant organic phase was washed with water and a saturated sodium chloride solution successively, the washed phase was dried over anhydrous magnesium sulfate, and the solvent was distilled out under reduced pressure. The resultant residue was purified by silica gel column chromatography [eluent; hexane:ethyl acetate=1:1] to yield 2.69 g of 4-isopropoxy-3-(3-isopropoxy-3-oxopropyl) benzoic acid as light yellowish brown solid.

NMR (90 MHz, CDCl$_3$) δ value: 1.22 (6H, d, J=6.1 Hz), 1.38 (6H, d, J=5.9 Hz), 2.49-2.67 (2H, m), 2.87-3.03 (2H, m), 4.50-5.23 (2H, m), 6.87 (1H, d, J=9.3 Hz), 7.92-8.03 (2H, m), 10.88 (1H, br)

Reference Example 3

10.0 g of resorcin, 87.8 g of potassium carbonate, and 54 mL of isopropyl iodide were suspended in 100 mL of N,N-dimethylformamide, and this suspension was stirred for 10 hours at 90 to 110° C. After the reaction mixture was filtered out, 43.9 g of potassium carbonate and 27 mL of isopropyl iodide were added to the filtrate, and this mixture was stirred for 3 hours at 120 to 130° C. The reaction mixture was added to a mixture of ethyl acetate and water, and adjusted to pH 2 with 6M hydrochloric acid, and then the organic phase was separated therefrom. After the resultant organic phase was washed with water and a saturated sodium chloride solution successively, the washed phase was dried over anhydrous magnesium sulfate, and the solvent was distilled out under reduced pressure. The resultant residue was purified by silica gel column chromatography [eluent; hexane:ethyl acetate=10:1] to yield 6.68 g of 1,3-diisopropoxybenzene as light brown oil.

NMR (90 MHz, CDCl$_3$) δ value: 1.32 (12H, d, J=6.1 Hz), 4.30-4.72 (2H, m), 6.42-6.51 (3H, m), 7.03-7.23 (1H, m)

Reference Example 4

70.0 g of salicylaldehyde and 158.5 g of potassium carbonate were suspended in 700 mL of N,N-dimethylformamide, to which 68 mL of 3-chloro-2-methyl-1-propene was added dropwise over 30 minutes at 70° C., and this mixture was stirred for 30 minutes at the same temperature. Then, the reaction mixture was added to a mixture of ethyl acetate and water, and adjusted to pH 3 with 6M hydrochloric acid, and then the organic phase was separated therefrom. After the resultant organic phase was washed with water and a saturated sodium chloride solution successively, the washed phase was dried over anhydrous magnesium sulfate, and the solvent was distilled out under reduced pressure. The resultant residue was dissolved in 350 mL of ethanol, to which 7.0 g of 5% palladium-carbon was added, and this mixture was stirred for 4 hours at 35° C. in a stream of hydrogen. After the reaction mixture was filtered through Celite, the solvent was distilled out under reduced pressure. The resultant residue was purified by silica gel column chromatography [eluent; hexane:toluene=2:1] to yield 92.4 g of 2-isobutoxybenzaldehyde as light yellow oil.

NMR (90 MHz, CDCl$_3$) δ value: 1.07 (6H, d, J=6.6 Hz), 2.0-2.2 (1H, m), 3.85 (2H, d, J=6.4 Hz), 6.9-7.1 (2H, m), 7.4-7.7 (1H, m), 7.83 (1H, dd, J=8.1, 2.0 Hz), 10.55 (1H, s)

Reference Example 5

0.92 g of 60% sodium hydride was suspended in 30 mL of tetrahydrofuran, to which 5.0 mL of ethyl diethylphosphonoacetate was added dropwise over 5 minutes at room temperature, and this mixture was stirred for 30 minutes at 40° C. Then, after 3.40 g of 2-isobutoxybenzaldehyde dissolved in 20 mL of tetrahydrofuran was added to the mixture dropwise over 20 minutes at room temperature, this mixture was stirred for one hour at the same temperature. The reaction mixture was added to a mixture of ethyl acetate and water, and the organic phase was separated therefrom. After the resultant organic phase was washed with water and a saturated sodium chloride solution successively, the washed phase was dried over anhydrous magnesium sulfate, and the solvent was distilled out under reduced pressure. The resultant residue was purified by silica gel column chromatography [eluent; hexane:ethyl acetate=9:1] to yield 4.30 g of ethyl (E)-3-(2-isobutoxyphenyl)-2-propenoate as light yellow oil.

NMR (90 MHz, CDCl$_3$) δ value: 1.06 (6H, d, J=6.6 Hz), 1.32 (3H, t, J=7.1 Hz), 1.8-2.4 (1H, m), 3.78 (2H, d, J=6.4 Hz), 4.25 (2H, q, J=7.1 Hz), 6.53 (1H, d, J=16.4 Hz), 6.8-7.6 (4H, m), 8.10 (1H, d, J=16.1 Hz)

Reference Example 6

1.50 g of ethyl (E)-3-(2-isobutoxyphenyl)-2-propenoate was dissolved in 15 mL of ethanol, to which 0.30 g of 5% palladium-carbon was added, and this mixture was stirred for one hour at room temperature in a stream of hydrogen. After the reaction mixture was filtered through Celite, the solvent was distilled out under reduced pressure. The resultant residue was purified by silica gel column chromatography [eluent; hexane:ethyl acetate=9:1] to yield 0.76 g of ethyl 3-(2-isobutoxyphenyl) propanoate as colorless oil.

NMR (90 MHz, CDCl$_3$) δ value: 1.04 (6H, d, J=6.6 Hz), 1.22 (3H, t, J=7.1 Hz), 1.9-2.3 (1H, m), 2.5-2.7 (2H, m), 2.9-3.1 (2H, m), 3.73 (2H, d, J=6.4 Hz), 4.12 (2H, q, J=6.8 Hz), 6.7-7.3 (4H, m)

Reference Example 7

12.8 g of ethyl 3-(2-isobutoxyphenyl)-2-propanoate was dissolved in 128 mL of methylene chloride, to which 11.2 mL of titanium tetrachloride and 5.1 mL of α,α-dichloromethyl methyl ether were successively added dropwise at 5 to 10° C., and this mixture was stirred for 30 minutes at room temperature. The reaction mixture was added to a mixture of methylene chloride and water, and the organic phase was separated therefrom. After the resultant organic phase was washed with water and a saturated sodium chloride solution successively, the washed phase was dried over anhydrous magnesium sulfate, and the solvent was distilled out under reduced pressure. The resultant residue was purified by silica gel column chromatography [eluent; hexane:ethyl acetate=10:1] to yield 13.4 g of ethyl 3-(5-formyl-2-isobutoxyphenyl) propanoate as light yellow oil.

NMR (90 MHz, CDCl$_3$) δ value: 1.07 (6H, d, J=6.6 Hz), 1.23 (3H, t, J=7.1 Hz), 2.0-2.4 (1H, m), 2.5-2.8 (2H, m), 2.9-3.1 (2H, m), 3.84 (2H, d, J=6.4 Hz), 4.13 (2H, q, J=7.1 Hz), 6.93 (1H, d, J=9.0 Hz), 7.7-7.9 (2H, m), 9.85 (1H, s)

Reference Example 8

13.9 g of ethyl 3-(5-formyl-2-isobutoxyphenyl) propanoate was dissolved in 139 mL of acetonitrile, to which 21.0 g of sodium dihydrogen phosphate dihydrate dissolved in 100 mL of water and 11.3 g of a 80% sodium chlorite dissolved in 39 mL of water and 11.3 mL of a 30% aq. hydrogen peroxide solution were successively added at 5 to 10° C., and this mixture was stirred for 4 hours at room temperature. Then, chloroform and water were added to the reaction mixture, and the organic phase was separated therefrom. After the resultant organic phase was washed with a 5% aqueous solution of sodium thiosulfate, water and a saturated sodium chloride solution successively, the washed phase was dried over anhydrous magnesium sulfate, and the solvent was distilled out under reduced pressure to yield 13.2 g of 4-isobutoxy-3-(3-ethoxy-3-oxopropyl) benzoic acid as light yellow solid.

NMR (90 MHz, $CDCl_3$) δ value: 1.07 (6H, d, J=6.6 Hz), 1.25 (3H, t, J=7.3 Hz), 2.0-2.4 (1H, m), 2.5-2.8 (2H, m), 2.9-3.1 (2H, m), 3.82 (2H, d, J=6.1 Hz), 4.14 (2H, q, J=7.1 Hz), 6.85 (1H, d, J=8.0 Hz), 7.9-8.1 (2H, m)

Reference Example 9

50 g of 2,4-dihydroxybenzoic acid, 269 g of potassium carbonate, 123 mL of dimethyl sulfate, and 500 mL of N,N-dimethylformamide were suspended together, and this suspension was stirred for 6.5 hours at 70 to 80° C. Further, 90 g of potassium carbonate and 61 mL of dimethyl sulfate were added to this suspension, which was stirred for another 4 hours at 110 to 115° C. This reaction mixture was added to a mixture of ethyl acetate and water, and adjusted to pH 2 with 6M hydrochloric acid, and then the organic phase was separated therefrom. After the resultant organic phase was washed with water and a saturated sodium chloride solution successively, the washed phase was dried over anhydrous magnesium sulfate, and the solvent was distilled out under reduced pressure. The resultant residue was purified by silica gel column chromatography [eluent; hexane:ethyl acetate=1:2] to yield 54 g of methyl 2,4-dimethoxybenzoate as yellow oil.

NMR (90 MHz, $CDCl_3$) δ value: 3.85 (6H, s), 3.89 (3H, s), 6.42-6.55 (2H, m), 7.85 (1H, d, J=9.3 Hz)

Reference Example 10

53 g of methyl 2,4-dimethoxybenzoate was dissolved in 160 mL of ethanol, to which 104 mL of a 5M aqueous solution of sodium hydroxide was added, and this mixture was stirred for 2 hours at 25 to 40° C. Then, chloroform and water were added to the reaction mixture, which was adjusted to pH 2 with 6M hydrochloric acid, and then the organic phase was separated therefrom. After the resultant organic phase was washed with water and a saturated sodium chloride solution successively, the washed phase was dried over anhydrous magnesium sulfate, and the solvent was distilled out under reduced pressure to yield 45 g of 2,4-dimethoxybenzoic acid as white solid.

NMR (90 MHz, $CDCl_3$) δ value: 3.88 (3H, s), 4.04 (3H, s), 6.53-6.69 (2H, m), 8.11 (1H, d, J=8.5 Hz), 10.34 (1H, br)

Reference Example 11

78 g of a 28% solution of sodium methoxide in methanol was added to 150 mL of a solution of 50 g of 3,4-dihydrocoumarin in methanol at room temperature, and then this mixture was stirred for 10 minutes at the same temperature. Then, 96 mL of dimethyl sulfate and 78 g of a 28% solution of sodium methoxide in methanol were successively added to the mixture, which was stirred for another 30 minutes at 20 to 40° C. The reaction mixture was added to a mixture of methylene chloride and water, and adjusted to pH 2 with 6M hydrochloric acid, and then the organic phase was separated therefrom. After the resultant organic phase was washed with water and a saturated sodium chloride solution successively, the washed phase was dried over anhydrous magnesium sulfate, and the solvent was distilled out under reduced pressure. The resultant residue was purified by silica gel column chromatography [eluent; hexane:ethyl acetate=1:1] to yield 61 g of methyl 3-(2-methoxyphenyl) propanoate as colorless oil.

NMR (90 MHz, $CDCl_3$) δ value: 2.50-2.69 (2H, m), 2.86-3.04 (2H, m), 3.66 (3H, s), 3.82 (3H, s), 6.79-6.94 (2H, m), 7.11-7.30 (2H, m)

Reference Example 12

9.05 g of hydroxylamine hydrochloride was dissolved in 84 mL of methanol, to which 40.64 g of a 28% solution of sodium methoxide in methanol was added at room temperature, and then this mixture was stirred for 10 minutes. Then, 21 mL of a solution of 7.00 g of methyl 2-hydroxy-4-methylsalicylate in methanol was added dropwise to the reaction mixture, which was stirred for one hour at room temperature and then another four hours while heating it under reflux. The reaction mixture was added to water, and adjusted to pH 5 with 6M hydrochloric acid, and then resultant precipitate was filtered out thereof. The resultant solid was washed with water and diisopropyl ether successively to yield 5.95 g of N,2-dihydroxy-4-methylbenzamide as light yellow solid.

NMR (400 MHz, DMSO-$d_6$) δ value: 2.26 (3H, s), 6.68 (1H, d, J=8.8 Hz), 6.72 (1H, s), 7.57 (1H, d, J=8.4 Hz), 9.27 (1H, s), 11.38 (1H, brs), 12.29 (1H, brs)

Reference Example 13

N,2-dihydroxy-5-methylbenzamide was obtained in a similar manner as in Reference Example 12.

NMR (400 MHz, DMSO-$d_6$) δ value: 2.22 (3H, s), 6.79 (1H, d, J=8.4 Hz), 7.20 (1H, d, J=8.4 Hz), 7.50 (1H, s), 9.29 (1H, brs), 11.33 (1H, brs), 11.95 (1H, brs)

Reference Example 14

44.0 g of N,2-dihydroxy-4-methylbenzamide was suspended in 880 mL of tetrahydrofuran, to which 147 mL of triethylamine was added dropwise at room temperature and then 28.7 mL of thionyl chloride was added dropwise at 5 to 10° C. successively, and this mixture was stirred for one hour at room temperature. The reaction mixture was added to water, and adjusted to pH 1 with 12M hydrochloric acid, and then resultant precipitate was filtered out thereof. The resultant solid was washed with water to yield 35.2 g of 6-methyl-1,2-benzisoxazol-3-ol as light yellow solid.

NMR (400 MHz, DMSO-$d_6$) δ value: 2.45 (3H, s), 7.14 (1H, d, J=8.0 Hz), 7.36 (1H, s), 7.59 (1H, d, J=8.4 Hz), 12.24 (1H, brs)

Reference Example 15

5-methyl-1,2-benzisoxazol-3-ol was obtained in a similar manner as in Reference Example 14.

NMR (400 MHz, CDCl$_3$) δ value: 2.47 (3H, s), 7.30 (1H, d, J=8.8 Hz), 7.42 (1H, d, J=8.8 Hz), 7.56 (1H, s)

Reference Example 16

20.0 g of methoxymethyl 6-methyl-1,2-benzisoxazol-3-yl ether was dissolved in 200 mL of benzene, to which 20.3 g of N-bromosuccinimide and 1.7 g of 2,2'-azobisisobutyronitrile were successively added at room temperature, and this mixture was stirred for 30 minutes while heating it under reflux. The reaction mixture was cooled to room temperature, and added to a mixture of ethyl acetate and water, and then the organic phase was separated therefrom. After the resultant organic phase was washed with a saturated aqueous solution of sodium hydrogen carbonate and a saturated sodium chloride solution successively, the washed phase was dried over anhydrous magnesium sulfate, and the solvent was distilled out under reduced pressure to yield 28.5 g of 6-(bromomethyl)-3-(methoxymethoxy)-1,2-benzisoxazole as light brown oil.

NMR (400 MHz, CDCl$_3$) δ value: 3.63 (3H, s), 4.59 (2H, s), 5.56 (2H, s), 7.33 (1H, dd, J=8.2, 0.8 Hz), 7.48 (1H, s), 7.65 (1H, d, J=8.0 Hz)

Reference Example 17

Compounds listed in Table 33 were obtained in a similar manner as in Reference Example 16.

TABLE 33

| Reference Example Number | $R^a$ | $R^b$ | $R^c$ | $R^d$ |
|---|---|---|---|---|
| 17(1) | H | H | SO$_2$NMe$_2$ | H |
| 17(2) | H | H | SO$_2$N(Boc)Me | H |
| 17(3) | H | H | SO$_2$N(Boc)$_2$ | H |
| 17(4) | H | H | SO$_3$Ph | H |
| 17(5) | H | H | P(O)(OEt)$_2$ | H |
| 17(6) | H | H | CONMe$_2$ | H |
| 17(7) | H | H | CON(Boc)Me | H |
| 17(8) | H | OMe | COOMe | H |
| 17(9) | H | COOMe | COOMe | H |
| 17(10) | H | O-i-Bu | COO-i-Bu | H |
| 17(11) | O-i-Pr | H | COO-i-Pr | H |
| 17(12) | H | F | COOMe | H |
| 17(13) | H | H | N(Boc)SO$_2$Me | H |
| 17(14) | H | OMe | COOMe | OMe |
| 17(15) | F | H | COOMe | H |
| 17(16) | Br | H | COOMe | H |
| 17(17) | OMOM | H | COOMe | H |

17(1)

yellow oil

17(2)

yellow oil

17(3)

NMR (400 MHz, CDCl$_3$) δ value: 1.49 (18H, s), 4.50 (2H, s), 7.56 (2H, d, J=8.4 Hz), 8.06 (2H, d, J=8.4 Hz)

17(4)

NMR (400 MHz, CDCl$_3$) δ value: 4.49 (2H, s), 6.97-7.02 (2H, m), 7.22-7.34 (3H, m), 7.54 (2H, d, J=8.4 Hz), 7.80-7.86 (2H, m)

17(5)

NMR (400 MHz, CDCl$_3$) δ value: 1.31-1.36 (6H, m), 4.08-4.16 (4H, m), 4.49 (2H, s), 7.48-7.51 (2H, m), 7.77-7.82 (2H, m)

17(6)

colorless oil

17(7)

light yellow oil

17(8)

yellow oil

NMR (400 MHz, CDCl$_3$) δ value: 3.89 (3H, s), 3.93 (3H, s), 4.47 (2H, s), 6.99-7.01 (2H, m), 7.77 (1H, d, J=8.4 Hz)

17(9)

NMR (400 MHz, CDCl$_3$) δ value: 3.90 (3H, s), 3.91 (3H, s), 4.47 (2H, s), 7.55 (1H, dd, J=8.0, 2.0 Hz) 7.70 (1H, d, J=8.0 Hz), 7.73 (1H, d, J=2.0 Hz)

17(10)

yellow oil

17(11)

NMR (90 MHz, CDCl$_3$) δ value: 1.36 (6H, d, J=6.3 Hz), 1.40 (6H, d, J=5.9 Hz), 4.54 (2H, s), 4.5-5.0 (1H, m), 5.0-5.5 (1H, m), 7.3-7.7 (3H, m)

17(12)

yellow oil

17(13)

NMR (400 MHz, CDCl$_3$) δ value: 1.47 (9H, s), 3.43 (3H, s), 4.48 (2H, s), 7.21 (2H, d, J=8.4 Hz), 7.44 (2H, d, J=8.4 Hz)

17(14)

yellow oil

17(15)

yellow oil

17(16)

NMR (400 MHz, CDCl$_3$) δ value: 3.93 (3H, s), 4.61 (2H, s), 7.53 (1H, d, J=8.0 Hz), 7.96 (1H, dd, J=8.0, 1.6 Hz), 8.25 (1H, d, J=1.6 Hz)

17(17)

NMR (400 MHz, CDCl$_3$) δ value: 3.53 (3H, s), 3.91 (3H, s), 4.56 (2H, s), 5.33 (2H, s), 7.40 (1H, d, J=8.0 Hz), 7.66 (1H, d, J=8.0 Hz), 7.74 (1H, s)

Reference Example 18

The following compounds were obtained in a similar manner as in Reference Example 16.

(1) 2-(chloromethyl)pyrazine

NMR (400 MHz, CDCl$_3$) δ value: 4.71 (2H, s), 8.55-8.58 (2H, m), 8.77 (1H, d, J=1.2 Hz)

(2) 5-[4-(bromomethyl)phenyl]-3-isoxazole methoxymethyl ether

NMR (400 MHz, CDCl$_3$) δ value: 3.58 (3H, s), 4.51 (2H, s), 5.37 (2H, s), 6.25 (1H, s), 7.48 (2H, d, J=8.8 Hz), 7.71 (2H, d, J=8.8 Hz)

(3) 3-[4-(bromomethyl)phenyl]-5-methyl-1,2,4-oxadiazole
NMR (400 MHz, CDCl$_3$) δ value: 2.66 (3H, s), 4.52 (2H, s), 7.51 (2H, d, J=8.4 Hz), 8.04 (2H, d, J=8.4 Hz)
(4) 5-(bromomethyl)-1,3-bis(methoxymethyl)-1,3-dihydro-2H-benzimidazol-2-one
light yellow solid
(5) 6-(bromomethyl)-1,2-benzisoxazol-3-yl methyl ether
NMR (400 MHz, CDCl$_3$) δ value: 4.19 (3H, s), 4.58 (2H, s), 7.31 (1H, dd, J=8.4, 1.2 Hz), 7.45 (1H, d, J=0.8 Hz), 7.60 (1H, d, J=8.0 Hz)
(6) 6-(bromomethyl)-2-methyl-1,2-benzisoxazol-3(2H)-one
NMR (400 MHz, CDCl$_3$) δ value: 3.67 (3H, s), 4.54 (2H, s), 7.26-7.31 (2H, m), 7.80 (1H, d, J=8.0 Hz)
(7) 6-(bromomethyl)-2-(methoxymethoxy)-1,2-benzisoxazol-3(2H)-one
NMR (400 MHz, CDCl$_3$) δ value: 3.50 (3H, s), 4.54 (2H, s), 5.33 (2H, s), 7.30-7.33 (2H, m), 7.83 (1H, d, J=8.0 Hz)
(8) 5-(bromomethyl)-3-(methoxymethoxy)-1,2-benzisoxazole
NMR (400 MHz, CDCl$_3$) δ value: 3.64 (3H, s), 4.61 (2H, s), 5.55 (2H, s), 7.44 (1H, d, J=8.8 Hz), 7.59 (1H, dd, J=8.8, 2.0 Hz), 7.70 (1H, d, J=2.0 Hz)
(9) tert-butyl 4-(bromomethyl)-1H-pyrazole-1-carboxylate
NMR (400 MHz, CDCl$_3$) δ value: 1.65 (9H, s), 4.39 (2H, s), 7.74 (1H, s), 8.10 (1H, s)
(10) ethyl 2-(bromomethyl)-1,3-thiazole-4-carboxylate
NMR (90 MHz, CDCl$_3$) δ value: 1.41 (3H, t, J=7.1 Hz), 4.44 (2H, q, J=7.1 Hz), 4.77 (2H, s), 8.23 (1H, s)
(11) ethyl 5-(chloromethyl)-2-pyrazinecarboxylate
NMR (400 MHz, CDCl$_3$) δ value: 1.47 (3H, t, J=7.2 Hz), 4.53 (2H, q, J=7.2 Hz), 4.77 (2H, s), 8.88 (1H, d, J=1.5 Hz), 9.26 (1H, d, J=1.5 Hz)
(12) tert-butyl 5-(bromomethyl)-1,3-dioxo-1,3-dihydro-2H-isoindole-2-carboxylate
NMR (400 MHz, CDCl$_3$) δ value: 1.63 (9H, s), 4.57 (2H, s), 7.81 (1H, dd, J=7.6, 1.6 Hz), 7.91-7.95 (2H, m)
(13) di(tert-butyl) 6-(bromomethyl)-2,4-dioxo-1,3(2H,4H)-quinazolinedicarboxylate
NMR (400 MHz, CDCl$_3$) δ value: 1.65 (9H, s), 1.73 (9H, s), 4.51 (2H, s), 7.00 (1H, d, J=8.4 Hz), 7.59 (1H, dd, J=8.6, 2.4 Hz), 8.07 (1H, d, J=2.0 Hz)
(14) 3-[4-(bromomethyl)phenyl]-4-methyl-1,2,4-oxadiazol-5(4H)-one
NMR (400 MHz, CDCl$_3$) δ value: 3.34 (3H, s), 4.53 (2H, s), 7.59 (2H, d, J=8.8 Hz), 7.61 (2H, d, J=8.8 Hz)

Reference Example 19

3.50 g of methyl 1H-benzimidazole-5-carboxylate hydrochloride and 6.9 mL of triethylamine were suspended in 35 mL of methylene chloride, to which 5.05 g of trityl chloride was added in small portions at 5 to 10° C., and this mixture was stirred for one hour at the same temperature. The reaction mixture was added to a mixture of ethyl acetate and water, and then the organic phase was separated therefrom. After the resultant organic phase was washed with water and a saturated sodium chloride solution successively, the washed phase was dried over anhydrous sodium sulfate, and the solvent was distilled out under reduced pressure. The resultant residue was purified by silica gel column chromatography [eluent; hexane:ethyl acetate=3:1] to yield 3.55 g of a mixture of methyl 1-trityl-1H-benzimidazole-5-carboxylate and methyl 3-trityl-3H-benzimidazole-5-carboxylate as white foam.
methyl 1-trityl-1H-benzimidazole-5-carboxylate
NMR (400 MHz, CDCl$_3$) δ value: 3.90 (3H, s), 6.49 (1H, d, J=8.8 Hz), 7.15-7.19 (6H, m), 7.31-7.34 (9H, m), 7.61 (1H, d, J=8.4 Hz), 7.97 (1H, s), 8.49 (1H, s)
methyl 3-trityl-3H-benzimidazole-5-carboxylate
NMR (400 MHz, CDCl$_3$) δ value: 3.75 (3H, s), 7.15-7.19 (7H, m), 7.31-7.34 (9H, m), 7.77 (1H, d, J=8.4 Hz), 7.87 (1H, d, J=8.4 Hz), 8.02 (1H, s)

Reference Example 20

The following compounds were obtained in a similar manner as in Reference Example 5.
(1) benzyl 4-[(E)-3-ethoxy-3-oxo-1-propenyl]-3-methoxybenzoate
NMR (400 MHz, CDCl$_3$) δ value: 1.34 (3H, t, J=7.1 Hz), 3.94 (3H, s), 4.27 (2H, q, J=7.1 Hz), 5.38 (2H, s), 6.59 (1H, d, J=16.0 Hz), 7.33-7.46 (5H, m), 7.54 (1H, d, J=8.0 Hz), 7.60 (1H, d, J=1.5 Hz), 7.66 (1H, dd, J=8.0, 1.5 Hz), 7.97 (1H, d, J=16.0 Hz)
(2) ethyl (E)-3-(4-formylphenyl)-2-propenoate
NMR (400 MHz, CDCl$_3$) δ value: 1.35 (3H, t, J=7.2 Hz), 4.29 (2H, q, J=7.2 Hz), 6.55 (1H, d, J=16.0 Hz), 7.68 (2H, d, J=8.4 Hz), 7.71 (1H, d, J=16.0 Hz), 7.90 (2H, d, J=8.4 Hz), 10.03 (1H, s)

Reference Example 21

The following compounds were obtained in a similar manner as in Reference Example 6.
(1) 2-[4-(methoxycarbonyl)phenyl]acetic acid
NMR (90 MHz, CDCl$_3$) δ value: 3.71 (2H, s), 3.91 (3H, s), 7.36 (2H, d, J=8.1 Hz), 8.01 (2H, d, J=8.4 Hz)
(2) ethyl 3-(4-formylphenyl)propanoate
light yellow oil
NMR (400 MHz, CDCl$_3$) δ value: 1.23 (3H, t, J=7.2 Hz), 2.66 (2H, t, J=7.8 Hz), 3.04 (2H, t, J=7.6 Hz), 4.13 (2H, q, J=7.2 Hz), 7.38 (2H, d, J=7.8 Hz), 7.81 (2H, d, J=8.0 Hz), 9.98 (1H, s)
(3) 3-cyclopentylphenol
NMR (400 MHz, CDCl$_3$) δ value: 1.54-1.81 (6H, m), 2.01-2.08 (2H, m), 2.89-2.99 (1H, m), 4.64 (1H, brs), 6.62-6.65 (1H, m), 6.72 (1H, t, J=2.0 Hz), 6.82 (1H, d, J=7.6 Hz), 7.15 (1H, t, J=7.6 Hz)
(4) 3-(cyclopentylmethyl)phenol
NMR (400 MHz, CDCl$_3$) δ value: 1.15-1.20 (2H, m), 1.49-1.73 (6H, m), 2.03-2.11 (1H, m), 2.56 (2H, d, J=7.2 Hz), 4.59 (1H, s), 6.63-6.66 (2H, m), 6.74-6.76 (1H, m), 7.11-7.15 (1H, m)
(5) 4-(3-ethoxy-3-oxopropyl)-3-methoxybenzoic acid
NMR (400 MHz, CDCl$_3$) δ value: 1.24 (3H, t, J=7.1 Hz), 2.62 (2H, t, J=7.6 Hz), 2.99 (2H, t, J=7.6 Hz), 3.90 (3H, s), 4.14 (2H, q, J=7.1 Hz), 7.25 (1H, d, J=7.8 Hz), 7.55 (1H, d, J=1.5 Hz), 7.66 (1H, dd, J=7.8, 1.5 Hz)

Reference Example 22

The following compounds were obtained in a similar manner as in Reference Example 7.
(1) methyl 3-formyl-1-benzothiophene-7-carboxylate
NMR (400 MHz, CDCl$_3$) δ value: 4.05 (3H, s), 7.62 (1H, dd, J=8.0, 7.6 Hz), 8.22 (1H, dd, J=7.6, 1.2 Hz), 8.46 (1H, s), 8.95 (1H, dd, J=8.0, 1.2 Hz), 10.18 (1H, s)
(2) methyl 3-formyl-1-benzothiophene-5-carboxylate
NMR (400 MHz, CDCl$_3$) δ value: 3.99 (3H, s), 7.95 (1H, dd, J=8.6, 0.8 Hz), 8.15 (1H, dd, J=8.6, 2.0 Hz), 8.40 (1H, s), 9.33 (1H, dd, J=2.0, 0.8 Hz), 10.19 (1H, s)

(3) methyl 2-(4-formylphenyl)acetate

NMR (90 MHz, CDCl₃) δ value: 3.6-3.8 (2H, m), 3.72 (3H, s), 7.46 (2H, d, J=8.4 Hz), 7.86 (2H, d, J=8.0 Hz), 10.01 (1H, s)

(4) methyl 3-(5-formyl-2-methoxyphenyl)propanoate

NMR (400 MHz, CDCl₃) δ value: 2.63 (2H, t, J=7.6 Hz), 2.99 (2H, t, J=7.6 Hz), 3.68 (3H, s), 3.92 (3H, s), 6.96 (1H, d, J=8.6 Hz), 7.70 (1H, d, J=2.0 Hz), 7.75 (1H, dd, J=8.6, 2.0 Hz), 9.86 (1H, s)

Reference Example 23

The following compounds were obtained in a similar manner as in Reference Example 8.

(1) 4-(cyclopentylmethyl)-2-methoxybenzoic acid

NMR (400 MHz, CDCl₃) δ value: 1.17-1.27 (2H, m), 1.52-1.74 (6H, m), 2.06-2.14 (1H, m), 2.67 (2H, d, J=7.6 Hz), 4.07 (3H, s), 6.85 (1H, s), 6.96 (1H, d, J=8.4 Hz), 8.08 (1H, d, J=8.0 Hz), 10.68 (1H, brs)

(2) 4-isopropyl-2-methoxybenzoic acid

NMR (400 MHz, CDCl₃) δ value: 1.28 (6H, d, J=7.2 Hz), 2.93-3.00 (1H, m), 4.08 (3H, s), 6.89 (1H, d, J=1.6 Hz), 7.02 (1H, dd, J=8.2, 2.0 Hz), 8.10 (1H, d, J=8.0 Hz), 10.72 (1H, brs)

(3) 4-cyclopentyl-2-methoxybenzoic acid

NMR (400 MHz, CDCl₃) δ value: 1.56-1.87 (6H, m), 2.07-2.14 (2H, m), 3.01-3.09 (1H, m), 4.08 (3H, s), 6.90 (1H, d, J=1.2 Hz), 7.02 (1H, dd, J=8.2, 1.6 Hz), 8.09 (1H, d, J=8.0 Hz), 10.68 (1H, brs)

Reference Example 24

0.770 g of 4-cyclopentyl-2-hydroxybenzaldehyde, 0.38 mL of iodomethane, and 0.839 g of potassium carbonate were suspended in 7.7 mL of N,N-dimethylformamide, and this mixture was stirred for 2 hours at 75° C. The reaction mixture, which was cooled to room temperature, was added to a mixture of ethyl acetate and water, and then adjusted to pH 3 with 6M hydrochloric acid, and the organic phase was separated therefrom. After the resultant organic phase was washed with water and a saturated sodium chloride solution successively, the washed phase was dried over anhydrous magnesium sulfate, and the solvent was distilled out under reduced pressure to yield 0.777 g of 4-cyclopentyl-2-methoxybenzaldehyde as yellow oil.

NMR (400 MHz, CDCl₃) δ value: 1.58-1.87 (6H, m), 2.05-2.13 (2H, m), 2.99-3.07 (1H, m), 3.93 (3H, s), 6.84 (1H, d, J=1.2 Hz), 6.91 (1H, dd, J=8.6, 1.2 Hz), 7.75 (1H, d, J=8.0 Hz), 10.40 (1H, s)

Reference Example 25

The following compounds were obtained in a similar manner as in Reference Example 24.

(1) 1-(benzyloxy)-3-bromobenzene

NMR (400 MHz, CDCl₃) δ value: 5.04 (2H, s), 6.89-6.91 (1H, m), 7.08-7.16 (3H, m), 7.31-7.43 (5H, m)

(2) 4-isopropyl-2-methoxybenzaldehyde

NMR (400 MHz, CDCl₃) δ value: 1.28 (6H, d, J=7.2 Hz), 2.91-2.98 (1H, m), 3.93 (3H, s), 6.82 (1H, s), 6.90 (1H, d, J=8.0 Hz), 7.76 (1H, d, J=8.0 Hz), 10.40 (1H, s)

(3) 4-(cyclopentylmethyl)-2-methoxybenzaldehyde

NMR (400 MHz, CDCl₃) δ value: 1.17-1.24 (2H, m), 1.53-1.74 (6H, m), 2.07-2.14 (1H, m), 2.65 (2H, d, J=7.2 Hz), 3.92 (3H, s), 6.78 (1H, s), 6.85 (1H, d, J=7.6 Hz), 7.74 (1H, d, J=8.0 Hz), 10.41 (1H, s)

(4) 3-(benzyloxy)benzaldehyde

NMR (400 MHz, CDCl₃) δ value: 5.13 (2H, s), 7.23-7.49 (9H, m), 9.98 (1H, s)

(5) 4-methyl-3-(4-methylphenyl)-1,2,4-oxadiazol-5(4H)-one

NMR (400 MHz, CDCl₃) δ value: 2.46 (3H, s), 3.32 (3H, s), 7.37 (2H, d, J=8.4 Hz), 7.50 (2H, d, J=8.4 Hz)

(6) 3-methoxy-6-methyl-1,2-benzisoxazole

NMR (400 MHz, CDCl₃) δ value: 2.48 (3H, s), 4.11 (3H, s), 7.07 (1H, dd, J=8.2, 0.4 Hz), 7.22 (1H, d, J=0.4 Hz), 7.48 (1H, d, J=8.0 Hz)

(7) 2,6-dimethyl-1,2-benzisoxazol-3(2H)-one

NMR (400 MHz, CDCl₃) δ value: 2.47 (3H, s), 3.68 (3H, s), 7.00 (1H, s), 7.07 (1H, d, J=8.0 Hz), 7.68 (1H, d, J=8.4 Hz)

Reference Example 26

Compounds listed in Table 34 were obtained in a similar manner as in Reference Example 9.

TABLE 34

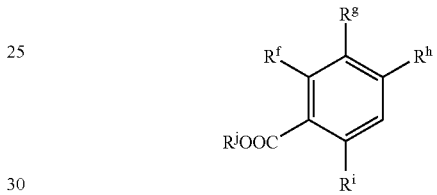

| Reference Example Number | $R^f$ | $R^g$ | $R^h$ | $R^i$ | $R^j$ |
|---|---|---|---|---|---|
| 26(1) | F | H | Me | H | Me |
| 26(2) | OMe | H | Me | H | Me |
| 26(3) | O-i-Bu | H | Me | H | i-Bu |
| 26(4) | OH | H | Me | H | Me |
| 26(5) | OMe | H | Me | OMe | Me |
| 26(6) | H | OH | Me | H | Me |
| 26(7) | H | Br | Me | H | Me |
| 26(8) | H | OMe | Me | H | Me |
| 26(9) | H | F | Me | H | Me |
| 26(10) | H | O-i-Pr | Me | H | i-Pr |
| 26(11) | H | Me | H | OH | Me |
| 26(12) | H | Me | Br | H | Me |
| 26(13) | H | CHO | H | H | Me |
| 26(14) | H | OMe | CHO | H | Bn |

26(1)

NMR (400 MHz, CDCl₃) δ value: 2.39 (3H, s), 3.91 (3H, s), 6.94 (1H, d, J=11.7 Hz), 6.99 (1H, d, J=7.8 Hz), 7.83 (1H, t, J=7.8 Hz)

26(2)

NMR (400 MHz, CDCl₃) δ value: 2.38 (3H, s), 3.87 (3H, s), 3.90 (3H, s), 6.78 (1H, s), 6.79 (1H, d, J=8.4 Hz), 7.72 (1H, d, J=8.4 Hz)

26(3)

NMR (400 MHz, CDCl₃) δ value: 1.00 (6H, d, J=6.8 Hz), 1.05 (6H, d, J=6.8 Hz), 2.06 (1H, sep, J=6.6 Hz), 2.14 (1H, sep, J=6.6 Hz), 2.36 (3H, s), 3.77 (2H, d, J=6.6 Hz), 4.06 (2H, d, J=6.8 Hz), 6.75 (1H, s), 6.76 (1H, d, J=8.0 Hz), 7.71 (1H, d, J=8.0 Hz)

26(4)

NMR (400 MHz, CDCl₃) δ value: 2.34 (3H, s), 3.93 (3H, s), 6.69 (1H, dd, J=8.2, 1.0 Hz), 6.79 (1H, s), 7.71 (1H, d, J=8.0 Hz), 10.70 (1H, s)

26(5)

NMR (400 MHz, CDCl$_3$) δ value: 2.35 (3H, s), 3.80 (6H, s), 3.89 (3H, s), 6.37 (2H, s)

26(6)

NMR (400 MHz, CDCl$_3$) δ value: 2.30 (3H, s), 3.91 (3H, s), 5.67 (1H, s), 7.18 (1H, d, J=8.0 Hz), 7.51 (1H, dd, J=7.6, 2.0 Hz), 7.56 (1H, s)

26(7)

NMR (400 MHz, CDCl$_3$) δ value: 2.44 (3H, s), 3.90 (3H, s), 7.29 (1H, d, J=7.6 Hz), 7.86 (1H, dd, J=7.6, 2.0 Hz), 8.19 (1H, d, J=2.0 Hz)

26(8)

NMR (400 MHz, CDCl$_3$) δ value: 3.99 (3H, s), 5.39 (2H, s), 7.34-7.47 (5H, m), 7.69 (1H, d, J=1.2 Hz), 7.71 (1H, d, J=8.0 Hz), 7.87 (1H, d, J=8.0 Hz), 10.51 (1H, s)

26(9)

NMR (400 MHz, CDCl$_3$) δ value: 2.33 (3H, d, J=1.7 Hz), 3.91 (3H, s), 7.25 (1H, t, J=8.0 Hz), 7.65 (1H, dd, J=10.0, 1.6 Hz), 7.72 (1H, dd, J=8.0, 1.6 Hz),

26(10)

NMR (90 MHz, CDCl$_3$) δ value: 1.36 (12H, d, J=6.4 Hz), 2.24 (3H, s), 4.4-4.9 (1H, m), 5.0-5.5 (1H, m), 7.16 (1H, d, J=8.1 Hz), 7.5-7.6 (2H, m)

26(11)

NMR (400 MHz, CDCl$_3$) δ value: 2.28 (3H, s), 3.94 (3H, s), 6.89 (1H, d, J=8.8 Hz), 7.26 (1H, d, J=8.8 Hz), 7.63 (1H, s), 10.56 (1H, s)

26(12)

NMR (400 MHz, CDCl$_3$) δ value: 2.44 (3H, s), 3.91 (3H, s), 7.60 (1H, d, J=8.4 Hz), 7.70 (1H, dd, J=8.2, 2.4 Hz), 7.90 (1H, d, J=2.4 Hz)

26(13)

NMR (90 MHz, CDCl$_3$) δ value: 3.97 (3H, s), 7.63 (1H, t, J=7.8 Hz), 8.10 (1H, dt, J=8.1, 1.4 Hz), 8.31 (1H, dt, J=7.2, 1.4 Hz), 8.54 (1H, t, J=1.4 Hz), 10.09 (1H, s)

26(14)

NMR (400 MHz, CDCl$_3$) δ value: 3.99 (3H, s), 5.39 (2H, s), 7.34-7.47 (5H, m), 7.69 (1H, d, J=1.2 Hz), 7.71 (1H, d, J=8.0 Hz), 7.87 (1H, d, J=8.0 Hz), 10.51 (1H, s)

Reference Example 27

The following compounds were obtained in a similar manner as in Reference Example 9.

(1) methyl 5-formyl-2-thiophenecarboxylate

NMR (90 MHz, CDCl$_3$) δ value: 3.94 (3H, s), 7.74 (1H, d, J=3.9 Hz), 7.85 (1H, d, J=3.9 Hz), 9.98 (1H, s)

(2) diethyl 2,5-pyridinedicarboxylate

NMR (90 MHz, CDCl$_3$) δ value: 1.43 (3H, t, J=7.1 Hz), 1.47 (3H, t, J=7.1 Hz), 4.46 (2H, q, J=7.1 Hz), 4.52 (2H, q, J=7.1 Hz), 8.20 (1H, d, J=8.4 Hz), 8.45 (1H, dd, J=8.2, 2.0 Hz), 9.33 (1H, d, J=2.0 Hz)

Reference Example 28

5.66 g of cyclopentyltriphenylphosphonim bromide was suspended in 25 mL of diethyl ether, to which 8.8 mL of a solution of n-butyllithium in n-hexane (1.56 M) was added dropwise at −30° C. After the reaction mixture was stirred for one hour at 5° C., 2.67 g of 3-(benzyloxy)benzaldehyde dissolved in 5 mL of diethyl ether was added to the reaction mixture, which was then stirred another one hour at room temperature. The reaction mixture was added to a mixture of methylene chloride and dilute hydrochloric acid, and then the organic phase was separated therefrom. After the resultant organic phase was washed with water and a saturated sodium chloride solution successively, the washed phase was dried over anhydrous magnesium sulfate, and the solvent was distilled out under reduced pressure. The resultant residue was purified by silica gel column chromatography [eluent; hexane:ethyl acetate=5:1] to yield 1.06 g of 1-(benzyloxy)-3-(cyclopentylidenemethyl)benzene as light yellow solid.

NMR (400 MHz, CDCl$_3$) δ value: 1.62-1.69 (2H, m), 1.73-1.78 (2H, m), 2.46-2.53 (4H, m), 5.07 (2H, s), 6.32 (1H, d, J=2.4 Hz), 6.79 (1H, d, J=8.0 Hz), 6.90-6.94 (2H, m), 7.20-7.45 (6H, m)

Reference Example 29

9.10 g of (4-bromo-3-methylphenyl)methanol was dissolved in 91 mL of methylene chloride and cooled to 5° C., to which 19.7 mL of N-ethyldiisopropylamine and 6.9 mL of chloromethyl methyl ether were successively added dropwise at 5 to 10° C., and then this mixture was stirred for 2.5 hours at room temperature. Water was added to the reaction mixture and adjusted to pH 7 with 6M hydrochloric acid, and then the organic phase was separated therefrom. After the resultant organic phase was washed with water and a saturated sodium chloride solution successively, the washed phase was dried over anhydrous sodium sulfate, and the solvent was distilled out under reduced pressure. The resultant residue was purified by silica gel column chromatography [eluent; hexane: ethyl acetate=5:1] to yield 10.44 g of 1-bromo-4-[(methoxymethoxy)methyl]-2-methylbenzene as yellow oil.

NMR (400 MHz, CDCl$_3$) δ value: 2.40 (3H, s), 3.41 (3H, s), 4.52 (2H, s), 4.71 (2H, s), 7.04 (1H, dd, J=8.2, 2.0 Hz), 7.23 (1H, d, J=1.6 Hz), 7.50 (1H, d, J=8.0 Hz)

Reference Example 30

The following compounds were obtained in a similar manner as in Reference Example 29.

(1) 1,3-bis(methoxymethyl)-5-methyl-1,3-dihydro-2H-benzimidazol-2-one

NMR (400 MHz, CDCl$_3$) δ value: 2.41 (3H, s), 3.36 (3H, s), 3.37 (3H, s), 5.33 (2H, s), 5.34 (2H, s), 6.94 (1H, d, J=7.2 Hz), 6.96 (1H, d, J=0.8 Hz), 7.05 (1H, d, J=8.0 Hz)

(2) methoxymethyl 6-methyl-1,2-benzisoxazol-3-yl ether

NMR (400 MHz, CDCl$_3$) δ value: 2.50 (3H, s), 3.63 (3H, s), 5.54 (2H, s), 7.11 (1H, dd, J=8.0, 0.8 Hz), 7.25 (1H, s), 7.54 (1H, d, J=8.0 Hz)

(3) methoxymethyl 5-methyl-1,2-benzisoxazol-3-yl ether

NMR (400 MHz, CDCl$_3$) δ value: 2.46 (3H, s), 3.63 (3H, s), 5.54 (2H, s), 7.33 (1H, d, J=8.8 Hz), 7.36 (1H, d, J=8.8 Hz), 7.45 (1H, s)

(4) 2-(methoxymethyl)-6-methyl-1,2-benzisoxazol-3(2H)-one

NMR (400 MHz, CDCl$_3$) δ value: 2.49 (3H, s), 3.44 (3H, s), 5.31 (2H, s), 7.05 (1H, d, J=0.8 Hz), 7.10 (1H, dd, J=8.0, 0.8 Hz), 7.72 (1H, d, J=8.0 Hz)

(5) (1-benzothiophen-5-ylmethoxy)methyl methyl ether

NMR (400 MHz, CDCl$_3$) δ value: 3.42 (3H, s), 4.71 (2H, s), 4.73 (2H, s), 7.31-7.36 (2H, m), 7.44 (1H, d, J=5.4 Hz), 7.81 (1H, s), 7.86 (1H, d, J=8.3 Hz)

(6) methyl 3-(methoxymethoxy)-4-methylbenzoate

NMR (400 MHz, CDCl$_3$) δ value: 2.30 (3H, s), 3.50 (3H, s), 3.89 (3H, s), 5.25 (2H, s), 7.20 (1H, d, J=8.0 Hz), 7.61 (1H, dd, J=8.0, 1.6 Hz), 7.68 (1H, d, J=1.6 Hz), (7) 3-(methoxymethoxy)-5-(4-methylphenyl)isoxazole NMR (400 MHz, CDCl$_3$) δ value: 2.38 (3H, s), 3.57 (3H, s), 5.35 (2H, s), 6.17 (1H, s), 7.23 (2H, d, J=8.0 Hz), 7.61 (2H, d, J=8.0 Hz)

Reference Example 31

4.00 g of 1-bromo-4-[(methoxymethoxy)methyl]-2-methylbenzene was dissolved in 40 mL of tetrahydrofuran, to which 11.5 mL of a solution of n-butyllithium in n-hexane (1.56 M) was added dropwise at −65 to −60° C., and then this mixture was stirred for 30 minutes at −65° C. Then, 20 mL of N,N-dimethylformamide was added dropwise thereto at −65 to −40° C., and a temperature of this reaction mixture was raised to room temperature over one hour and was stirred for another one hour at room temperature. Water was added to the reaction mixture and adjusted to pH 5 with 6M hydrochloric acid, followed by addition thereto of ethyl acetate, and then the organic phase was separated therefrom. After the resultant organic phase was washed with water and a saturated sodium chloride solution successively, the washed phase was dried over anhydrous magnesium sulfate, and the solvent was distilled out under reduced pressure. The resultant residue was purified by silica gel column chromatography [eluent; hexane:ethyl acetate=5:1] to yield 1.54 g of 4-[(methoxymethoxy)methyl]-2-methylbenzaldehyde as colorless oil.

NMR (400 MHz, CDCl$_3$) δ value: 2.68 (3H, s), 3.43 (3H, s), 4.63 (2H, s), 4.76 (2H, s), 7.26 (1H, s), 7.35 (1H, d, J=7.6 Hz), 7.79 (1H, d, J=7.6 Hz), 10.26 (1H, s)

Reference Example 32

The following compounds were obtained in a similar manner as in Reference Example 31.
(1) diethyl 4-methylphenylphosphonate NMR (400 MHz, CDCl$_3$) δ value: 1.30-1.36 (6H, m), 2.40 (3H, s), 4.07-4.16 (4H, m), 7.26-7.29 (2H, m), 7.68-7.73 (2H, m)

(2) 2-(hydroxymethyl)-1-benzothiophene-5-carboaldehyde

NMR (400 MHz, CDCl$_3$) δ value: 2.12 (1H, brs), 4.98 (2H, s), 7.34 (1H, s), 7.83 (1H, dd, J=8.4, 1.6 Hz), 7.94 (1H, d, J=8.0 Hz), 8.20 (1H, d, J=1.2 Hz), 10.08 (1H, s)

(3) ethyl 5-(hydroxymethyl)-1-benzothiophene-2-carboxylate

NMR (400 MHz, CDCl$_3$) δ value: 1.42 (3H, t, J=7.1 Hz), 1.80 (1H, brs), 4.41 (2H, q, J=7.1 Hz), 4.82 (2H, d, J=5.1 Hz), 7.46 (1H, dd, J=8.6, 1.6 Hz), 7.83-7.86 (2H, m), 8.03 (1H, s)

(4) 2-fluoro-4-methylbenzoic acid

NMR (400 MHz, CDCl$_3$) δ value: 2.42 (3H, s), 6.98 (1H, d, J=12.0 Hz), 7.04 (1H, d, J=7.8 Hz), 7.92 (1H, t, J=7.8 Hz)

Reference Example 33

2.90 g of 3-cyclopentylphenol was dissolved in 14.5 mL of toluene, to which 0.21 mL of tin tetrachloride and 1.7 mL of tri-n-butylamine were added at room temperature in a stream of nitrogen, and then this mixture was stirred for 30 minutes at room temperature followed by addition thereto of 1.18 g of paraformaldehyde, and this mixture was stirred for 1.5 hours at 80° C. Then, the reaction mixture was cooled to room temperature and poured into water, to which methylene chloride was added, and then the organic phase was separated therefrom. After the resultant organic phase was washed with water and a saturated sodium chloride solution successively, the washed phase was dried over anhydrous magnesium sulfate, and the solvent was distilled out under reduced pressure. The resultant residue was purified by silica gel column chromatography [eluent; hexane:ethyl acetate=10:1] to yield 0.77 g of 4-cyclopentyl-2-hydroxybenzaldehyde as yellow oil.

NMR (400 MHz, CDCl$_3$) δ value: 1.57-1.84 (6H, m), 2.04-2.11 (2H, m), 2.97-3.05 (1H, m), 6.86 (1H, s), 6.90 (1H, dd, J=7.8, 1.6 Hz), 7.45 (1H, d, J=8.0 Hz), 9.83 (1H, s), 11.04 (1H, s)

Reference Example 34

The following compounds were obtained in a similar manner as in Reference Example 33.
(1) 2-hydroxy-4-isopropylbenzaldehyde NMR (90 MHz, CDCl$_3$) δ value: 1.26 (6H, d, J=6.8 Hz), 2.79-3.06 (1H, m), 6.85-6.94 (2H, m), 7.47 (1H, d, J=8.5 Hz), 9.84 (1H, s), 11.03 (1H, s)

(2) 4-(cyclopentylmethyl)-2-hydroxybenzaldehyde

NMR (400 MHz, CDCl$_3$) δ value: 1.16-1.21 (2H, m), 1.52-1.73 (6H, m), 2.06-2.14 (1H, m), 2.62 (2H, d, J=7.6 Hz), 6.80 (1H, s), 6.83 (1H, dd, J=8.0, 1.6 Hz), 7.44 (1H, d, J=8.0 Hz), 9.83 (1H, s), 11.04 (1H, s)

Reference Example 35

1.61 mL of cyclopentanecarboxylic acid was dissolved in 5 mL of tetrahydrofuran, and this mixture was added dropwise to 50 mL of solution of lithium diisopropylamide in tetrahydrofuran prepared from 20.9 mL of n-butyllithium in n-hexane (1.56 M) and 4.58 mL of diisopropylamine at −30° C., and then this mixture was stirred for one hour at 50° C. and for another one hour at room temperature. After the reaction mixture was cooled to −30° C., a solution of 5.00 g of methyl 4-(bromomethyl)-2-methoxybenzoate in 5 mL of tetrahydrofuran was added dropwise to this mixture, which was then stirred for 1.5 hours at −10° C. and for another 1.5 hours at room temperature. A saturated aqueous solution of ammonium chloride and diethyl ether were successively added to the reaction mixture, and the organic phase was separated therefrom. A saturated aqueous solution of sodium hydrogen carbonate was added to the resultant organic phase, from which an aqueous phase was separated, followed by adjustment to pH 2 with 6M hydrochloric acid, and then the organic layer was separated therefrom by adding chloroform thereto. After the resultant organic phase was washed with water and a saturated sodium chloride solution successively, the washed phase was dried over anhydrous magnesium sulfate, and the solvent was distilled out under reduced pressure. The resultant residue was purified by silica gel column chromatography [eluent; hexane:ethyl acetate=3:2] to yield 0.718 g of 1-[3-methoxy-4-(methoxycarbonyl)benzyl]-cyclopentanecarboxylic acid as colorless oil.

NMR (400 MHz, CDCl$_3$) δ value: 1.62-1.72 (6H, m), 2.05-2.12 (2H, m), 3.00 (2H, s), 3.84 (3H, s), 3.87 (3H, s), 6.78-6.80 (3H, m), 7.71 (1H, d, J=8.0 Hz)

Reference Example 36

1.50 g of 1-[3-methoxy-4-(methoxycarbonyl)-benzyl]cyclopentanecarboxylic acid was dissolved in 15 mL of tetrahydrofuran, to which 10.3 mL of a 1M solution of borane in tetrahydrofuran was added dropwise at 5 to 10° C., and then this mixture was stirred for one hour at room temperature. Then, acetone and water were successively added dropwise to the reaction mixture, which was added to a mixture of ethyl acetate and water, and the organic phase was separated therefrom. After the resultant organic phase was washed with a saturated aqueous solution of sodium hydrogen carbonate, water, and a saturated sodium chloride solution successively, the washed phase was dried over anhydrous magnesium sulfate, and the solvent was distilled out under reduced pressure. The resultant residue was purified by silica gel column chromatography [eluent; hexane:ethyl acetate=1:1] to yield 0.564 g of methyl 4-{[1-(hydroxymethyl) cyclopentyl]methyl}-2-methoxybenzoate as colorless oil.

NMR (400 MHz, CDCl$_3$) δ value: 1.38-1.66 (9H, m), 2.74 (2H, s), 3.32 (2H, s), 3.88 (3H, s), 3.90 (3H, s), 6.83-6.86 (2H, m), 7.72 (1H, d, J=8.4 Hz)

Reference Example 37

1.16 g of methyl 4-{[1-(hydroxymethyl) cyclopentyl]methyl}-2-methoxybenzoate and 0.764 g of 4-(dimethylamino) pyridine were dissolved in 10 mL of methylene chloride, to which a solution of 0.953 g of para-toluenesulfonyl chloride in 10 mL of methylene chloride was added dropwise at 0° C., and then this mixture was stirred for one hour at room temperature. Further, 1.53 g of 4-(dimethylamino)pyridine and a solution of 1.91 g of para-toluenesulfonyl chloride in 15 mL of methylene chloride was added thereto, and this mixture was stirred for another one hour at room temperature. The reaction mixture was added to water, and the organic phase was separated therefrom. After the resultant organic phase was washed with water and a saturated sodium chloride solution successively, the washed phase was dried over anhydrous magnesium sulfate, and the solvent was distilled out under reduced pressure. The resultant residue was purified by silica gel column chromatography [eluent; hexane:ethyl acetate=2:1] to yield 1.58 g of methyl 2-methoxy-4-{[1-({[(4-methylphenyl)sulfonyl]oxy}methyl)-cyclopentyl]methyl} benzoate as colorless oil.

NMR (400 MHz, CDCl$_3$) δ value: 1.33-1.36 (2H, m), 1.47-1.53 (4H, m), 1.59-1.63 (2H, m), 2.46 (3H, s), 2.71 (2H, s), 3.66 (2H, s), 3.88 (6H, s), 6.64 (1H, dd, J=8.0, 1.6 Hz), 6.80 (1H, d, J=1.6 Hz), 7.35 (2H, d, J=8.0 Hz), 7.61 (1H, d, J=8.0 Hz), 7.77-7.80 (2H, m)

Reference Example 38

Phenyl 4-methylbenzenesulfonate was obtained in a similar manner as in Reference Example 37.

NMR (400 MHz, CDCl$_3$) δ value: 2.45 (3H, s), 6.96-6.99 (2H, m), 7.22-7.32 (5H, m), 7.70 (2H, d, J=8.8 Hz)

Reference Example 39

1.58 g of methyl 2-methoxy-4-{[1-({[(4-methylphenyl)sulfonyl]oxy}methyl)cyclopentyl]methyl} benzoate, 0.716 g of zinc dust, and 1.64 g of sodium iodide were suspended in 16 mL of N,N-dimethylformamide, and this mixture was stirred for 2.5 hours at 115° C. The reaction mixture was cooled to room temperature, to which diethyl ether was added, and filtered through Celite. The filtrate was added to a mixture of ethyl acetate and dilute hydrochloric acid, and the organic phase was separated therefrom. After the resultant organic phase was washed with an aqueous solution of sodium thiosulfate, water and a saturated sodium chloride solution successively, the washed phase was dried over anhydrous magnesium sulfate, and the solvent was distilled out under reduced pressure. The resultant residue was purified by silica gel column chromatography [eluent; hexane:ethyl acetate=2:1] to yield 0.725 g of methyl 2-methoxy-4-[(1-methylcyclopentyl)methyl] benzoate as colorless oil.

NMR (400 MHz, CDCl$_3$) δ value: 0.90 (3H, s), 1.30-1.34 (2H, m), 1.49-1.55 (2H, m), 1.65-1.68 (4H, m), 2.62 (2H, s), 3.88 (3H, s), 3.90 (3H, s), 6.75-6.79 (2H, m), 7.71 (1H, d, J=8.0 Hz)

Reference Example 40

8.75 g of copper (II) bromide was suspended in 40 mL of acetonitrile, to which a solution of 5.82 mL of tert-butyl nitrite in 5 mL of acetonitrile was added dropwise at room temperature in a stream of nitrogen and then a suspension of 5.00 g of 4-amino-2-hydroxybenzoic acid in 100 mL of acetonitrile was added dropwise in an ice bath, and this suspension was stirred for 2 hours at 5 to 10° C. The reaction mixture was added dropwise to a mixture of ice and 6M hydrochloric acid, to which diethyl ether was added, and the organic phase was separated therefrom. After the resultant organic phase was washed with 6M hydrochloric acid, water, and a saturated sodium chloride solution successively, the washed phase was dried over anhydrous magnesium sulfate, and the solvent was distilled out under reduced pressure to yield 7.84 g of 4-bromo-2-hydroxybenzoic acid as black solid.

NMR (400 MHz, DMSO-d$_6$) δ value: 7.13 (1H, dd, J=8.4, 2.0 Hz), 7.22 (1H, d, J=2.0 Hz), 7.71 (1H, d, J=8.4 Hz), 10.5-10.7 (1H, br), 11.1-11.5 (1H, br)

Reference Example 41

1.85 g of magnesium was suspended in 15 mL of diethyl ether, to which a catalytic amount of iodine was added and then a solution of 20.00 g of 1-(benzyloxy)-3-bromobenzene in 40 mL of diethyl ether was added dropwise and this mixture was stirred for 8 hours while heating it under reflux. The reaction mixture was cooled to 5° C., to which a solution of 6.72 mL of cyclopentanone in 20 mL of diethyl ether was added dropwise, and this mixture was stirred for one hour at room temperature. Then an aqueous solution of ammonia chloride was added to the ice-cooled reaction mixture, and the organic phase was separated therefrom. After the resultant organic phase was washed with water and a saturated sodium chloride solution successively, the washed phase was dried over anhydrous magnesium sulfate, and the solvent was distilled out under reduced pressure. The resultant residue was purified by silica gel column chromatography [eluent; hexane:ethyl acetate=10:1] to yield 7.65 g of 1-[3-(benzyloxy)phenyl] cyclopentanol as yellow oil.

NMR (400 MHz, CDCl$_3$) δ value: 1.52 (1H, s), 1.79-1.88 (2H, m), 1.93-2.04 (6H, m), 5.08 (2H, s), 6.85 (1H, ddd, J=8.4, 2.8, 1.2 Hz), 7.08 (1H, ddd, J=7.6, 1.6, 0.8 Hz), 7.16-7.17 (1H, m), 7.24-7.46 (6H, m)

Reference Example 42

10.55 g of methyl 4-bromo-3-methylbenzoate was dissolved in 110 mL of tetrahydrofuran, to which 1.31 g of lithium aluminium hydride was added dropwise in small portions at −30 to −20° C., and this mixture was stirred for 15 minutes at −20° C. Then a mixed solution of methanol and water (4:1) was added dropwise to the reaction mixture, and this mixture was stirred for 30 minutes at room temperature. The reaction mixture, to which water was added, was adjusted to pH 7 with 6M hydrochloric acid followed by addition of ethyl acetate, and the organic phase was separated therefrom. After the resultant organic phase was washed with water and a saturated sodium chloride solution successively, the washed phase was dried over anhydrous magnesium sulfate, and the solvent was distilled out under reduced pressure to yield 9.20 g of (4-bromo-3-methylphenyl)methanol as brown oil.

NMR (400 MHz, CDCl$_3$) δ value: 1.74 (1H, brs), 2.40 (3H, s), 4.62 (2H, s), 7.04 (1H, dd, J=8.2, 2.0 Hz), 7.23 (1H, d, J=2.0 Hz), 7.50 (1H, d, J=8.0 Hz)

Reference Example 43

A mixture of (1-trityl-1H-benzimidazol-5-yl)methanol and (1-trityl-1H-benzimidazol-6-yl)methanol was obtained in a similar manner as in Reference Example 42.

(1-trityl-1H-benzimidazol-5-yl)methanol

NMR (400 MHz, CDCl$_3$) δ value: 2.05 (1H, brs), 4.71 (2H, s), 6.46 (1H, d, J=8.4 Hz), 6.94 (1H, dd, J=8.4, 1.6 Hz), 7.16-7.19 (6H, m), 7.31-7.32 (9H, m), 7.73 (1H, d, J=1.6 Hz), 7.88 (1H, s)

(1-trityl-1H-benzimidazol-6-yl)methanol

NMR (400 MHz, CDCl$_3$) δ value: 1.56 (1H, brs), 4.45 (2H, s), 6.44 (1H, s), 7.16-7.19 (6H, m), 7.31-7.32 (10H, m), 7.73 (1H, d, J=1.6 Hz), 7.88 (1H, s)

Reference Example 44

4.00 g of 2-amino-5-methylbenzoic acid was dissolved in 40 mL of 1,4-dioxane, to which 5.5 mL of triethylamine and 6.8 mL of diphenylphosphoryl azide were successively added, and this mixture was stirred for 1.5 hours while heating it under reflux. The reaction mixture, to which a mixture of ethyl acetate and water was added, was adjusted to pH 7 with 1M hydrochloric acid, and the organic phase was separated therefrom. After the resultant organic phase was washed with water and a saturated sodium chloride solution successively, the washed phase was dried over anhydrous sodium sulfate, and the solvent was distilled out under reduced pressure to yield 2.96 g of 5-methyl-1,3-dihydro-2H-benzimidazol-2-one as light yellow solid.

NMR (400 MHz, DMSO-d$_6$) δ value: 2.27 (3H, s), 6.72-6.75 (2H, m), 6.80 (1H, d, J=8.0 Hz), 10.47 (1H, s), 10.51 (1H, s)

Reference Example 45

1.00 g of methyl 3-formyl-1-benzothiophene-7-carboxylate was dissolved in a mixed solution of 15 mL of ethanol and 15 mL of tetrahydrofuran, to which 86 mg of sodium borohydride was added at room temperature, and this solution was stirred for one hour at the same temperature. After acetone was added dropwise to the reaction mixture, from which the solvent was distilled out under reduced pressure, followed by addition of ethyl acetate and water, and this mixture was adjusted to pH 6 with 6M hydrochloric acid, and the organic phase was separated therefrom. After the resultant organic phase was washed with water and a saturated sodium chloride solution successively, the washed phase was dried over anhydrous magnesium sulfate, and the solvent was distilled out under reduced pressure to yield 0.97 g of methyl 3-(hydroxymethyl)-1-benzothiophene-7-carboxylate as light yellow solid.

NMR (400 MHz, CDCl$_3$) δ value: 1.73 (1H, brs), 4.03 (3H, s), 4.97 (2H, s), 7.47-7.53 (2H, m), 8.11 (1H, d, J=8.0 Hz), 8.14 (1H, d, J=8.0 Hz)

Reference Example 46

Compounds listed in Table 35 were obtained in a similar manner as in Reference Example 45.

TABLE 35

| Reference Example Number | $R^m$ | $R^n$ |
|---|---|---|
| 46(1) | H | CH$_2$CH$_2$COOEt |
| 46(2) | H | CH=CHCOOEt |
| 46(3) | COOMe | H |
| 46(4) | H | SMe |
| 46(5) | CH$_2$CH$_2$COOMe | OMe |
| 46(6) | —OCH$_2$O— | |

46(1)

NMR (400 MHz, CDCl$_3$) δ value: 1.24 (3H, t, J=7.2 Hz), 1.69 (1H, brs), 2.61 (2H, t, J=7.6 Hz), 2.95 (2H, t, J=7.6 Hz), 4.12 (2H, q, J=7.2 Hz), 4.66 (2H, s), 7.20 (2H, d, J=8.0 Hz), 7.29 (2H, d, J=8.0 Hz)

46(2)

NMR (400 MHz, CDCl$_3$) δ value: 1.34 (3H, t, J=7.1 Hz), 2.00 (1H, brs), 4.26 (2H, q, J=7.1 Hz), 4.72 (2H, s), 6.42 (1H, d, J=16.1 Hz), 7.38 (2H, d, J=8.1 Hz), 7.51 (2H, d, J=8.1 Hz), 7.66 (1H, d, J=16.1 Hz)

46(3)

NMR (90 MHz, CDCl$_3$) δ value: 2.02 (1H, brs), 3.92 (3H, s), 4.75 (2H, s), 7.34-7.62 (2H, m), 7.90-8.02 (2H, m)

46(4)

NMR (90 MHz, CDCl$_3$) δ value: 1.77 (1H, brs), 2.48 (3H, s), 4.64 (2H, s), 7.16-7.38 (4H, m)

46(5)

NMR (400 MHz, CDCl$_3$) δ value: 1.71 (1H, brs), 2.61 (2H, t, J=7.6 Hz), 2.93 (2H, t, J=7.6 Hz), 3.67 (3H, s), 3.82 (3H, s), 4.59 (2H, s), 6.82 (1H, d, J=8.3 Hz), 7.15 (1H, d, J=2.2 Hz), 7.19 (1H, dd, J=8.3, 2.2 Hz)

46(6)

NMR (400 MHz, CDCl$_3$) δ value: 1.58-1.63 (1H, m), 4.58 (2H, d, J=6.0 Hz), 5.96 (2H, s), 6.78 (1H, d, J=8.0 Hz), 6.82 (1H, dd, J=8.0, 1.6 Hz), 6.87 (1H, d, J=1.6 Hz)

Reference Example 47

The following compounds were obtained in a similar manner as in Reference Example 45.

(1) 1-[4-(hydroxymethyl)phenyl]-4-methyl-2,3-piperazinedione

NMR (400 MHz, DMSO-d$_6$) δ value: 2.99 (3H, s), 3.67 (2H, dd, J=6.8, 4.8 Hz), 3.92 (2H, dd, J=6.8, 4.8 Hz), 4.50 (2H, d, J=5.6 Hz), 5.22 (1H, t, J=5.8 Hz), 7.31-7.36 (4H, m)

(2) 3-[4-(hydroxymethyl)phenyl]-1,3-oxazolidin-2-one

NMR (400 MHz, DMSO-d$_6$) δ value: 4.05 (2H, t, J=8.2 Hz), 4.41-4.47 (4H, m), 5.14 (1H, t, J=5.8 Hz), 7.32 (2H, d, J=8.0 Hz), 7.51 (1H, dd, J=9.0, 2.2 Hz), 7.52 (1H, dd, J=9.0, 2.2 Hz)

(3) methyl 3-(hydroxymethyl)-1-benzothiophene-5-carboxylate

NMR (400 MHz, CDCl$_3$) δ value: 2.01 (1H, brs), 3.96 (3H, s), 4.99 (2H, s), 7.47 (1H, s), 7.89 (1H, d, J=8.4 Hz), 8.01 (1H, dd, J=8.4, 1.6 Hz), 8.54 (1H, d, J=1.2 Hz)

(4) methyl 5-(hydroxymethyl)-2-thiophenecarboxylate
NMR (90 MHz, CDCl$_3$) δ value: 2.3-2.5 (1H, m), 3.87 (3H, s), 4.85 (2H, d, J=4.9 Hz), 6.98 (1H, dd, J=3.7, 0.7 Hz), 7.66 (1H, d, J=3.7 Hz)

(5) 1-benzothiophen-5-ylmethanol
NMR (400 MHz, CDCl$_3$) δ value: 1.78 (1H, brs), 4.80 (2H, s), 7.31-7.36 (2H, m), 7.45 (1H, d, J=5.6 Hz), 7.81 (1H, s), 7.86 (1H, d, J=8.4 Hz)

Reference Example 48

Benzyl 2-(4-formylphenyl)acetate was obtained in a similar manner as in Reference Example 9.
NMR (90 MHz, CDCl$_3$) δ value: 3.76 (2H, s), 5.15 (2H, s), 7.16-7.55 (7H, m), 7.76-7.89 (2H, m), 10.00 (1H, s)

Reference Example 49

29.7 g of hydroxylamine hydrochloride was dissolved in 100 mL of methanol, to which 82.4 g of a 28% solution of sodium methoxide in methanol was added at room temperature, and this solution was stirred for one hour at the same temperature. 10.0 g of 4-methylbenzonitrile was added to this mixture, which was then stirred for 2 hours at room temperature. The reaction mixture was concentrated under reduced pressure, to which water was added, and adjusted to pH 8 with 6M hydrochloric acid, followed by addition thereto of ethyl acetate, and the organic phase was separated therefrom. After the resultant organic phase was washed with water and a saturated sodium chloride solution successively, the washed phase was dried over anhydrous magnesium sulfate, and the solvent was distilled out under reduced pressure to yield 11.6 g of N'-hydroxy-4-methylbenzenecarboxyimidamide as white solid.
NMR (400 MHz, CDCl$_3$) δ value: 2.37 (3H, s), 4.87 (2H, brs), 8.31 (1H, brs), 7.20 (2H, d, J=8.0 Hz), 7.51 (2H, d, J=8.0 Hz)

Reference Example 50

1.00 g of N'-hydroxy-4-methylbenzenecarboxyimidamide was dissolved in 14 mL of N,N-dimethylformamide, to which 0.59 mL of pyridine was added at room temperature and then 1.28 g of 2-ethylhexyl chloroformate was added at 5° C., this solution was stirred for one hour at the same temperature. The reaction mixture was added to a mixture of water and ethyl acetate, and the organic phase was separated therefrom. After the resultant organic phase was washed with water and a saturated sodium chloride solution successively, the washed phase was dried over anhydrous sodium sulfate, and the solvent was distilled out under reduced pressure. 14 mL of xylene was added to the resultant residue, and which was stirred for one hour while heating it under reflux. The reaction mixture was cooled to room temperature, from which resultant precipitate was filtered out, and the resultant precipitate was washed with hexane and then with diisopropyl ether to yield 0.78 g of 3-(4-methylphenyl)-1,2,4-oxadiazol-5(4H)-one as white solid.
NMR (400 MHz, DMSO-d$_6$) δ value: 2.38 (3H, s), 7.39 (2H, d, J=8.4 Hz), 7.70 (2H, d, J=8.4 Hz), 12.90 (1H, brs)

Reference Example 51

2.00 g of N'-hydroxy-4-methylbenzenecarboxyimidamide was dissolved in 40 mL of acetic anhydride, and this solution was stirred for 1.5 hours while heating it under reflux. After the reaction mixture was cooled to room temperature, the solvent was distilled out thereof under reduced pressure, and then the resultant residue was purified by silica gel column chromatography to yield 1.20 g of 5-methyl-3-(4-methylphenyl)-1,2,4-oxadiazole as yellow solid.
NMR (400 MHz, CDCl$_3$) δ value: 2.41 (3H, s), 2.65 (3H, s), 7.28 (2H, d, J=8.0 Hz), 7.94 (2H, d, J=8.0 Hz)

Reference Example 52

1.00 g of 4-methyl-1H-pyrazole and 2.5 mL of triethylamine were dissolved in 10 mL of tetrahydrofuran, to which 3.1 mL of di-tert-butyl dicarbonate and 73 mg of 4-(dimethylamino)pyridine were successively added, and this solution was stirred for 30 minutes at room temperature. The reaction mixture was added to a mixture of water and ethyl acetate, and adjusted to pH 7 with 6M hydrochloric acid, and then the organic phase was separated therefrom. After the resultant organic phase was washed with water and a saturated sodium chloride solution successively, the washed phase was dried over anhydrous magnesium sulfate, and the solvent was distilled out under reduced pressure to yield 2.23 g of tert-butyl 4-methyl-1H-pyrazole-1-carboxylate as light yellow oil.
NMR (400 MHz, CDCl$_3$) δ value: 1.64 (9H, s), 2.09 (3H, s), 7.54 (1H, s), 7.84 (1H, s)

Reference Example 53

The following compounds were obtained in a similar manner as in Reference Example 52.
(1) di-tert-butyl 6-methyl-2,4-dioxo-1,3-(2H,4H)-quinazolinedicarboxylate
NMR (400 MHz, CDCl$_3$) δ value: 1.64 (9H, s), 1.73 (9H, s), 2.38 (3H, s), 6.90 (1H, d, J=8.0 Hz), 7.36 (1H, dd, J=8.4, 2.0 Hz), 7.85 (1H, d, J=2.0 Hz)
(2) tert-butyl methyl[(4-methylphenyl)sulfonyl]carbamate
NMR (400 MHz, CDCl$_3$) δ value: 1.35 (9H, s), 2.44 (3H, s), 3.35 (3H, s), 7.31 (2H, d, J=8.0 Hz), 7.78 (2H, d, J=8.4 Hz)
(3) tert-butyl methyl(4-methylbenzoyl)-carbamate
NMR (400 MHz, CDCl$_3$) δ value: 1.19 (9H, s), 2.39 (3H, s), 3.29 (3H, s), 7.19 (2H, d, J=8.0 Hz), 7.42 (2H, d, J=8.4 Hz)
(4) tert-butyl 4-methylphenyl-(methylsulfonyl)carbamate
NMR (400 MHz, CDCl$_3$) δ value: 1.48 (9H, s), 2.37 (3H, s), 3.41 (3H, s), 7.11 (2H, d, J=7.6 Hz), 7.20 (2H, d, J=7.6 Hz)
(5) tert-butyl 5-methyl-1,3-dioxo-1,3-dihydro-2H-isoindole-2-carboxylate
NMR (400 MHz, CDCl$_3$) δ value: 1.63 (9H, s), 2.54 (3H, s), 7.59 (1H, dd, J=7.6, 0.8 Hz), 7.73 (1H, d, J=0.8 Hz), 7.82 (1H, d, J=7.6 Hz)
(6) tert-butyl 3-hydroy-1-pyrrolidinecarboxylate
NMR (90 MHz, CDCl$_3$) δ value: 1.46 (9H, s), 1.8-2.1 (3H, m), 3.2-3.6 (4H, m), 4.3-4.6 (1H, m)

Reference Example 54

16.5 g of 1-benzothiophene-5-carbaldehyde and 49.5 mL of ethylene glycol were dissolved in 165 mL of toluene, to which 0.30 g of para-toluenesulfonic acid monohydrate was added, and this solution was stirred for 7 hours while heating it under reflux. The reaction mixture was cooled to room temperature, to which an aqueous solution of sodium hydroxide was added, and then the organic phase was separated therefrom. After the resultant organic phase was washed with water and a saturated sodium chloride solution successively, the washed phase was dried over anhydrous magnesium sulfate, and the solvent was distilled out under reduced pressure. The resultant residue was purified by silica gel column chromatography [eluent; hexane:ethyl acetate=5:1] to yield 15.8 g of 2-(1-benzothiophen-5-yl)-1,3-dioxolane as yellow oil.

NMR (400 MHz, CDCl$_3$) δ value: 4.03-4.18 (4H, m), 5.95 (1H, s), 7.34 (1H, d, J=5.6 Hz), 7.45-7.48 (2H, m), 7.89 (1H, d, J=8.4 Hz), 7.94 (1H, s)

Reference Example 55

3.83 g of silver nitrate was dissolved in 10 mL of water, to which a solution of 1.81 g of sodium hydroxide in 10 mL of water was added dropwise and then a solution of 2.00 g of 2-methyl-1,3-benzothiazole-5-carbaldehyde in 20 mL of tetrahydrofuran was added dropwise at room temperature, and this solution was stirred for 30 minutes at the same temperature. The reaction mixture was filtered through Celite, and 6M hydrochloric acid was added to the filtrate to adjust its pH value to 3.5 followed by addition of ethyl acetate, and then the organic phase was separated therefrom. After the resultant organic phase was washed with a saturated sodium chloride solution, the washed phase was dried over anhydrous magnesium sulfate, and the solvent was distilled out under reduced pressure. The resultant residue was dissolved in 30 mL of methylene chloride, to which 20 μL of N,N-dimethylformamide and 1.5 mL of oxalyl chloride were added successively, and this solution was stirred for 30 minutes at room temperature. The reaction mixture, to which 20 mL of methanol was added dropwise, was stirred for 30 minutes at room temperature, and after water was added thereto, the pH value of this mixture was adjusted to 7 with a 5M solution of sodium hydroxide in water, and then the organic phase was separated therefrom. After the resultant organic phase was washed with a saturated sodium chloride solution, the washed phase was dried over anhydrous magnesium sulfate, and the solvent was distilled out under reduced pressure to yield 1.90 g of methyl 2-methyl-1,3-benzothiazole-5-carboxylate as light yellow solid.

NMR (400 MHz, CDCl$_3$) δ value: 2.87 (3H, s), 3.97 (3H, s), 7.88 (1H, d, J=8.4 Hz), 8.03 (1H, dd, J=8.4, 1.6 Hz), 8.61 (1H, d, J=1.6 Hz)

Reference Example 56

The following compounds were obtained in a similar manner as in Reference Example 55.
(1) methyl 1-benzothiophene-5-carboxylate
    NMR (400 MHz, CDCl$_3$) δ value: 3.96 (3H, s), 7.43 (1H, dd, J=5.6, 0.8 Hz), 7.52 (1H, d, J=5.6 Hz), 7.92 (1H, dd, J=8.6, 0.8 Hz), 8.01 (1H, dd, J=8.6, 1.6 Hz), 8.54 (1H, d, J=1.2 Hz)
(2) methyl 4-[2-(benzyloxy)-2-oxoethyl] benzoate
    NMR (90 MHz, CDCl$_3$) δ value: 3.72 (2H, s), 3.91 (3H, s), 5.14 (2H, s), 7.33-7.46 (7H, m), 7.90-8.04 (2H, m)

Reference Example 57

10.85 g of methyl 3-bromo-4-(bromomethyl)benzoate was dissolved in 108 mL of N,N-dimethylformamide, to which 3.46 g of potassium acetate was added at room temperature, and this solution was stirred for 17.5 hours at the same temperature. The reaction mixture was added to a mixture of water and ethyl acetate, and then the organic phase was separated therefrom. After the resultant organic phase was washed with water and a saturated sodium chloride solution, the washed phase was dried over anhydrous magnesium sulfate, and the solvent was distilled out under reduced pressure. The resultant residue was purified by silica gel column chromatography [eluent; hexane:ethyl acetate=10:1] to yield 6.43 g of methyl 4-[(acetyloxy)methyl]-3-bromobenzoate as white solid.

NMR (400 MHz, CDCl$_3$) δ value: 2.18 (3H, s), 3.93 (3H, s), 5.22 (2H, s), 7.47 (1H, d, J=8.0 Hz), 7.98 (1H, dd, J=8.0, 1.2 Hz), 8.24 (1H, d, J=1.2 Hz)

Reference Example 58

5.30 g of methyl 4-[(acetyloxy)methyl]-3-bromobenzoate was dissolved in 50 mL of hexamethylphosphoramide, to which 6.6 mL of tetramethyltin and 0.26 g of bis(triphenylphosphine)-palladium(II) dichloride were added at room temperature in a stream of nitrogen, and this solution was stirred for 3 hours at 70° C. The reaction mixture was cooled to room temperature, and was added to a mixture of water and diethyl ether, and then the organic phase was separated therefrom. After the resultant organic phase was washed with water and a saturated sodium chloride solution, the washed phase was dried over anhydrous magnesium sulfate, and the solvent was distilled out under reduced pressure. The resultant residue was purified by silica gel column chromatography [eluent; hexane:ethyl acetate=5:1] to yield 4.17 g of methyl 4-[(acetyloxy)methyl]-3-methylbenzoate as brown oil.

NMR (400 MHz, CDCl$_3$) δ value: 2.13 (3H, s), 2.38 (3H, s), 3.91 (3H, s), 5.15 (2H, s), 7.8-7.9 (2H, m), 7.40 (1H, d, J=8.4 Hz)

Reference Example 59

1.00 g of methyl 4-[(acetyloxy)methyl]-3-methylbenzoate was dissolved in 10 mL of methanol, to which a solution of 0.365 g of sodium methoxide in 7 mL of methanol was added dropwise at 5 to 7° C., and this solution was stirred for 30 minutes at 50° C. The reaction mixture was concentrated under reduced pressure, followed by successive addition of ethyl acetate and water, and then the organic phase was separated therefrom. After the resultant organic phase was washed with water and a saturated sodium chloride solution, the washed phase was dried over anhydrous magnesium sulfate, and the solvent was distilled out under reduced pressure to yield 0.79 g of methyl 4-(hydroxymethyl)-3-methylbenzoate as yellow oil.

NMR (400 MHz, CDCl$_3$) δ value: 1.78 (1H, brs), 2.36 (3H, s), 3.91 (3H, s), 4.75 (2H, s), 7.48 (1H, d, J=8.0 Hz), 7.84 (1H, s), 7.87 (1H, d, J=8.0 Hz)

Reference Example 60

Methyl 2-(hydroxymethyl)-1,3-benzothiazole-5-carboxylate was obtained in a similar manner as in Reference Example 59.

NMR (400 MHz, CDCl$_3$) δ value: 3.97 (4H, brs), 5.11 (2H, s), 7.94 (1H, d, J=8.0 Hz), 8.06 (1H, dd, J=8.4, 1.6 Hz), 8.63 (1H, d, J=1.6 Hz)

Reference Example 61

1.00 g of 5-methyl-2-benzofuran-1,3-dione was suspended in 10 mL of chlorobenzene, to which 1.3 mL of 1,1,1,3,3,3-hexamethyldisilazane was added at room temperature, and this suspension was stirred for 10.5 hours while heating it under reflux. The reaction mixture was cooled to room temperature, and resultant precipitate was filtered out therefrom to yield 0.169 g of 5-methyl-1H-isoindole-1,3(2H)-dione as light yellow solid.

NMR (400 MHz, CDCl₃) δ value: 2.53 (3H, s), 7.49 (1H, brs), 7.55 (1H, dd, J=7.8, 0.8 Hz), 7.67 (1H, d, J=0.8 Hz), 7.75 (1H, d, J=8.0 Hz)

Reference Example 62

1.00 g of 1H-benzimidazole-5-carboxylic acid was suspended in a mixed solvent of 10 mL of tetrahydrofuran and 20 μL of N,N-dimethylformamide, to which 1.6 mL of oxalyl chloride was added dropwise at room temperature, and this suspension was stirred for one hour at room temperature. The reaction mixture, to which 10 mL of methanol was added, was stirred for another one hour at room temperature and then for 30 minutes at 50° C., and this mixture was concentrated under reduced pressure. The resultant solid was washed with diisopropyl ether to yield 1.25 g of methyl 1H-benzimidazole-5-carboxylate hydrochloride as gray solid.

NMR (400 MHz, DMSO-d₆) δ value: 3.92 (3H, s), 7.95 (1H, d, J=8.4 Hz), 8.11 (1H, d, J=8.4 Hz), 8.39 (1H, s), 9.56 (1H, s)

Reference Example 63

3.00 g of 5-methyl-2-benzofuran-1,3-dione was suspended in 30 mL of methanol, to which 0.2 mL of sulfuric acid was added at room temperature, and this suspension was stirred for 2.5 hours while heating it under reflux. The reaction mixture was cooled to room temperature, and poured into ice water followed by addition of ethyl acetate, and then the organic phase was separated therefrom. After the resultant organic phase was washed with water and a saturated sodium chloride solution successively, the washed phase was dried over anhydrous magnesium sulfate, and then the solvent was distilled out under reduced pressure to yield 2.95 g of dimethyl 4-methylphthalate as light yellow oil.

NMR (400 MHz, CDCl₃) δ value: 2.42 (3H, s), 3.88 (3H, s), 3.91 (3H, s), 7.33 (1H, d, J=8.0 Hz) 7.47 (1H, s), 7.67 (1H, d, J=8.0 Hz)

Reference Example 64

The following compounds were obtained in a similar manner as in Reference Example 63.
(1) ethyl 5-methyl-2-pyrazinecarboxylate
NMR (400 MHz, CDCl₃) δ value: 1.46 (3H, t, J=7.2 Hz), 2.67 (3H, s), 4.51 (2H, q, J=7.2 Hz), 8.59 (1H, d, J=1.2 Hz), 9.19 (1H, d, J=1.2 Hz)
(2) methyl 3-(2-methoxy-2-oxoethyl)benzoate
NMR (90 MHz, CDCl₃) δ value: 3.68 (2H, s), 3.70 (3H, s), 3.92 (3H, s), 7.39-7.47 (2H, m), 7.91-7.96 (2H, m)

Reference Example 65

0.34 g of 60% sodium hydride was added to a solution of 1.00 g of 1-methyl-2,3-piperazinedione in 10 mL of N,N-dimethylformamide, and this mixture was stirred for 10 minutes at 50° C. Then, 0.88 mL of 4-fluorobenzaldehyde was added thereto and the mixture was stirred for 30 minutes at 120° C. The mixture was cooled to room temperature, and the solvent was distilled out thereof under reduced pressure. The resultant residue was purified by silica gel column chromatography [eluent; chloroform:ethanol=15:1] to yield 0.80 g of 4-(4-methyl-2,3-dioxo-1-piperazinyl)benzaldehyde as white solid.

NMR (400 MHz, DMSO-d₆) δ value: 3.01 (3H, s), 3.70 (2H, t, J=5.8 Hz), 4.05 (2H, t, J=5.6 Hz), 7.65 (2H, d, J=8.4 Hz), 7.96 (2H, d, J=7.6 Hz), 9.99 (1H, s)

Reference Example 66

4-(2-oxo-1,3-oxazolidin-3-yl)benzaldehyde was obtained in a similar manner as in Reference Example 65.
NMR (400 MHz, CDCl₃) δ value: 4.14 (2H, t, J=8.0 Hz), 4.55 (2H, t, J=8.0 Hz), 7.74 (2H, dd, J=9.0, 2.2 Hz), 7.91 (2H, dd, J=9.2, 2.2 Hz), 9.96 (1H, s)

Reference Example 67

7.00 g of 4-methylbenzenesulfonyl chloride was dissolved in 70 mL of methylene chloride, to which 3.59 g of dimethylamine hydrochloride was added at room temperature and 12.8 mL of triethylamine was added dropwise in an ice bath, and then this solution was stirred for one hour at room temperature. The reaction mixture, to which water was added, was adjusted to pH 3 with 6M hydrochloric acid, and then the organic phase was separated therefrom. After the resultant organic phase was washed with water and a saturated sodium chloride solution successively, the washed phase was dried over anhydrous magnesium sulfate, and the solvent was distilled out thereof under reduced pressure to yield 6.75 g of N,N,4-trimethylbenzenesulfonamide as white solid.

NMR (400 MHz, CDCl₃) δ value: 2.44 (3H, s), 2.68 (6H, s), 7.34 (2H, d, J=8.4 Hz), 7.66 (2H, d, J=8.4 Hz)

Reference Example 68

The following compounds were obtained in a similar manner as in Reference Example 67.
(1) N-(4-methylphenyl)methanesulfonamide
NMR (400 MHz, DMSO-d₆) δ value: 2.23 (3H, s), 2.89 (3H, s), 7.10 (2H, d, J=8.8 Hz), 7.14 (2H, d, J=8.8 Hz), 9.53 (1H, s)
(2) [bis(tert-butoxycarbonyl)amino](4-methylphenyl)dioxo-λ⁶-sulfane
NMR (400 MHz, CDCl₃) δ value: 1.48 (18H, s), 2.45 (3H, s), 7.33 (2H, d, J=8.0 Hz), 7.96 (2H, d, J=8.4 Hz)
(3) N,4-dimethylbenzenesulfonamide
NMR (400 MHz, CDCl₃) δ value: 2.43 (3H, s), 2.65 (3H, d, J=5.6 Hz), 4.47 (1H, d, J=4.8 Hz), 7.32 (2H, d, J=8.4 Hz), 7.75 (2H, d, J=8.4 Hz)

Reference Example 69

99.3 g of ethyl (E)-3-(4-methylphenyl)-2-propenoate was dissolved in 400 mL of chloroform, to which a solution of 21.7 mL of bromine in 100 mL of chloroform was added dropwise in an ice bath, and then this solution was stirred for 30 minutes at room temperature. An aqueous solution of sodium thiosulfate was then added to the reaction mixture, and the organic phase was separated therefrom. After the resultant organic phase was washed with water and a saturated sodium chloride solution successively, the washed phase was dried over anhydrous magnesium sulfate, and the solvent was distilled out therefrom under reduced pressure to yield 146.34 g of ethyl 2,3-dibromo-3-(4-methylphenyl)propanoate as light yellow solid.

NMR (400 MHz, CDCl₃) δ value: 1.37 (3H, t, J=6.8 Hz), 2.36 (3H, s), 4.35 (2H, q, J=6.8 Hz), 4.83 (1H, d, J=12.0 Hz), 5.33 (1H, d, J=12.0 Hz), 7.19 (2H, d, J=7.8 Hz), 7.29 (2H, d, J=7.8 Hz)

Reference Example 70

0.35 g of ethyl 2,3-dibromo-3-(4-methylphenyl)propanoate and 0.083 g of hydroxylamine hydrochloride was suspended in 7 mL of methanol, to which 0.19 g of a 28% solution of sodium methoxide in methanol was added at room temperature, and then this solution was stirred for 12 hours at the same temperature. The reaction mixture, to which water was added, was adjusted to pH 1 with 6M hydrochloric acid followed by addition of ethyl acetate, and the organic phase was separated therefrom. After the resultant organic phase was washed with water and a saturated sodium chloride solution successively, the washed phase was dried over anhydrous magnesium sulfate, and the solvent was distilled out therefrom under reduced pressure. The resultant residue was purified by silica gel column chromatography [eluent; hexane: ethyl acetate=4:1] to yield 0.12 g of 5-(4-methylphenyl)-3-isoxazolol as yellow oil.

NMR (400 MHz, CDCl$_3$) δ value: 2.41 (3H, s), 6.16 (1H, s), 7.2-7.3 (3H, m), 7.62 (2H, d, J=8.0 Hz)

Reference Example 71

2.50 g of methyl 3-methoxy-4-methylbenzoate was dissolved in 25 mL of benzene, to which 2.72 g of N-bromosuccinimide and 0.23 g of 2,2'-azobisisobutyronitrile were successively added at room temperature, and this solution was stirred for one hour while heating it under reflux. After 3.90 g of hexamethylenetetramine dissolved in 7.8 mL of acetic acid and 7.8 mL of water was added dropwise to the reaction mixture, benzene was distilled out therefrom, and then the mixture was stirred for one hour while heating it under reflux. The reaction mixture, which was cooled to room temperature, was added to a mixture of chloroform and water and then adjusted to pH 7 with a 20% aqueous solution of sodium hydroxide, and the organic phase was separated therefrom. After the resultant organic phase was successively washed with water, a saturated aqueous solution of sodium hydrogen carbonate, and a saturated sodium chloride solution, the washed phase was dried over anhydrous magnesium sulfate, and the solvent was distilled out under reduced pressure. The resultant residue was purified by silica gel column chromatography [eluent; hexane:ethyl acetate=3:1] to yield 1.74 g of methyl 4-formyl-3-methoxybenzoate as white solid.

NMR (400 MHz, CDCl$_3$) δ value: 3.96 (3H, s), 4.00 (3H, s), 7.67 (1H, s), 7.68 (1H, d, J=7.8 Hz), 7.88 (1H, d, J=7.8 Hz), 10.52 (1H, s)

Reference Example 72

2-methyl-1,3-benzothiazole-5-carboaldehyde was obtained in a similar manner as in Reference Example 71.

NMR (400 MHz, CDCl$_3$) δ value: 2.89 (3H, s), 7.90 (1H, dd, J=8.4, 1.6 Hz), 7.97 (1H, d, J=8.4 Hz), 8.40 (1H, d, J=1.2 Hz), 10.13 (1H, s)

Reference Example 73

1.72 g of methyl 4-formyl-3-methoxybenzoate was dissolved in 8.6 mL of methanol, to which 2.6 mL of a 20% aqueous solution of sodium hydroxide was added at room temperature, and this solution was stirred for one hour at the same temperature. The reaction mixture, to which water was added, was adjusted to pH 2 with 6M hydrochloric acid, and resultant precipitate was filtered out therefrom and washed with water to yield 1.49 g of 4-formyl-3-methoxybenzoic acid as light yellow solid.

NMR (400 MHz, DMSO-d$_6$) δ value: 3.99 (3H, s), 7.62 (1H, d, J=8.0 Hz), 7.68 (1H, d, J=1.2 Hz), 7.79 (1H, d, J=8.0 Hz), 10.40 (1H, s), 13.51 (1H, brs)

Reference Example 74

The following compounds were obtained in a similar manner as in Reference Example 73.
(1) 5-(ethoxycarbonyl)-2-pyridinecarboxylic acid
NMR (90 MHz, DMSO-d$_6$) δ value: 1.36 (3H, t, J=7.1 Hz), 3.60 (1H, brs), 4.39 (2H, q, J=7.1 Hz), 8.16 (1H, d, J=8.1 Hz), 8.46 (1H, dd, J=8.2, 2.3 Hz), 9.16-9.18 (1H, m)
(2) 2-[3-(methoxycarbonyl)phenyl]acetic acid
NMR (90 MHz, CDCl$_3$) δ value: 3.71 (2H, s), 3.96 (3H, s), 7.39-7.54 (2H, m), 7.93-8.01 (2H, m), 9.52 (1H, brs)
(3) 2-(4-formylphenyl)acetic acid
light yellow oil
(4) 2-methoxy-4-[(1-methylcyclopentyl)-methyl]benzoic acid
NMR (400 MHz, CDCl$_3$) δ value: 0.91 (3H, s), 1.32-1.37 (2H, m), 1.49-1.56 (2H, m), 1.67-1.70 (4H, m), 2.67 (2H, s), 4.07 (3H, s), 6.82 (1H, s), 6.94 (1H, d, J=8.0 Hz), 8.08 (1H, d, J=7.6 Hz), 10.70 (1H, brs)

Reference Example 75

1.58 g of 4-(3-ethoxy-3-oxopropyl)-3-methoxybenzoic acid was dissolved in 16 mL of tetrahydrofuran, to which 0.96 mL of triethylamine was added dropwise at −10° C. and then 0.63 mL of ethyl chloroformate was added dropwise at −20° C., followed by addition thereto of 0.47 g of sodium borohydride in an ice bath, and this solution was stirred for 30 minutes at the same temperature. The reaction mixture, to which water was added dropwise before adding ethyl acetate and water thereto, was adjusted to pH 2 with 6M hydrochloric acid, and the organic phase was separated therefrom. After the resultant organic phase was washed with water and a saturated sodium chloride solution successively, the washed phase was dried over anhydrous magnesium sulfate, and the solvent was distilled out under reduced pressure to yield 1.49 g of ethyl 3-[4-(hydroxymethyl)-2-methoxyphenyl]propanoate as white solid.

NMR (400 MHz, CDCl$_3$) δ value: 1.24 (3H, t, J=7.1 Hz), 2.58 (2H, t, J=7.6 Hz), 2.85 (1H, brs), 2.92 (2H, t, J=7.6 Hz), 3.83 (3H, s), 4.11 (2H, q, J=7.1 Hz), 4.65 (2H, s), 6.84 (1H, d, J=7.6 Hz), 6.88 (1H, s), 7.11 (1H, d, J=7.6 Hz)

Reference Example 76

The following compounds were obtained in a similar manner as in Reference Example 75.
(1) methyl 4-(2-hydroxyethyl)benzoate
NMR (90 MHz, CDCl$_3$) δ value: 1.55 (1H, brs), 2.92 (2H, t, J=6.7 Hz), 3.77-4.03 (2H, m), 3.91 (3H, s), 7.30 (2H, d, J=7.7 Hz), 7.98 (2H, j, d, J=8.1 Hz)
(2) methyl 3-(2-hydroxyethyl)benzoate
NMR (90 MHz, CDCl$_3$) δ value: 1.42 (1H, t, J=5.9 Hz), 2.93 (2H, t, J=6.7 Hz), 3.80-4.00 (2H, m), 3.92 (3H, s), 7.37-7.44 (2H, m), 7.85-7.96 (2H, m)

Reference Example 77

5.00 g of 4-bromobenzaldehyde was dissolved in 100 mL of N,N-dimethylformamide, to which 2.9 mL of ethyl acrylate, 0.30 g of palladium(II) acetate, 0.35 g of triphenylphosphine, 13.20 g of potassium acetate, and 8.70 g of tetra-n-butylammonium bromide were added, and this solution was stirred for 2.5 hours at 90° C. The reaction mixture was added to a mixture of ethyl acetate and water, and adjusted to pH 2 with 6M hydrochloric acid, and the organic phase was separated therefrom. After the resultant organic phase was washed with water and a saturated sodium chloride solution successively, the washed phase was dried over anhydrous magnesium sulfate, and the solvent was distilled out under reduced pressure. The resultant residue was purified by silica gel column chromatography [eluent; hexane:ethyl acetate=2:1] to yield 4.75 g of ethyl (E)-3-(4-formylphenyl)-2-propenoate as yellow solid.

NMR (400 MHz, CDCl$_3$) δ value: 1.35 (3H, t, J=7.2 Hz), 4.29 (2H, q, J=7.2 Hz), 6.55 (1H, d, J=16.0 Hz), 7.68 (2H, d, J=8.4 Hz), 7.71 (1H, d, J=16.0 Hz), 7.90 (2H, d, J=8.4 Hz), 10.03 (1H, s)

Reference Example 78

4.00 g of methyl 3-(hydroxymethyl)benzoate was dissolved in 80 mL of methylene chloride, to which 9.47 g of triphenylphosphine was added in small portions in an ice bath followed by addition of 12.00 g of carbon tetrabromide in small portions, and this solution was stirred for one hour at room temperature. The reaction mixture was concentrated under reduced pressure, and the resultant residue was purified by silica gel column chromatography [eluent; hexane:ethyl acetate=2:1] to yield 5.02 g of methyl 3-(bromomethyl)benzoate as colorless oil.

NMR (90 MHz, CDCl$_3$) δ value: 3.93 (3H, s), 4.52 (2H, s), 7.42-8.07 (4H, m)

Reference Example 79

0.924 g of sodium cyanide was dissolved in 15 mL of dimethylsulfoxide, to which a solution of 4.00 g of methyl 3-(bromomethyl)benzoate in 5 mL of dimethylsulfoxide was added in an ice bath, and this solution was stirred for 2 hours at room temperature. The reaction mixture was added to a mixture of ethyl acetate and water, and the organic phase was separated therefrom. After the resultant organic phase was washed with water and a saturated sodium chloride solution successively, the washed phase was dried over anhydrous magnesium sulfate, and concentrated under reduced pressure to yield 3.00 g of methyl 3-(cyanomethyl)benzoate as orange oil.

NMR (90 MHz, CDCl$_3$) δ value: 3.81 (2H, s), 3.94 (3H, s), 7.46-7.54 (2H, m), 7.99-8.06 (2H, m)

Reference Example 80

12.2 mL of (S)-(−)-α-pinene was dissolved in 30 mL of tetrahydrofuran, to which a 1M solution of borane in tetrahydrofuran was added dropwise in an ice bath, and this solution was stirred for 2 hours at 5 to 10° C. Then, after a solution of 4.59 g of 1,3-cyclopentadiene in 4 mL of tetrahydrofuran was added dropwise thereto in an ice bath, the solution was stirred for 14 hours at room temperature. The reaction mixture was ice-cooled, to which 1.2 mL of water, 6.9 mL of 20% sodium hydroxide, and 6.9 mL of a 30% aqueous solution of hydrogen peroxide were successively added dropwise, and then the reaction mixture was cooled to room temperature followed by addition of sodium chloride, and the organic phase was separated therefrom. The resultant organic phase was concentrated under reduced pressure, to which diethyl ether and a 1M aqueous solution of silver nitrate were added, and after this mixture was stirred for 30 minutes at room temperature, the reaction mixture was permitted to stand and the organic phase was separated therefrom. The resultant organic phase was washed with a 1M aqueous solution of silver nitrate followed by addition of sodium chloride, and then filtered. The filtrate was dried over anhydrous magnesium sulfate, and the solvent was distilled out under reduced pressure to yield 0.83 g of 3-cyclopenten-1-ol as light yellow oil.

NMR (400 MHz, CDCl$_3$) δ value: 1.73 (1H, brs), 2.29-2.36 (2H, m), 2.61-2.69 (2H, m), 4.51-4.54 (1H, m), 5.72 (2H, s)

Reference Example 81

2.00 g of 2-amino-5-methylbenzoic acid was suspended in 20 mL of water, to which 1.18 g of potassium cyanate was added and a mixture of 0.23 mL of acetic acid and 1 mL of water were added dropwise, and this suspension was stirred for 1.5 hours at 50° C. Then, after a solution of 1.42 g of sodium hydroxide in 2 mL of water was added drowise, to which 40 mL of water and 20 mL of 1,4-dioxane were added, and this solution was stirred for 3.5 hours while heating it under reflux. The reaction mixture was ice-cooled, from which precipitated solid was filtered, and then 30 mL of water and 3 mL of 6M of hydrochloric acid were added to the resultant solid, which was then stirred for 1.5 hours while heating it under reflux. The reaction mixture was cooled to room temperature, from which resultant precipitate was filtered and washed with water to yield 1.17 g of 6-methyl-2,4-(1H,3H)-quinazolinedione as white solid.

NMR (400 MHz, DMSO-d$_6$) δ value: 2.32 (3H, s), 7.07 (1H, d, J=8.4 Hz), 7.46 (1H, dd, J=8.4, 2.0 Hz), 7.69 (1H, d, J=0.8 Hz), 11.09 (1H, brs), 11.18 (1H, brs)

Reference Example 82

0.636 g of sodium borohydride was added to 22 mL of ice-cooled ethanol, to which a solution of 1.09 g of calcium chloride in 14 mL of ethanol was added dropwise, followed by addition of 1.20 g of 5-(ethoxycarbonyl)-2-pyridinecarboxylic acid ½ calcium salt, and this mixture was stirred for one hour at room temperature. The reaction mixture, to which 2.8 mL of concentrated sulfuric acid was added, was stirred for 6 hours while heating it under reflux. The reaction mixture was cooled to room temperature and concentrated under reduced pressure followed by successive addition of a saturated aqueous solution of sodium hydrogen carbonate and chloroform, and then the organic phase was separated therefrom. The resultant organic phase was washed with a saturated sodium chloride solution and dried over anhydrous magnesium sulfate, and the solvent was distilled out under reduced pressure to yield 0.34 g of ethyl 5-(hydroxymethyl)-2-pyridinecarboxylate as light yellow solid.

NMR (90 MHz, CDCl$_3$) δ value: 1.45 (3H, t, J=7.1 Hz); 2.32 (1H, brs), 4.48 (2H, q, J=7.1 Hz), 4.84 (2H, s), 7.86 (1H, dd, J=8.1, 2.0 Hz), 8.13 (1H, d, J=7.9 Hz), 8.71 (1H, d, J=1.3 Hz)

Reference Example 83

23.30 g of sodium hydroxide was dissolved in 118 mL of water and was ice-cooled, to which 9.23 mL of bromine was added dropwise over 20 minutes and then a solution of 9.80 g of 1-(2-fluoro-4-methoxyphenyl)-1-ethanone in 88 mL of 1,4-dioxane was added dropwise over one hour at −10° C. The resultant reaction mixture was cooled to room temperature, to which water was added, and then an aqueous phase was separated therefrom. A solution of 7.23 g of sodium thiosulfate in 100 mL of water was added to the aqueous phase, and then 12M hydrochloric acid was further added until the pH value of this aqueous phase reached 2. The resultant precipitate was filtered therefrom and washed with water to yield 8.20 g of 2-fluoro-4-methoxybenzoic acid as white solid.

NMR (400 MHz, DMSO-d$_6$) δ value: 3.83 (3H, s), 6.84-6.92 (2H, m), 7.83 (1H, t, J=8.8 Hz), 12.86 (1H, brs)

Reference Example 84

1.70 g of 4-(methoxymethoxymethyl)-2-methylbenzaldehyde was dissolved in 10 mL of acetonitrile, to which 3.69 g of sodium dihydrogen phosphate dihydrate dissolved in 7 mL of water and 1.58 g of a 80% sodium chlorite dissolved in 3 mL of water and a 1.5 mL of 30% aqueous solution of hydrogen peroxide were successively added at 5 to 10° C., and then this solution was stirred for 20 minutes at room temperature. Then, ethyl acetate and water were added to the reaction mixture, and the organic phase was separated therefrom. After the resultant organic phase was washed with water and a saturated sodium chloride solution successively, the washed phase was dried over anhydrous magnesium sulfate, and the solvent was distilled out under reduced pressure. The resultant residue was dissolved in 18 mL of methanol, to which 9 mL of 6M hydrochloric acid was added, and this mixture was stirred for 4.5 hours while heating it under reflux. The reaction mixture was cooled to room temperature, and poured into a mixture of chloroform and water, then the organic phase was separated therefrom. After the resultant organic phase was washed with water and a saturated sodium chloride solution successively, the washed phase was dried over anhydrous magnesium sulfate, and the solvent was distilled out under reduced pressure. The resultant residue was purified by silica gel column chromatography [eluent; hexane:ethyl acetate=1:1] to yield 1.30 g of methyl 4-(hydroxymethyl)-2-methylbenzoate as light yellow oil.

NMR (400 MHz, CDCl$_3$) δ value: 1.89 (1H, brs), 2.61 (3H, s), 3.87 (3H, s), 4.71 (2H, s), 7.22-7.26 (2H, m), 7.91 (1H, d, J=8.0 Hz)

Reference Example 85

14.17 g of 4-bromo-2-hydroxybenzoic acid, 16.3 mL of iodomethane, and 27.07 g of potassium carbonate were suspended in 142 mL of N,N-dimethylformamide, and this suspension was stirred for 5 hours at 75° C. In addition, 4.1 mL of iodomethane and 9.02 g of potassium carbonate were added thereto, and the mixture was stirred for 30 minutes at 105° C. The reaction mixture was cooled to room temperature, added to a mixture of ethyl acetate and ice cooled water, and adjusted to pH 2 with 6M hydrochloric acid for separation of the organic phase. After the resultant organic phase was washed with water and a saturated sodium chloride solution successively, the washed phase was dried over anhydrous magnesium sulfate, and the solvent was distilled out under reduced pressure. The resultant residue was purified by silica gel column chromatography [eluent; hexane:ethyl acetate=3:1] to yield 5.62 g of yellow oil. The resultant oil was dissolved in 30 mL of methanol, to which 10 mL of a 20% aqueous solution of sodium hydroxide was added, and this mixture was stirred for one hour at room temperature. The reaction mixture, to which water was added, was adjusted to pH 2 with 6M hydrochloric acid followed by addition of chloroform, and the organic phase was separated therefrom. After the resultant organic phase was washed with water and a saturated sodium chloride solution successively, the washed phase was dried over anhydrous magnesium sulfate, and the solvent was distilled out under reduced pressure. The resultant residue was purified by silica gel column chromatography [eluent; toluene:ethyl acetate=5:1] to yield 5.62 g of 4-bromo-2-methoxybenzoic acid as light yellow solid.

NMR (400 MHz, DMSO-d$_6$) δ value: 3.84 (3H, s), 7.20 (1H, dd, J=8.0, 1.6 Hz), 7.33 (1H, d, J=1.6 Hz), 7.58 (1H, d, J=8.0 Hz), 12.81 (1H, brs)

Reference Example 86

4-isobutoxy-2-methylbenzoic acid was obtained in a similar manner as in Reference Example 85.

NMR (90 MHz, DMSO-d$_6$) δ value: 0.98 (6H, d, J=6.6 Hz), 1.7-2.3 (1H, m), 2.52 (3H, s), 3.79 (2H, d, J=6.4 Hz), 6.77-6.84 (2H, m), 7.84 (1H, d, J=9.3 Hz)

Reference Example 87

2.20 g of methyl 2-methyl-1,3-benzothiazole-5-carboxylate was dissolved in 165 mL of benzene, to which 16.63 g of N-bromosuccinimide and 1.22 g of 2,2'-azobisisobutyronitrile were successively added at room temperature, and this solution was stirred for 15 hours while heating it under reflux. The reaction mixture was cooled to room temperature, and then the solvent was distilled out under reduced pressure. The resultant residue was dissolved in 22 mL of N,N-dimethylformamide, to which 5.21 g of potassium acetate was added at room temperature, and this solution was stirred for 30 minutes at the same temperature. The reaction mixture was added to a mixture of water and ethyl acetate, and then the organic phase was separated therefrom. After the resultant organic phase was washed with water and a saturated sodium chloride solution successively, the washed phase was dried over anhydrous magnesium sulfate, and the solvent was distilled out under reduced pressure. The resultant residue was purified by silica gel column chromatography [eluent; hexane:ethyl acetate=5:1] to yield 0.64 g of methyl 2-[(acetyloxy)methyl]-1,3-benzothiazole-5-carboxylate as yellow solid.

NMR (400 MHz, CDCl$_3$) δ value: 2.22 (3H, s), 3.98 (3H, s), 5.51 (2H, s), 7.95 (1H, d, J=8.4 Hz), 8.10 (1H, dd, J=8.4, 1.6 Hz), 8.70 (1H d, J=1.6 Hz)

Reference Example 88

3.00 g of 4-methylbenzoic acid was suspended in a mixed solvent of 30 mL of methylene chloride and 20 μL of N,N-dimethylformamide, to which 2.9 mL of oxalyl chloride was added dropwise at room temperature, and this suspension was stirred for 5.5 hours at room temperature. Then, 1.79 g of monomethylamine hydrochloride was added to the reaction mixture, to which 15.4 mL of triethylamine was added dropwise in an ice bath, and the mixture was stirred for one hour at room temperature. The reaction mixture, to which water was added, was adjusted to pH 3 with 6M hydrochloric acid, and then the organic phase was separated therefrom. After the resultant organic phase was washed with water and a saturated sodium chloride solution successively, the washed phase was dried over anhydrous magnesium sulfate, and the solvent was distilled out under reduced pressure. The resultant residue was purified by silica gel column chromatography [eluent; chloroform:acetone=5:1] to yield 2.11 g of N,4-dimethylbenzamide as light orange solid.

NMR (400 MHz, CDCl$_3$) δ value: 2.39 (3H, s), 3.01 (3H, d, J=4.8 Hz), 6.11 (1H, brs), 7.23 (2H, d, J=7.6 Hz), 7.66 (2H, d, J=8.0 Hz)

Reference Example 89

N,N,4-trimethylbenzamide was obtained in a similar manner as in Reference Example 88.

NMR (400 MHz, CDCl$_3$) δ value: 2.37 (3H, s), 2.99 (3H, brs), 3.10 (3H, brs), 7.19 (2H, d, J=7.6 Hz), 7.32 (2H, d, J=8.0 Hz)

Reference Example 90

1.00 g of 2-[4-(bromomethyl)phenyl]acetic acid was suspended in 5 mL of a 4M solution of hydrogen chloride in ethanol, and this suspension was stirred for 2 hours at room temperature. The reaction mixture was concentrated under reduced pressure to yield 0.954 g of ethyl 2-[4-(bromomethyl)phenyl]acetate as light brown oil.

NMR (400 MHz, CDCl$_3$) δ value: 1.25 (3H, t, J=7.2 Hz), 3.61 (2H, s), 4.15 (2H, q, J=7.2 Hz), 4.57 (2H, s), 7.28 (2H, d, J=7.8 Hz), 7.34 (2H, d, J=7.9 Hz)

Reference Example 91

5.00 g of ethanethioamide was suspended in 50 mL of ethanol, to which 9.3 mL of ethyl 3-bromo-2-oxopropanoate was added dropwise at room temperature, and this suspension was stirred for one hour while heating it under reflux. The reaction mixture was cooled to room temperature and added to a mixture of ethyl acetate and water, followed by separation of the organic phase therefrom. After the resultant organic phase was washed with water and a saturated sodium chloride solution successively, the washed phase was dried over anhydrous magnesium sulfate, and the solvent was distilled out under reduced pressure to yield 2.30 g of ethyl 2-methyl-1,3-thiazole-4-carboxylate as white solid.

NMR (90 MHz, CDCl$_3$) δ value: 1.40 (3H, t, J=7.1 Hz), 2.77 (3H, s), 4.42 (2H, q, J=7.1 Hz), 8.04 (1H, s)

Reference Example 92

25.0 g of 2-sulfanylbenzoic acid was suspended in 125 mL of ethanol, to which 14.3 g of sodium hydroxide and 31.7 mL of 2-bromo-1,1-diethoxyethane was successively added and this suspension was stirred for 3.5 hours while heating it under reflux. The reaction mixture was concentrated under reduced pressure, and the resultant residue was dissolved in 250 mL of N,N-dimethylformamide, to which 15.1 mL of iodomethane and 67.2 g of potassium carbonate were added, and then this mixture was stirred for one hour at room temperature. The reaction mixture was added to a mixture of ethyl acetate and water, from which the organic phase was separated. After the resultant organic phase was washed with water and a saturated sodium chloride solution successively, the washed phase was dried over anhydrous magnesium sulfate, and the solvent was distilled out under reduced pressure. The resultant residue was purified by silica gel column chromatography [eluent; hexane:ethyl acetate=2:1] to yield yellow oil. This product was dissolved in 250 mL of toluene, to which 100 mL of a 85% phosphoric acid was added, and this solution was stirred for 4.5 hours while heating it under reflux. The reaction mixture was cooled to room temperature, to which water was added, and filtered through Celite to separate the organic phase therefrom. After the resultant organic phase was washed with water and a saturated sodium chloride solution successively, the washed phase was dried over anhydrous magnesium sulfate, and the solvent was distilled out under reduced pressure. Purification by silica gel column chromatography [eluent; hexane:ethyl acetate=10:1] to yield 20.5 g of methyl 1-benzothiophene-7-carboxylate as yellow oil.

NMR (400 MHz, CDCl$_3$) δ value: 4.03 (3H, s), 7.40 (1H, d, J=5.6 Hz), 7.45 (1H, t, J=7.6 Hz), 7.58 (1H, d, J=5.6 Hz), 8.03 (1H, dd, J=8.2, 0.8 Hz), 8.11-8.13 (1H, m)

Reference Example 93

4.42 g of 2-(hydroxymethyl)-1-benzothiophene-5-carbaldehyde was suspended in 44 mL of methylene chloride, to which 20.0 mL of N-ethyldiisopropylamine and 5.2 mL of chloromethyl methyl ether were successively added dropwise at 25 to 30° C., and this mixture was stirred for one hour at room temperature. The reaction mixture was poured into water, and adjusted to pH 7.5 with 6M hydrochloric acid, and then the organic phase was separated therefrom. After the resultant organic phase was washed with water and a saturated sodium chloride solution successively, the washed phase was dried over anhydrous sodium sulfate, and the solvent was distilled out under reduced pressure to yield 5.40 g of brown oil. The resultant oil was dissolved in 20 mL of tetrahydrofuran, and this solution was added dropwise to 40 mL of an aqueous suspension of silver oxide prepared from 7.62 g of silver nitrate and 3.78 g of sodium hydroxide in an ice bath, and then this mixture was stirred for 1.5 hours at room temperature. The reaction mixture was filtered through Celite, and the filtrate to which 6M hydrochloric acid was added was adjusted to pH 2 followed by addition thereto of ethyl acetate, and then the organic phase was separated therefrom. After the resultant organic phase was washed with a saturated sodium chloride solution, the washed phase was dried over anhydrous magnesium sulfate, and the solvent was distilled out under reduced pressure. 6.00 g of the resultant yellow solid was dissolved in 60 mL of N,N-dimethylformamide, to which 7.90 g of potassium carbonate and 2.1 mL of iodomethane were added, and this mixture was stirred for 30 minutes at room temperature. The reaction mixture was added to a mixture of ethyl acetate and water, and then the organic phase was separated therefrom. After the resultant organic phase was washed with water and a saturated sodium chloride solution successively, the washed phase was dried over anhydrous magnesium sulfate, and the solvent was distilled out under reduced pressure to yield yellow solid. The resultant solid was dissolved in 50 mL of methanol, to which 10 mL of 6M hydrochloric acid was added, and this mixture was stirred for 30 minutes while heating it under reflux. The reaction mixture was cooled to room temperature and poured into a mixture of ethyl acetate and water for separation of the organic phase. After the resultant organic phase was washed with a saturated aqueous solution of sodium hydrogen carbonate, water, and a saturated sodium chloride solution successively, the washed phase was dried over anhydrous magnesium sulfate, and the solvent was distilled out under reduced pressure to yield 3.50 g of methyl 2-(hydroxymethyl)-1-benzothiophene-5-carboxylate as yellow solid.

NMR (400 MHz, CDCl$_3$) δ value: 2.03 (1H, t, J=5.4 Hz), 3.96 (3H, s), 4.96 (2H, d, J=4.8 Hz), 7.29 (1H, s), 7.86 (1H, d, J=8.8 Hz), 7.97 (1H, dd, J=8.8, 1.6 Hz), 8.43 (1H, d, J=1.6 Hz)

INDUSTRIAL APPLICABILITY

The novel benzophenone derivatives and the salts thereof in accordance with this invention have excellent anti-arthritic activities and inhibitory effect on bone destruction caused by arthritis, and moreover, provide high safety as well as excellent pharmacokinetics in vivo and thus are useful as therapeutic agent for arthritis. The preventive/therapeutic agent for diseases in which excessive expression of AP-1 is involved and inhibitors against AP-1 activity, which contain the above benzophenone derivatives or the salts thereof, are useful as preventive/therapeutic agent for diseases in which excessive expression of AP-1 is involved because of their inhibitory activity on AP-1 activity.

The invention claimed is:

1. A benzophenone derivative represented by the following general formula:

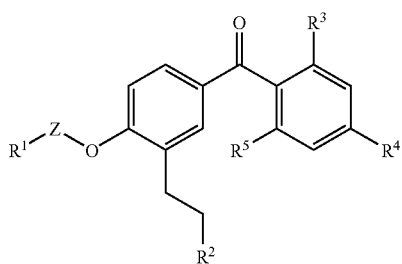

wherein
R$^1$ represents a substituted or unsubstituted heterocyclic group, a substituted phenyl group, or a substituted or unsubstituted alkyl group;
Z represents a substituted or unsubstituted alkylene group;
R$^2$ represents a substituted or unsubstituted heterocyclic group, a substituted or unsubstituted heterocyclic carbonyl group or a protected or unprotected carboxyl group;
R$^3$ represents a hydrogen atom, a halogen atom, a cyano group, a nitro group, a protected or unprotected carboxyl group, a protected or unprotected hydroxyl group, a protected or unprotected amino group, a mercapto group, a carbamoyl group or a substituted or unsubstituted alkyl, alkenyl, cycloalkyl, aryl, aralkyl, alkoxy, aryloxy, acyl, alkoxycarbonyl, aryloxycarbonyl, alkylthio, alkylsulfinyl, alkylsulfonyl, alkylamino, acylamino, alkylsulfonylamino, arylsulfonylamino or heterocyclic group;
R$^4$ represents a substituted or unsubstituted alkoxy, cycloalkyloxy, cycloalkenyloxy, alkyl, cycloalkyl, heterocyclic-oxy or heterocyclic group;
R$^5$ represents a hydrogen atom, a halogen atom or a hydroxyl group,
provided that, when R$^1$ represents a substituted or unsubstituted alkyl group, R$^4$ represents a substituted or unsubstituted cycloalkyloxy group, an alkoxy group substituted with a substituted or unsubstituted phenyl or heterocyclic group or a substituted or unsubstituted heterocyclic-oxy group,
or a salt thereof.

2. The benzophenone derivative or a salt thereof according to claim 1, wherein R$^1$ is a substituted or unsubstituted heterocyclic group or a substituted phenyl group; R$^2$ is a carboxyl group protected or unprotected with an alkyl group; R$^3$ is a protected or unprotected hydroxyl group; R$^4$ is a substituted or unsubstituted cycloalkyloxy group; R$^5$ is a hydrogen atom; and Z is an alkylene group.

3. The benzophenone derivative or a salt thereof according to claim 1 or 2, wherein R$^1$ is a substituted or unsubstituted heterocyclic group; R$^2$ is a carboxyl group; and R$^3$ is a hydroxyl group.

4. The benzophenone derivative or a salt thereof according to claim 1, wherein R$^1$ is a substituted or unsubstituted heterocyclic group or a substituted phenyl group; R$^2$ is a carboxyl group protected with a substituted alkyl group; R$^3$ is a protected or unprotected hydroxyl group; R$^4$ is a substituted or unsubstituted cycloalkyloxy group; R$^5$ is a hydrogen group; and Z is an alkylene group.

5. The benzophenone derivative or a salt thereof according to claim 1 or 4, wherein R$^1$ is a substituted or unsubstituted heterocyclic group; R$^2$ is a carboxyl group protected with a substituted alkyl group; and R$^3$ is a hydroxyl group.

6. A composition comprising:
a compound or a salt thereof according to claim 1, and an additive selected from the group consisting of an excipient, a carrier and a diluent.

7. A composition comprising
a compound or a salt thereof according to claim 1, and
an additive selected from the group consisting of an excipient, a carrier and a diluent,
wherein the composition is a therapeutic agent for an autoimmune disease and the autoimmune disease is one selected from the group consisting of rheumatoid arthritis, systemic lupus erythematosus, scleroderma, Behcet's disease, rheumatic fever, polymyositis, periarteritis nodosa, Sjogren's syndrome, active chronic hepatitis and glomerulonephritis.

8. The composition according to claim 7, wherein the autoimmune disease is rheumatoid arthritis.

9. A method for the treatment of a disease in which excessive expression of AP-1 is involved, comprising administering to a patient in need thereof an effective dose of an AP-1 inhibitor comprising a compound or a salt thereof according to claim 1, wherein the disease in which excessive expression of AP-1 is involved is one or more selected from the group consisting of rheumatoid arthritis, systemic lupus erythematosus, scleroderma, Behcet's disease, rheumatic fever, polymyositis, periarteritis nodosa, Sjögren's syndrome, active chronic hepatitis and glomerulonephritis.

10. A benzophenone derivative according to claim 1 wherein the benzophenone derivative is 3-{5-[4-(cyclopentyloxy)-2-hydroxybenzoyl]-2-[(3-hydroxyl-1,2-benzisoxazol-6-yl)methoxy}phenyl}propanoic acid.

11. A benzophenone derivative according to claim 1 wherein the benzophenone derivative is 2-(4-morpholinyl)ethyl 3-{5-[4-(cyclopentyloxy)-2-hydroxybenzoyl]-2-[(3-hydroxy-1,2-benzisoxazol-6-yl)methoxy]phenyl}propanoate.

12. A benzophenone derivative according to claim 1 wherein the benzophenone derivative is 4-({2-(2-carboxyethyl)-4-[4-(cyclopentyloxy)-2-hydroxybenzoyl]phenoxy}methyl)benzoic acid.

13. A benzophenone derivative according to claim 1 wherein the benzophenone derivative is 3-(5-[4-(cyclopentyloxy)-2-hydroxybenzoyl]-2-{[4-(3-hydroxy-5-isoxazolyl)benzyl]oxy}phenyl)propanoic acid.

14. The composition according to claim 6, wherein the benzophenone derivative represented by the formula:

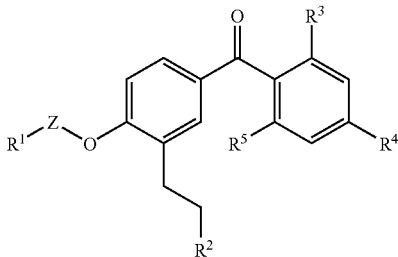

is at least one selected from the group consisting of 3-{5-[4-(cyclopentyloxy)-2-hydroxybenzoyl]-2-[(3-hydroxyl-1,2-benzisoxazol-6-yl)methoxy]phenyl}propanoic acid, 2-(4-morpholinyl)ethyl 3-{5-[4-(cyclopentyloxy)-2-hydroxybenzoyl]-2-[(3-hydroxy-1,2-benzisoxazol-6-yl)methoxy]phenyl}propanoate, 4-({2-(2-carboxyethyl)-4-[4-(cyclopentyloxy)-2-hydroxybenzoyl]phenoxy}methyl)benzoic acid and 3-(5-[4-(cyclopentyloxy)-2-hydroxybenzoyl]-2-{[4-(3-hydroxy-5-isoxazolyl)benzyl]oxy}phenyl)propanoic acid.

15. The composition according to claim 7, wherein the benzophenone derivative represented by the formula:

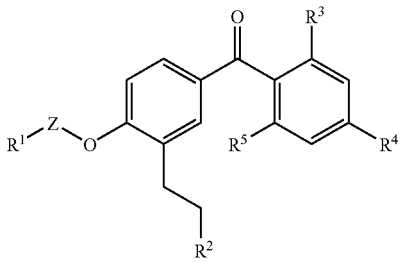

is at least one selected from the group consisting of 3-{5-[4-(cyclopentyloxy)-2-hydroxybenzoyl]-2-[(3-hydroxyl-1,2-benzisoxazol-6-yl)methoxy]phenyl}propanoic acid, 2-(4-morpholinyl)ethyl 3-{5-[4-(cyclopentyloxy)-2-hydroxybenzoyl]-2-[(3-hydroxy-1,2-benzisoxazol-6-yl)methoxy]phenyl}propanoate, 4-({2-(2-carboxyethyl)-4-[4-(cyclopentyloxy)-2-hydroxybenzoyl]phenoxy}methyl)benzoic acid and 3-(5-[4-(cyclopentyloxy)-2-hydroxybenzoyl]-2-{[4-(3-hydroxy-5-isoxazolyl)benzyl]oxy}phenyl)propanoic acid.

16. The method for the treatment of a disease in which excessive expression of AP-1 is involved according to claim 9 wherein the benzophenone derivative represented by the formula:

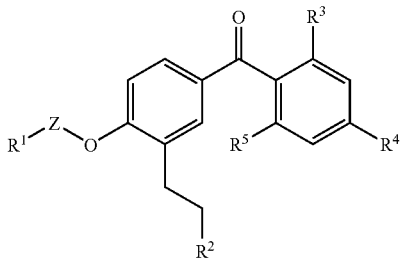

is at least one selected from the group consisting of 3-{5-[4-(cyclopentyloxy)-2-hydroxybenzoyl]-2-[(3-hydroxyl-1,2-benzisoxazol-6-yl)methoxy]phenyl}propanoic acid, 2-(4-morpholinyl)ethyl 3-{5-[4-(cyclopentyloxy)-2-hydroxybenzoyl]-2-[(3-hydroxy-1,2-benzisoxazol-6-yl)methoxy]phenyl}propanoate, 4-({2-(2-carboxyethyl)-4-[4-(cyclopentyloxy)-2-hydroxybenzoyl]phenoxy}methyl)benzoic acid and 3-(5-[4-(cyclopentyloxy)-2-hydroxybenzoyl]-2-{[4-(3-hydroxy-5-isoxazolyl)benzyl]oxy}phenyl)propanoic acid.

17. The method of treatment of a disease according to claim 9, wherein the disease in which excessive expression of AP-1 is involved is rheumatoid arthritis.

* * * * *